United States Patent
Kim et al.

(10) Patent No.: US 10,741,771 B2
(45) Date of Patent: Aug. 11, 2020

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si, Chungcheongnam-do (KR)

(72) Inventors: Yu Ri Kim, Wonju-si (KR); Sun-Hee Lee, Cheonan-si (KR); Won Sam Kim, Hwaseong-si (KR); Hye Ryeong Kim, Cheonan-si (KR); Ho Young Jung, Gimpo-si (KR); Jung Hwan Park, Hwaseong-si (KR); Sun Pil Hwang, Ansan-si (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 0 days.

(21) Appl. No.: 15/112,115

(22) PCT Filed: Jan. 14, 2015

(86) PCT No.: PCT/KR2015/000364
§ 371 (c)(1),
(2) Date: Jul. 15, 2016

(87) PCT Pub. No.: WO2015/108325
PCT Pub. Date: Jul. 23, 2015

(65) Prior Publication Data
US 2016/0380206 A1 Dec. 29, 2016

(30) Foreign Application Priority Data

Jan. 16, 2014 (KR) .................. 10-2014-0005580
Jul. 10, 2014 (KR) .................. 10-2014-0086820
Jan. 8, 2016 (KR) .................. 10-2016-0002635

(51) Int. Cl.
*H01L 51/00* (2006.01)
*C09K 11/06* (2006.01)
(Continued)

(52) U.S. Cl.
CPC ........ *H01L 51/0071* (2013.01); *C07D 495/14* (2013.01); *C09K 11/06* (2013.01);
(Continued)

(58) Field of Classification Search
None
See application file for complete search history.

(56) References Cited

U.S. PATENT DOCUMENTS 6,465,115 B2 10/2002 Shi et al.
6,596,415 B2 7/2003 Shi et al.
(Continued)

FOREIGN PATENT DOCUMENTS

KR 10-2010-0122798 A 11/2010
KR 10-2013-0009765 A 1/2013
(Continued)

OTHER PUBLICATIONS

Machine English translation of Eom et al. (KR-10-2014-0111719). Mar. 27, 2019.*
(Continued)

*Primary Examiner* — Jay Yang
(74) *Attorney, Agent, or Firm* — Vorys, Sater, Seymour & Pease LLP; Mih Suhn Koh

(57) ABSTRACT

A compound represented by Formula 1 is disclosed. An organic electric element includes a first electrode, a second electrode, and an organic material layer between the first electrode and the second electrode. The organic material layer includes the compound represented by Formula 1. When the organic electric element includes the compound in the organic material layer, luminescence efficiency, stability, and life span can be improved.

9 Claims, 1 Drawing Sheet

(51) Int. Cl.
  *C07D 495/14* (2006.01)
  *H01L 51/50* (2006.01)
  *H01L 51/56* (2006.01)

(52) U.S. Cl.
  CPC ...... *H01L 51/0067* (2013.01); *H01L 51/0072* (2013.01); *C09K 2211/1029* (2013.01); *C09K 2211/1044* (2013.01); *C09K 2211/1059* (2013.01); *C09K 2211/1092* (2013.01); *H01L 51/0005* (2013.01); *H01L 51/5056* (2013.01); *H01L 51/5088* (2013.01); *H01L 51/56* (2013.01)

(56) References Cited

U.S. PATENT DOCUMENTS

| | | | | |
|---|---|---|---|---|
| 2007/0231503 | A1* | 10/2007 | Hwang | C09K 11/06 428/1.1 |
| 2008/0026135 | A1 | 1/2008 | Bentsen et al. | |
| 2013/0328021 | A1 | 12/2013 | Lim et al. | |
| 2015/0034914 | A1* | 2/2015 | Lee | H01L 51/0067 257/40 |

FOREIGN PATENT DOCUMENTS

| | | | |
|---|---|---|---|
| KR | 10-2013-0110051 A | | 10/2013 |
| KR | 10-2014-0000611 A | | 1/2014 |
| KR | 10-2014-0097044 A | | 8/2014 |
| KR | 10-2014-0111719 | * | 9/2014 |
| WO | WO-2013/154325 A1 | * | 10/2013 |
| WO | WO-2014/142467 A1 | * | 9/2014 |

OTHER PUBLICATIONS

Kelgtermans et al., "Synthesis of Functionalized Dioxa-aza[7]helicenes Using Palladium Catalyzed Arylations", Organic Letters, (2012), vol. 14, No. 6, pp. 1500-1503.
Korean Office Action for Korean Application No. 10-2014-0086820, dated Nov. 9, 2015, six pages.
Korean Office Action for Korean Application No. 10-2014-0086820, dated May 12, 2016, four pages.
International Search Report for PCT Application No. PCT/KR2015/000364, dated Apr. 21, 2015, three pages; with English translation, two pages.
Office Action issued in corresponding KR application KR 10-2016-0002635; 8 pages, dated Jun. 13, 2019.

* cited by examiner

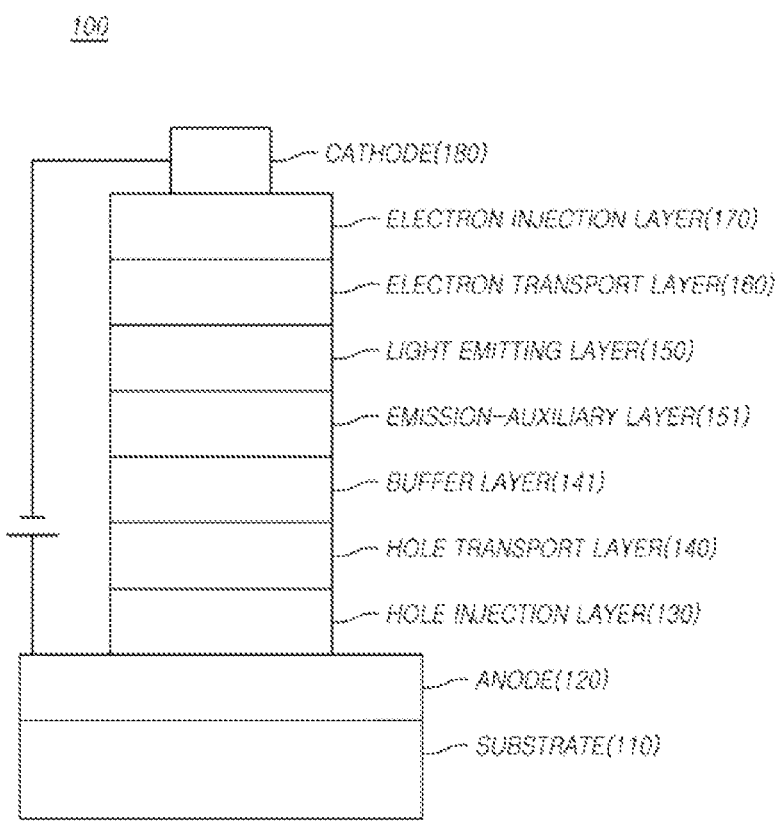

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This application claims priority from and the benefit under 35 U.S.C. 5129(a) of Korean Patent Application No. 10-2014-0005580 filed on Jan. 16, 2014, and Korean Patent Application No. 10-2014-0086820 filed on Jul. 10, 2014, the contents of which are hereby incorporated by reference for all purposes as if fully set forth herein.

BACKGROUND

Technical Field

The present invention relates to compounds for organic electric elements, organic electric elements using the same, and electronic devices thereof.

Background Art

In general, an organic light emitting phenomenon refers to a phenomenon in which electric energy is converted into light energy using an organic material. An organic electric element utilizing the organic light emitting phenomenon typically has a structure comprising an anode, a cathode, and an organic material layer interposed therebetween. In many cases, the organic material layer has a multilayered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function.

Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and yellow and orange light emitting materials required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to deterioration in color purity or a reduction in luminescence efficiency. On account of this, a host/dopant system may be used as the light emitting material in order to enhance the color purity and increase the luminescence efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given. Therefore it is required to develop a light emitting material that has high thermal stability and can achieve efficiently a charge balance in the light-emitting layer Further, in order to solve the emission problem with a hole transport layer in a recent organic electric element, an emission-auxiliary layer is present between the hole transport layer and a light emitting layer, and it is time to develop different emission-auxiliary layers according to respective light emitting layers (R, G, B).

In general, an electron transferred from an electron transport layer to a light emitting layer and a hole transferred from a hole transport layer to the light emitting layer are recombined to form an exciton. However, since a material used in a hole transporting layer should have a low HOMO value, it mainly has a low T1 value. Due to this, excitons generated from a light emitting layer are transported to the hole transporting layer, resulting in a charge unbalance in the light emitting layer. Thus, light emission occurs at an interface of the hole transporting layer.

When light emission at an interface of the hole transporting layer, the organic electroluminescent device also suffers from the disadvantage of a reduction in color purity, efficiency, and lifespan. Therefore, there is an urgent need to develop an emission-auxiliary layer which has a high T1 value and the HOMO level of which is between the HOMO energy level of a hole transport layer and the HOMO energy level of a light emitting layer.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new materials for an organic material layer.

The background art of the present inventions are disclosed in the documents below.

PRIOR ART

1. U.S. Pat. No. 6,596,415 (2003 Jul. 22)
2. U.S. Pat. No. 6,465,115 (2002 Oct. 15)

3. International Publication No. WO2009/148015 (2009 Dec. 10)

SUMMARY

In order to solve one or more of the above-mentioned problems occurring in the prior art, an aspect of the present invention is to provide a compound which allows an organic electric element to have high luminescence efficiency, low driving voltage, high heat-resistant, and to be improved in color purity and life span, an organic electric element using the same, and an electronic device including the organic electric element.

In accordance with an aspect of the present invention, the compound represented by the following formula is provided.

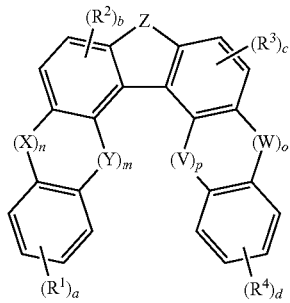

In another aspect of the present invention, organic electric elements using the compound represented by the formula above and electronic devices including the organic electric element are provided.

By using the compound according to embodiments of the present invention, an organic electric element according to one or more embodiments of the present invention not only has high luminescence efficiency, low driving voltage and high heat-resistant, but can also be significantly improved in color purity, and life span.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "haloalkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R'' are all hydrogen in the structural formula below. Also, "substituted fluorenyl group" or "substituted fluorenylene group" means, functional group which at least any one of R, R' and R'' is a functional group other than hydrogen and spiro compound which R and R' can be linked together with the carbone to which they are attached to form spiro compound.

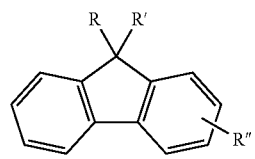

Unless otherwise stated, the term "aryl group" or "arylene group" as used herein has, but not limited to, 6 to 60 carbon atoms. Herein, the aryl group or arylene group means a monocyclic or polycyclic aromatic group, and may also be formed in conjunction with an adjacent group. Examples of "aryl group" or "arylene group" may include a phenyl group, a biphenyl group, a fluorene group, or a spirofluorene group.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P, and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

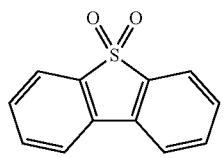 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Otherwise specified, the Formulas used in the present invention are as defined in the index definition of the substituent of the following Formula.

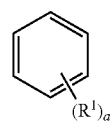

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent R's may be the same and different, and are linked to the benzene ring as follows. when a is an integer of 4 to 6, the substituents R's may be the same and different, and are linked to the benzene ring in a similar manner to that when a is an integer of 2 or 3, hydrogen atoms linked to carbon constituents of the benzene ring being not represented as usual.

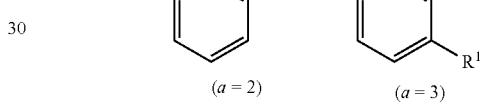

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For example, the inventive compound may be used as the light emitting layer 150, the hole transport layer 140, and/or the emission-auxiliary layer 151.

Since depending on the type and position of a substituent to be attached, a band gap, electrical properties, interfacial properties, and the like may vary even in the same core, it is very important what the types of core and a combination of substituent attached to the core are. Specially, long life span and high efficiency can be simultaneously achieved when an optimal combination of energy levels and T1 values, inherent material properties (mobility, interfacial properties, etc.), and the like among the respective layers included in the organic material layer is given.

As already described above, in order to solve the emission problem with a hole transport layer in a conventional organic electric element, an emission-auxiliary layer is preferably formed between the hole transport layer and a light emitting layer, and it is time to develop different emission-auxiliary layers according to respective light emitting layers (R, G, B). However, even when a similar core is used, it is very difficult to infer the characteristics of an emission-auxiliary layer if a used organic material layer varies because the correlation between the emission-auxiliary layer and a hole transport layer and the correlation between the emission-auxiliary layer and a light emitting layer (host) mused be discovered.

Accordingly, in the present invention, a combination of energy levels and T1 values, inherent material properties (mobility, interfacial properties, etc.), and the like among the respective layers included in the organic material layer is optimized by forming a light emitting layer and/or an emission-auxiliary layer by using the compound represented by Formula 1, and thus the life span and efficiency of the organic electric element can be improved at the same time.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be comprised between the hole transport layer 140 and the light emitting layer 150.

And also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R(Red), G(Green), B(Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

[Formula 1]

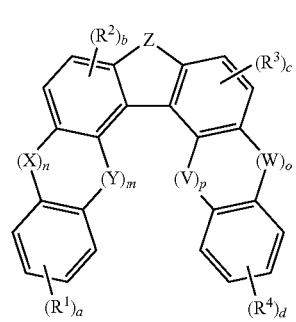

In formula 1 above, each of the symbols may be defined as follows:

Z is S or $N(R^5)$;

V, W, X and Y are each independently $N(R^6)$, S or O, provided that at least one of X, Y, V and W is not $N(R^6)$ when Z is $NR^5$, thereby excluding the compounds where all of X, Y, V, W, and Z are amine groups; m, n, o and p are each independently an integer of 0 or 1, wherein m+n is 1 or more and o+p is 1 or more, and wherein m=0, n=0, o=0 or p=0, in each case, means that the corresponding bridge X, Y, V or W is not present.

For example, if m+n is 1 or more, at least one of X and Y may be $N(R^6)$, S or O. Likewise, if o+p may be 1 or more, at least one of V and W may be $N(R^6)$, S or O. That is, the compound where m+n is 0 and/or o+p is 0 is excluded. Accordingly, the ring including X and Y may be a five-membered ring or a six-membered ring, and the ring including V and W may be a five-membered ring or a six-membered ring.

Specifically, i) when Z is $N(R^5)$, at least one of V and W is selected from $N(R^6)$, S or O and at least one of X and Y is selected from $N(R^6)$, S or O, with the proviso that the compounds where all of V, W, X and Y are $NR^6$ are excluded; and ii) when Z is S, at least one of V and W is selected from $N(R^6)$, S or O, and at least one of X and Y is selected from $N(R^6)$, S or O. In either case, however, at least one of X and Y is present and at least one of V and W is present.

$R^5$ and $R^6$ above are each independently selected from the group consisting of a $C_6$-$C_{60}$ aryl group; a fluorenylene group; a $C_2$-$C_{60}$ heterocyclic group containing at least one heteroatom selected from the group consisting of O, N, S, Si, and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; -L'-$N(Ar^1)$ $(Ar^2)$; and a combination thereof.

Preferably, $R^5$ and $R^6$ may be each independently, a $C_6$-$C_{25}$ aryl group, a $C_3$-$C_{12}$ heterocyclic group, a fluorenylene group, or -L'-$N(Ar^1)$ $(Ar^2)$, preferably a $C_6$, $C_{10}$, or $C_{12}$ aryl group; a $C_3$, $C_4$, $C_8$, or $C_{12}$ heterocyclic group, particularly, a phenyl, a biphenyl, a naphthyl, a fluorenyl unsubstituted or substituted with methyl or phenyl, a spirobifluorenyl, a triazinyl unsubstituted or substituted with phenyl, a pyrimidinyl unsubstituted or substituted with phenyl, a quinazolinyl or a dibenzothienyl unsubstituted or substituted with phenyl, naphthyl, biphenyl, terphenyl, phenanthrenyl, triphenyl, fluorenyl, carbazole, dibenzothienyl or dibenzofuryl.

Preferably, $R^5$ and $R^6$ may be optionally substituted with one or more substituent(s) selected from the group consisting of deuterium; halogen; a silan group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group.

In Formula 1 above, $R^1$ to $R^4$ may be each independently selected from the group consisting of hydrogen; deuterium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; -L'-$N(Ar^1)$ $(Ar^2)$; and a combination thereof.

Each of a and d above may be an integer of 0 to 4, each of b and c may be an integer of 0 to 2.

When a is 2 or more the plurality of $R^1$ may be the same or different from each other, when b is 2 the plurality of $R^2$ may be the same or different from each other, when c is 2 the plurality of $R^3$ may be the same or different from each other, and when d is 2 or more the plurality of $R^4$ may be the same or different from each other.

Preferably, $R^1$ to $R^4$ may be each independently, hydrogen, a $C_6$-$C_{18}$ aryl group, a $C_3$-$C_{12}$ heterocyclic group, or a diphenyl amine group, preferably a $C_6$ aryl group, a $C_5$ or $C_{12}$ heterocyclic group, particularly phenyl, pyridyl, carbazole unsubstituted or substituted with phenyl.

Further, any two adjacent groups of $R^1$ to $R^4$ may optionally form a ring that may be a mono- or poly-cyclic ring, where the other two of $R^1$ to $R^4$ not forming a ring may be the same as defined above. Preferably, $R^1$ to $R^4$ may be optionally substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; and a $C_8$-$C_{20}$ arylalkenyl group.

L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group containing at least one heteroatom selected from the group consisting of O, N, S, Si, and P; and a combination thereof.

Preferably, L' may be a single bond, a $C_6$-$C_{18}$ arylene group, a $C_3$-$C_{12}$ heterocyclic group, or a fluorenylene group, preferably a $C_6$ or $C_{12}$ arylene group, a $C_4$ or $C_{12}$ heterocyclic group, particularly a phenylene group, a biphenylene group, a fluorenylene group unsubstituted or substituted with methyl, a pyrimidinyl group, a carbazolylene group unsubstituted or substituted with a phenyl or dibenzothienyl group.

Preferably, L' may be optionally substituted with one or more substituent(s) selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; and a $C_8$-$C_{20}$ arylalkenyl group.

$Ar^1$ and $Ar^2$ above may be each independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; a $C_2$-$C_{60}$ heterocyclic group containing at least one heteroatom selected from the group consisting of O, N, S, Si, and P; and a combination thereof.

Preferably, $Ar^1$ and $Ar^2$ may be each independently, a $C_6$-$C_{18}$ aryl group, a $C_3$-$C_{12}$ heterocyclic group, or a fluorenyl group, preferably a $C_6$, $C_{10}$ or $C_{12}$ aryl group, a $C_3$ or $C_{12}$ heterocyclic group, particularly phenyl, naphthyl, biphenyl, fluorenyl unsubstituted or substituted with methyl or phenyl, triazinyl or dibenzothienyl unsubstituted or substituted with phenyl.

Preferably, $Ar^1$ and $Ar^2$ may be optionally substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; and a $C_8$-$C_{20}$ arylalkenyl group.

Particularly, Formula 1 above, in accordance with the combination of m, n, o and p, may be represented by any one of Formulas 2 to 4 below. Formula 2 is an example of Formula 1 wherein m is 1, n is 0, o is 0, and p is 1. Formula 3 is an example of Formula 1 wherein m is 0, n is 1, o is 1, and p is 0. Formula 4 is an example of Formula 1 wherein m is 0, n is 1, o is 0, and p is 1.

[Formula 2]

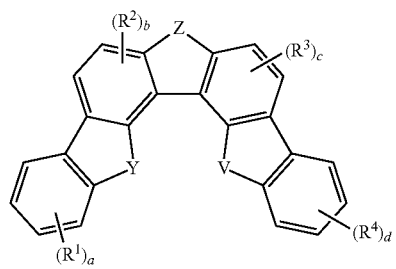

[Formula 3]

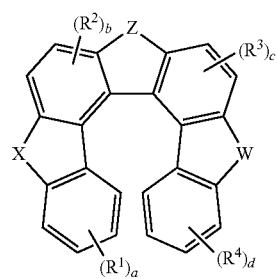

[Formula 4]

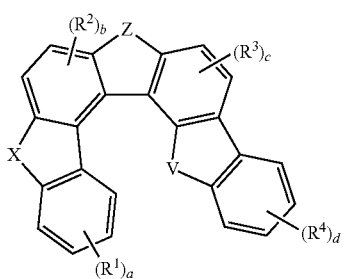

In Formula 2 to Formula 4, V, W, X, Y, Z, $R^1$ to $R^4$, a, b, c and d may be the same as defined in Formula 1 above.

More particularly, the compound represented by Formula 1 above may be any one of the following compounds.

1-1

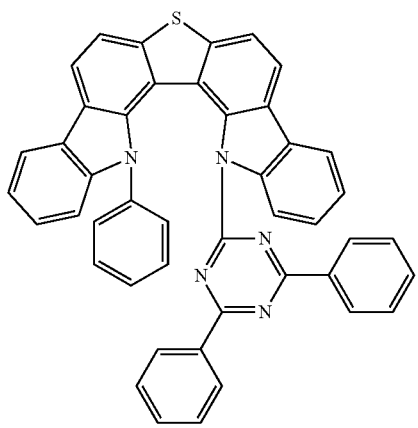

1-2

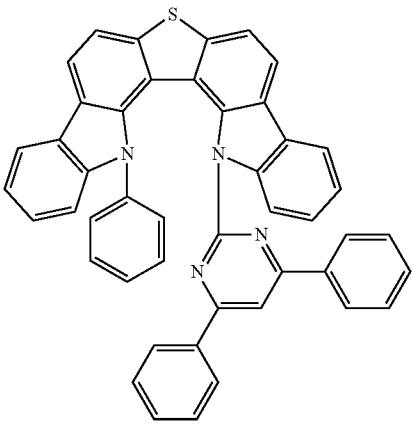

1-3

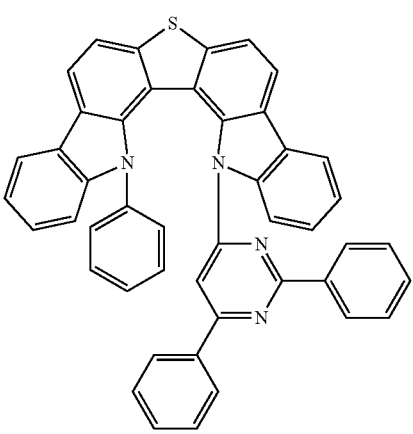

1-4

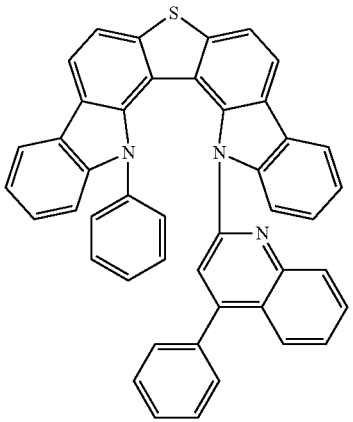

1-5
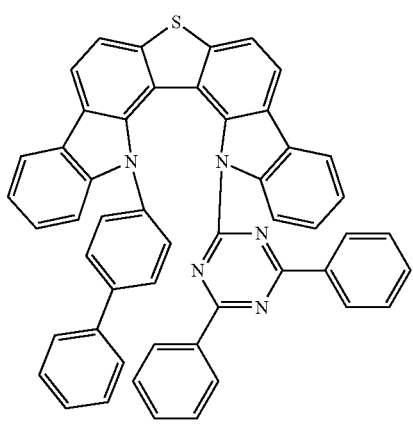
1-6
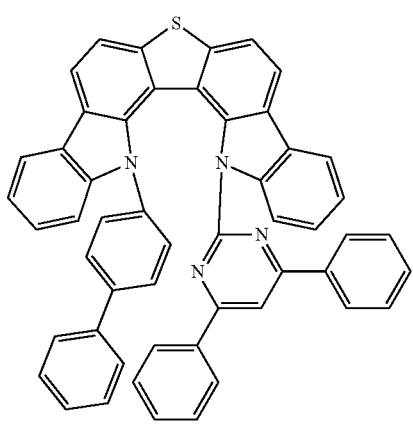
1-7
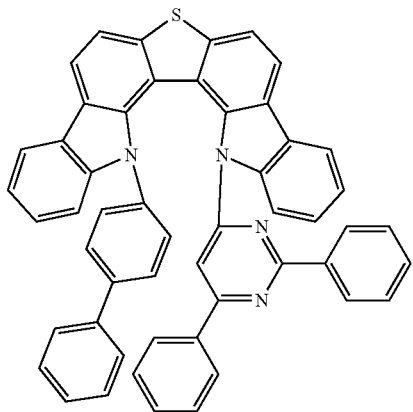
1-8
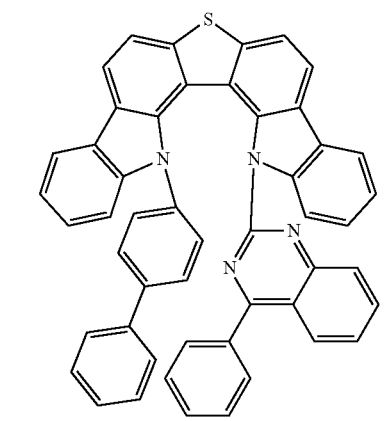
1-9
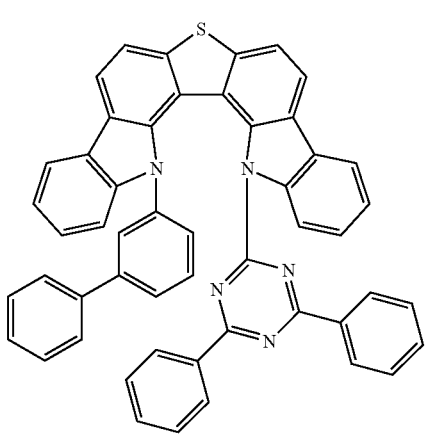
1-10
1-11
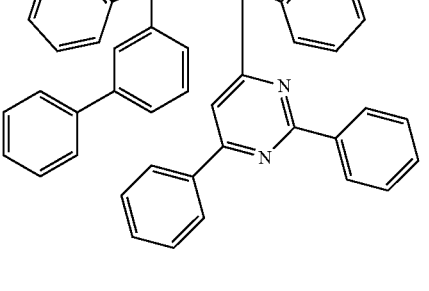

1-12
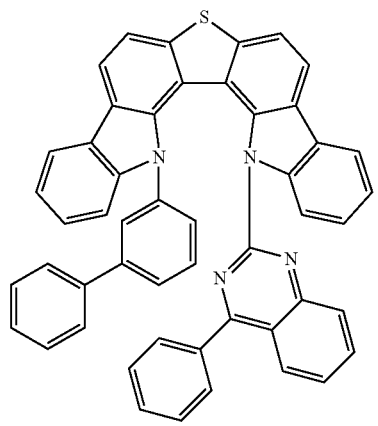
1-13
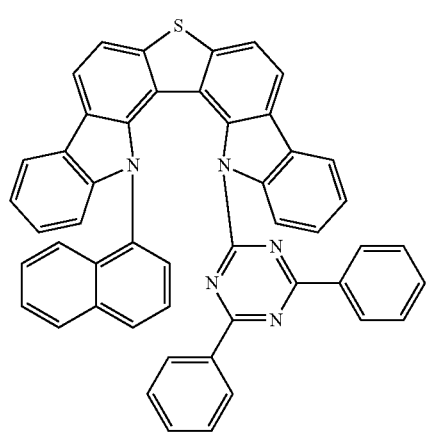
1-14
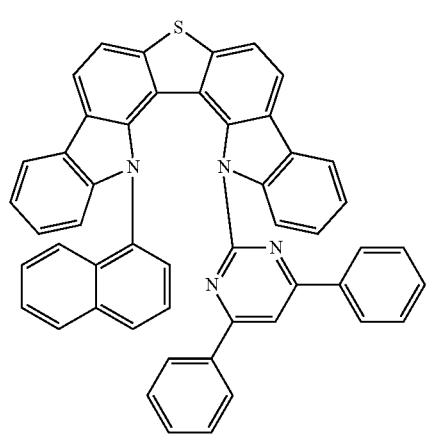
1-15
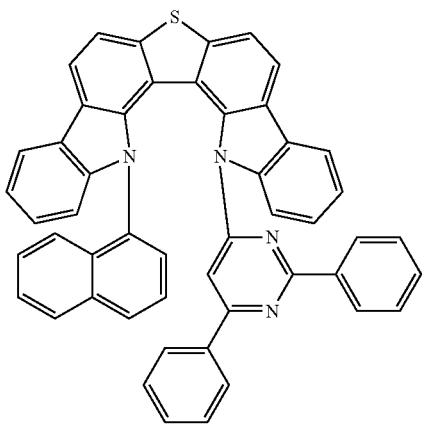
1-16
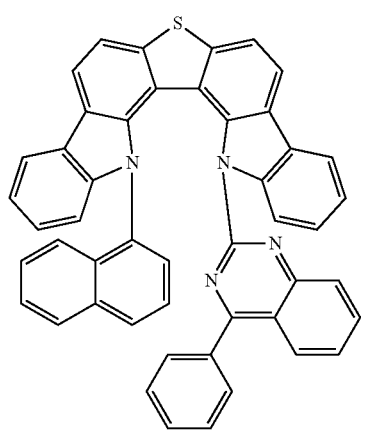
1-17
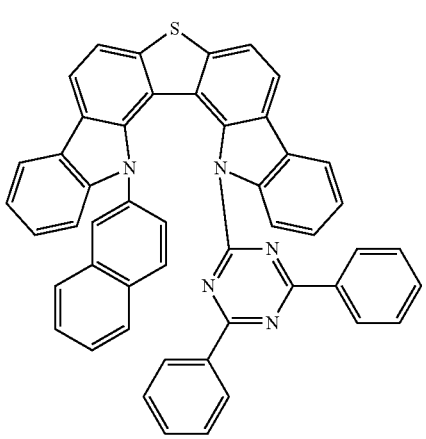

1-18
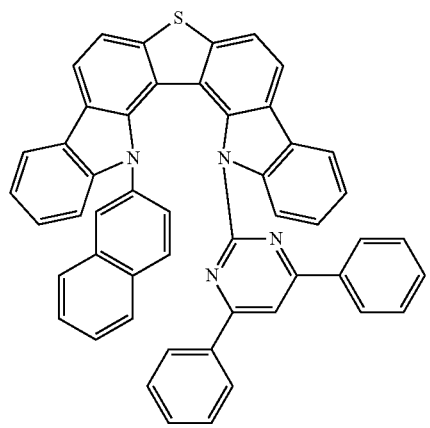
1-19
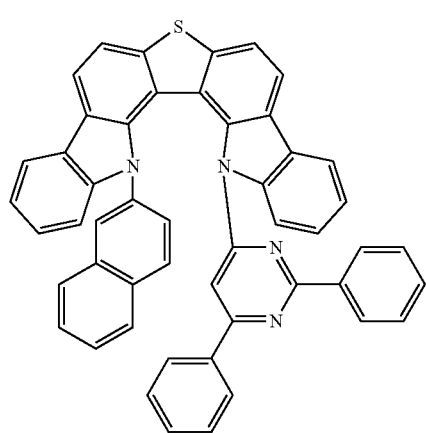
1-20
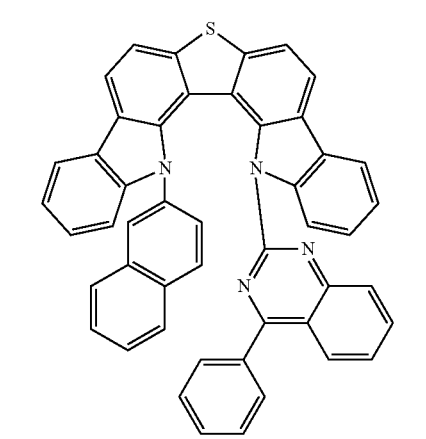
1-21
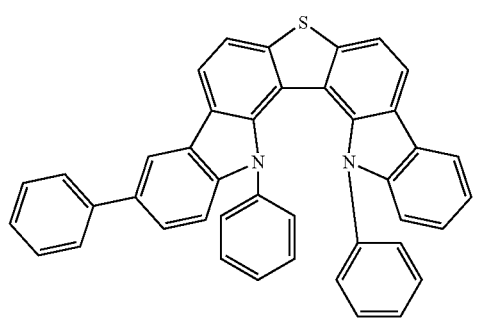
1-22
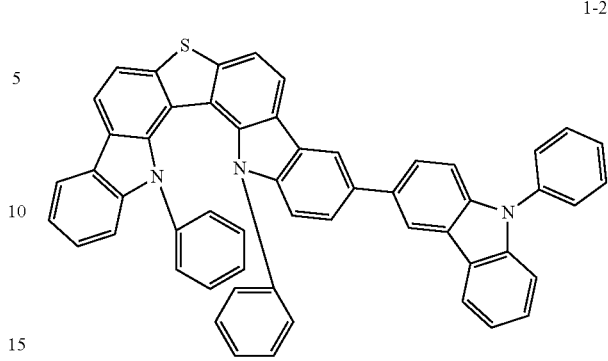
1-23
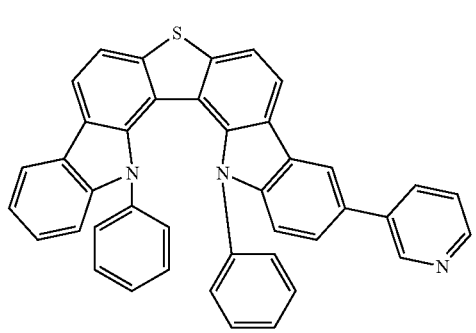
1-24
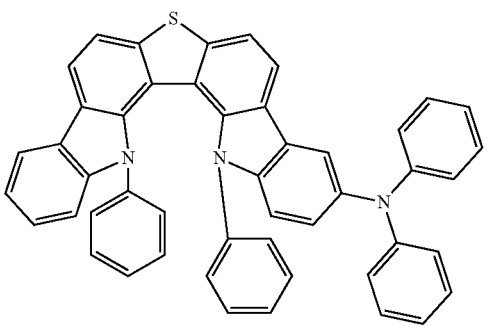
2-1
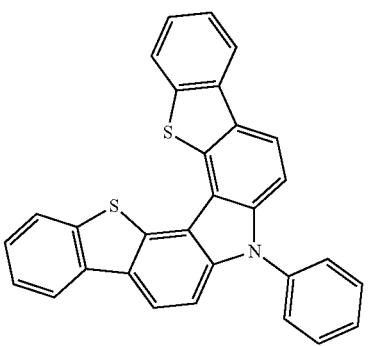

-continued
2-2
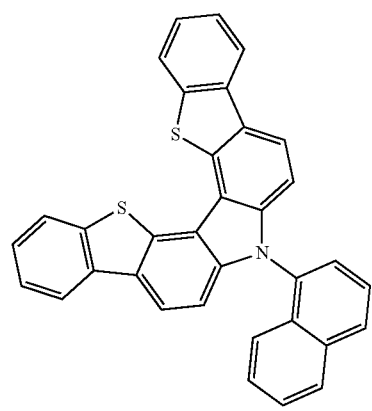
2-3
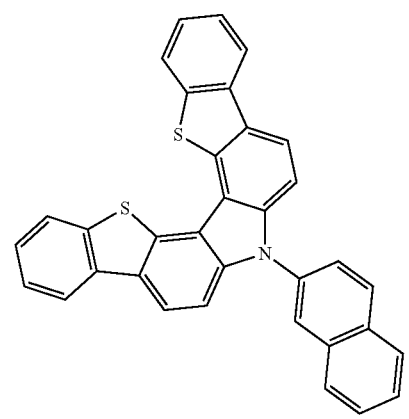
2-4
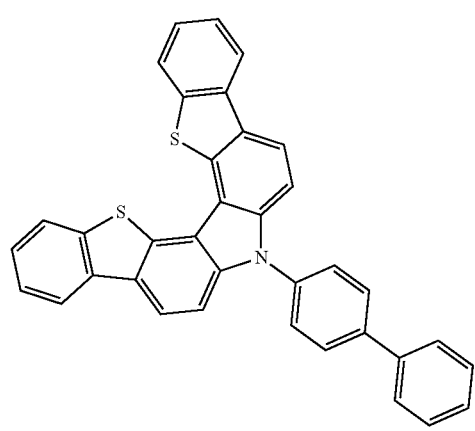
-continued
2-5
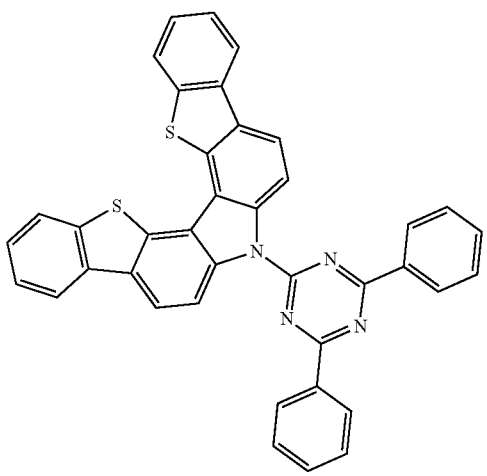
2-6
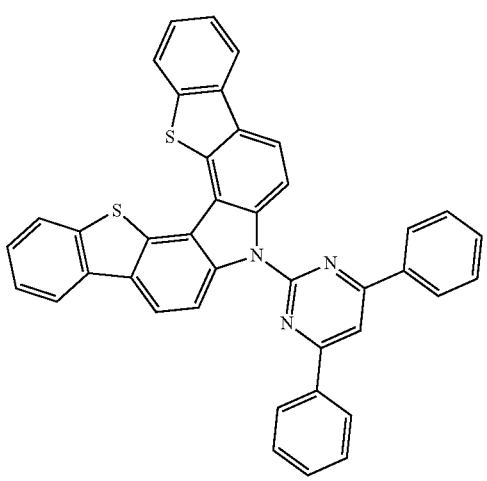
2-7
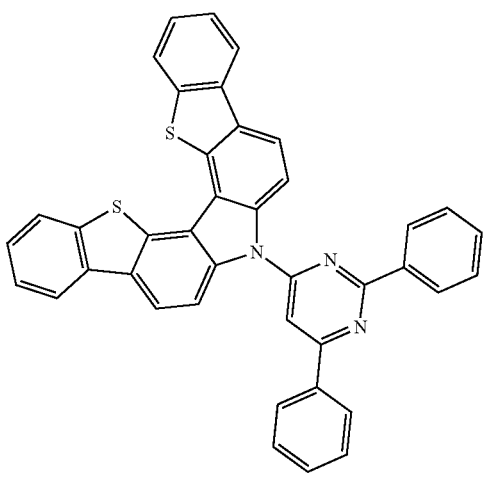

2-8
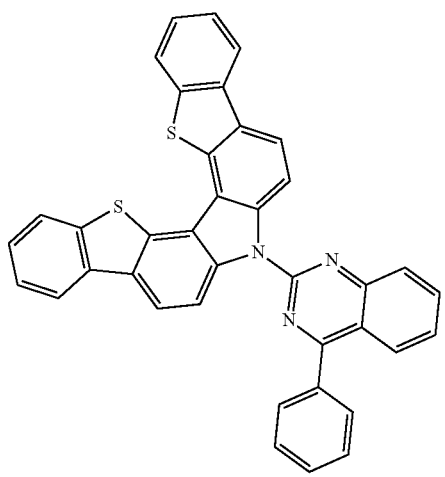
2-11
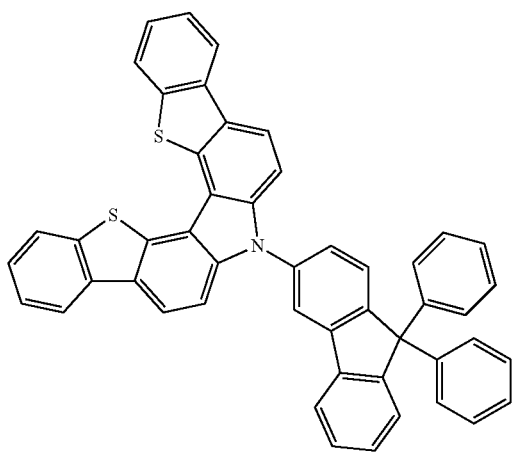
2-9
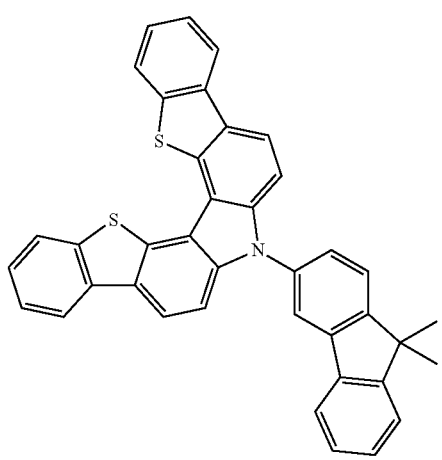
2-12
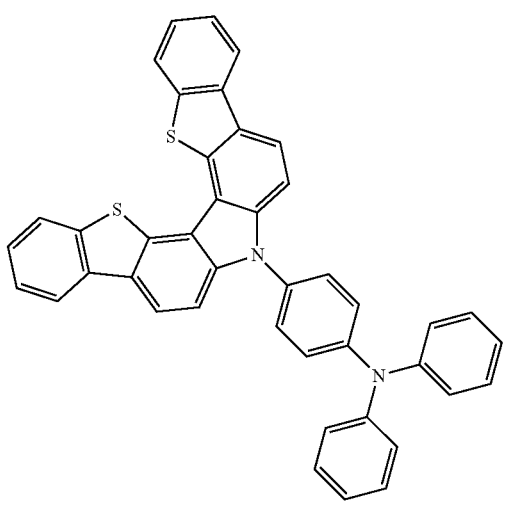
2-10
2-13

2-14
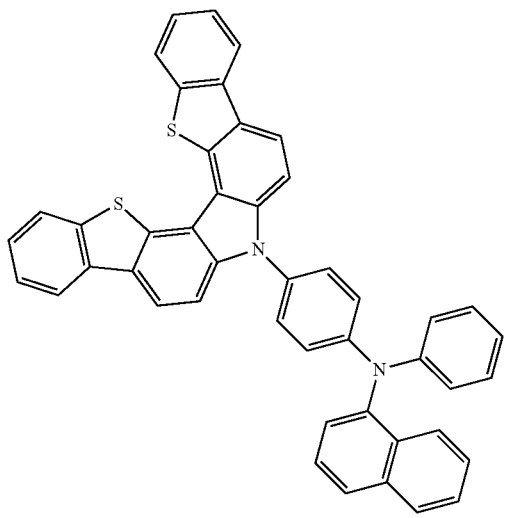
2-15
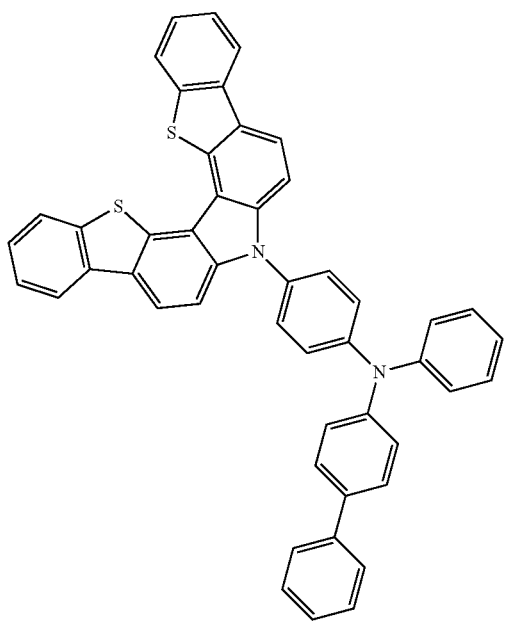
2-16
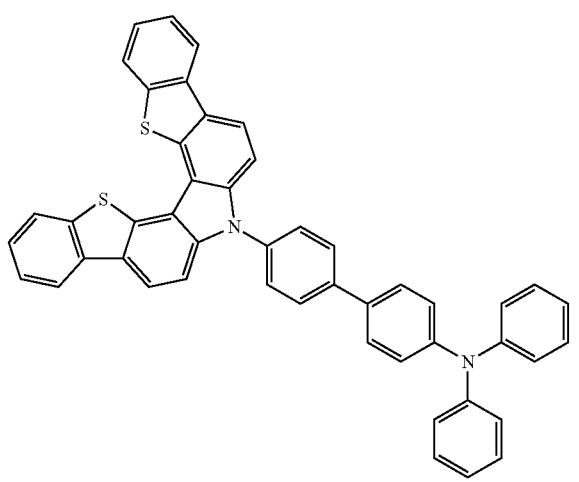
2-17
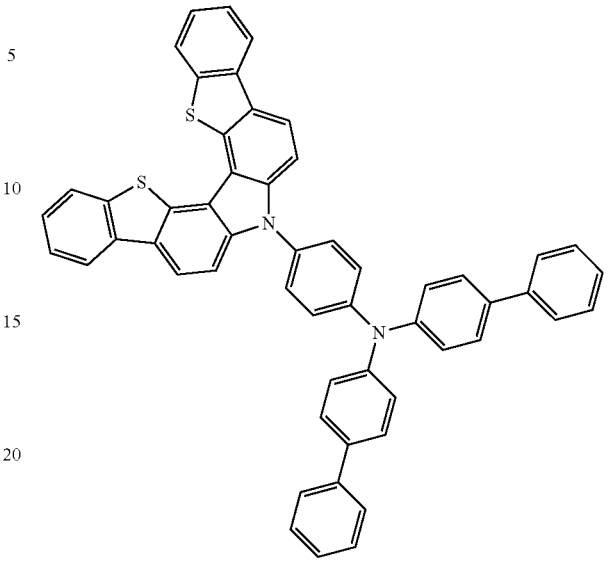
2-18
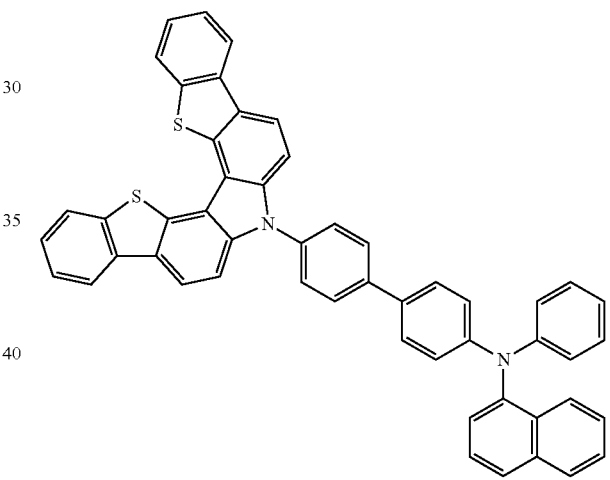
2-19
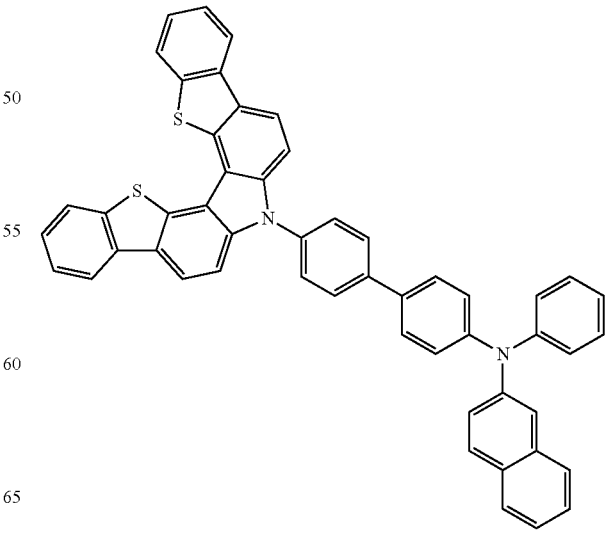

2-20
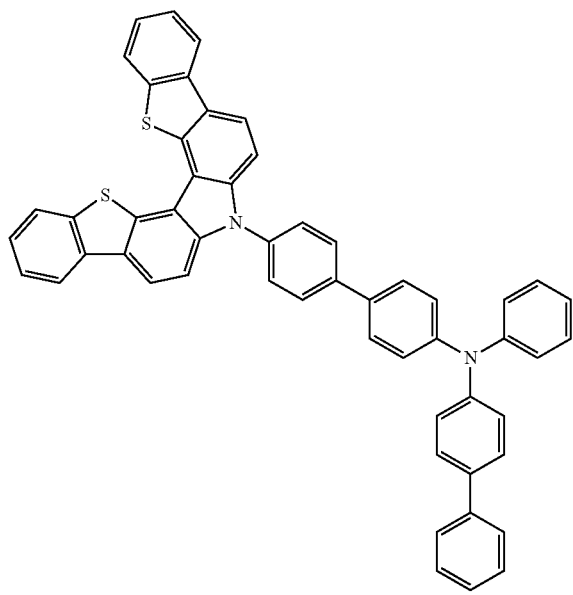
2-22
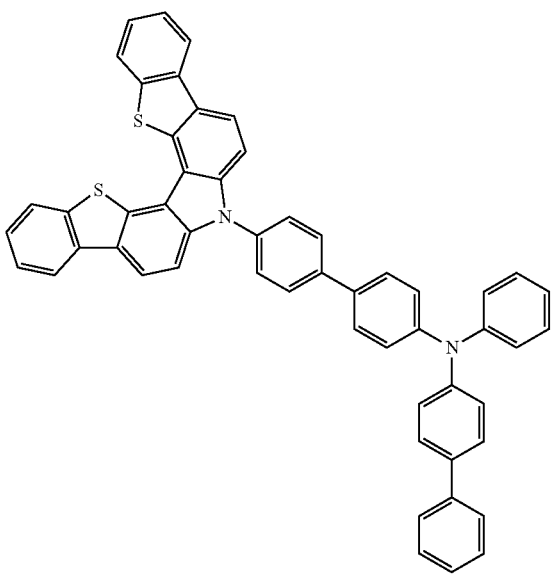
2-21
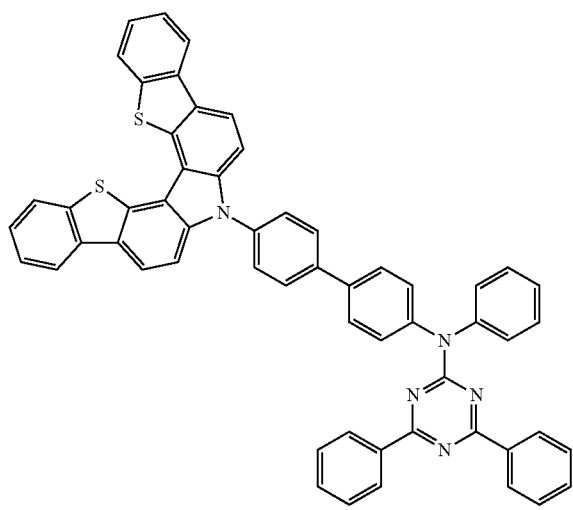
2-23
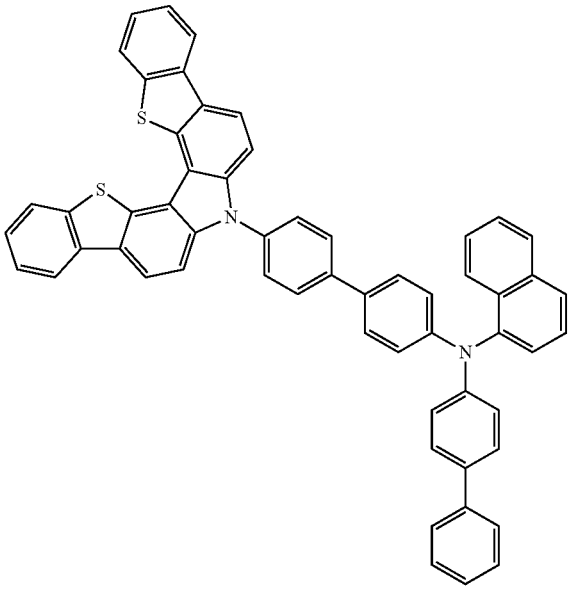

2-24
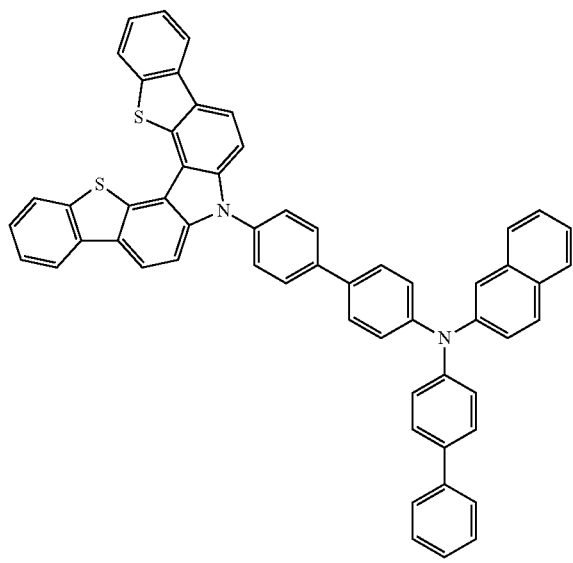
2-25
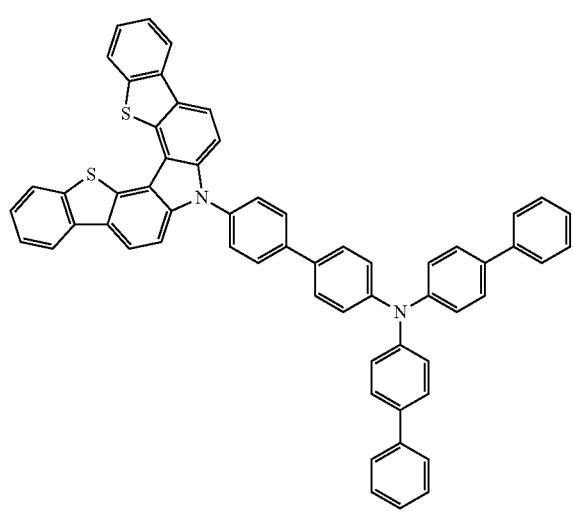
2-26
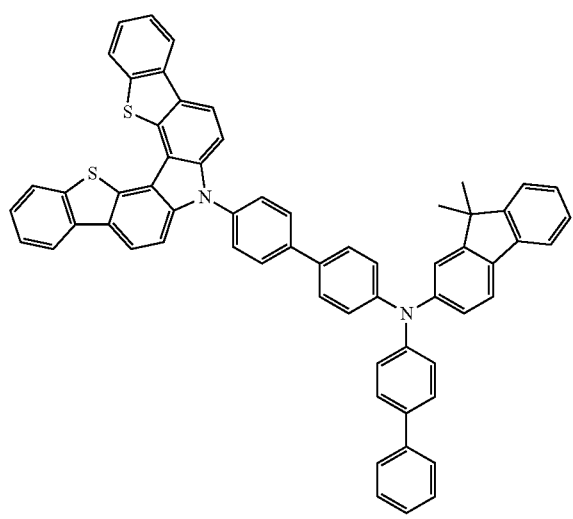
2-27
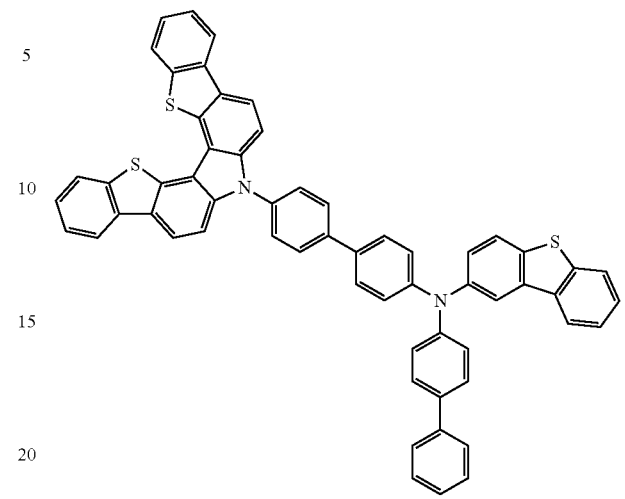
2-28
2-29
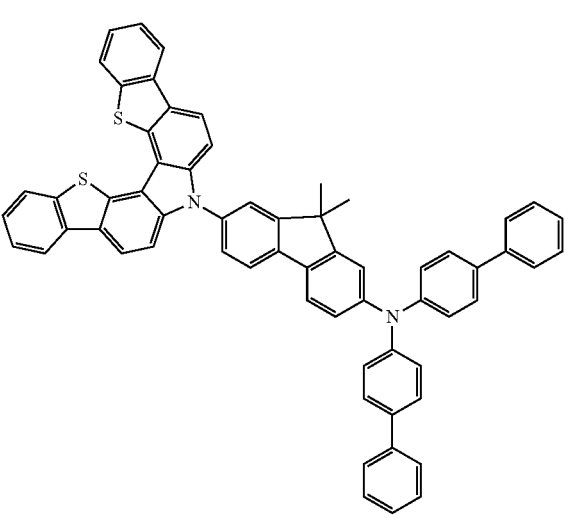

-continued
2-30
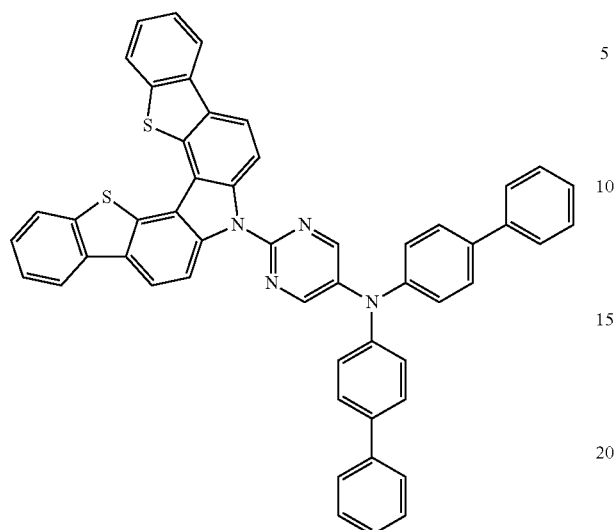
2-31
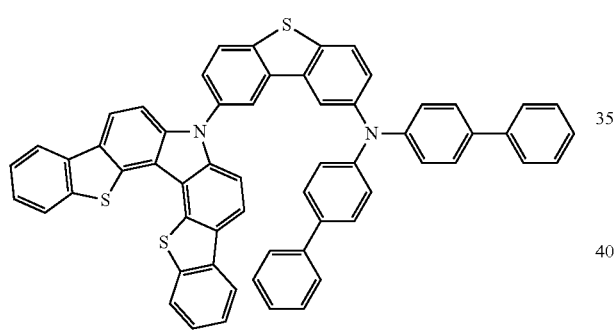
2-32
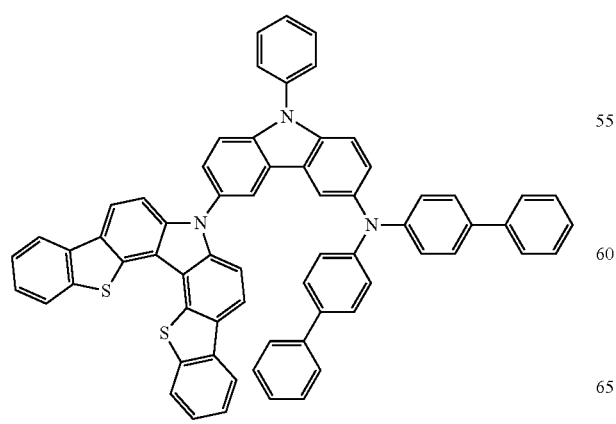
-continued
2-33
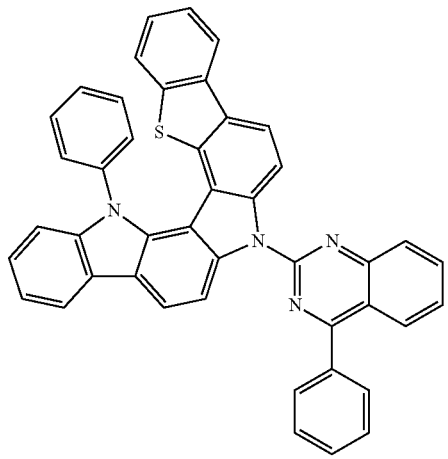
2-34
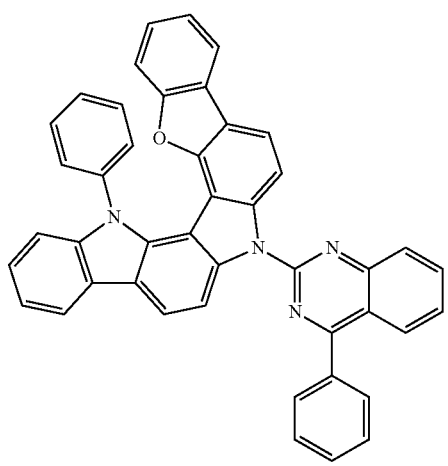
2-35
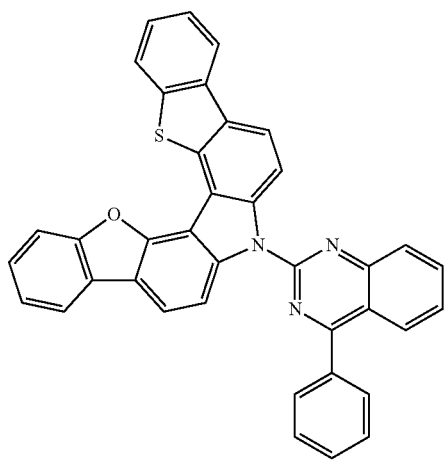

31
-continued
2-36
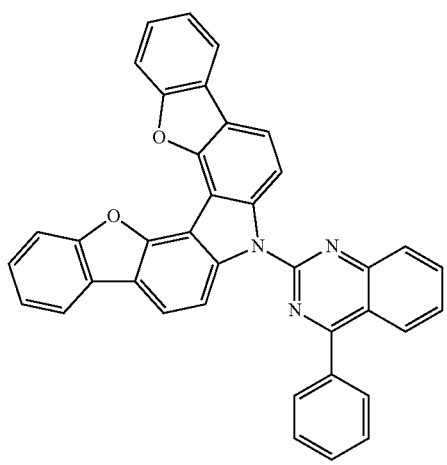
2-37
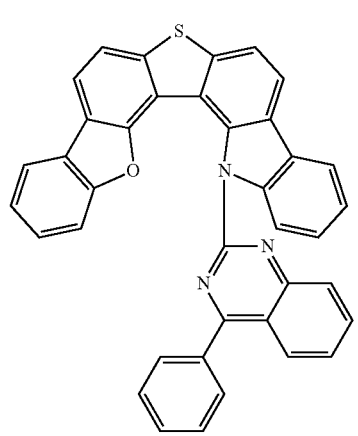
2-38
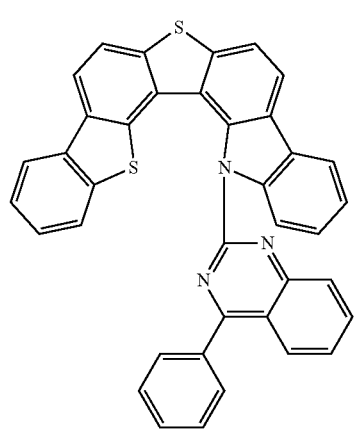
2-39
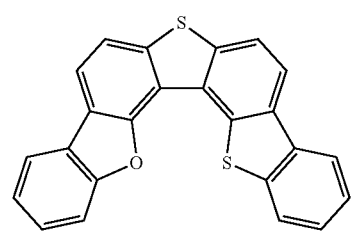
32
-continued
2-40
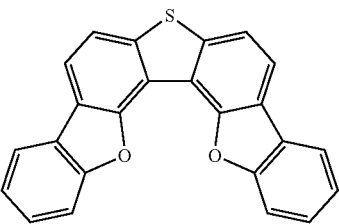
3-1
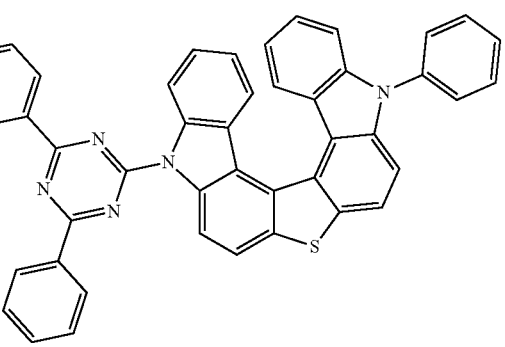
3-2
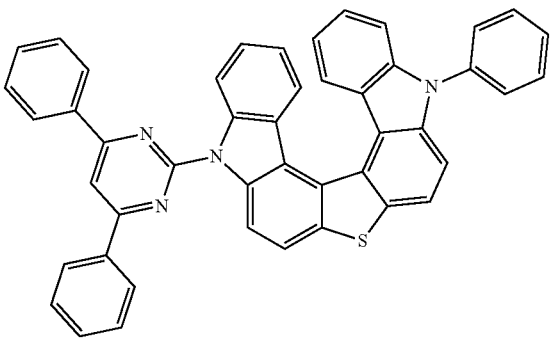
3-3
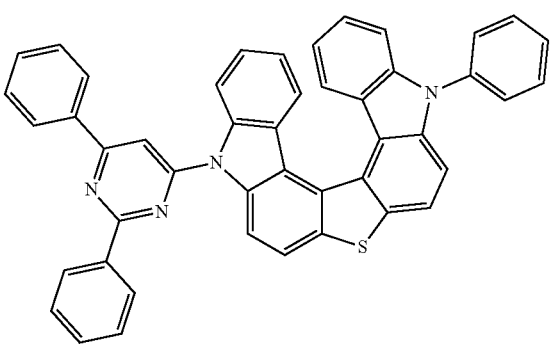

3-4
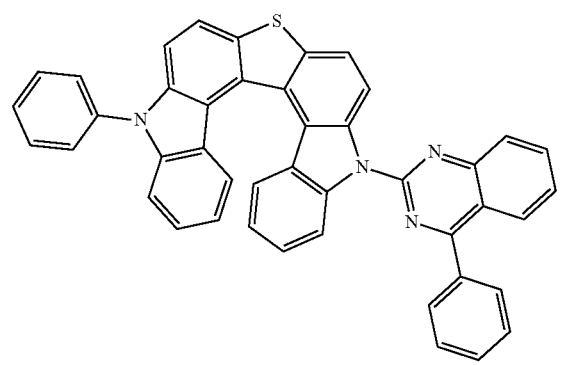
3-5
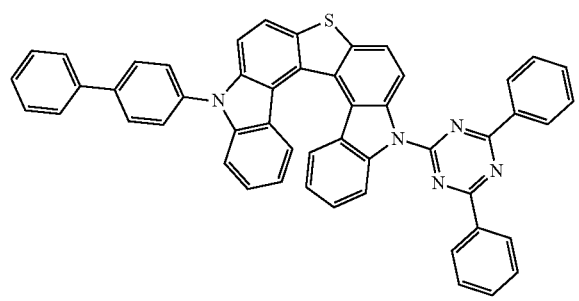
3-6
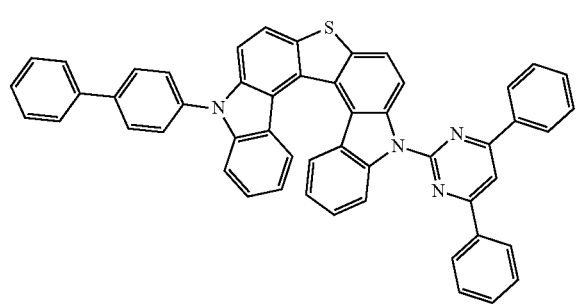
3-8
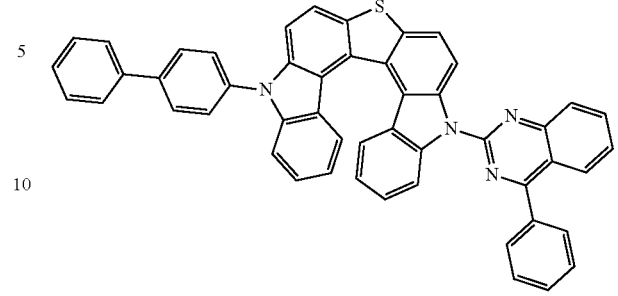
3-9
3-10
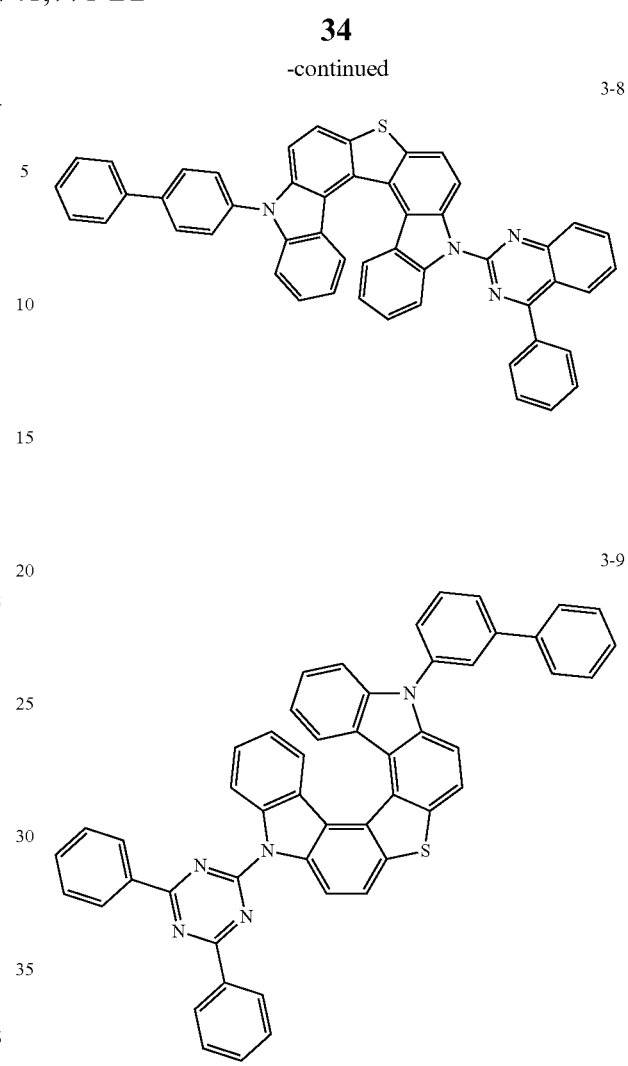
3-7
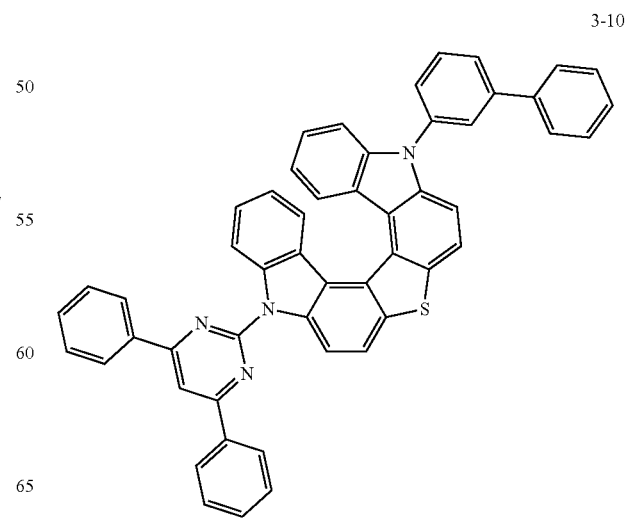

-continued
3-11
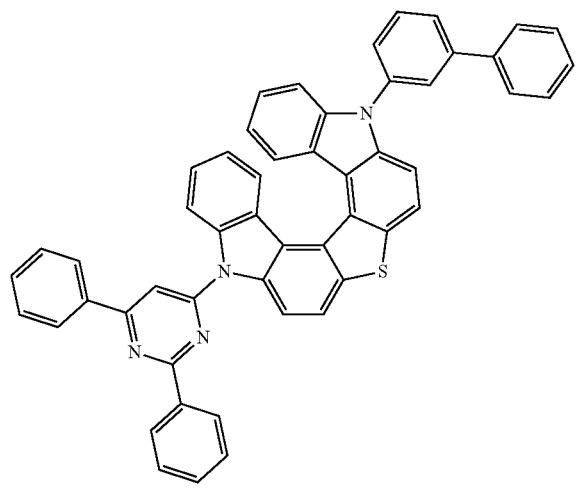
3-12
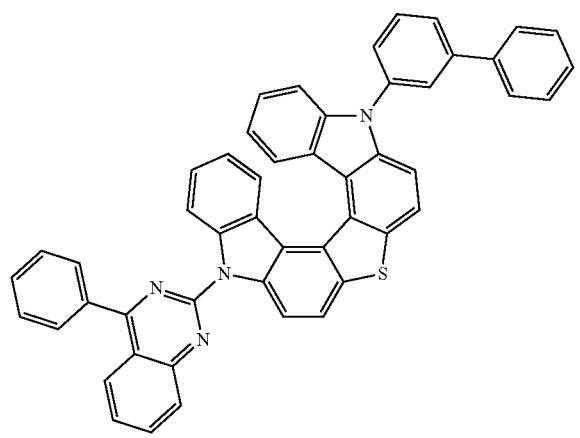
3-13
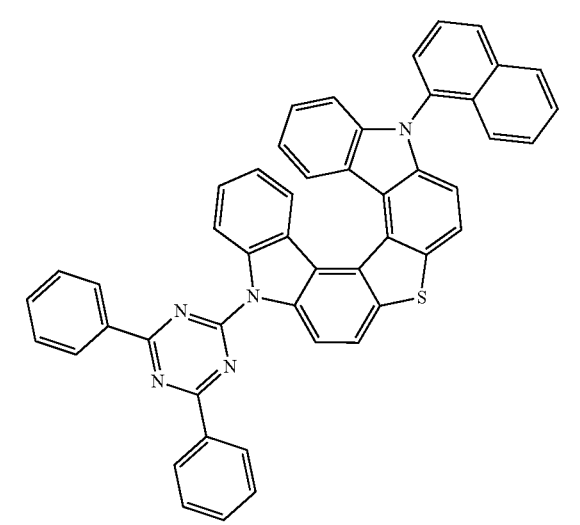
-continued
3-14
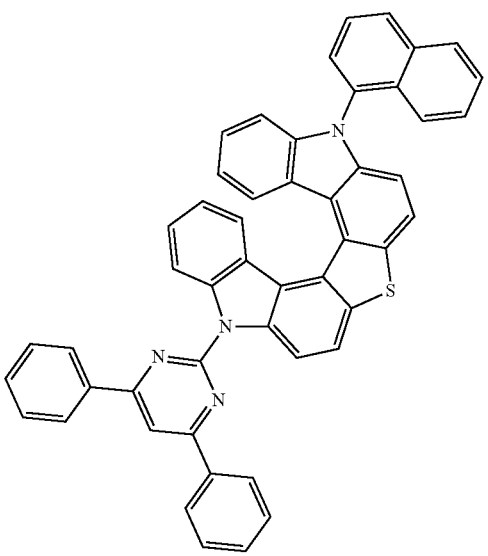
3-15
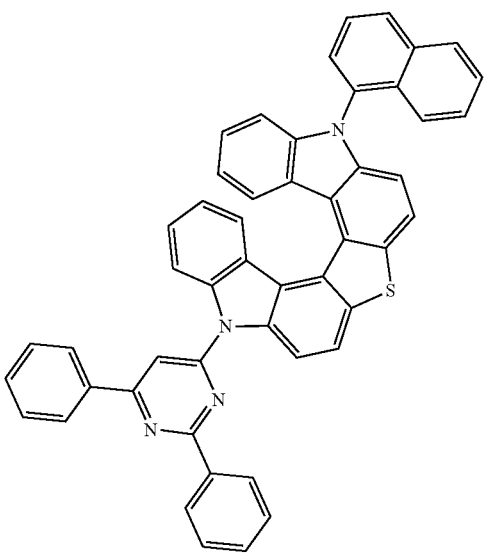
3-16
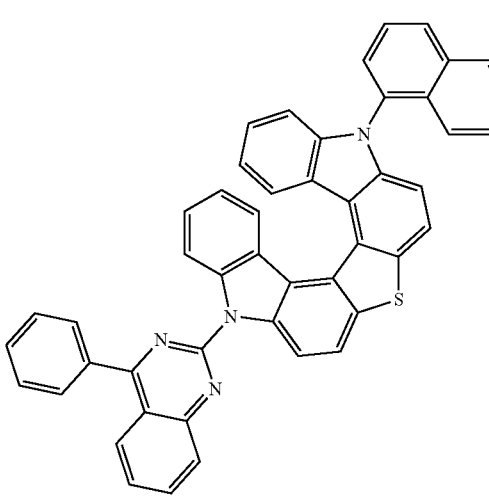

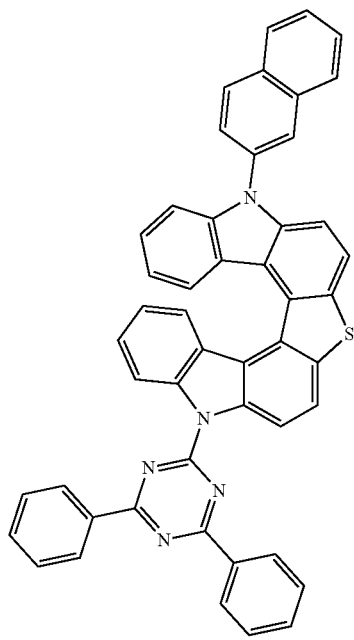
3-17
3-18
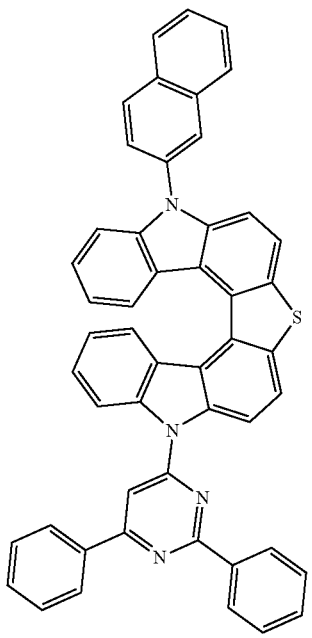
3-19
3-20

3-21
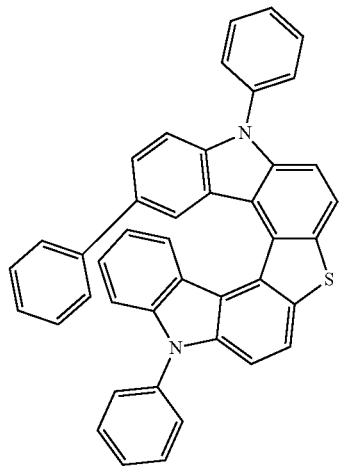
3-22
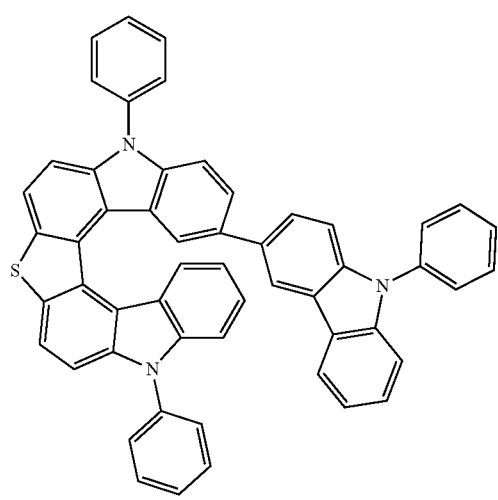
3-23
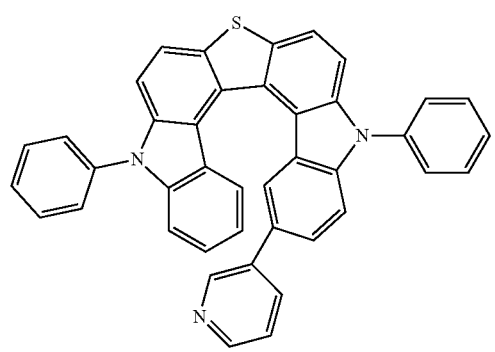
3-24
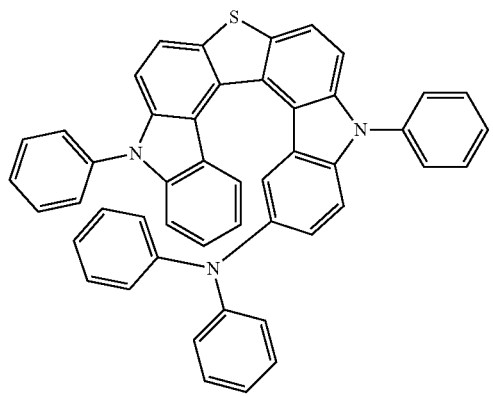
4-1
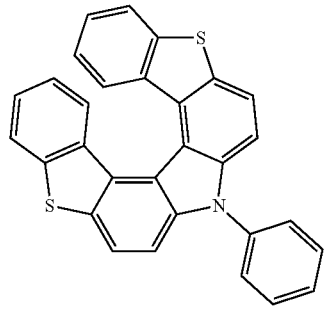
4-2
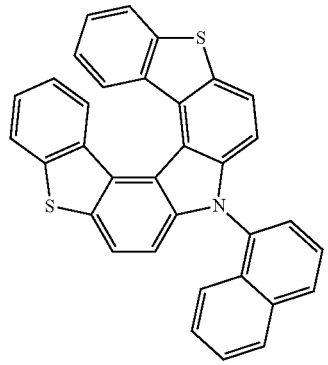
4-3
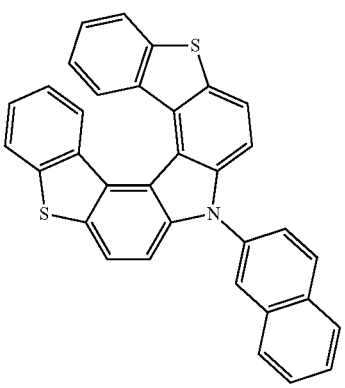

4-4
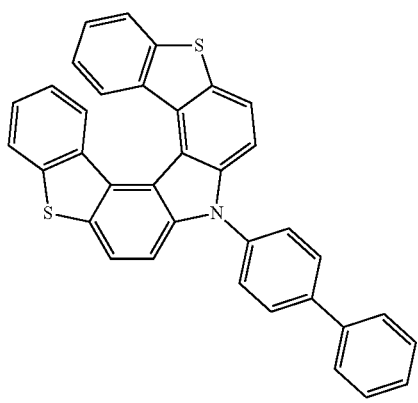
4-5
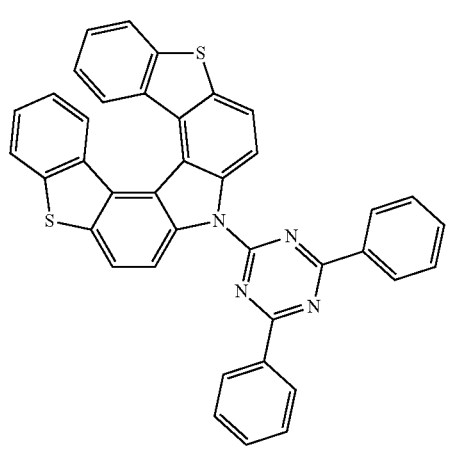
4-6
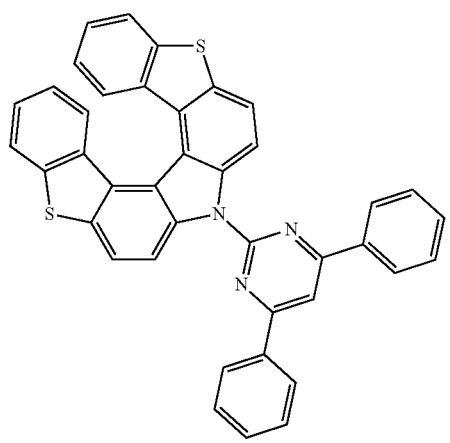
4-7
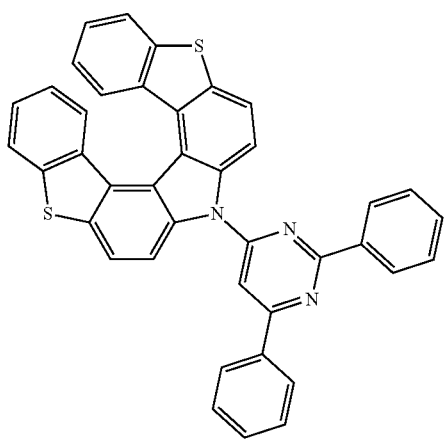
4-8
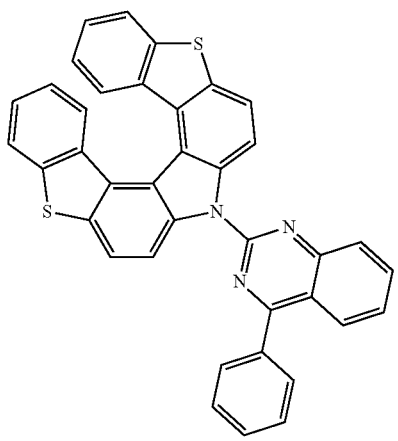
4-9
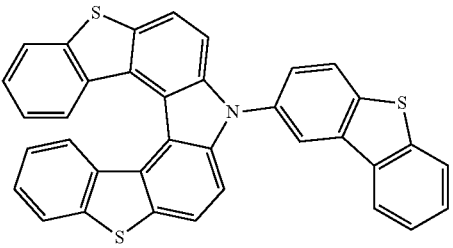
4-10
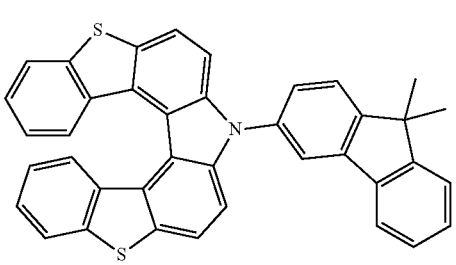

-continued
4-11
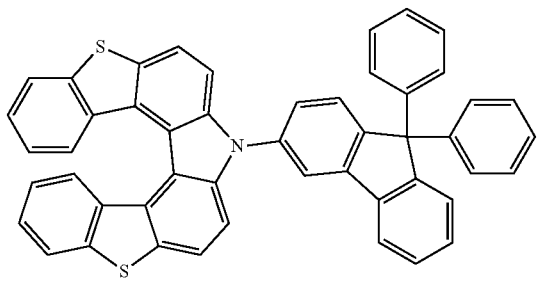
4-12
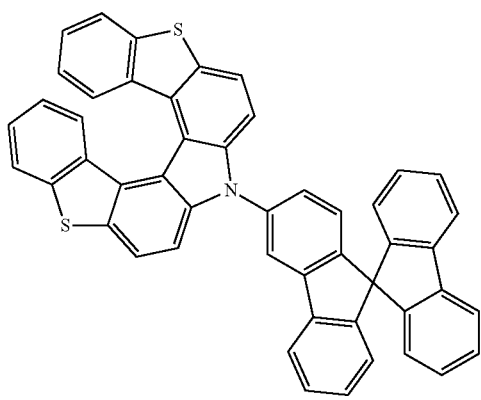
4-13
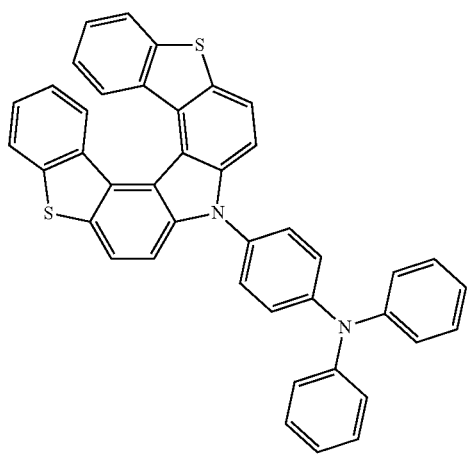
4-14
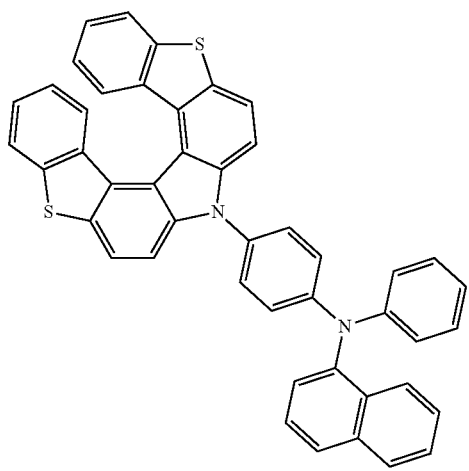
-continued
4-15
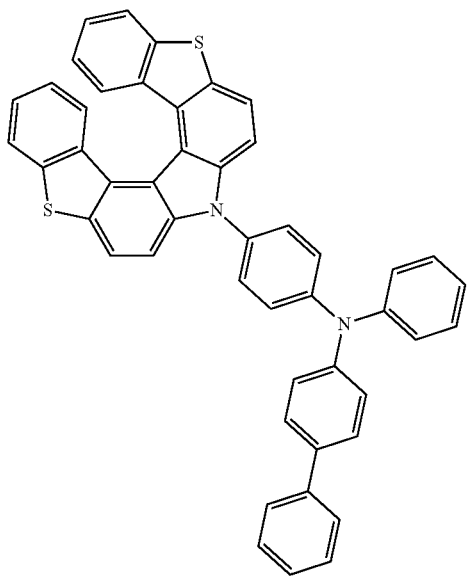
4-16
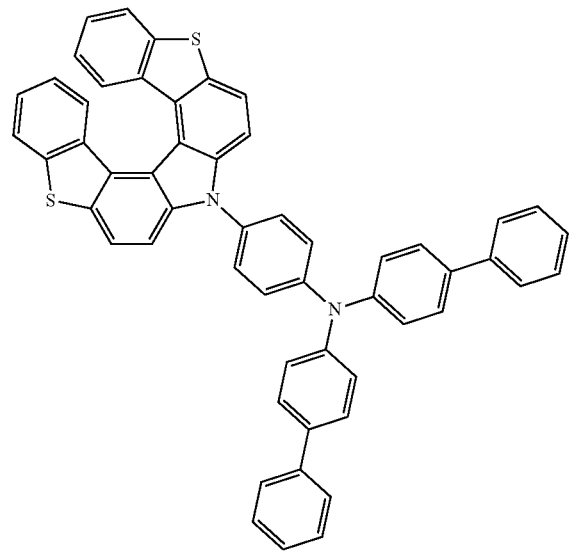
4-17
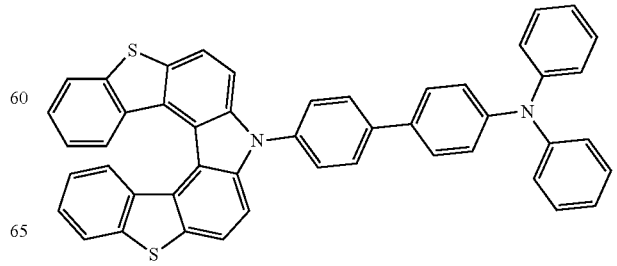

-continued
4-18
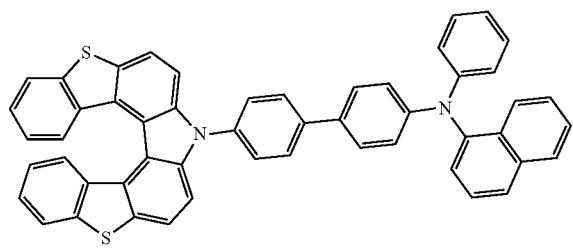
4-19
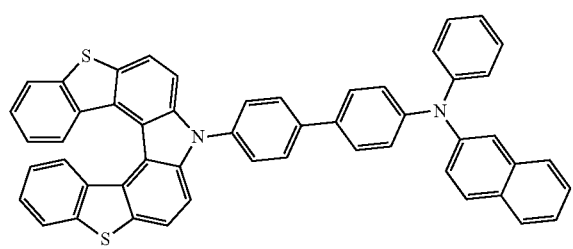
4-20
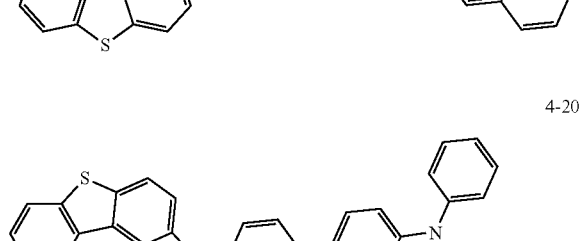
4-21
4-22
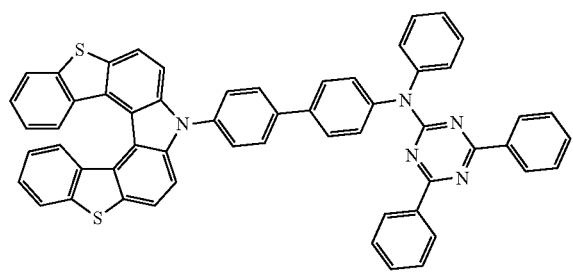
-continued
4-23
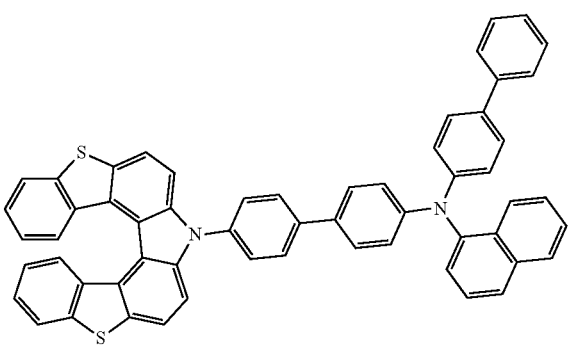
4-24
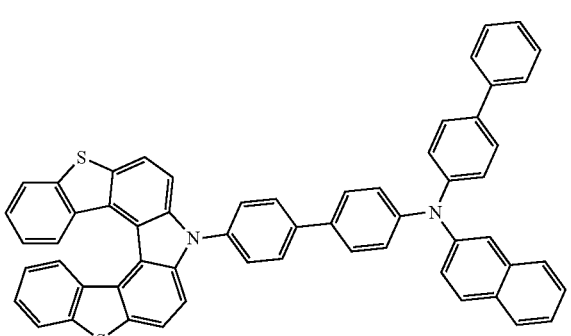
4-25
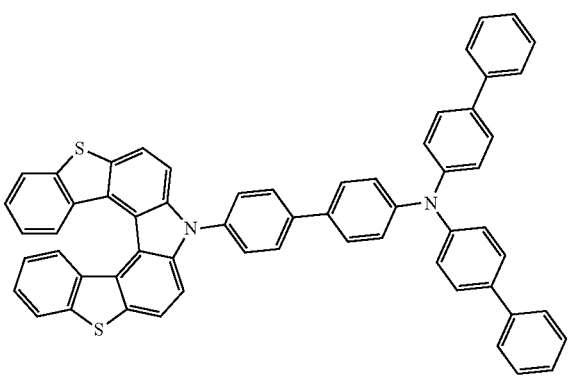
4-26
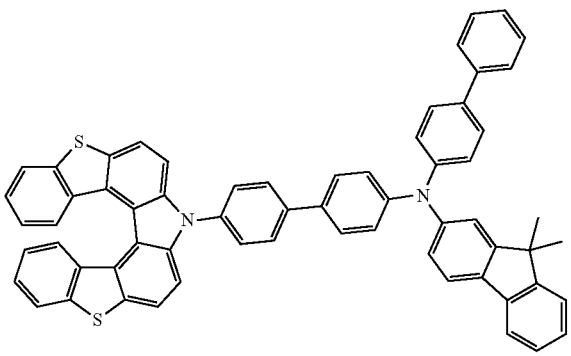

4-27
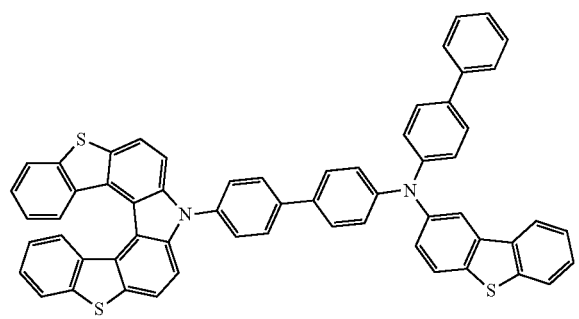
4-28
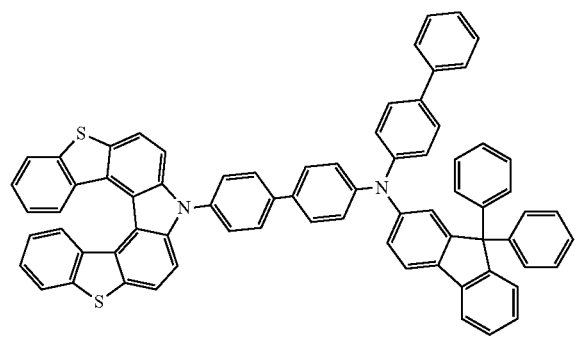
4-29
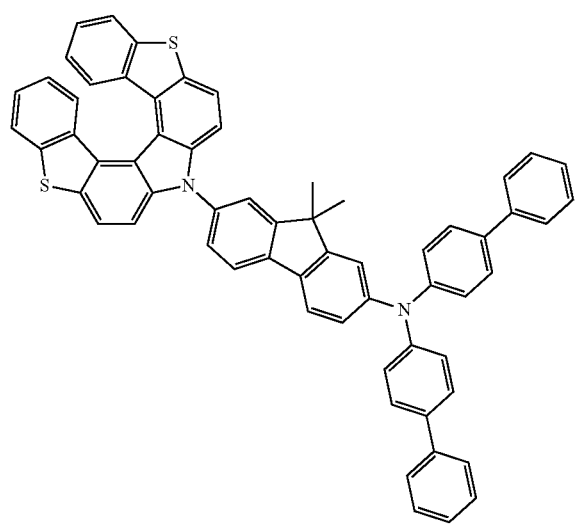
4-30
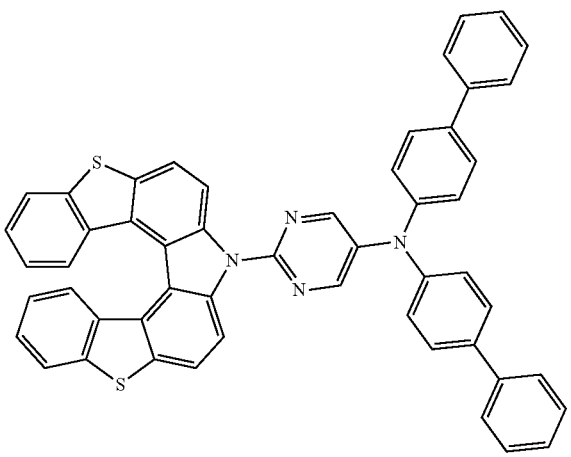
4-31
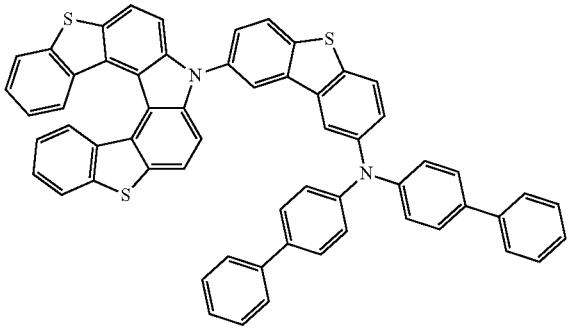
4-32
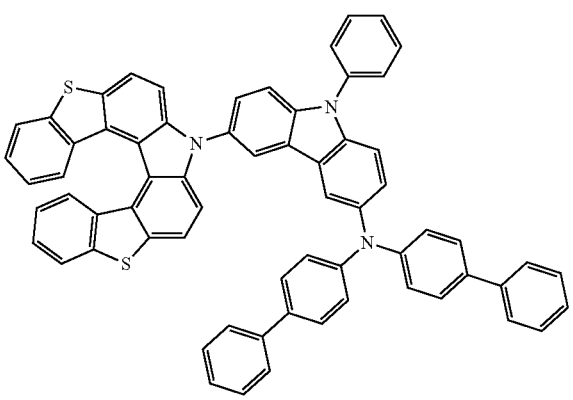

-continued
4-33
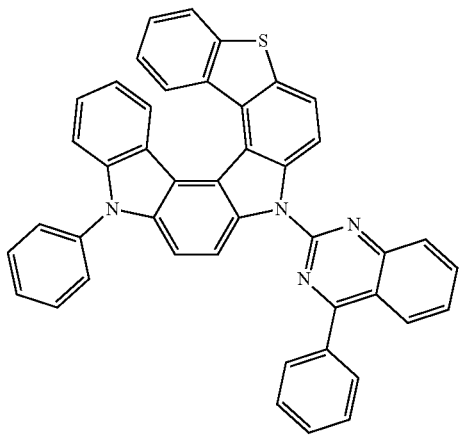
4-34
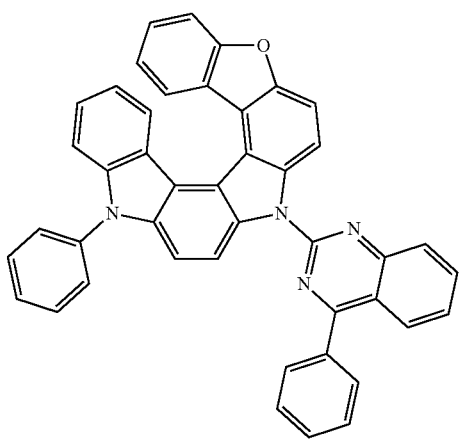
4-35
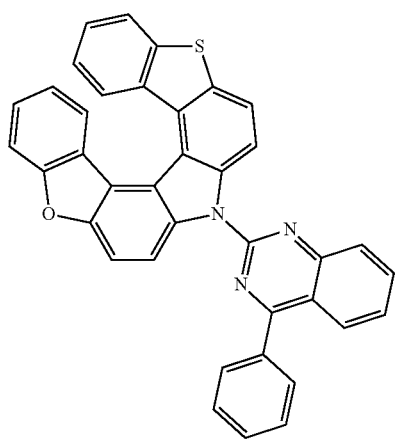
-continued
4-36
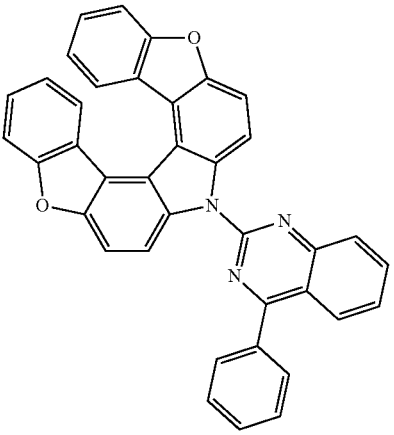
4-37
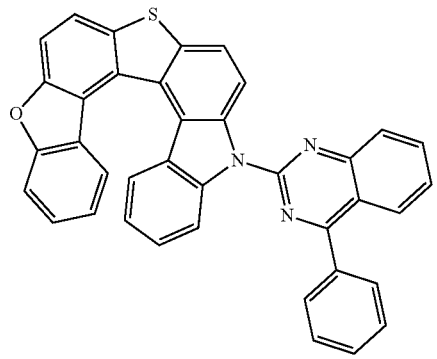
4-38
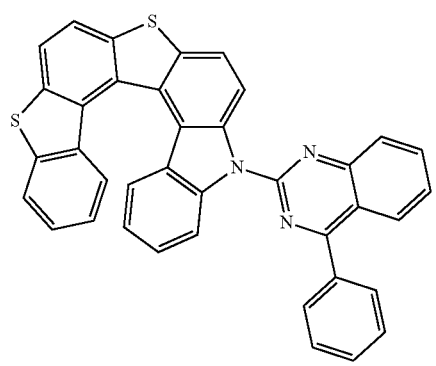
4-39
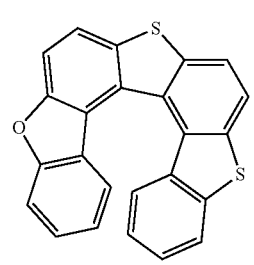

-continued
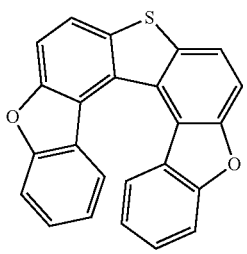
4-40
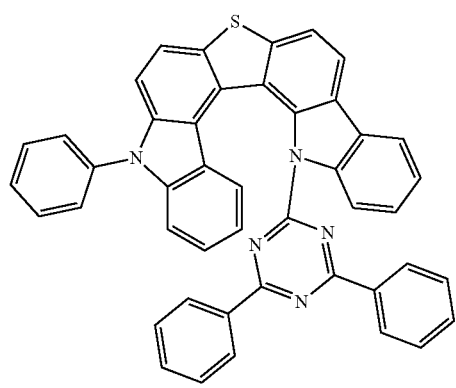
5-1
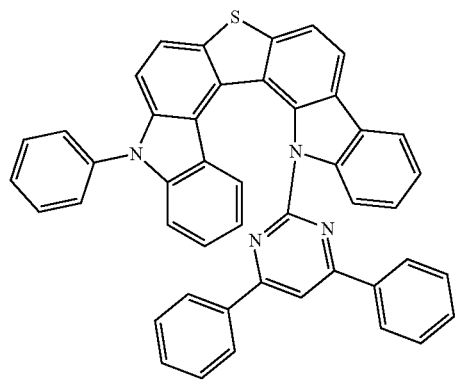
5-2
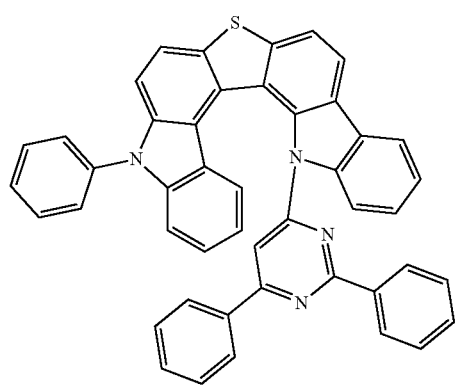
5-3
-continued
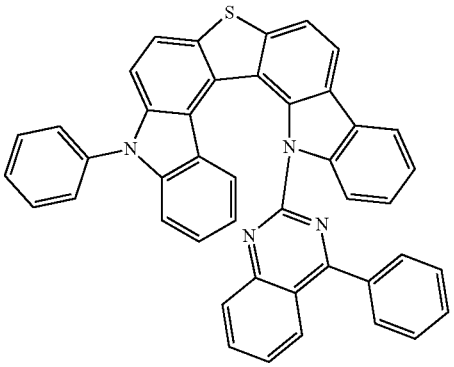
5-4
5-5
5-6
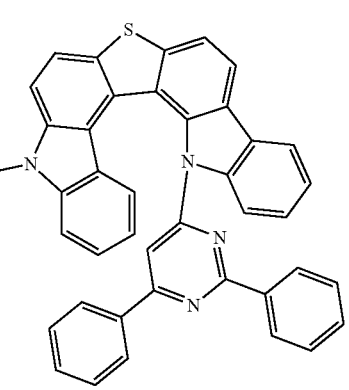
5-7

5-8
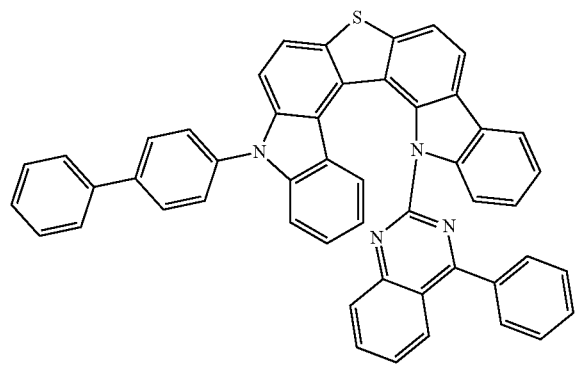
5-9
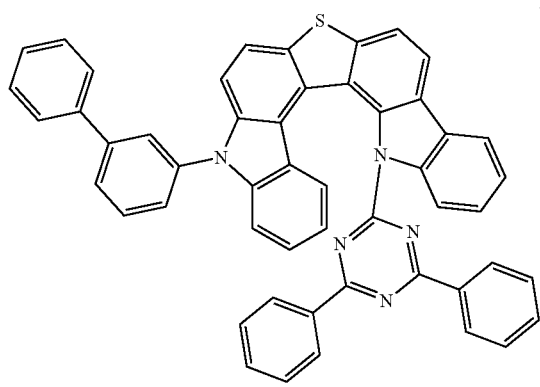
5-10
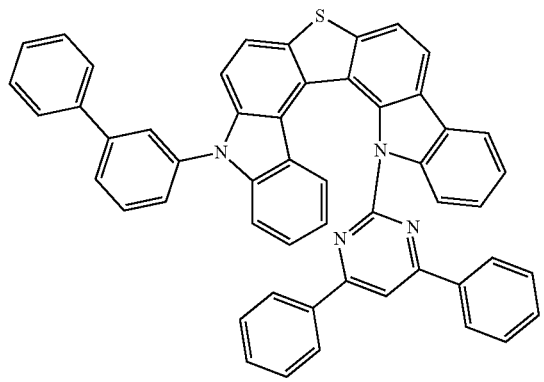
5-11
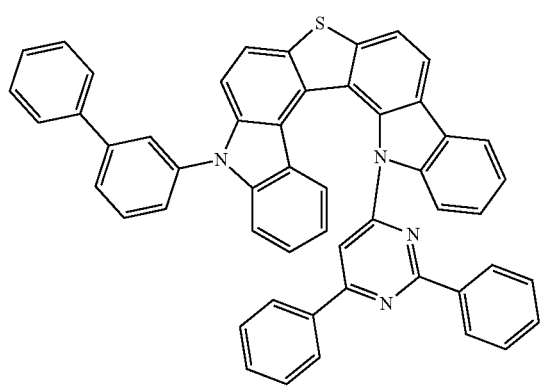
5-12
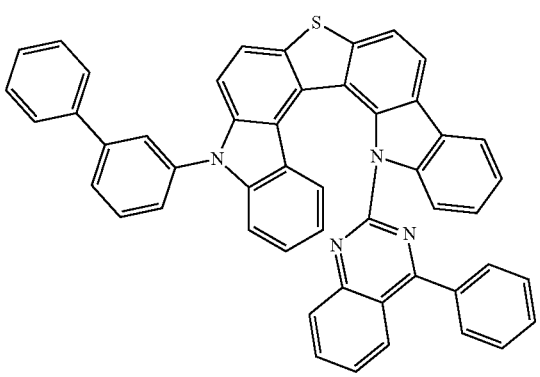
5-13
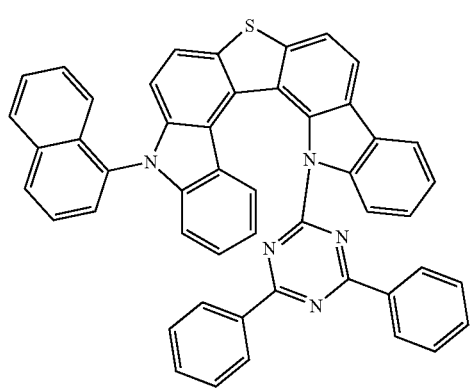
5-14
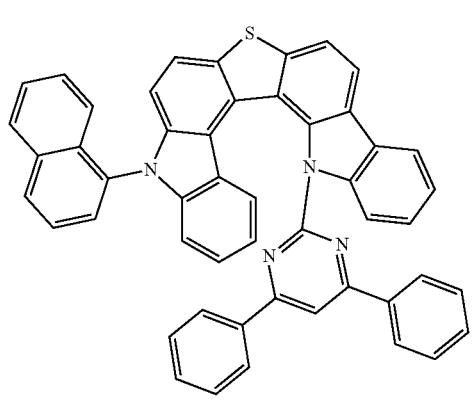
5-15
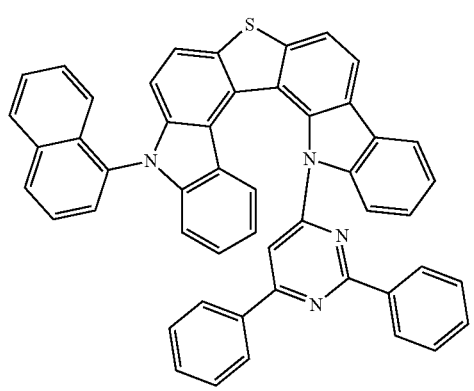

5-16
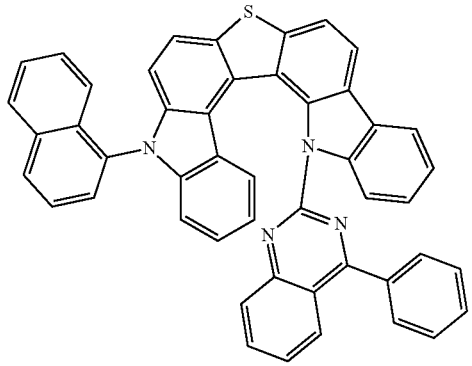
5-17
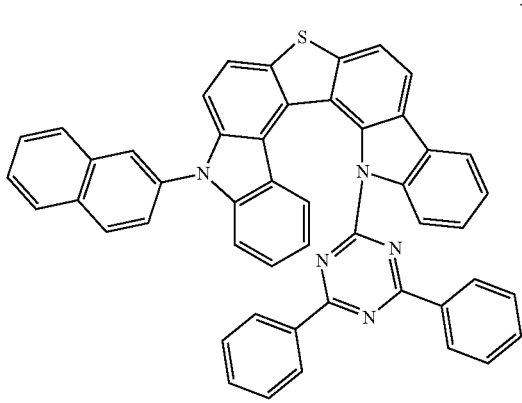
5-18
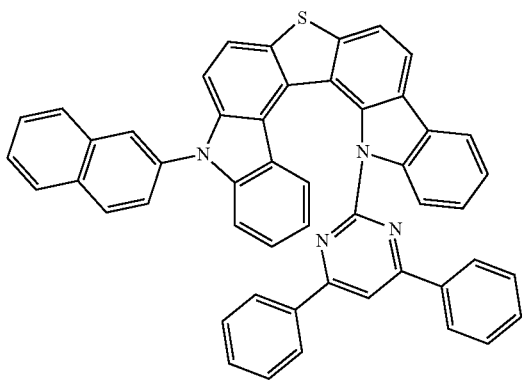
5-19
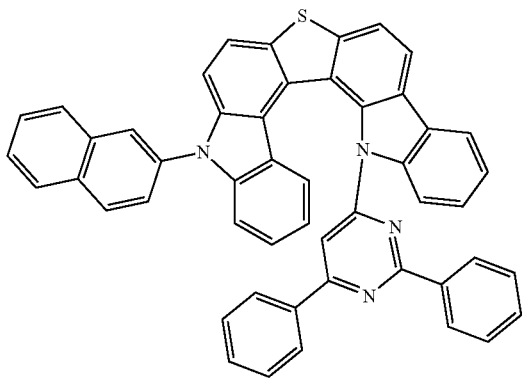
5-20
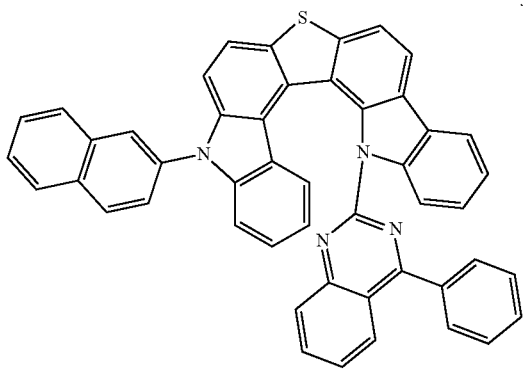
5-21
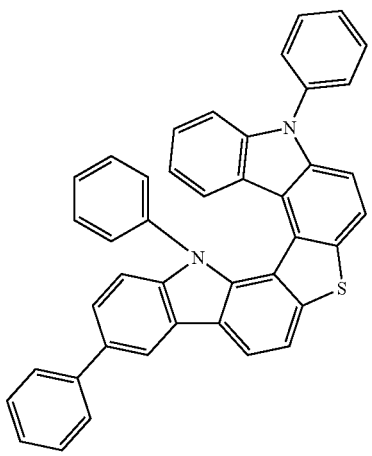
5-22
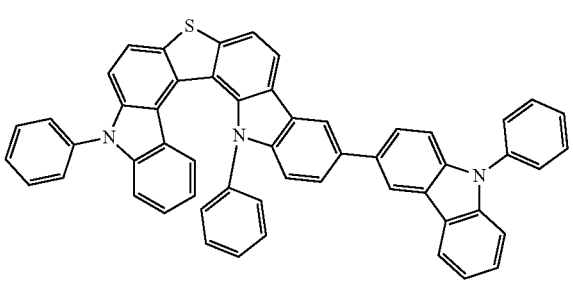
5-23
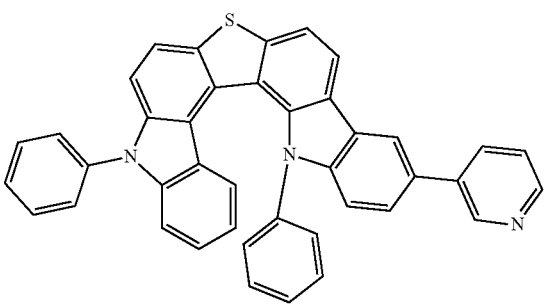

-continued
5-24
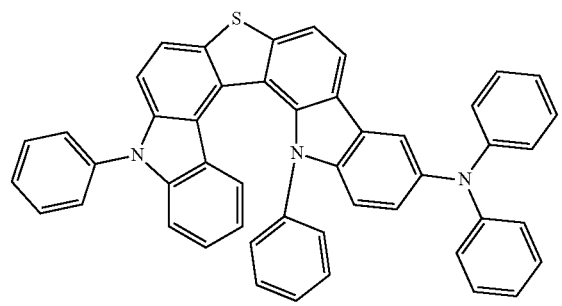
6-1
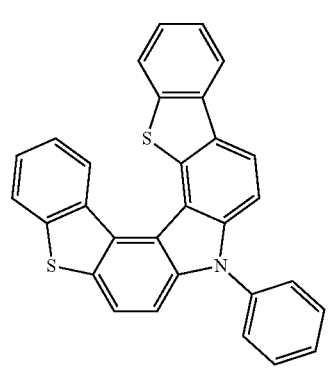
6-2
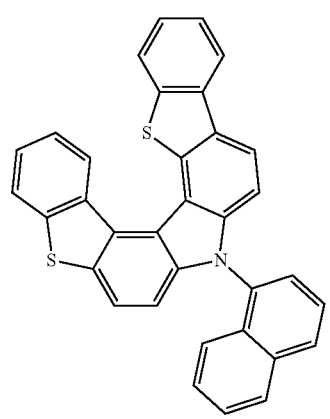
6-3
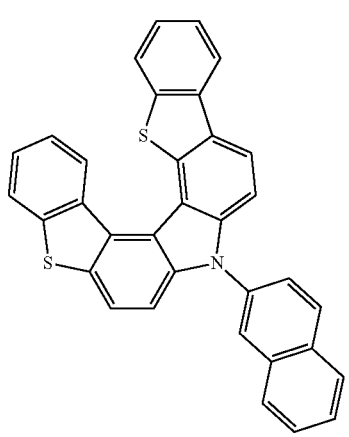
-continued
6-4
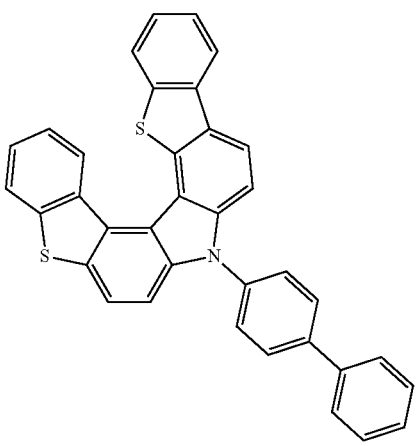
6-5
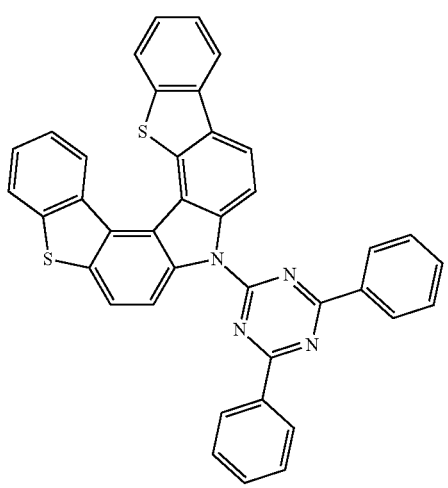
6-6
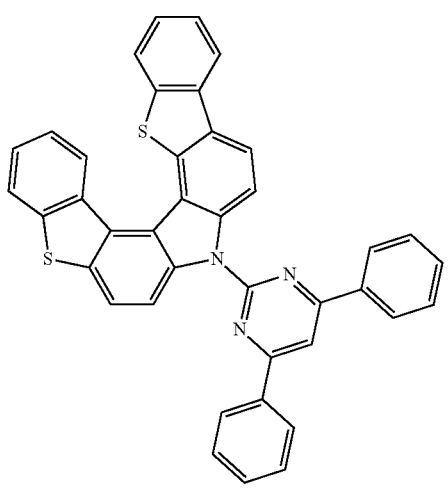

6-7
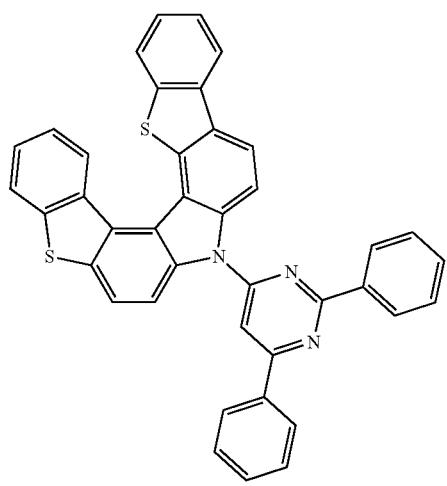
6-8
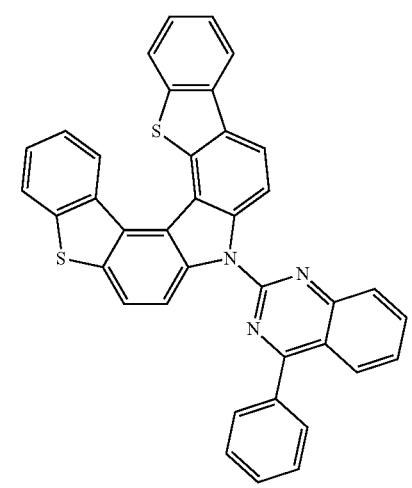
6-9
6-10
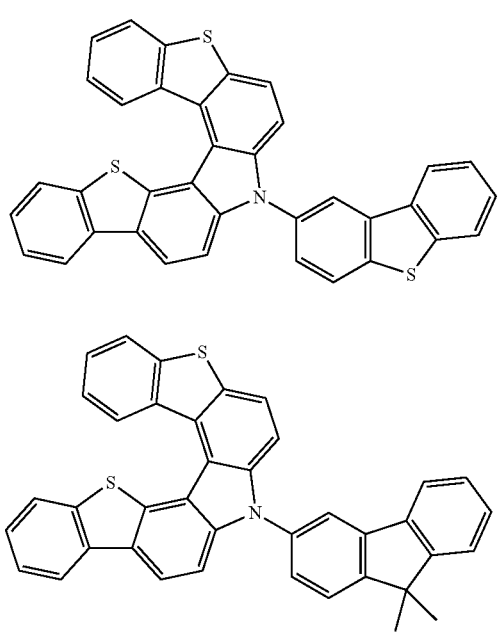
6-11
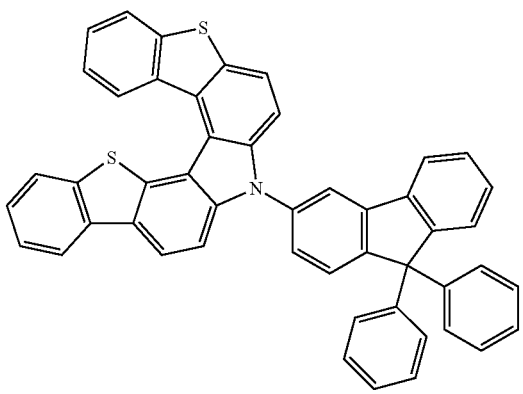
6-12
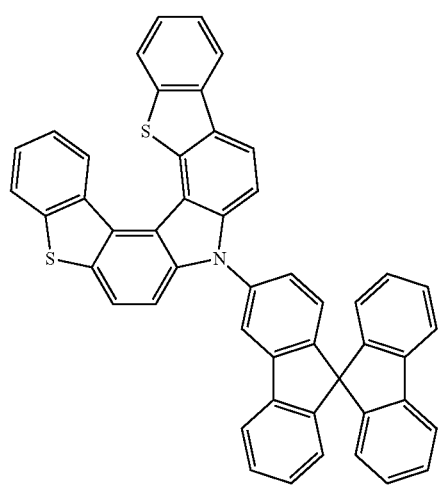
6-13
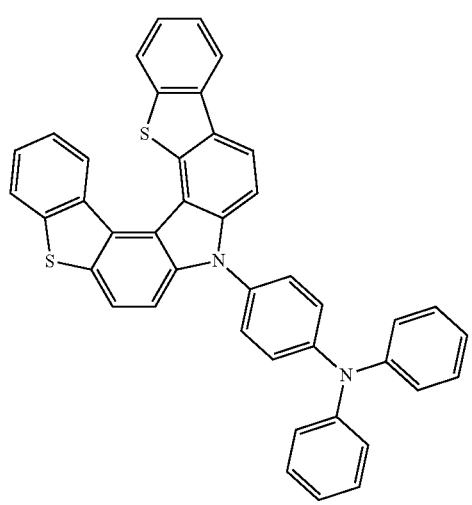

6-14
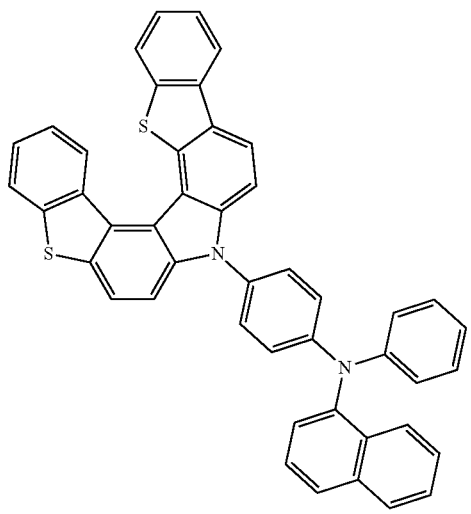
6-15
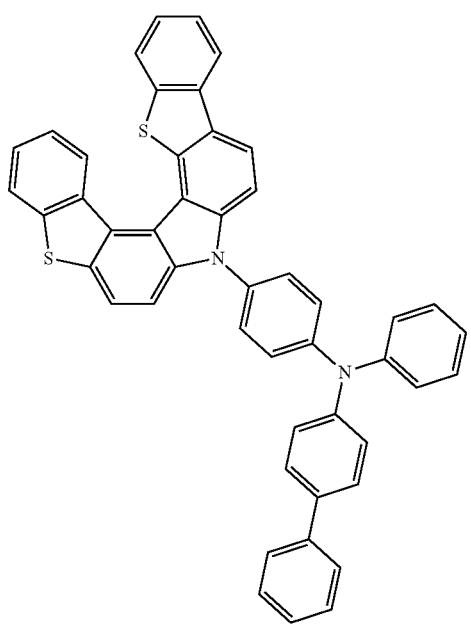
6-16
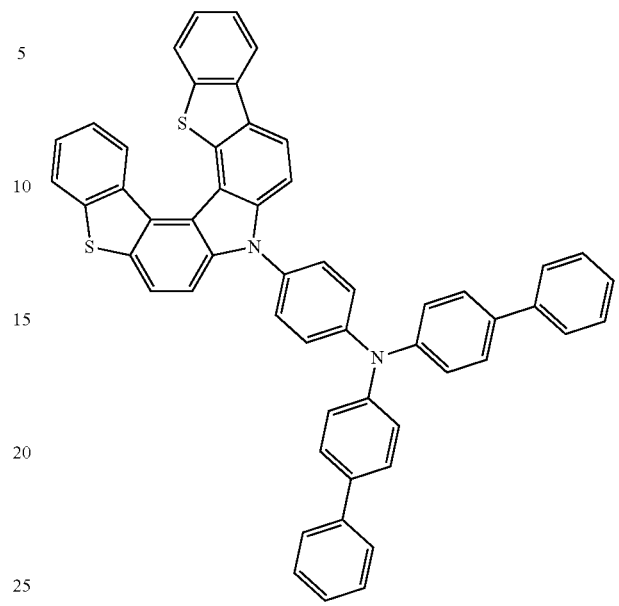
6-17
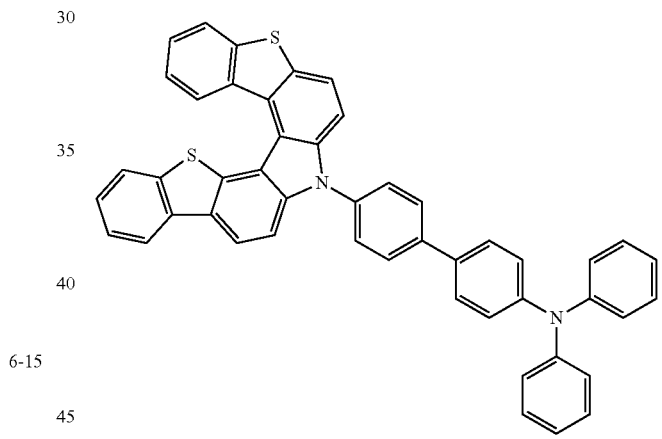
6-18
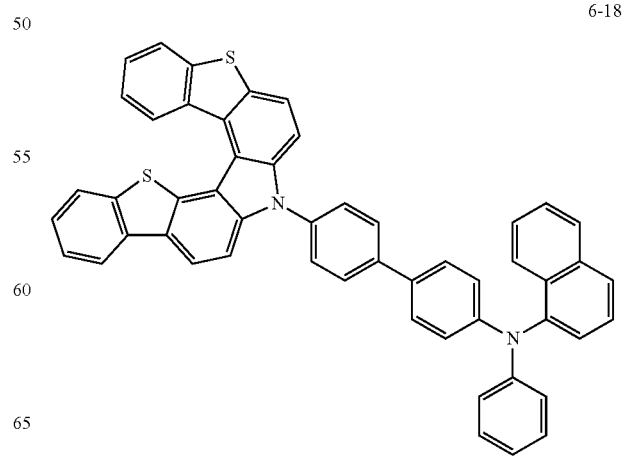

-continued
6-19
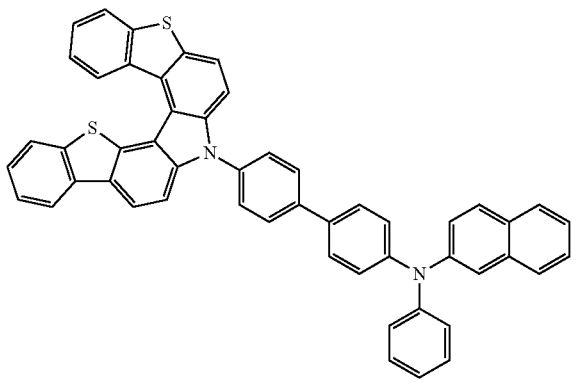
6-20
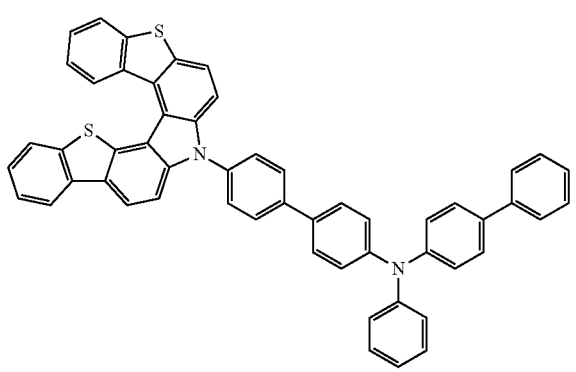
6-21
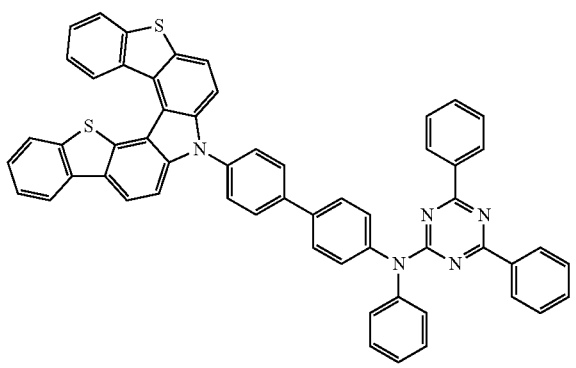
6-22
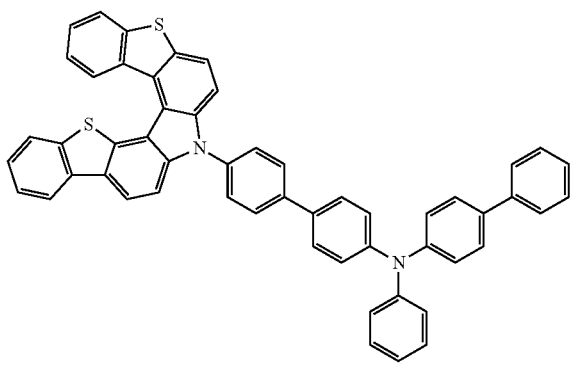
6-23
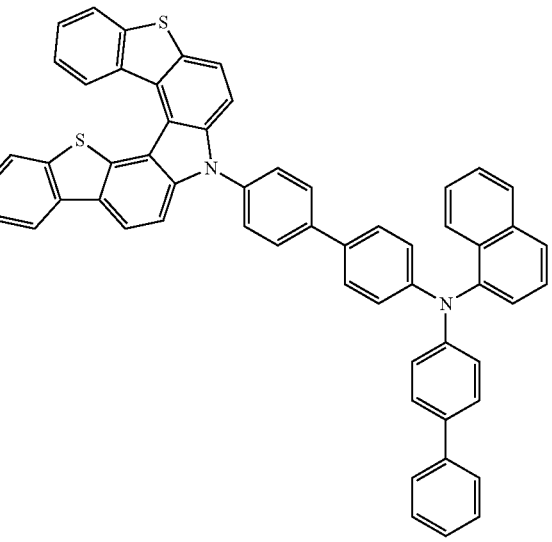
6-24
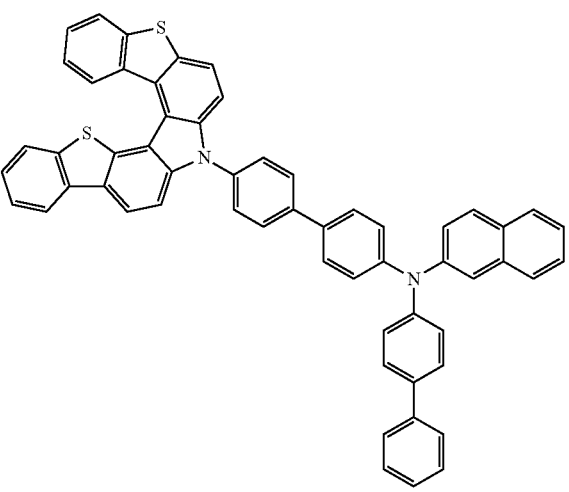
6-25
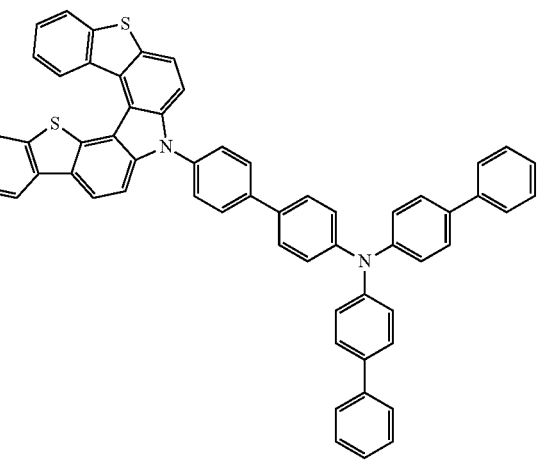

6-26
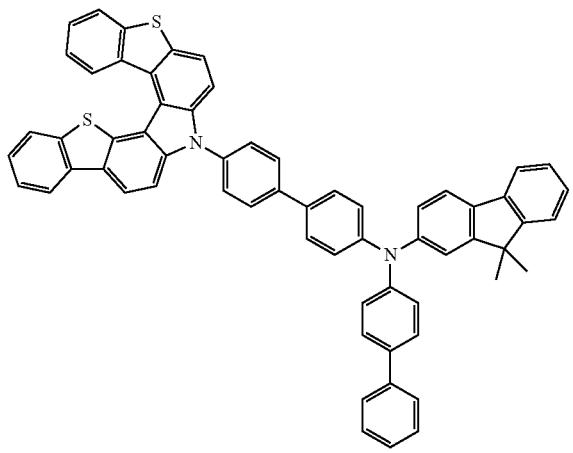
6-29
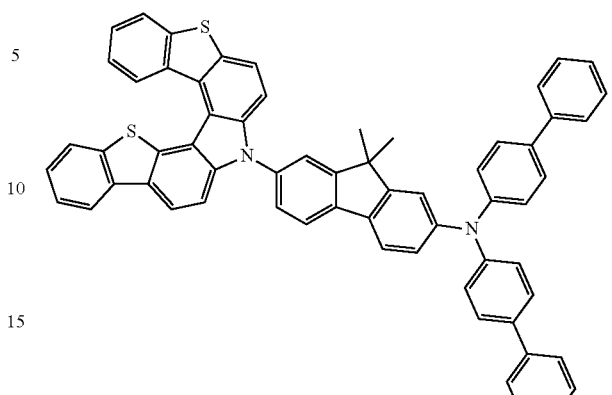
6-27
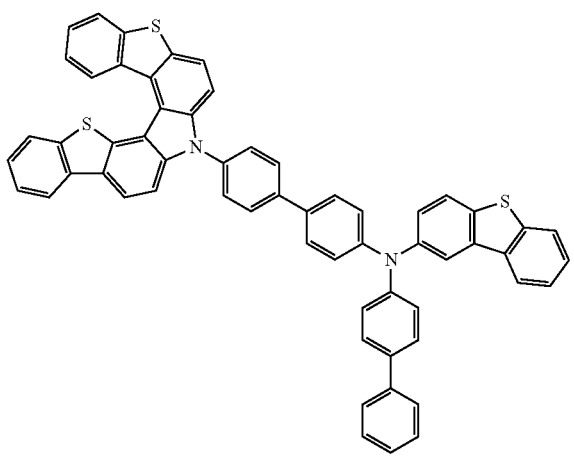
6-30
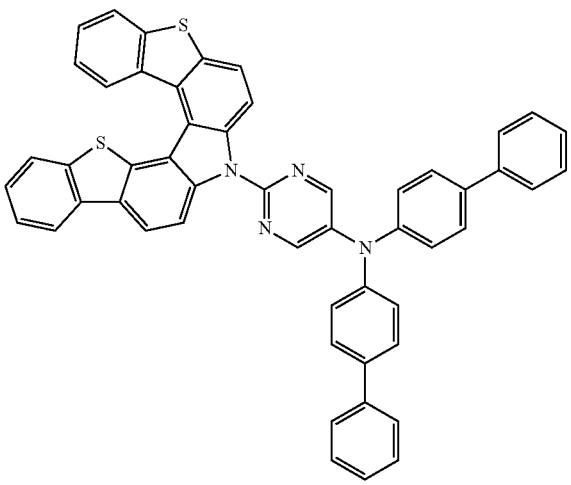
6-28
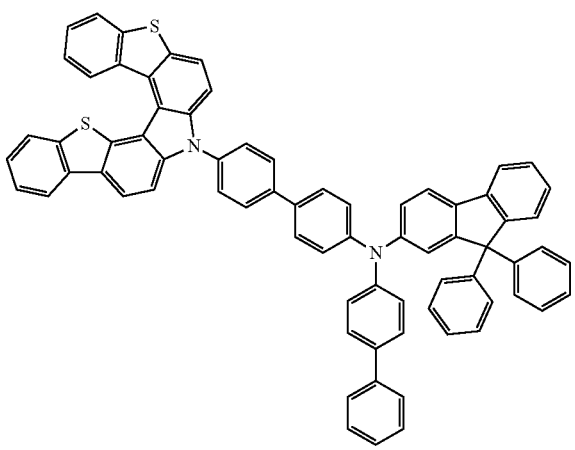
6-31
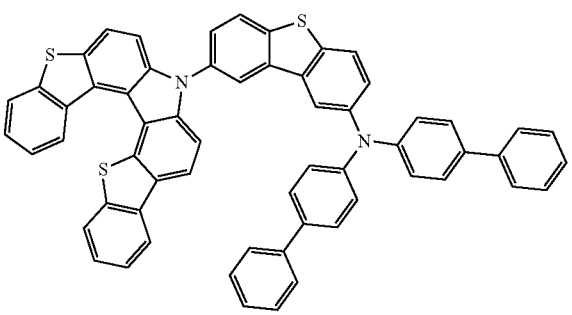

6-32
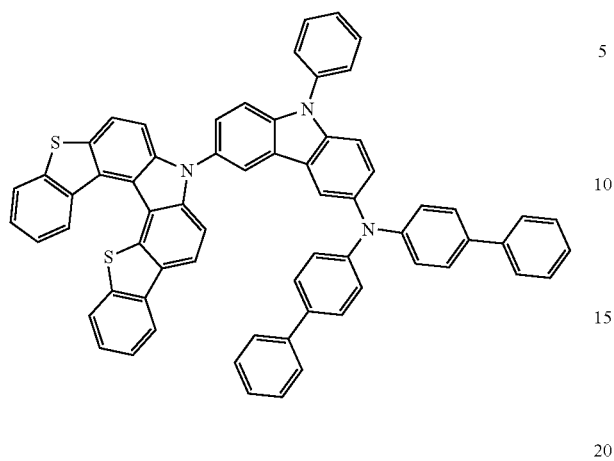
6-35
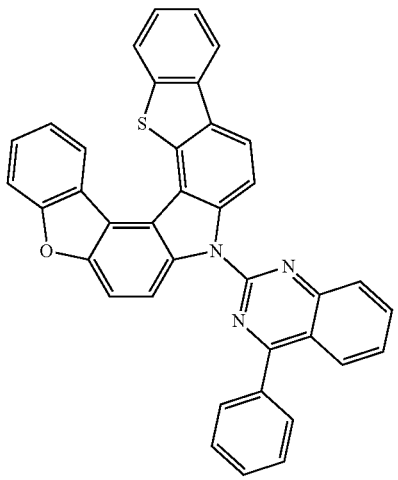
6-33
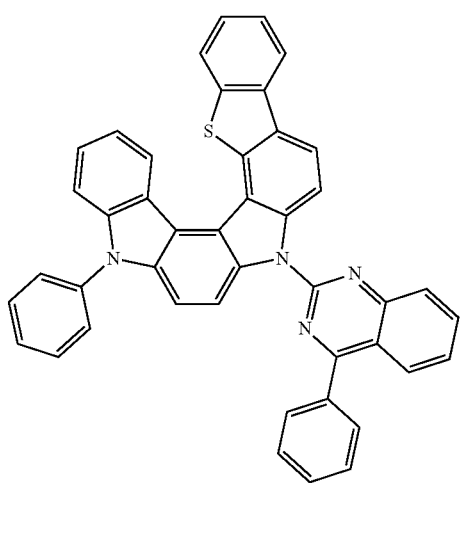
6-36
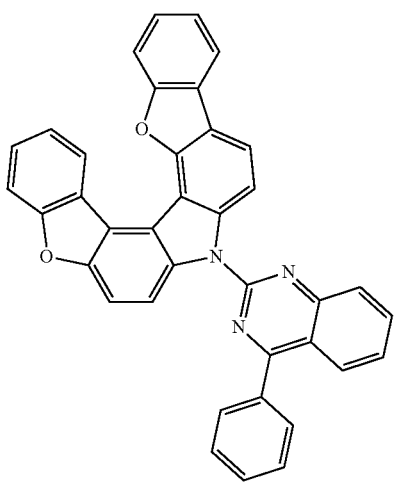
6-34
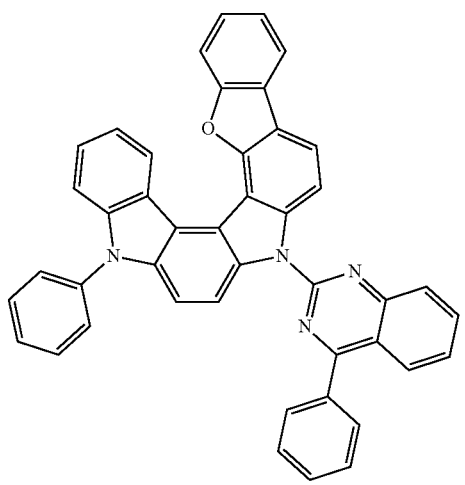
6-37
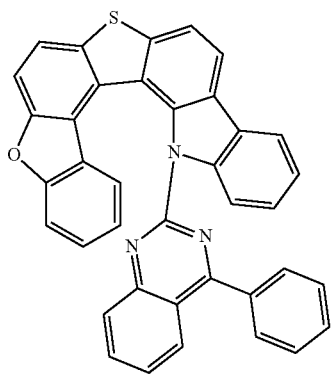

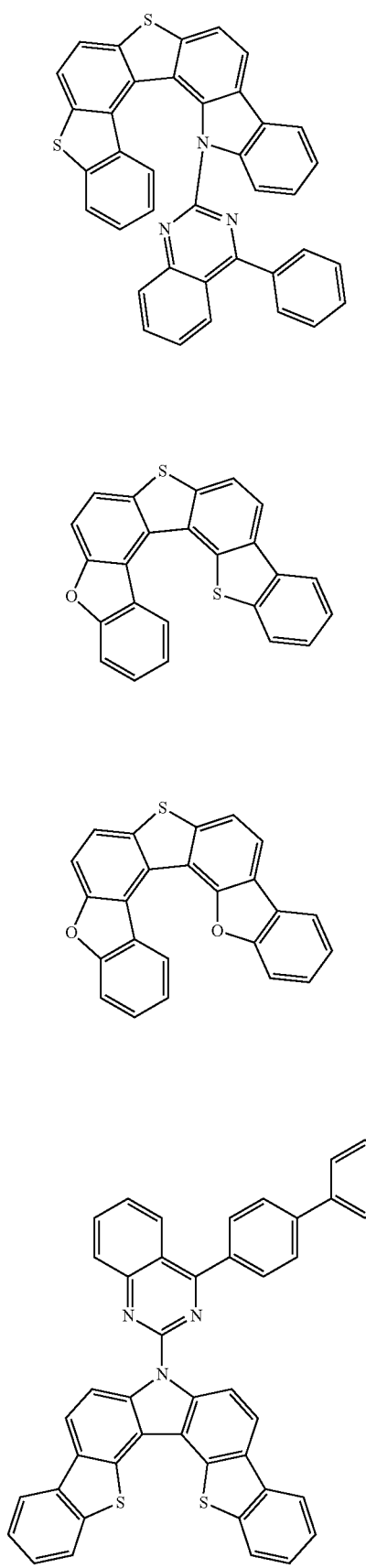

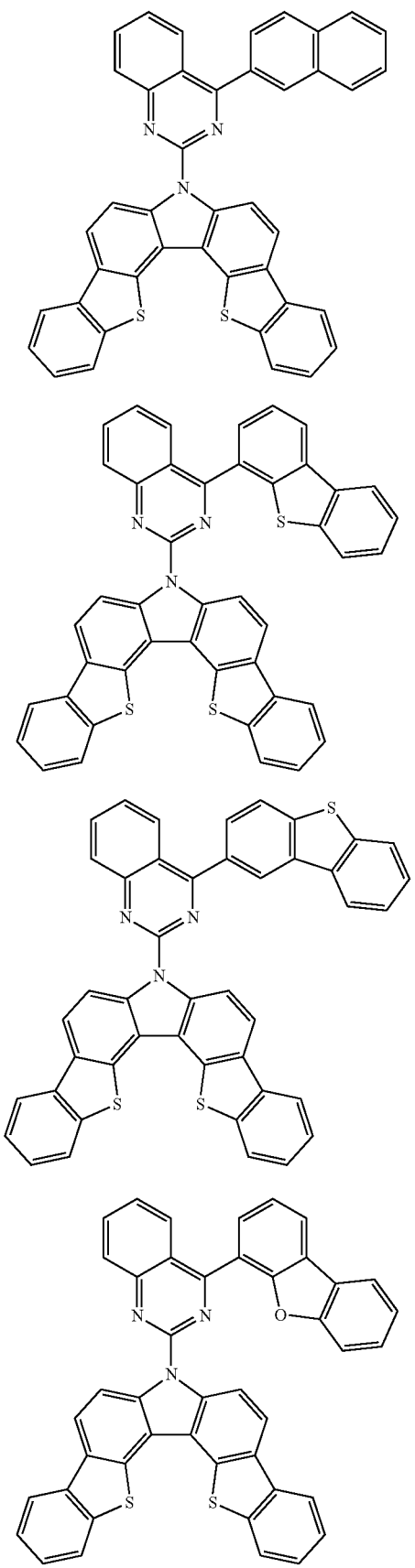
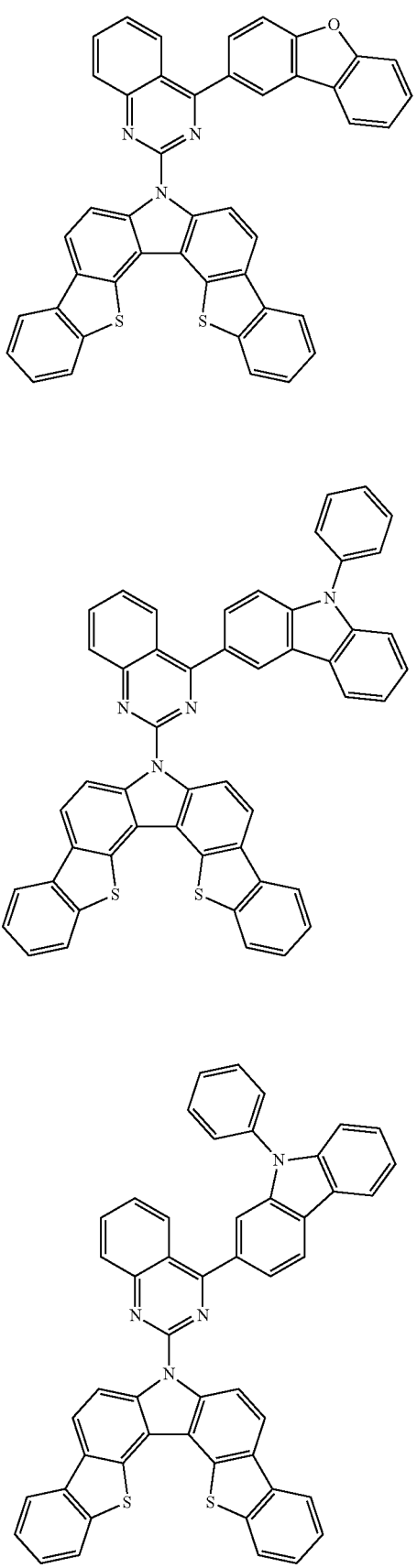

7-12
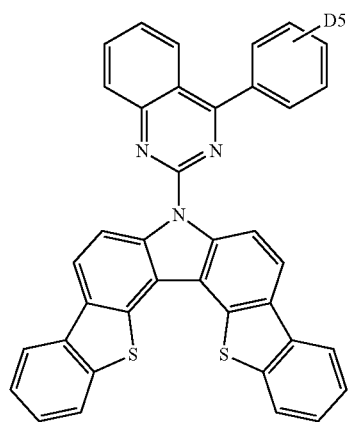
7-13
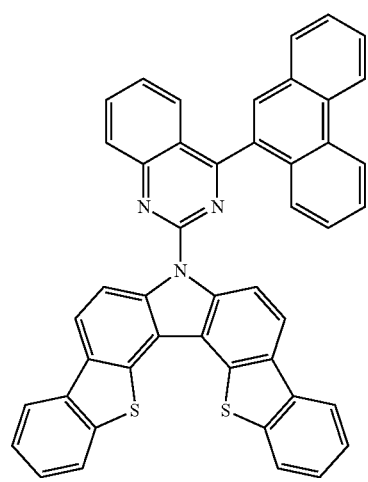
7-14
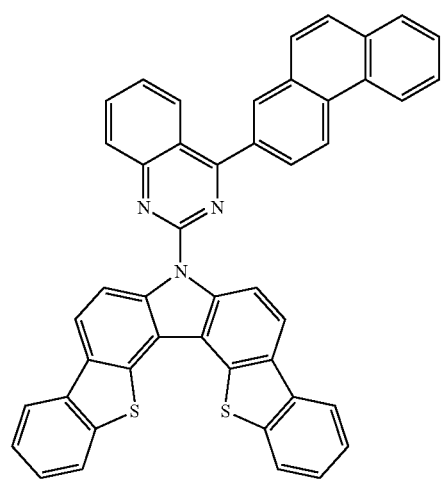
7-15
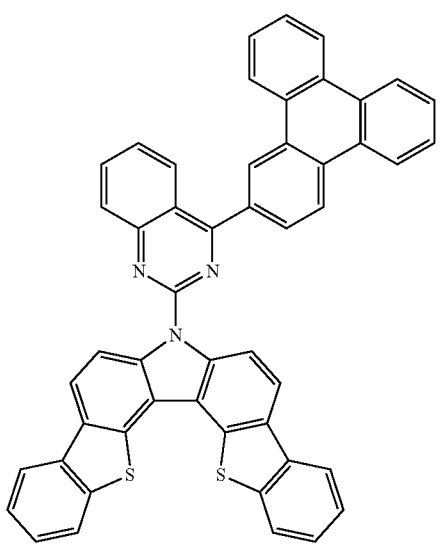
7-16
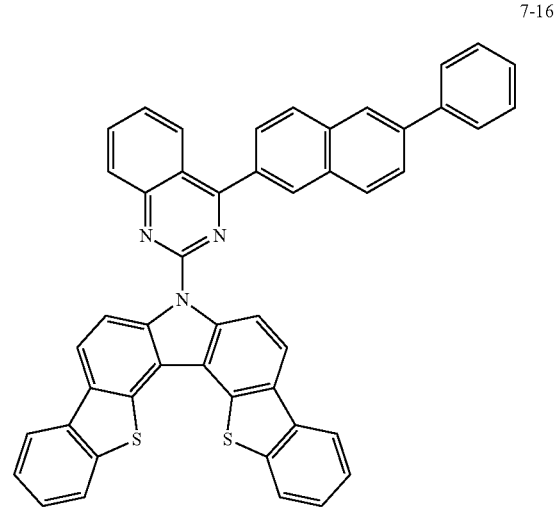
7-17
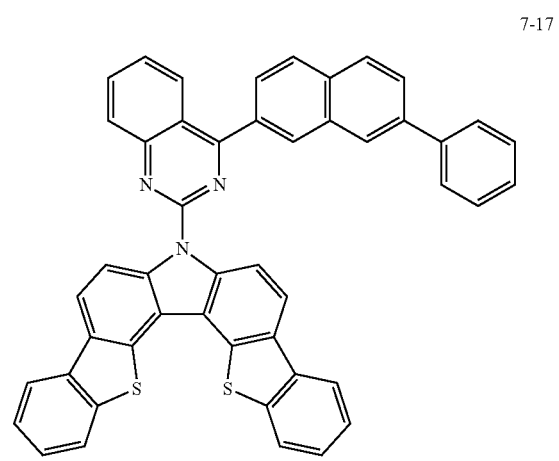

7-18
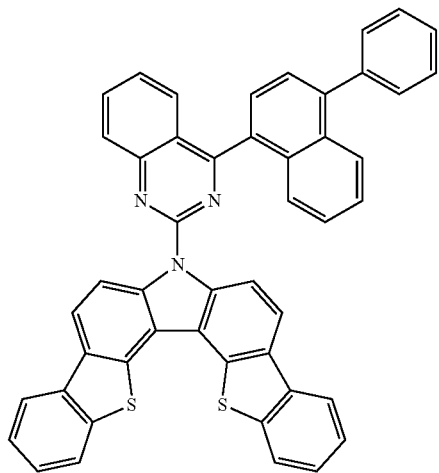
7-19
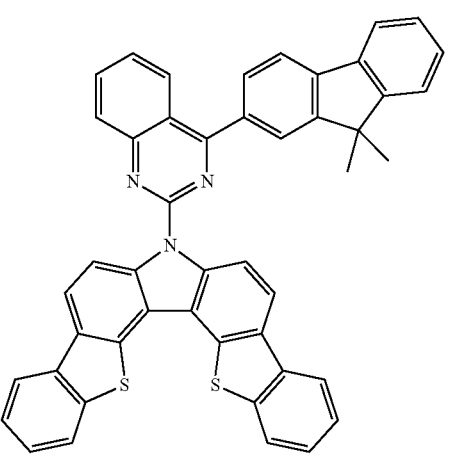
7-20
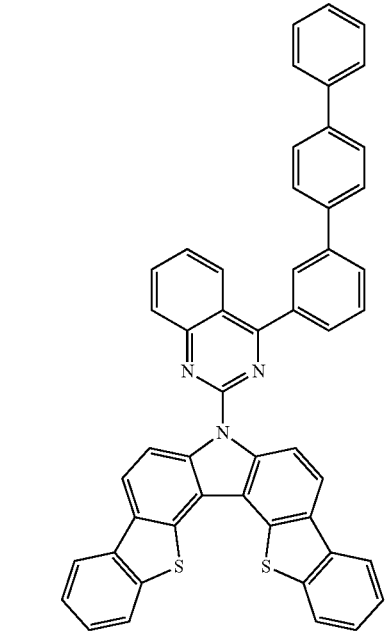
7-21
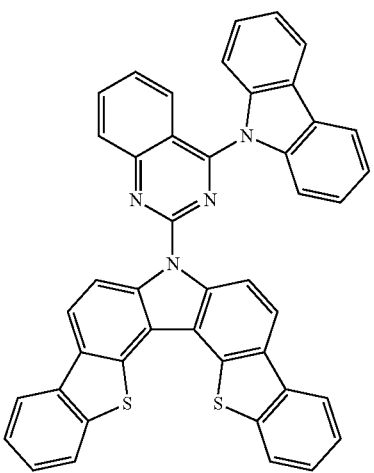
7-22
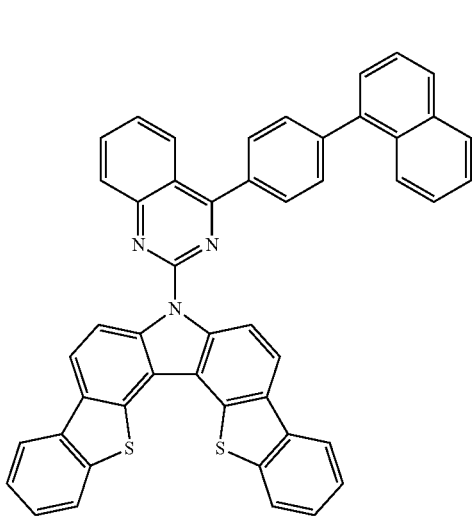
7-23
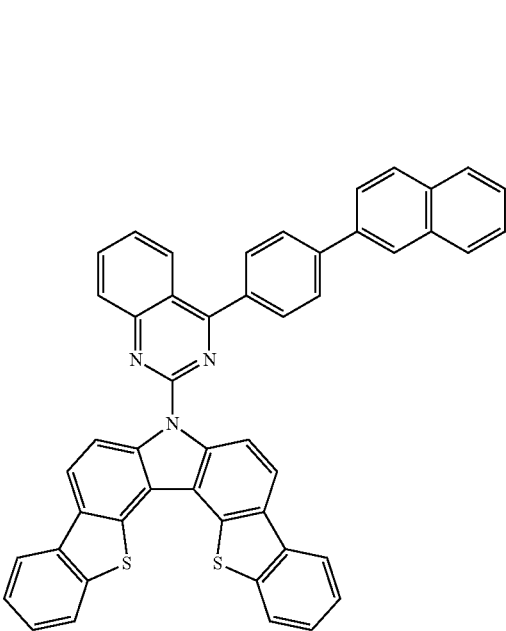

7-24
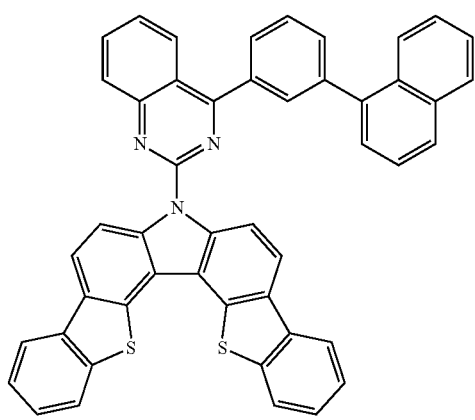
8-1
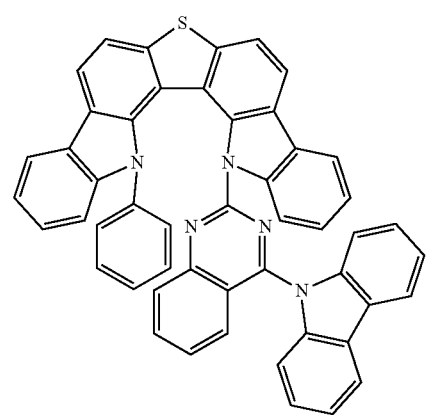
8-2
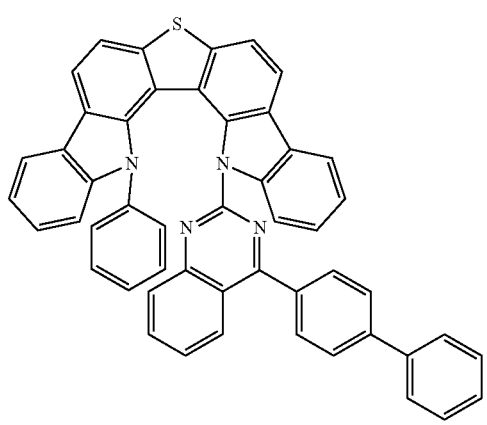
8-3
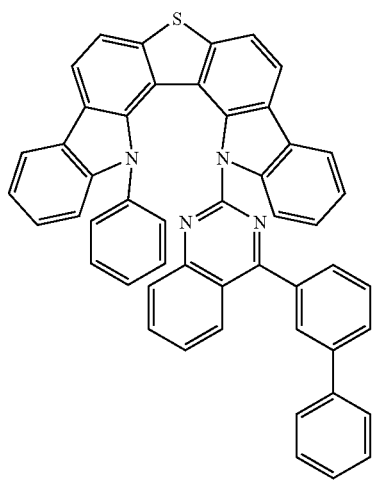
8-4
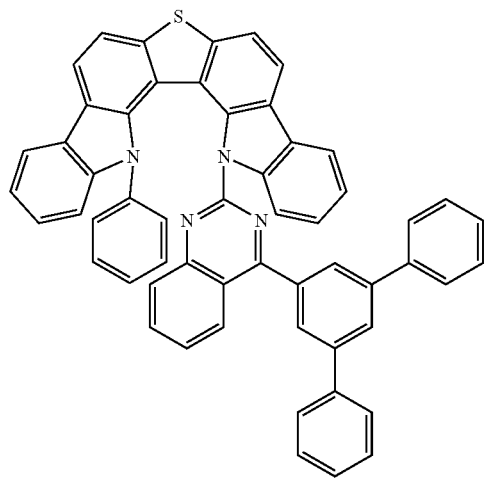
8-5
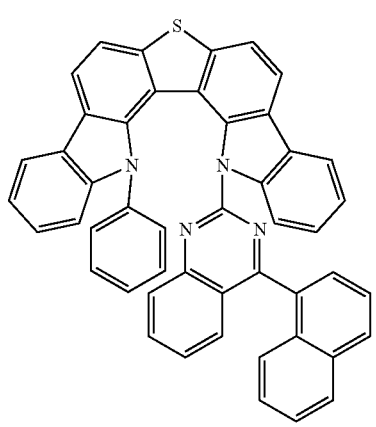

8-6
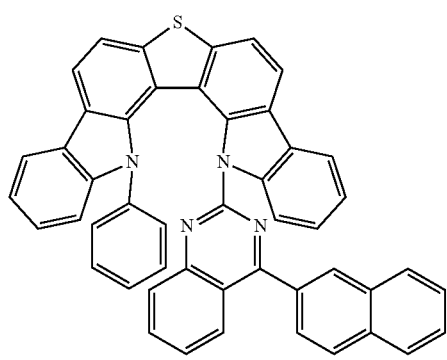
8-7
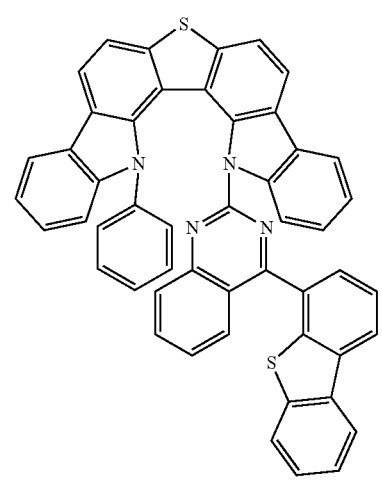
8-8
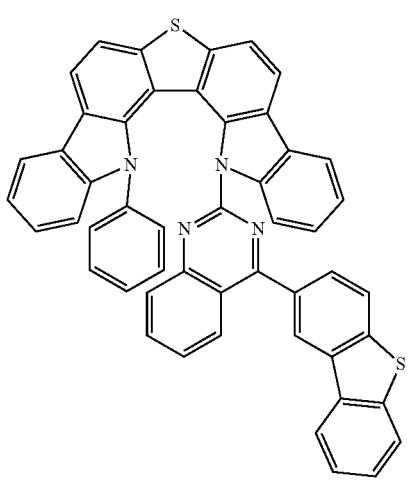
8-9
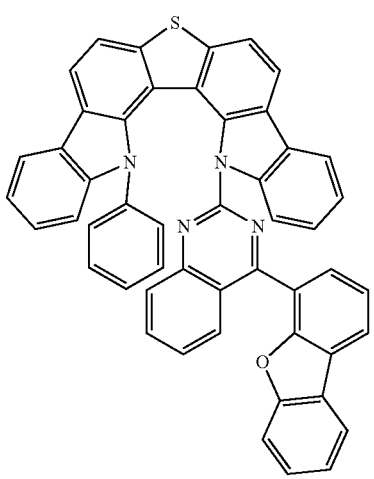
8-10
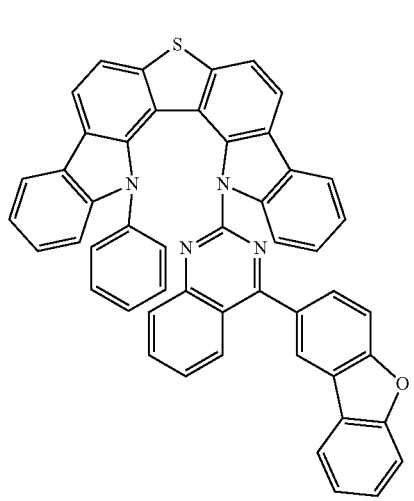
8-11
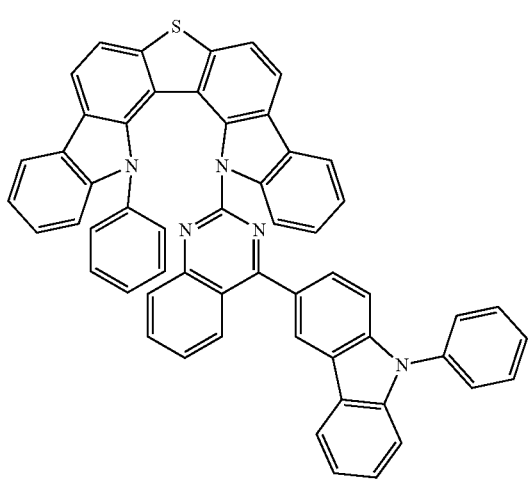

8-12
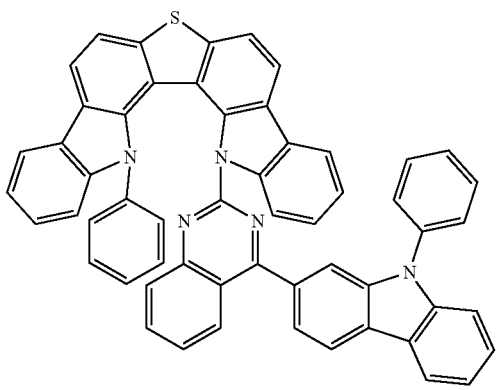
8-13
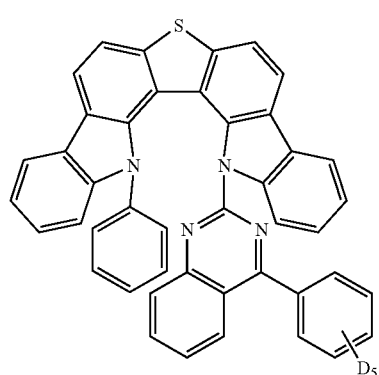
8-14
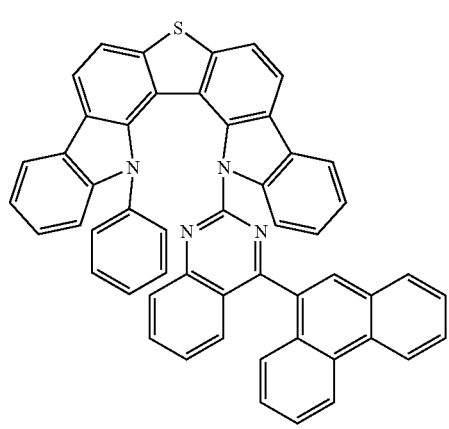
8-15
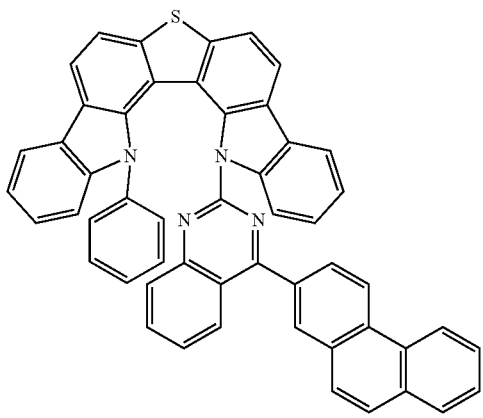
8-16
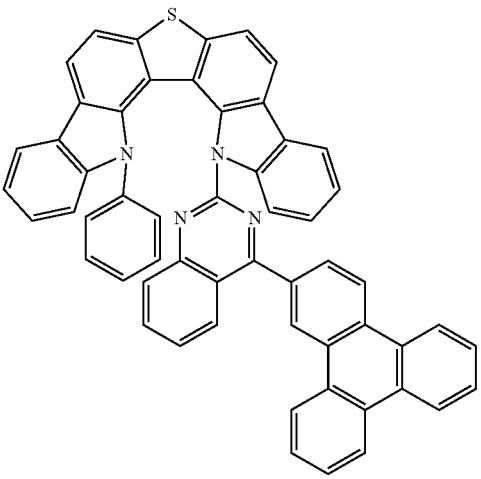
8-17
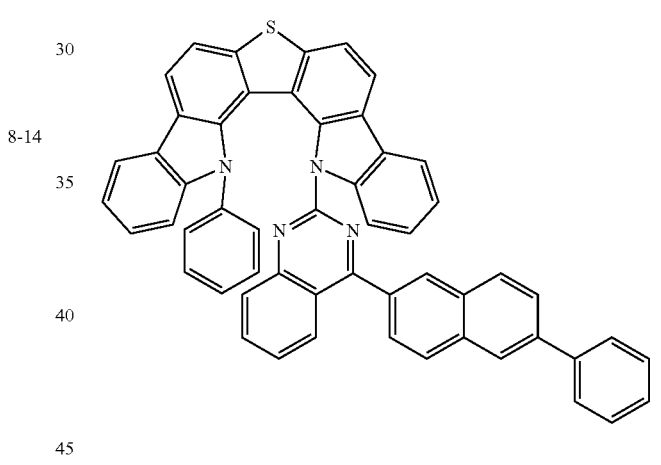
8-18
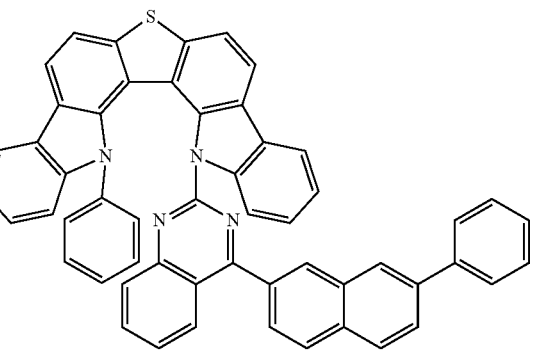

8-19

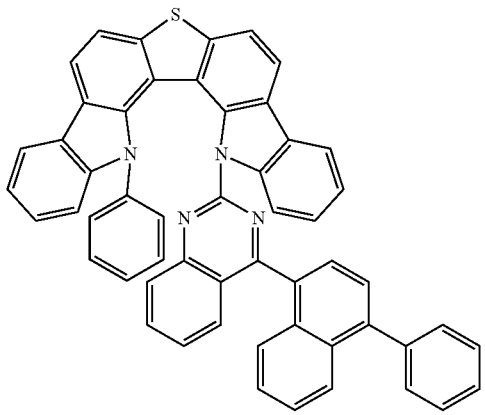

8-20

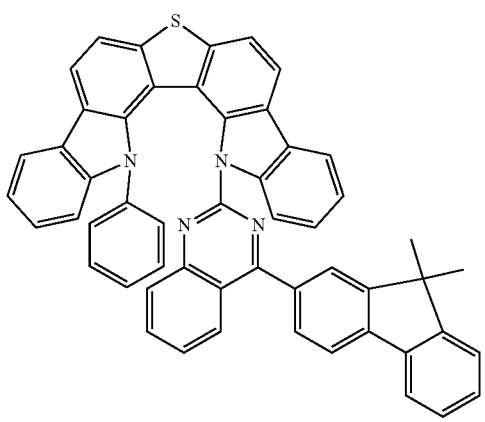

In another aspect of the present invention, a compound for an organic electric element represented by Formula 1 above is provided.

In another aspect of the present invention, an organic electric element comprising the compound represented by Formula 1 above is provided.

The organic electric element can comprise a first electrode, a second electrode, and an organic material layer disposed between the first electrode and the second electrode. The organic material layer can comprise the compound represented by Formula 1. The compound represented Formula 1 can be contained in at least one layer of a hole injection layer, a hole transport layer, an emission-auxiliary layer, or a light emitting layer of the organic material layer. The compound represented by Formula 1 may be used a material in the hole injection layer, a material in the hole transport layer, a material in the emission-auxiliary layer, or a material in the light emitting layer.

Specifically, the organic electric element comprising the organic material layer comprising at least one of the compounds represented by Formula 2 to 4 is provided, more specially, the organic electric element comprising the organic material layer comprising at least one of the compounds represented by individual Formula 1-1 to 1-24, 2-1 to 2-40, 3-1 to 3-24, 4-1 to 4-40, 5-1 to 5-24, 6-1 to 6-40, 7-1 to 7-24 and 8-1 to 8-20 is provided.

Furthermore, the compounds comprising of an organic material layer can be one kind or two or more different kinds of the compounds represented by Formula 1 above.

As an example, an emission-auxiliary layer or a light emitting layer of an organic material layer may be formed of a compound 1-1 or comprised a mixture of the compound 1-1 and 1-3.

In another aspect of the present invention, the present invention provides an organic electric element further including at least a layer to improve luminescence efficiency which is formed on at least one of the sides the first and second electrodes, which is opposite to the organic material layer.

Hereinafter, Synthesis Examples of the inventive compound represented by Formula 1 above and Preparation Examples of an organic electric element will be described in detail by way of example. However, the following examples are only for illustrative purposes and are not intended to limit the scope of the invention.

SYNTHESIS EXAMPLE

As an example, the compounds of the present invention can be prepared according to, but not limited to, the following reaction scheme 1 or reaction scheme 3 depending on Z of Formula 1.

I. Synthesis Example of the Product 1 (Z=S)

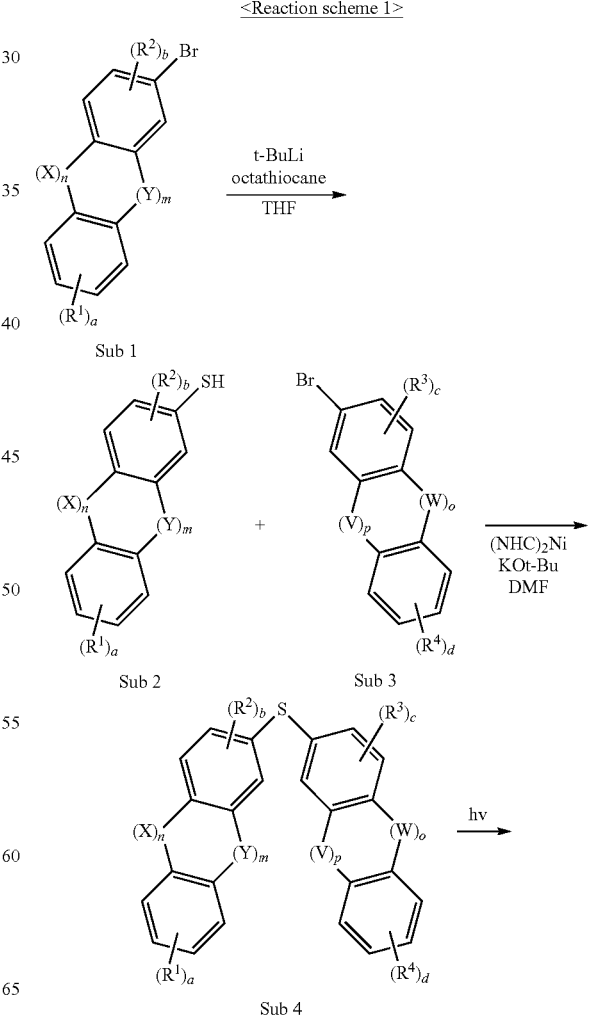

-continued

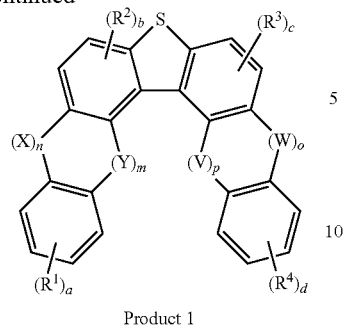

Product 1

1. Synthesis Example of Sub 1

When X or Y of Sub 1 is NR$^6$, it can be synthesized according to, but not limited to, the following Reaction scheme 2.

<Reaction scheme 2>

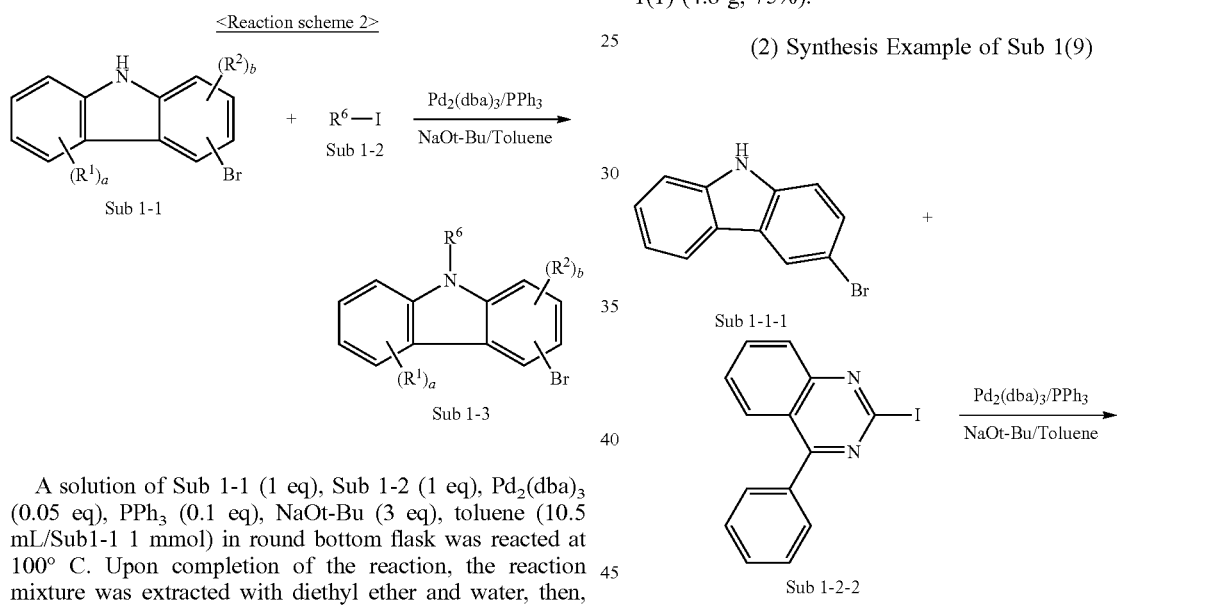

A solution of Sub 1-1 (1 eq), Sub 1-2 (1 eq), Pd$_2$(dba)$_3$ (0.05 eq), PPh$_3$ (0.1 eq), NaOt-Bu (3 eq), toluene (10.5 mL/Sub1-1 1 mmol) in round bottom flask was reacted at 100° C. Upon completion of the reaction, the reaction mixture was extracted with diethyl ether and water, then, dried over MgSO$_4$, concentrated. The concentrate was separated by a silica gel column chromatography and recrystallization to obtain Sub 1-3.

(1) Synthesis Example of Sub 1(1)

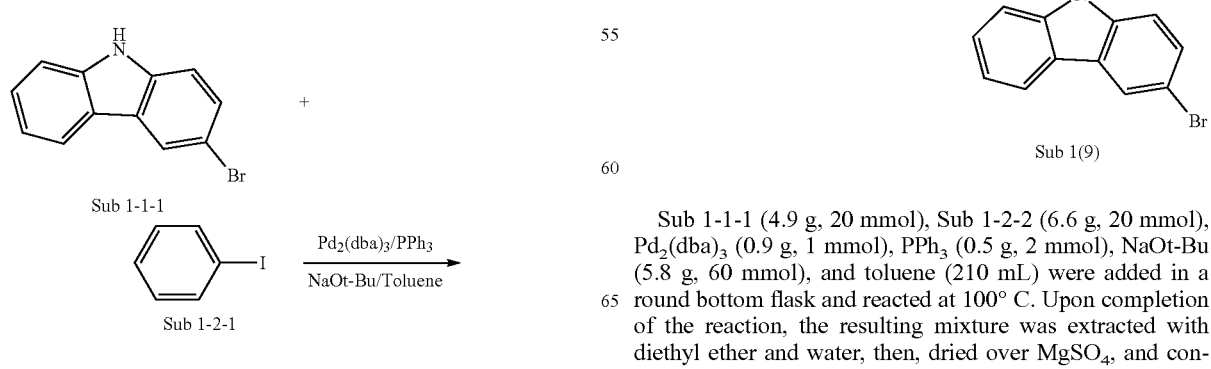

-continued

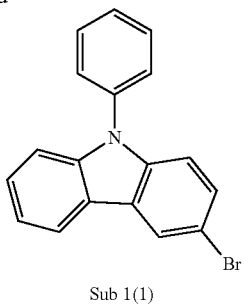

Sub 1(1)

Sub 1-1-1 (4.9 g, 20 mmol), Sub 1-2-1 (4.1 g, 20 mmol), Pd$_2$(dba)$_3$ (0.9 g, 1 mmol), PPh$_3$ (0.5 g, 2 mmol), NaOt-Bu (5.8 g, 60 mmol), and toluene (210 mL) were added in a round bottom flask and reacted at 100° C. Upon completion of the reaction, the resulting mixture was extracted with diethyl ether and water, then, dried over MgSO$_4$ and concentrated. The concentrate was separated by a silica gel column chromatography and recrystallized to obtain Sub 1(1) (4.8 g, 75%).

(2) Synthesis Example of Sub 1(9)

Sub 1-1-1 (4.9 g, 20 mmol), Sub 1-2-2 (6.6 g, 20 mmol), Pd$_2$(dba)$_3$ (0.9 g, 1 mmol), PPh$_3$ (0.5 g, 2 mmol), NaOt-Bu (5.8 g, 60 mmol), and toluene (210 mL) were added in a round bottom flask and reacted at 100° C. Upon completion of the reaction, the resulting mixture was extracted with diethyl ether and water, then, dried over MgSO$_4$, and concentrated. The concentrate was separated by a silica gel column chromatography and recrystallized to obtain Sub 1(9) (6.2 g, 69%).
Examples of Sub 1 compounds include, but are not limited to, the following compounds, and FD-MS data of the compounds are given in Table 1 below.
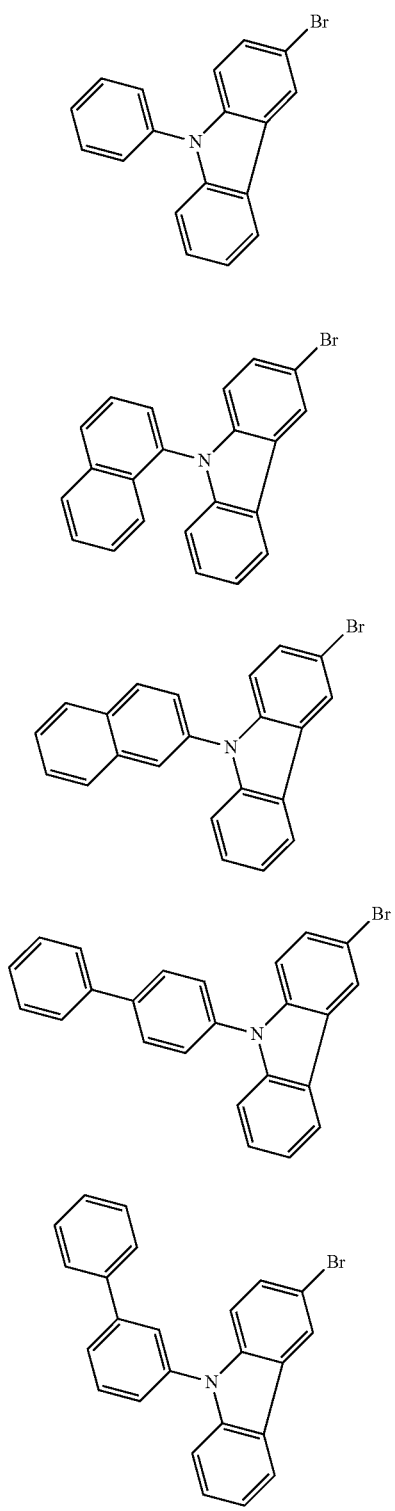
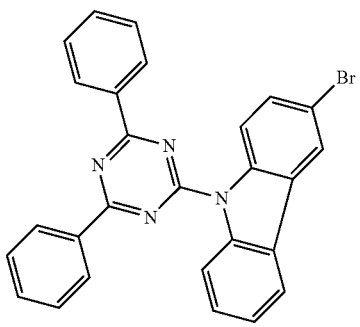
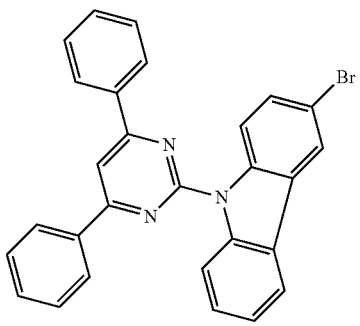
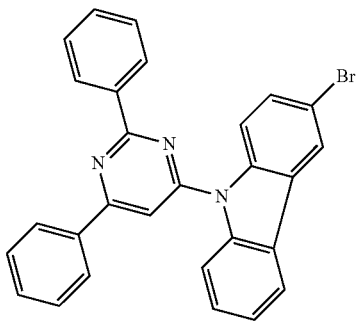
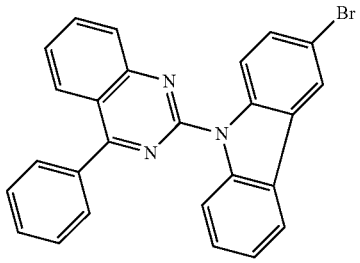
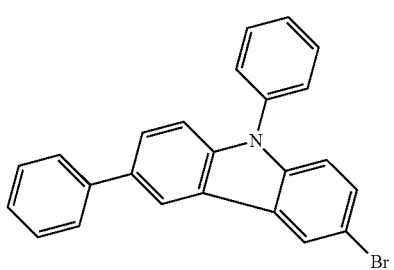

-continued
Sub 1(11)
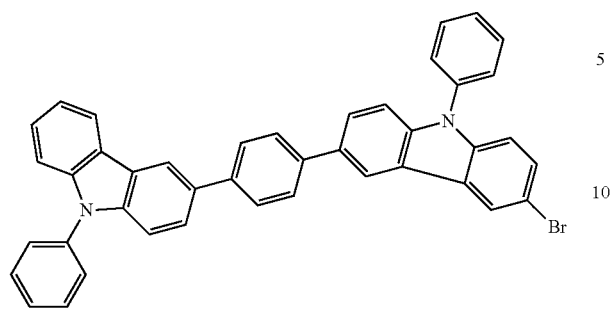
Sub 1(12)
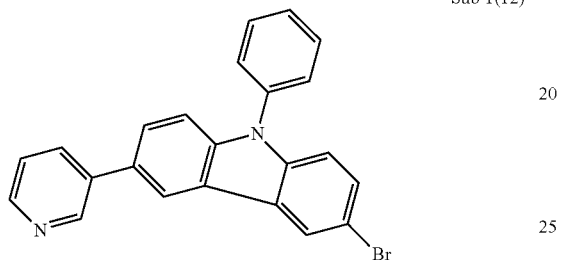
Sub 1(13)
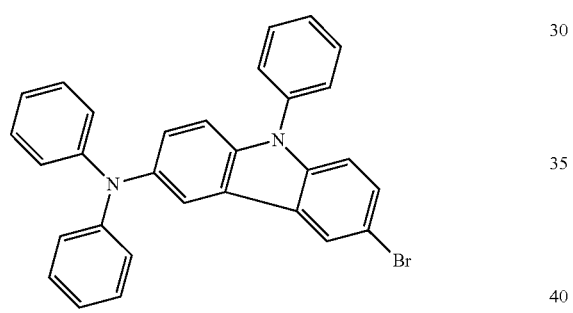
Sub 1(14)
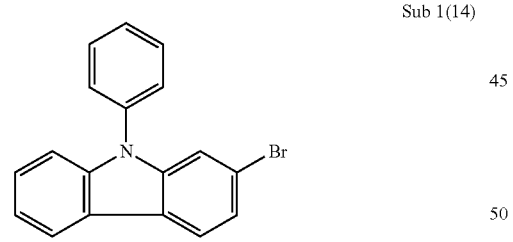
Sub 1(15)
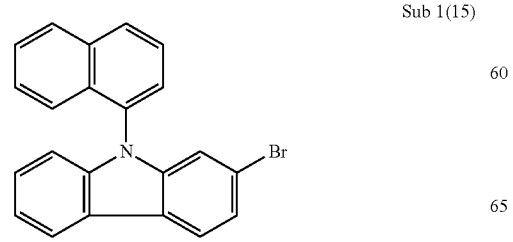
-continued
Sub 1(16)
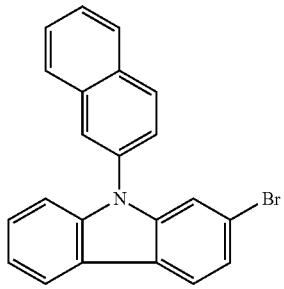
Sub 1(17)
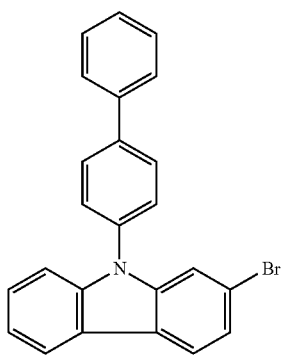
Sub 1(18)
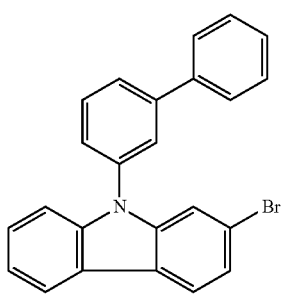
Sub 1(19)
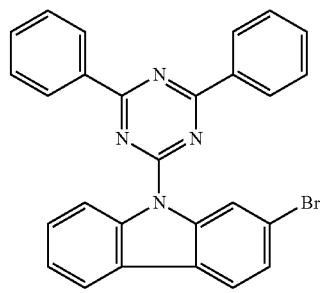
Sub 1(20)
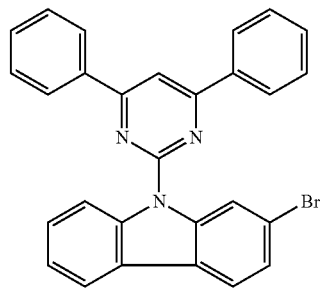

Sub 1(21)
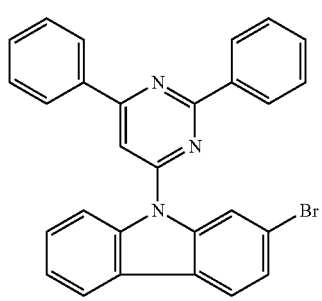
Sub 1(24)
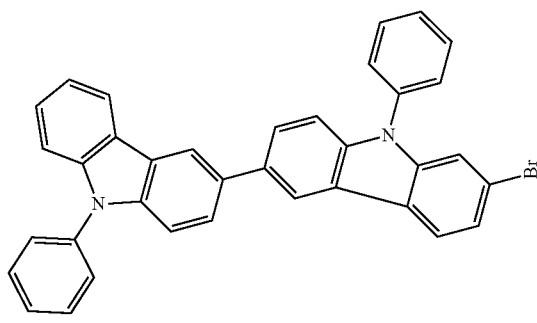
Sub 1(22)
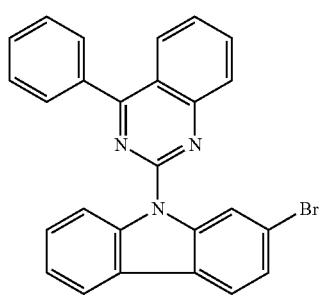
Sub 1(25)
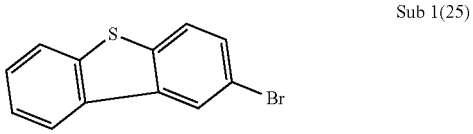
Sub 1(26)
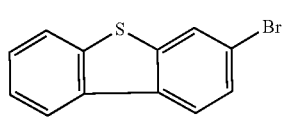
Sub 1(27)
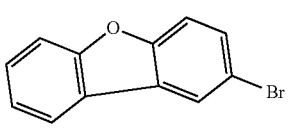
Sub 1(23)
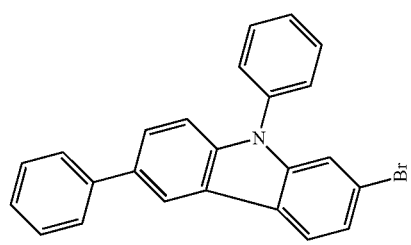
Sub 1(28)
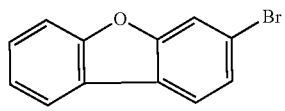

| Compound | FD-MS | Compound | FD-MS |
|---|---|---|---|
| Sub 1(1) | m/z = 321.02($C_{18}H_{12}BrN$ = 322.20) | Sub 1(2) | m/z = 371.03($C_{22}H_{14}BrN$ = 372.26) |
| Sub 1(3) | m/z = 371.03($C_{22}H_{14}BrN$ = 372.26) | Sub 1(4) | m/z = 397.05($C_{24}H_{16}BrN$ = 398.29) |
| Sub 1(5) | m/z = 397.05($C_{24}H_{16}BrN$ = 398.29) | Sub 1(6) | m/z = 476.06($C_{27}H_{17}BrN_4$ = 477.35) |
| Sub 1(7) | m/z = 475.07($C_{28}H_{18}BrN_3$ = 476.37) | Sub 1(8) | m/z = 475.07($C_{28}H_{18}BrN_3$ = 476.37) |
| Sub 1(9) | m/z = 449.05($C_{26}H_{16}BrN_3$ = 450.33) | Sub 1(10) | m/z = 397.05($C_{24}H_{16}BrN$ = 398.29) |
| Sub 1(11) | m/z = 562.10($C_{36}H_{23}BrN_2$ = 563.49) | Sub 1(12) | m/z = 398.04($C_{23}H_{15}BrN_2$ = 399.28) |
| Sub 1(13) | m/z = 488.09($C_{30}H_{21}BrN_2$ = 489.41) | Sub 1(14) | m/z = 321.02($C_{18}H_{12}BrN$ = 322.20) |
| Sub 1(15) | m/z = 371.03($C_{22}H_{14}BrN$ = 372.26) | Sub 1(16) | m/z = 371.03($C_{22}H_{14}BrN$ = 372.26) |
| Sub 1(17) | m/z = 397.05($C_{24}H_{16}BrN$ = 398.29) | Sub 1(18) | m/z = 397.05($C_{24}H_{16}BrN$ = 398.29) |
| Sub 1(19) | m/z = 476.06($C_{27}H_{17}BrN_4$ = 477.35) | Sub 1(20) | m/z = 475.07($C_{28}H_{18}BrN_3$ = 476.37) |
| Sub 1(21) | m/z = 475.07($C_{28}H_{18}BrN_3$ = 476.37) | Sub 1(22) | m/z = 449.05($C_{26}H_{16}BrN_3$ = 450.33) |
| Sub 1(23) | m/z = 397.05($C_{24}H_{16}BrN$ = 398.29) | Sub 1(24) | m/z = 562.10($C_{36}H_{23}BrN_2$ = 563.49) |
| Sub 1(25) | m/z = 261.95($C_{12}H_7BrS$ = 263.15) | Sub 1(26) | m/z = 261.95($C_{12}H_7BrS$ = 263.15) |
| Sub 1(27) | m/z = 245.97($C_{12}H_7BrO$ = 247.09) | Sub 1(28) | m/z = 245.97($C_{12}H_7BrO$ = 247.09) |

2. Synthesis Example of Sub 2

A mixture of Sub 1 (1 eq) and tert-butyl lithium (1.1 eq) was stirred at −78° C. for 1 hr. After increasing the reaction temperature to room temperature, to the solution was added octathiocane (1.5 eq) and stirred for 3 hr. And then to the solution was added HCl and stirred for 30 min again. Upon completion of the reaction, the reaction solution was extracted with $CH_2Cl_2$ and water, dried over $MgSO_4$, concentrated. The concentrate was separated by a silica gel column chromatography and recrystallized to obtain Sub 2.

3. Synthesis Example of Sub 3

Sub 3 was prepared in the same way, but not limited to, as Synthesis example of Sub 1.

4. Synthesis Example of Sub 4

A mixture of Sub 2 (1 eq.), Sub 3 (1 eq.), potassium tert-butoxide (1.1 eq.), $(NHC)_2Ni$ (0.04 eq.) in DMF was stirred for 16 hr at 110° C. Upon completion of the reaction, the resulting solution was cooled to room temperature, extracted with $CH_2Cl_2$ and washed with water, dried over anhydrous $MgSO_4$ to remove a trace amount of water, filtered under pressure and concentrated. The concentrate was separated by a silica gel column chromatography and recrystallized to obtain Sub 4.

5. Synthesis Example of Product 1

A mixture of Sub 4 (1 eq), $I_2$ (1.25 eq) and cyclohexane was added in Hanovia photoreactor with 1450 W medium pressure Hg lamp, and stirred under argon for 20 min. After that, to the resulting mixture was added propylene oxide (6 eq) and irradiated for 30 min. Upon completion of the reaction, the reactant was cooled to room temperature, and extracted with $CH_2Cl_2$, washed with water, dried over anhydrous $MgSO_4$ to remove a trace amount of water. Then, the organic layer was filtered under pressure and concentrated. The concentrate was separated by a silica gel column chromatography and recrystallized to obtain Product 1.

(1) Synthesis Example of Product 1-8

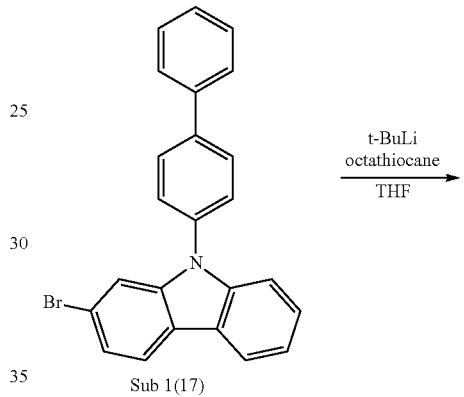

Sub 1(17)

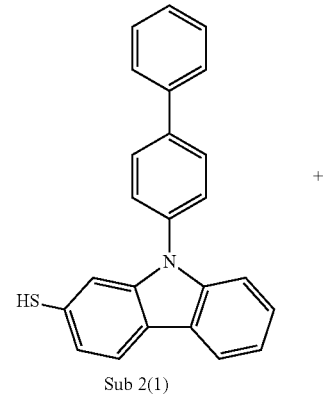

Sub 2(1)

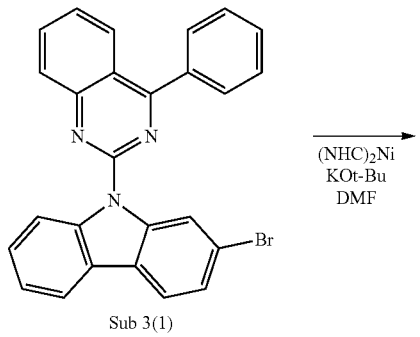

Sub 3(1)

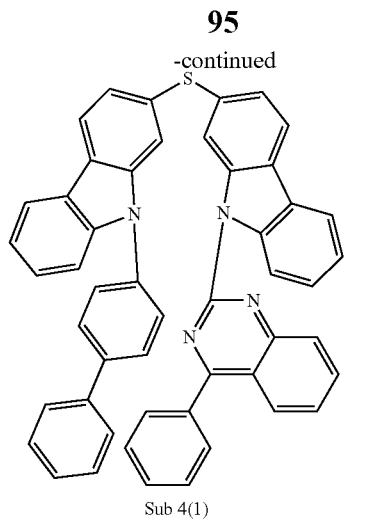

Sub 4(1)

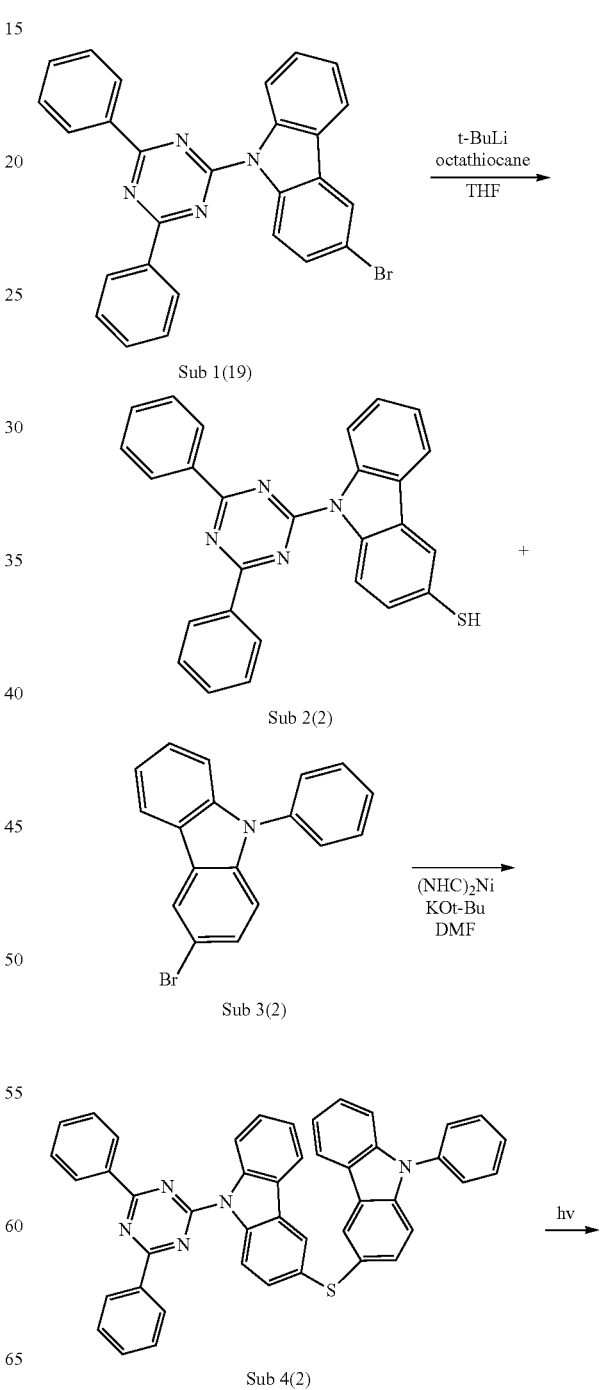

1-8

1) Synthesis Example of Sub 2(1)

A solution of Sub 1(17) (8.0 g, 20 mmol), tert-butyl lithium (1.4 g, 22 mmol) was stirred at −78° C. for 1 hr. After raising the reaction temperature to room temperature, to the solution was added octathiocane (7.7 g, 30 mmol) and stirred for 3 hr. And HCl was added to the solution and stirred for 30 min again. Upon completion of the reaction, the reactant was extracted with $CH_2Cl_2$ and water, dried over $MgSO_4$ and concentrated. The concentrate was separated by a silica gel column chromatography and recrystallization to obtain Sub 2(1) (4.6 g, 65%).

2) Synthesis Example of Sub 4(1)

A solution of Sub 2(1) (7.0 g, 20 mmol), Sub 3(1) (9.0 g, 20 mmol), potassium tert-butoxide (2.5 g, 22 mmol), $(NHC)_2$ Ni (0.67 g, 0.8 mmol) in DMF was stirred at 110° C. for 16 hr. Upon completion of the reaction, the reactant was cooled to room temperature, extracted with $CH_2Cl_2$, washed with water, dried over $MgSO_4$ to remove trace amount of water and filtered under vacuum concentrated. The concentrate was separated by a silica gel column chromatography and recrystallization to obtain Sub 4(1) (9.8 g, 68%).

3) Synthesis Example of the Compound 1-8

A solution of Sub 4(1) (14.4 g, 20 mmol), $I_2$ (6.34 g, 25 mmol), and cyclohexane in Hanovia photoreactor with 1450 W medium pressure Hg lamp was stirred under argon for 20 min. Then, propylene oxide (7.0 g, 120 mmol) was added to the reaction solution and irradiated for 30 min. Upon completion of the reaction, the reactant was cooled to room temperature, extracted with $CH_2Cl_2$, washed with water, dried over anhydrous $MgSO_4$ to remove trace amount of water, filtered under pressure and concentrated. The concentrate was separated by a silica gel column chromatography and recrystallization to obtain Product 1-8 (9.3 g, 65%).

(2) Synthesis Example of the Compound 3-1

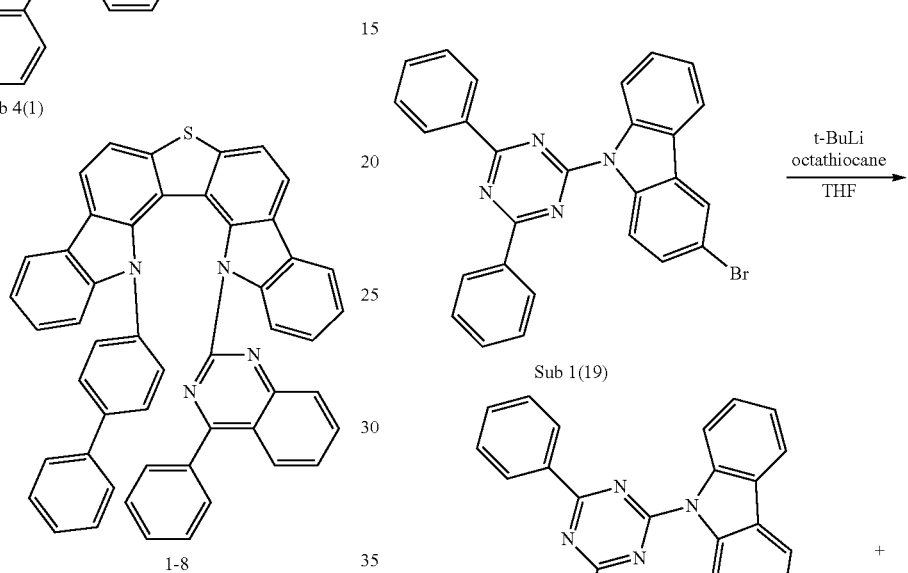

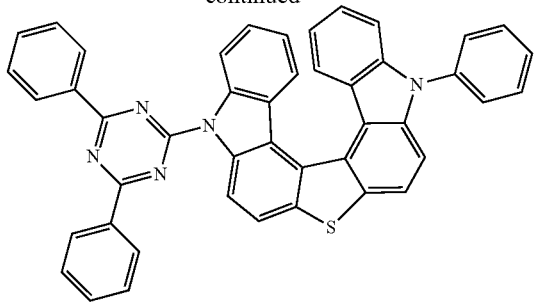

3-1

1) Synthesis Example of Sub 2(2)

A solution of Sub 1(19) (9.5 g, 20 mmol), tert-butyl lithium (1.4 g, 22 mmol) was stirred at −78° C. for 1 hr. After raising the reaction temperature to room temperature, to the solution was added octathiocane (7.7 g, 30 mmol) and stirred for 3 hr. And HCl was added to the solution and stirred for 30 min again. Upon completion of the reaction, the reactant was extracted with $CH_2Cl_2$ and water, dried over MgSO4 and concentrated. The concentrate was separated by a silica gel column chromatography and recrystallization to obtain Sub 2(2) (5.8 g, 67%).

2) Synthesis Example of Sub 4(2)

A solution of Sub 2(2) (8.6 g, 20 mmol), Sub 3(2) (9.0 g, 20 mmol), potassium tert-butoxide (2.5 g, 22 mmol), $(NHC)_2$ Ni (0.67 g, 0.8 mmol) in DMF was stirred at 110° C. for 16 hr. Upon completion of the reaction, the reactant was cooled to room temperature, extracted with $CH_2Cl_2$, washed with water, dried over $MgSO_4$ to remove trace amount of water and filtered under vacuum concentrated. The concentrate was separated by a silica gel column chromatography and recrystallization to obtain Sub 4(2) (9.4 g, 70%).

3) Synthesis Example of the Compound 3-1

A solution of Sub 4(2) (13.4 g, 20 mmol), $I_2$ (6.34 g, 25 mmol), and cyclohexane in Hanovia photoreactor with 1450 W medium pressure Hg lamp was stirred under argon for 20 min. Then, propylene oxide (7.0 g, 120 mmol) was added to the reaction solution and irradiated for 30 min. Upon completion of the reaction, the reactant was cooled to room temperature, extracted with $CH_2Cl_2$, washed with water, dried over anhydrous $MgSO_4$ to remove trace amount of water, filtered under pressure and concentrated. The concentrate was separated by a silica gel column chromatography and recrystallization to obtain Product 3-1(8.7 g, 65%).

(3) Synthesis Example of the Compound 6-39

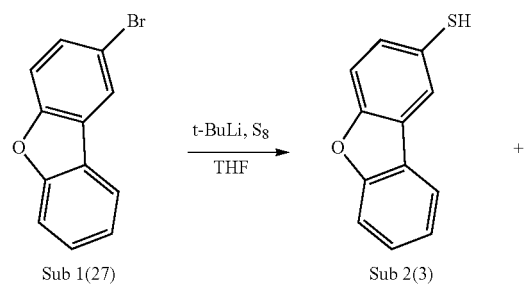

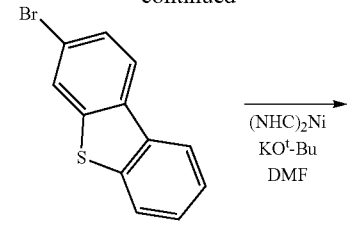

Sub 3(3)

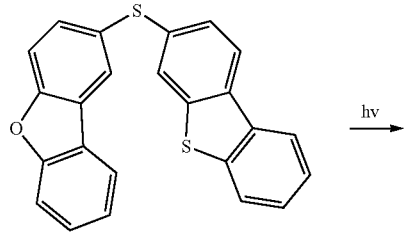

Sub 4(3)

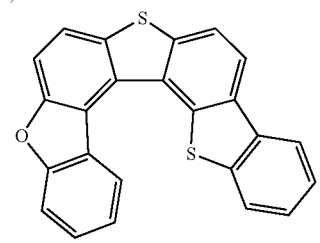

6-39

1) Synthesis Example of Sub 2(3)

A solution of Sub 1(27) (4.9 g, 20 mmol), tert-butyl lithium (1.4 g, 22 mmol) was stirred at −78° C. for 1 hr. Then, after raising the reaction temperature to room temperature, to the solution was added octathiocane (7.7 g, 30 mmol) and stirred for 3 hr. And HCl was added to the solution and stirred for 30 min again. Upon completion of the reaction, the reactant was extracted with $CH_2Cl_2$ and water, dried over MgSO4 and concentrated. The concentrate was separated by a silicagel column chromatography and recrystallization to obtain Sub 2(3) (2.5 g, 62%).

2) Synthesis Example of Sub 4(3)

A solution of Sub 2(3) (4.0, 20 mmol), Sub 3(3) (5.3, 20 mmol), potassium tert-butoxide (2.5 g, 22 mmol), $(NHC)_2Ni$ (0.67 g, 0.8 mmol) in DMF was stirred at 110° C. for 16 hr. Upon completion of the reaction, the reactant was cooled to room temperature, extracted with $CH_2Cl_2$, washed with water, dried over $MgSO_4$ to remove trace amount of water and filtered under vacuum concentrated. The concentrate was separated by a silicagel column chromatography and recrystallization to obtain Sub 4(3) (5.0 g, 66%).

3) Synthesis Example of the Compound 6-39

A solution of Sub 4(3) (7.7 g, 20 mmol), $I_2$ (6.34 g, 25 mmol), and cyclohexane in Hanovia photoreactor with 1450 W medium pressure Hg lamp was stirred under argon for 20 min. Then, propylene oxide (7.0 g, 120 mmol) was added to the reaction solution and irradiated for 30 min. Upon completion of the reaction, the reactant was cooled to room temperature, extracted with CH$_2$Cl$_2$, washed with water, dried over anhydrous MgSO$_4$ to remove trace amount of water, filtered under pressure and concentrated. The concentrate was separated by a silica gel column chromatography and recrystallization to obtain Product 6-39 (4.6 g, 61%).

II. Synthesis Example of the Product 2 (Z=NR$^5$)

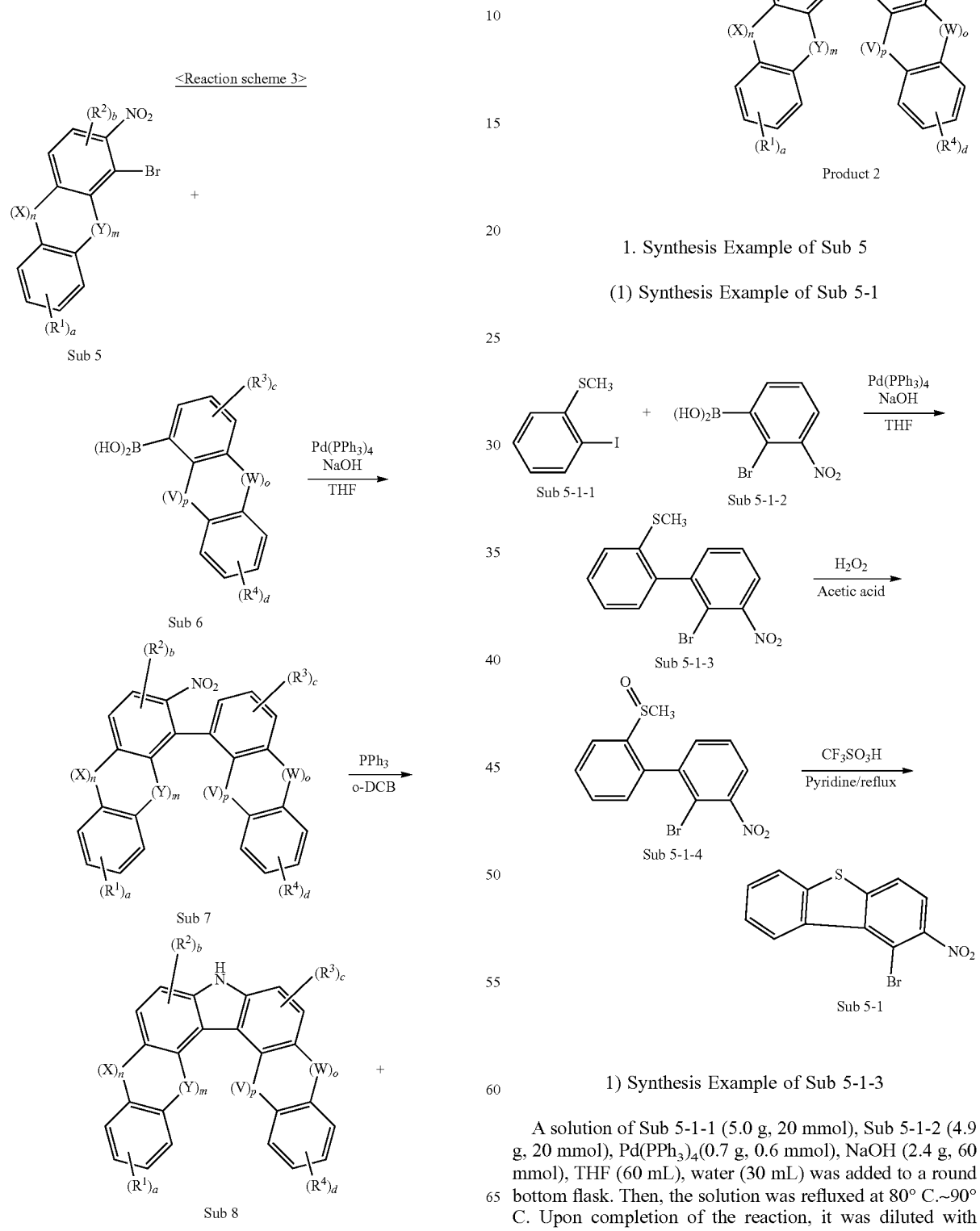

1. Synthesis Example of Sub 5

(1) Synthesis Example of Sub 5-1

1) Synthesis Example of Sub 5-1-3

A solution of Sub 5-1-1 (5.0 g, 20 mmol), Sub 5-1-2 (4.9 g, 20 mmol), Pd(PPh$_3$)$_4$ (0.7 g, 0.6 mmol), NaOH (2.4 g, 60 mmol), THF (60 mL), water (30 mL) was added to a round bottom flask. Then, the solution was refluxed at 80° C.~90° C. Upon completion of the reaction, it was diluted with distilled water at room temperature, extracted with methylene chloride and water. The organic layer was dried over MgSO$_4$ and after concentrating, the concentrate was separated by a silica gel column chromatography and recrystallization to obtain Sub 5-1-3 (3.9 g, 60%).

2) Synthesis Example of Sub 5-1-4

A solution of hydrogen peroxide in acetic acid was dropwised to another solution of Sub 5-1-3 (6.5 g, 20 mmol) in acetic acid and the reactant was stirred at room temperature for 6 hr. Upon completion of the reaction, acetic acid was removed by using apparatus for vacuum and then separated by a silica gel column chromatography to obtain Sub 5-1-4 (4.6 g, 68%).

3) Synthesis Example of Sub 5-1

A mixture of Sub 5-1-4 (6.8 g, 20 mmol) in an excessive amount of trifluoromethanesulfonic acid was stirred at room temperature for 24 hr, added slowly a solution of water and pyridine (8:1), then refluxed for 30 min. After completion of the reaction, the reactant was cooled, extracted with CH$_2$Cl$_2$, washed with water and dried over anhydrous MgSO$_4$ to remove trace amount of water and then filtered under pressure and concentrated. The concentrate was separated by a silica gel column chromatography and recrystallization to obtain Sub 5-1(4.1 g, 67%).

(2) Synthesis Example of Sub 5-2 completion of the reaction, it was diluted with distilled water at room temperature, extracted with methylene chloride and water. The organic layer was dried over MgSO$_4$ and after concentrating, the concentrate was separated by a silica gel column chromatography and recrystallization to obtain Sub 5-2-3 (4.0 g, 62%).

2) Synthesis Example of Sub 5-2-4

A solution of hydrogen peroxide in acetic acid was dropwised to another solution of Sub 5-2-3 (6.5 g, 20 mmol) in acetic acid and then the reactant was stirred at room temperature for 6 hr. Upon completion of the reaction, acetic acid was removed by using apparatus for vacuum and then the concentrate was separated by a silica gel column chromatography to obtain Sub 5-2-4 (4.8 g, 70%).

3) Synthesis Example of Sub 5-2

A mixture of Sub 5-2-4 (6.8 g, 20 mmol) in an excessive amount of trifluoromethanesulfonic acid were stirred at room temperature for 24 hr, added slowly a solution of water and pyridine (8:1), then refluxed for 30 min. After completion of the reaction, the reactant was cooled, extracted with CH$_2$Cl$_2$, washed with water and dried over anhydrous MgSO$_4$ to remove trace amount of water and then filtered under pressure and concentrated. The concentrate was separated by a silica gel column chromatography and recrystallization to obtain Sub 5-2(4.4 g, 72%).

(3) Synthesis Example of Sub 5-3

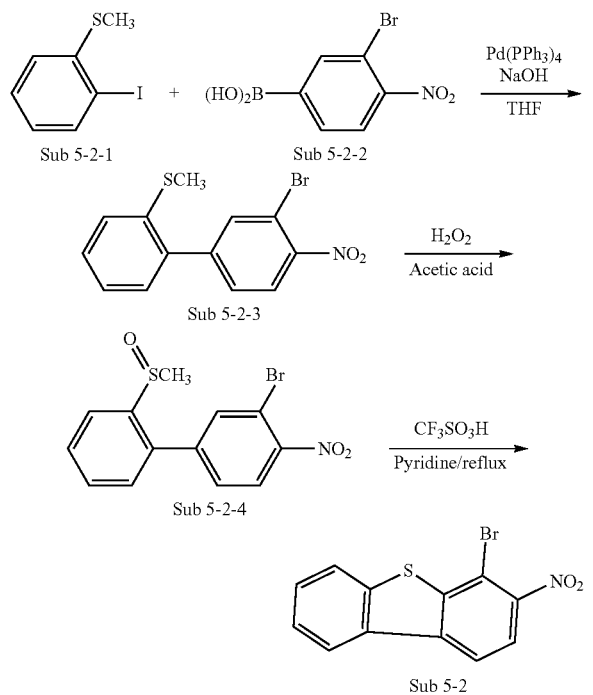

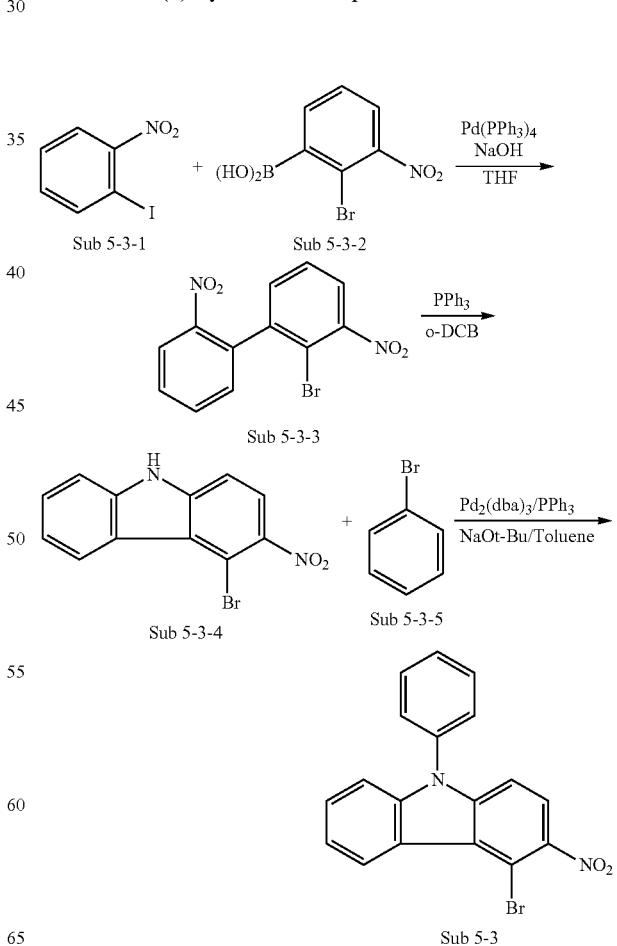

1) Synthesis Example of Sub 5-2-3

Sub 5-2-1 (5.0 g, 20 mmol), Sub 5-2-2 (4.9 g, 20 mmol), Pd(PPh$_3$)$_4$(0.7 g, 0.6 mmol), NaOH (2.4 g, 60 mmol), THF (60 mL), water (30 mL) were added to a round bottom flask. Then, the solution was refluxed at 80° C.~90° C. Upon 1) Synthesis example of Sub 5-3-3 Sub 5-3-1 (5.0 g, 20 mmol), Sub 5-3-2 (4.9 g, 20 mmol), Pd(PPh₃)₄(0.7 g, 0.6 mmol), NaOH (2.4 g, 60 mmol), THF (60 mL), water (30 mL) were added to a round bottom flask. Then, the solution was refluxed at 80° C.~90° C. Upon completion of the reaction, it was diluted with distilled water at room temperature, extracted with methylene chloride and water. The organic layer was dried over MgSO₄ and after concentrating, the concentrate was separated by a silica gel column chromatography and recrystallization to obtain Sub 5-3-3 (4.3 g, 66%).

2) Synthesis Example of Sub 5-3-4

A solution of hydrogen peroxide in acetic acid was dropwised to another solution of Sub 5-3-3 (6.5 g, 20 mmol) in acetic acid and the reactant was stirred at room temperature for 6 hr. Upon completion of the reaction, acetic acid was removed by using apparatus for vacuum and then separated by a silica gel column chromatography to obtain Sub 5-3-4 (4.1 g, 70%).

3) Synthesis Example of Sub 5-3

Sub 5-3-4 (5.8 g, 20 mmol), Sub 5-3-5 (3.1 g, 20 mmol), pd₂(dba)₃ (0.9 g, 1 mmol), PPh₃ (0.5 g, 2 mmol), NaOt-Bu (5.8 g, 60 mmol), toluene (210 mL) were added to a round bottom flask, and reacted at 100° C. Upon completion of the reaction, it was extracted with ether and water, then, the organic layer was dried over MgSO₄ and concentrated. The concentrate was separated by a silica gel column chromatography and recrystallization to obtain Sub 5-3 (5.4 g, 74%).

(4) Synthesis Example of Sub 5-4

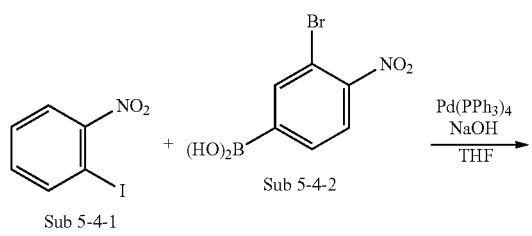

Sub 5-4-1 + Sub 5-4-2 →(Pd(PPh₃)₄ / NaOH / THF)

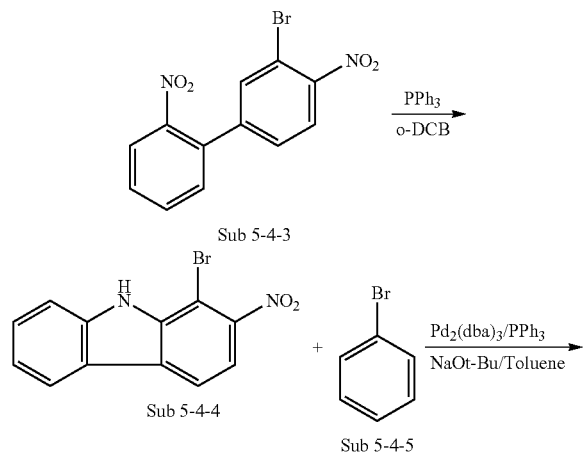

Sub 5-4-3 →(PPh₃ / o-DCB)

Sub 5-4-4 + Sub 5-4-5 →(Pd₂(dba)₃/PPh₃ / NaOt-Bu/Toluene)

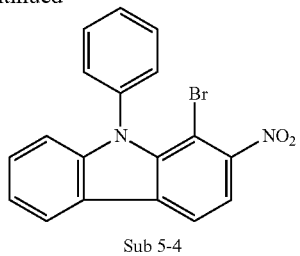

Sub 5-4

1) Synthesis Example of Sub 5-4-3

A solution of Sub 5-4-1 (5.0 g, 20 mmol), Sub 5-4-2 (4.9 g, 20 mmol), Pd(PPh₃)₄(0.7 g, 0.6 mmol), NaOH (2.4 g, 60 mmol), THF (60 mL), water (30 mL) in a round bottom flask was refluxed at 80° C.~90° C. Upon completion of the reaction, it was diluted with distilled water at room temperature, extracted with methylene chloride and water. The organic layer was dried over MgSO₄ and after concentrated, the concentrated product was separated by a silica gel column chromatography and recrystallization to obtain Sub 5-4-3 (4.3 g, 67%).

2) Synthesis Example of Sub 5-4-4

A solution of Sub 5-4-3 (6.5 g, 20 mmol) and triphenylphosphine (15.7 g, 60 mmol) in o-dichlorobenzene was refluxed for 24 hr. Upon completion of the reaction, the solvent was removed by vacuum-distillation. The concentrate was separated by a silica gel column chromatography and recrystallization to obtain Sub 5-4-4 (4.0 g, 69%).

3) Synthesis Example of Sub 5-4

A solution of Sub 5-4-4 (5.8 g, 20 mmol), Sub 5-4-5 (3.1 g, 20 mmol), pd₂(dba)₃ (0.9 g, 1 mmol), PPh₃ (0.5 g, 2 mmol), NaOt-Bu (5.8 g, 60 mmol), toluene (210 mL) in a round bottom flask were reacted at 100° C. Upon completion of the reaction, the reactant was extracted with ether and water, dried over MgSO₄ and concentrated. The concentrate was separated by a silica gel column chromatography and recrystallization to obtain Sub 5-4(5.5 g, 75%).

2. Synthesis Example of Sub 6

(1) Synthesis Example of Sub 6-1

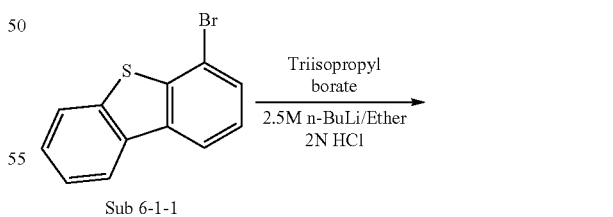

Sub 6-1-1 →(Triisopropyl borate / 2.5M n-BuLi/Ether / 2N HCl)

Sub 6-1

To a dissolving solution of Sub 6-1-1 (5.4 g, 20 mmol) in anhydrous ether was slowly added n-BuLi (2.5M in hexane) (1.4 g, 22 mmol) at −78° C., and stirred for 30 min. After that, Triisopropyl borate (5.6 g, 30 mmol) was dropwised to the reactant at −78° C. After stirring at room temperature, it was added water and 2N HCl. Upon completion of the reaction, the reactant was extracted with ethyl acetate and water, dried over MgSO$_4$ and concentrated. The concentrate was separated by a silica gel column chromatography and recrystallization to obtain Sub 6-1(3.3 g, 73%).

(2) Synthesis Example of Sub 6-2

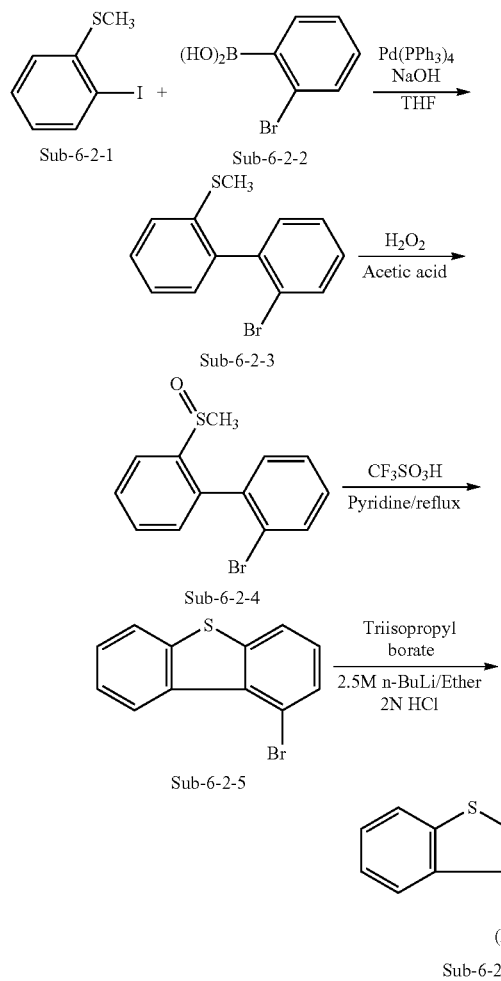

1) Synthesis Example of Sub 6-2-3

A solution of Sub 6-2-1 (5.0 g, 20 mmol), Sub 6-2-2 (4.0 g, 20 mmol), Pd(PPh$_3$)$_4$(0.7 g, 0.6 mmol), NaOH (2.4 g, 60 mmol), THF (60 mL), water (30 mL) in round bottom flask was refluxed at 80° C.~90° C. Upon completion of the reaction, it was diluted with distilled water at room temperature, extracted with methylene chloride and water. The organic layer was dried over MgSO$_4$. After concentrating, the concentrate was separated by a silica gel column chromatography and recrystallization to obtain Sub 6-2-3(3.8 g, 68%).

2) Synthesis Example of Sub 6-2-4

A solution of hydrogen peroxide in acetic acid was dropwised to another solution of Sub 6-2-3 (5.6 g, 20 mmol) in acetic acid and stirred at room temperature for 6 hr. Upon completion of the reaction, acetic acid was removed by using apparatus for vacuum and then separated by a silica gel column chromatography to obtain Sub 6-2-4 (4.3 g, 72%).

3) Synthesis Example of Sub 6-2-5

A solution of Sub 6-2-4 (5.9 g, 20 mmol) in an excessive amount of trifluoromethanesulfonic acid was stirred at room temperature for 24 hr, added slowly a solution of water and pyridine (8:1), then refluxed for 30 min. After completion of the reaction, the reactant was cooled, extracted with CH$_2$Cl$_2$, washed with water and dried over anhydrous MgSO$_4$ to remove trace amount of water and then filtered under pressure and concentrated. The concentrated product was separated by a silica gel column chromatography and recrystallization to obtain Sub 6-2-5 (3.8 g, 73%).

4) Synthesis Example of Sub 6-2

To a dissolving solution of Sub 6-2-5 (5.3 g, 20 mmol) in anhydrous ether was slowly added n-BuLi (2.5M in hexane) (1.4 g, 22 mmol) at −78° C., and stirred for 30 min. After that, Triisopropyl borate (5.6 g, 30 mmol) was dropwised to the reactant at −78° C. After stirring at room temperature, it was added water and 2N HCl. Upon completion of the reaction, the reactant was extracted with ethyl acetate and water, dried over MgSO$_4$ and concentrated. The concentrate was separated by a silica gel column chromatography and recrystallization to obtain Sub 6-2(3.4 g, 75%).

(3) Synthesis Example of Sub 6-3

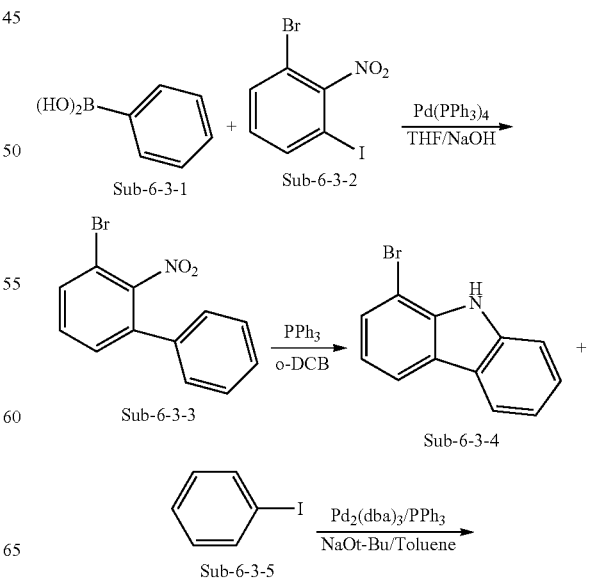

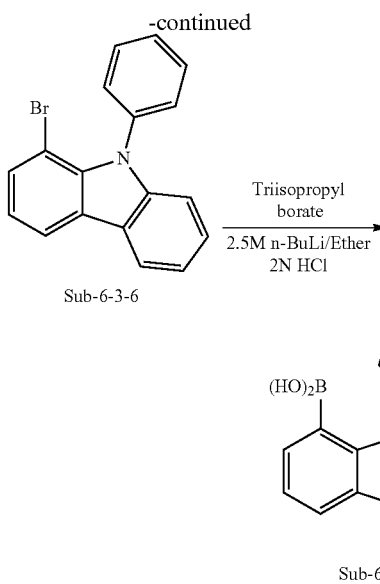

Sub-6-3-6

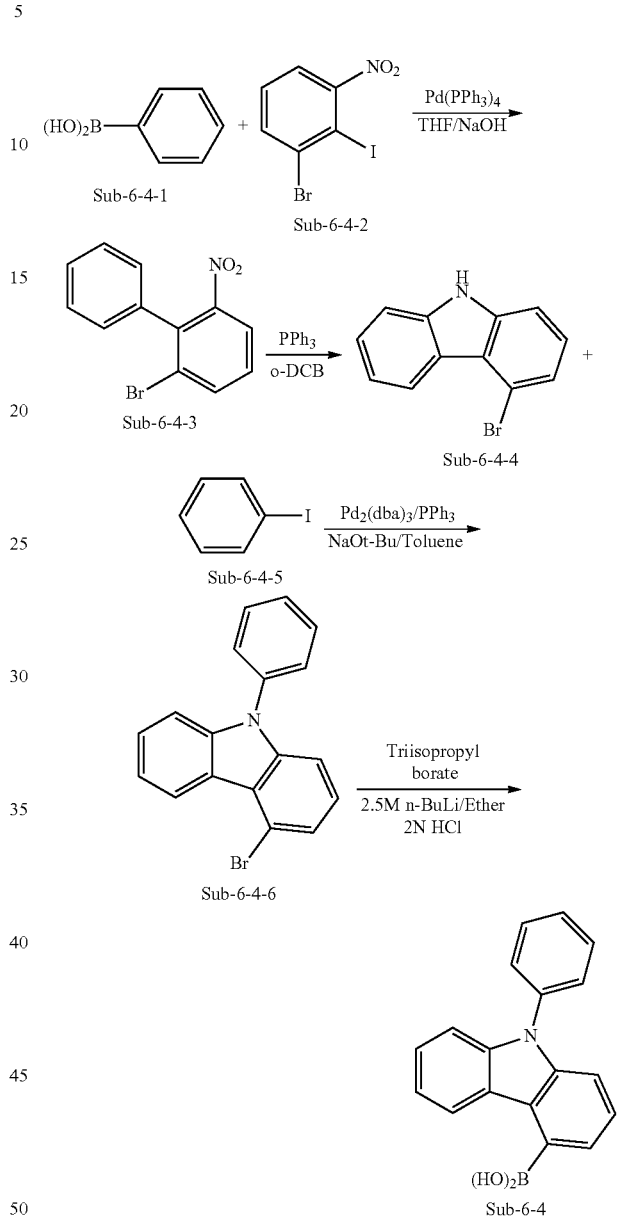

1) Synthesis Example of Sub 6-3-3

A solution of Sub 6-3-1 (2.4 g, 20 mmol), Sub 6-3-2 (6.6 g, 20 mmol), Pd(PPh$_3$)$_4$(0.7 g, 0.6 mmol), NaOH (2.4 g, 60 mmol), THF (60 mL), water (30 mL) in a round bottom flask was refluxed at 80° C.~90° C. Upon completion of the reaction, it was diluted with distilled water, extracted with methylene chloride and water. The organic layer was dried over MgSO$_4$ and concentrated. The concentrate was separated by a silica gel column chromatography and recrystallization to obtain Sub 6-3-3 (3.1 g, 55%).

2) Synthesis Example of Sub 6-3-4

A solution of Sub 6-3-3 (5.6 g, 20 mmol), triphenylphosphine (15.7 g, 60 mmol) in o-dichlorobenzene was refluxed for 24 hr. Upon completion of the reaction, solvent was removed by vacuum distillation. The concentrate was separated by a silica gel column chromatography and recrystallization to obtain Sub 6-3-4 (2.8 g, 58%).

3) Synthesis Example of Sub 6-3-6

A solution of Sub 6-3-4 (4.9 g, 20 mmol), Sub 6-3-5 (4.1 g, 20 mmol), pd$_2$(dba)$_3$ (0.9 g, 1 mmol), PPh$_3$ (0.5 g, 2 mmol), NaOt-Bu (5.8 g, 60 mmol), toluene (210 mL) was reacted at 100° C. Upon completion of the reaction, the reactant was extracted with ether and water, dried over MgSO$_4$ and concentrated. The concentrate was separated by a silica gel column chromatography and recrystallization to obtain Sub 6-3-6(4.6 g, 73%).

4) Synthesis Example of Sub 6-3

To a dissolving solution of Sub 6-3-6 (6.4 g, 20 mmol) in anhydrous ether was slowly added n-BuLi (2.5M in hexane) (1.4 g, 22 mmol) at −78° C., and stirred for 30 min. After that, Triisopropyl borate (5.6 g, 30 mmol) was dropwised to the reactant at −78° C. After stirring at room temperature, it was added water and 2N HCl. Upon completion of the reaction, the reactant was extracted with ethyl acetate and water, dried over MgSO$_4$ and concentrated. The concentrate was separated by a silica gel column chromatography and recrystallization to obtain Sub 6-3(3.8 g, 68%).

(4) Synthesis Example of Sub 6-4

1) Synthesis Example of Sub 6-4-3

A solution of Sub 6-4-1 (2.4 g, 20 mmol), Sub 6-4-2 (6.6 g, 20 mmol), Pd(PPh$_3$)$_4$(0.7 g, 0.6 mmol), NaOH (2.4 g, 60 mmol), THF (60 mL), water (30 mL) in a round bottom flask was refluxed at 80° C.~90° C. Upon completion of the reaction, it was diluted with distilled water, extracted with methylene chloride and water. The organic layer was dried over MgSO$_4$ and concentrated. The concentrate was separated by a silica gel column chromatography and recrystallization to obtain Sub 6-4-3 (3.1 g, 56%).

2) Synthesis Example of Sub 6-4-4

A solution of Sub 6-4-3 (5.6 g, 20 mmol), triphenylphosphine (15.7 g, 60 mmol) in o-dichlorobenzene was refluxed for 24 hr. Upon completion of the reaction, solvent was removed by vacuum distillation. The concentrate was separated by a silica gel column chromatography and recrystallization to obtain Sub 6-4-4 (3.0 g, 60%).

3) Synthesis Example of Sub 6-4-6

A solution of Sub 6-4-4 (4.9 g, 20 mmol), Sub 6-4-5 (4.1 g, 20 mmol), pd$_2$(dba)$_3$ (0.9 g, 1 mmol), PPh$_3$ (0.5 g, 2 mmol), NaOt-Bu (5.8 g, 60 mmol), toluene (210 mL) was reacted at 100° C. Upon completion of the reaction, the reactant was extracted with ether and water, dried over MgSO$_4$ and concentrated. The concentrate was separated by a silica gel column chromatography and recrystallization to obtain Sub 6-4-6(4.8 g, 75%).

4) Synthesis Example of Sub 6-4

To a dissolving solution of Sub 6-4-6 (6.4 g, 20 mmol) in anhydrous ether was slowly added n-BuLi (2.5M in hexane) (1.4 g, 22 mmol) at −78° C., and stirred for 30 min. After that, Triisopropyl borate (5.6 g, 30 mmol) was dropwised to the reactant at −78° C. After stirring at room temperature, it was added water and 2N HCl. Upon completion of the reaction, the reactant was extracted with ethyl acetate and water, dried over MgSO$_4$ and concentrated. The concentrate was separated by a silica gel column chromatography and recrystallization to obtain Sub 6-4(4.1 g, 71%).

3. Synthesis Example of Sub 7

A solution of Sub 5 (1 eq), Sub 6 (1 eq), Pd(PPh$_3$)$_4$(0.03 eq), NaOH (3 eq), THF, water in a round bottom flask was refluxed at 80° C.~90° C. Upon completion of the reaction, it was diluted with distilled water, extracted with methylene chloride and water. The organic layer was dried over MgSO$_4$ and concentrated. The concentrate was separated by a silica gel column chromatography and recrystallization to obtain Sub 7.

(1) Synthesis Example of Sub 7-1

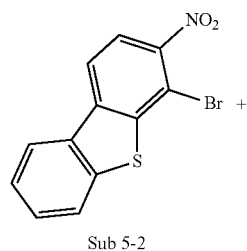

Sub 5-2

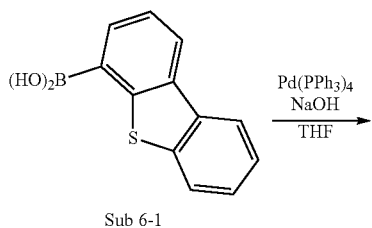

Sub 6-1

-continued

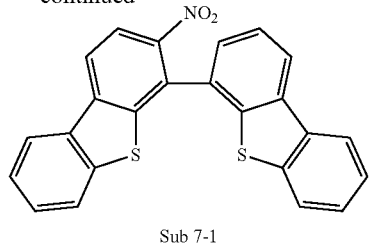

Sub 7-1

A solution of Sub 5-2 (6.2 g, 20 mmol), Sub 6-1 (4.6 g, 20 mmol), Pd(PPh$_3$)$_4$(0.7 g, 0.6 mmol), NaOH (2.4 g, 60 mmol), THF (60 mL), water (30 mL) in a round bottom flask was refluxed at 80° C.~90° C. Upon completion of the reaction, it was diluted with distilled water, extracted with methylene chloride and water. The organic layer was dried over MgSO$_4$ and concentrated. The concentrate was separated by a silica gel column chromatography and recrystallization to obtain Sub 7-1(5.8 g, 71%).

(2) Synthesis Example of Sub 7-2

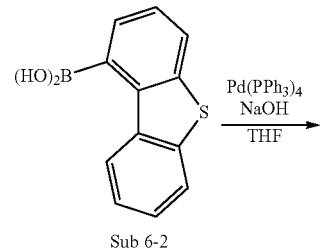

Sub 5-1

Sub 6-2

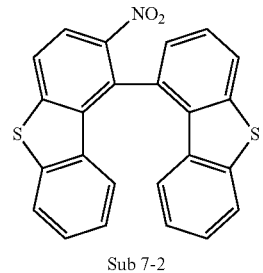

Sub 7-2

A solution of Sub 5-1 (6.2 g, 20 mmol), Sub 6-2 (4.6 g, 20 mmol), Pd(PPh$_3$)$_4$(0.7 g, 0.6 mmol), NaOH (2.4 g, 60 mmol), THF (60 mL), water (30 mL) in a round bottom flask was refluxed at 80° C.~90° C. Upon completion of the reaction, it was diluted with distilled water, extracted with methylene chloride and water. The organic layer was dried over MgSO$_4$ and concentrated. The concentrate was separated by a silica gel column chromatography and recrystallization to obtain Sub 7-2(5.7 g, 69%).

(3) Synthesis Example of Sub 7-3

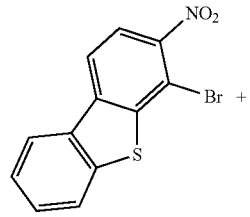

Sub 5-2

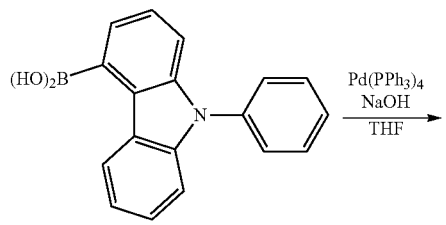

Sub 6-4

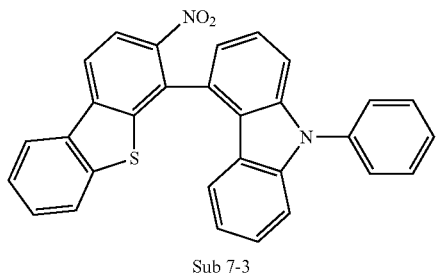

Sub 7-3

A solution of Sub 5-2 (6.2 g, 20 mmol), Sub 6-4 (5.7 g, 20 mmol), Pd(PPh₃)₄(0.7 g, 0.6 mmol), NaOH (2.4 g, 60 mmol), THF (60 mL), water (30 mL) in a round bottom flask was refluxed at 80° C.~90° C. Upon completion of the reaction, upon completion of the reaction, it was diluted with distilled water, extracted with methylene chloride and water. The organic layer was dried over MgSO₄ and concentrated. The concentrate was separated by a silica gel column chromatography and recrystallization to obtain Sub 7-3(6.2 g, 66%).

4. Synthesis Example of Sub 8

A solution of Sub 7 (1 eq), triphenylphosphine (3 eq) in o-dichlorobenzene was refluxed for 24 hr. Upon completion of the reaction, solvent was removed by vacuum distillation. The concentrate was separated by a silica gel column chromatography and recrystallization to obtain Sub 8.

(1) Synthesis Example of Sub 8-1

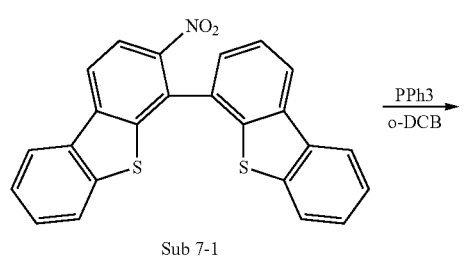

Sub 7-1

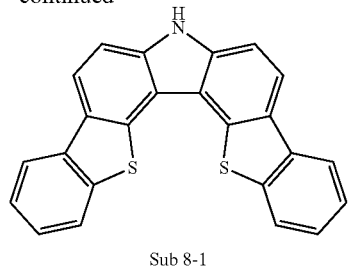

Sub 8-1

A solution of Sub 7-1 (8.2 g, 20 mmol), triphenylphosphine (15.7 g, 60 mmol) in o-dichlorobenzene was refluxed for 24 hr. Upon completion of the reaction, solvent was removed by vacuum distillation. The concentrate was separated by a silica gel column chromatography and recrystallization to obtain Sub 8-1 (5.2 g, 68%).

(2) Synthesis Example of Sub 8-2

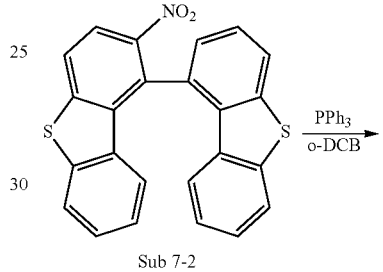

Sub 7-2

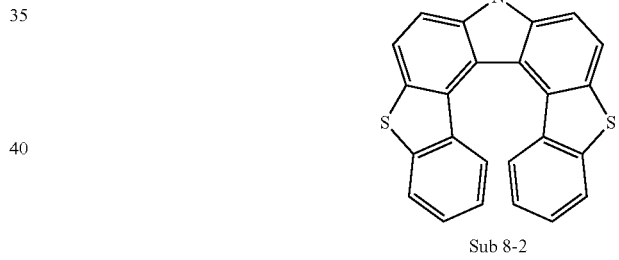

Sub 8-2

A solution of Sub 7-2 (8.2 g, 20 mmol), triphenylphosphine (15.7 g, 60 mmol) in o-dichlorobenzene was refluxed for 24 hr. Upon completion of the reaction, solvent was removed by vacuum distillation. The concentrate was separated by a silica gel column chromatography and recrystallization to obtain Sub 8-2 (5.1 g, 67%).

(3) Synthesis Example of Sub 8-3

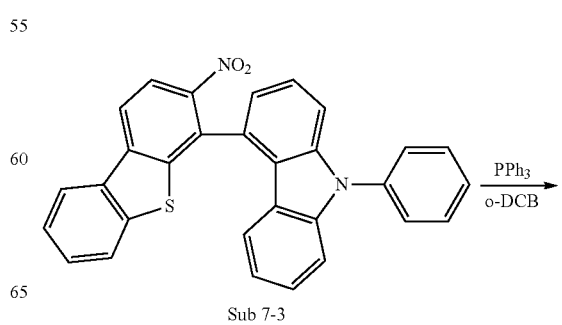

Sub 7-3

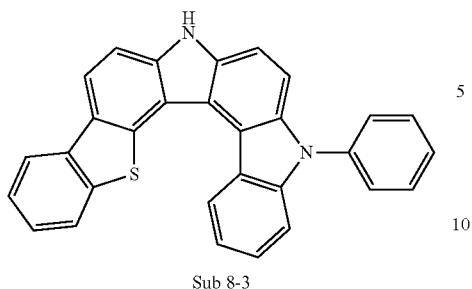

Sub 8-3

A solution of Sub 7-3 (9.4 g, 20 mmol), triphenylphosphine (15.7 g, 60 mmol) in o-dichlorobenzene was refluxed for 24 hr. Upon completion of the reaction, solvent was removed by vacuum distillation. The concentrate was separated by a silica gel column chromatography and recrystallization to obtain Sub 8-3 (5.1 g, 65%).

5. Example of Sub 9

Examples of Sub 9 compounds include, but are not limited to, the following compounds, and FD-MS data of the compounds are given in Table 2 below.

Sub 9-1

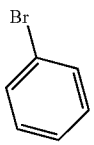

Sub 9-2

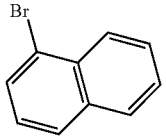

Sub 9-3

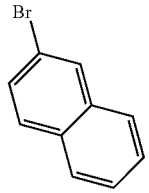

Sub 9-4

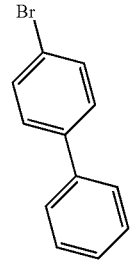

Sub 9-5

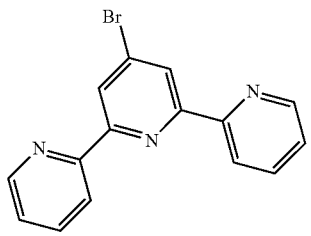

Sub 9-6

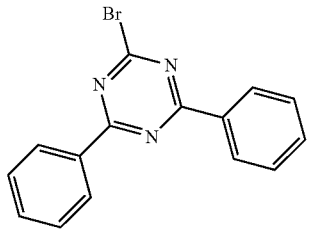

Sub 9-7

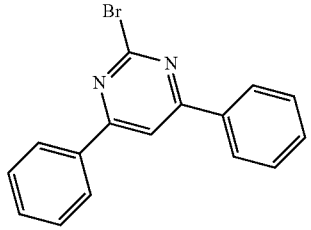

Sub 9-8

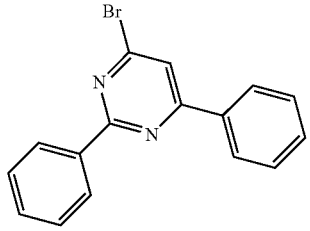

Sub 9-9

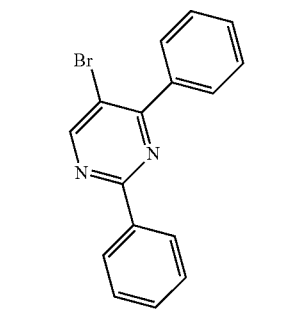

Sub 9-10

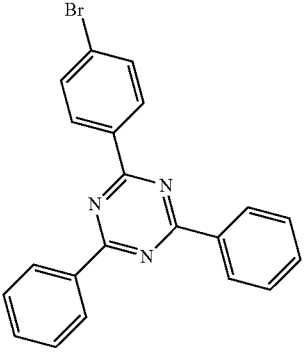

-continued
Sub 9-11
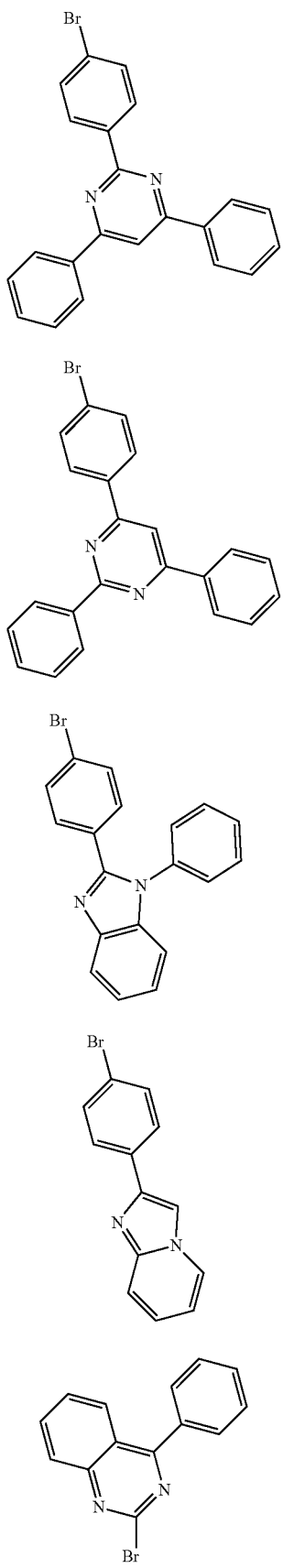
Sub 9-12
Sub 9-13
Sub 9-14
Sub 9-15
-continued
Sub 9-16
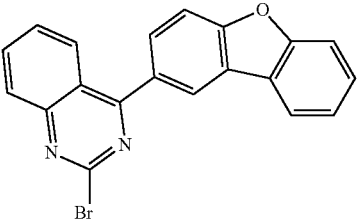
Sub 9-17
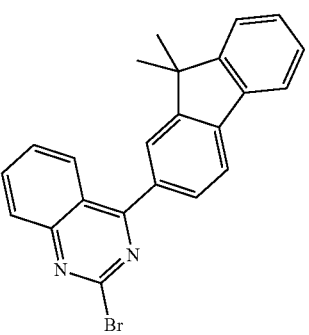
Sub 9-18
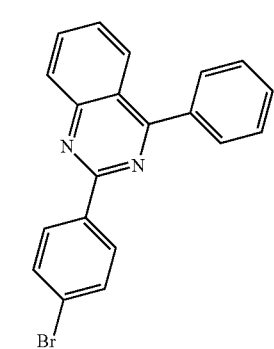
Sub 9-19
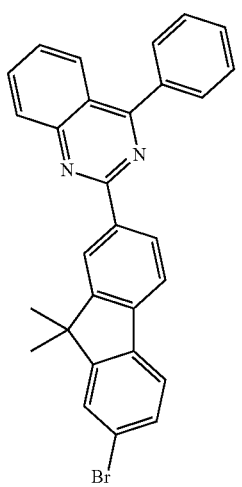
Sub 9-20
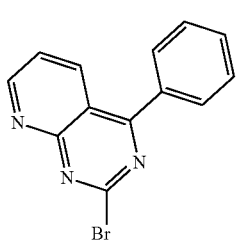

Sub 9-21
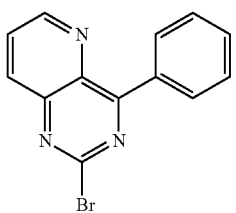
Sub 9-22
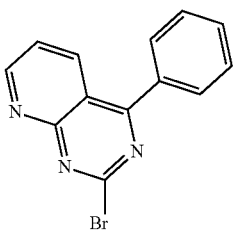
Sub 9-23
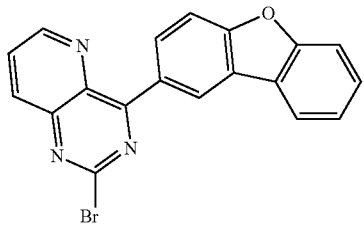
Sub 9-24
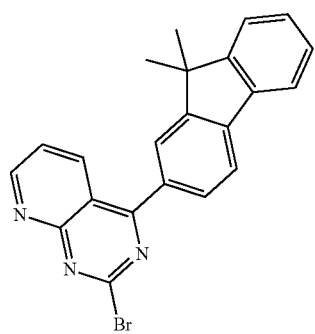
Sub 9-25
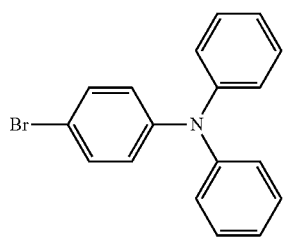
Sub 9-26
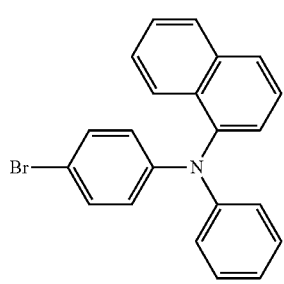
Sub 9-27
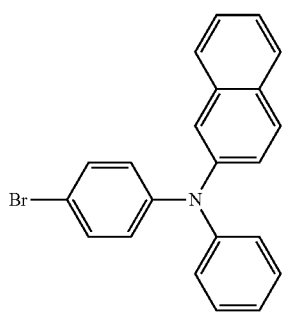
Sub 9-28
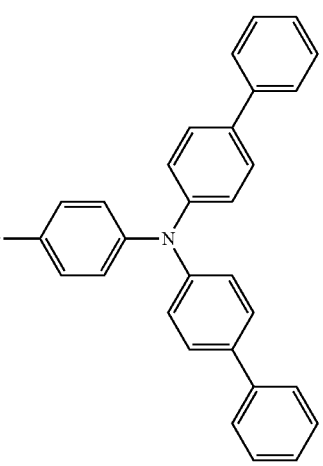
Sub 9-29
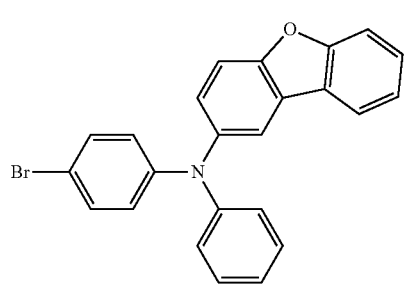
Sub 9-30
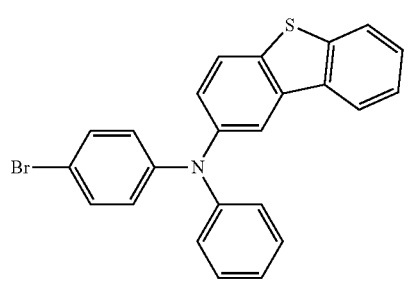

Sub 9-31

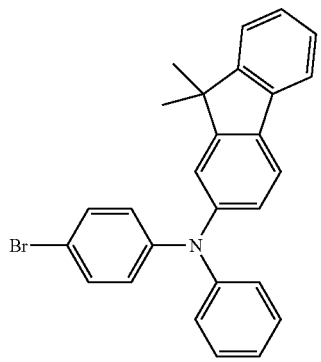

Sub 9-33

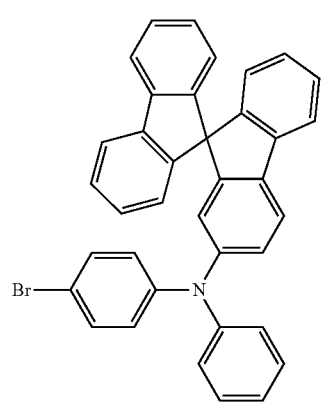

Sub 9-32

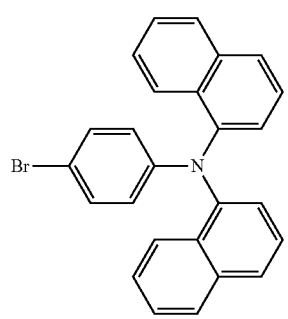

Sub 9-34

TABLE 2

| Compound | FD-MS | Compound | FD-MS |
| --- | --- | --- | --- |
| Sub 9-1 | m/z = 155.96($C_6H_5Br$ = 157.01) | Sub 9-2 | m/z = 205.97($C_{10}H_7Br$ = 207.07) |
| Sub 9-3 | m/z = 205.97($C_{10}H_7Br$ = 207.07) | Sub 9-4 | m/z = 231.99($C_{12}H_9Br$ = 233.10) |
| Sub 9-5 | m/z = 309.02($C_{17}H_{12}BrN$ = 310.19) | Sub 9-6 | m/z = 311.01($C_{15}H_{10}BrN_3$ = 312.16) |
| Sub 9-7 | m/z = 310.01($C_{16}H_{11}BrN_2$ = 311.18) | Sub 9-8 | m/z = 310.01($C_{16}H_{11}BrN_2$ = 311.18) |
| Sub 9-9 | m/z = 310.01($C_{16}H_{11}BrN_2$ = 311.18) | Sub 9-10 | m/z = 387.04($C_{21}H_{14}BrN_3$ = 388.26) |
| Sub 9-11 | m/z = 386.04($C_{22}H_{15}BrN_2$ = 387.27) | Sub 9-12 | m/z = 386.04($C_{22}H_{15}BrN_2$ = 387.27) |
| Sub 9-13 | m/z = 348.03($C_{19}H_{13}BrN_2$ = 349.22) | Sub 9-14 | m/z = 271.99($C_{13}H_9BrN_2$ = 273.13) |
| Sub 9-15 | m/z = 283.99($C_{14}H_9BrN_2$ = 285.14) | Sub 9-16 | m/z = 374.01($C_{20}H_{11}BrN_2O$ = 375.22) |
| Sub 9-17 | m/z = 400.06($C_{23}H_{17}BrN_2$ = 401.30) | Sub 9-18 | m/z = 360.03($C_{20}H_{13}BrN_2$ = 361.23) |
| Sub 9-19 | m/z = 476.09($C_{29}H_{21}BrN_2$ = 477.39) | Sub 9-20 | m/z = 284.99($C_{13}H_8BrN_3$ = 286.13) |
| Sub 9-21 | m/z = 284.99($C_{13}H_8BrN_3$ = 286.13) | Sub 9-22 | m/z = 284.99($C_{13}H_8BrN_3$ = 286.13) |
| Sub 9-23 | m/z = 375.00($C_{19}H_{10}BrN_3O$ = 376.2) | Sub 9-24 | m/z = 401.05($C_{22}H_{16}BrN_3$ = 402.29) |
| Sub 9-25 | m/z = 323.03($C_{18}H_{14}BrN$ = 324.21) | Sub 9-26 | m/z = 373.05($C_{22}H_{16}BrN$ = 374.27) |
| Sub 9-27 | m/z = 373.05($C_{22}H_{16}BrN$ = 374.27) | Sub 9-28 | m/z = 475.09($C_{30}H_{22}BrN$ = 476.41) |
| Sub 9-29 | m/z = 413.04($C_{24}H_{16}BrNO$ = 414.3) | Sub 9-30 | m/z = 429.02($C_{24}H_{16}BrNS$ = 430.36) |
| Sub 9-31 | m/z = 439.09($C_{27}H_{22}BrN$ = 440.37) | Sub 9-32 | m/z = 563.12($C_{37}H_{26}BrN$ = 564.51) |
| Sub 9-33 | m/z = 561.11($C_{37}H_{24}BrN$ = 562.50) | Sub 9-34 | m/z = 423.06($C_{26}H_{18}BrN$ = 424.33) |

6. Synthesis Example of Product 2

A solution of Sub 8 (1 eq), Sub 9 (1 eq), Pd₂(dba)₃ (0.05 eq), PPh₃ (0.1 eq), NaOt-Bu (3 eq), toluene (10.5 mL/Sub 8 1 mmol) in a round bottom flask was reacted at 100° C. Upon completion of the reaction, it was extracted with ether and water, dried over MgSO₄. After concentrating, the residue was purified by silica gel column and recrystallization to obtain final product 2.

(1) Synthesis Example of Product 2-5

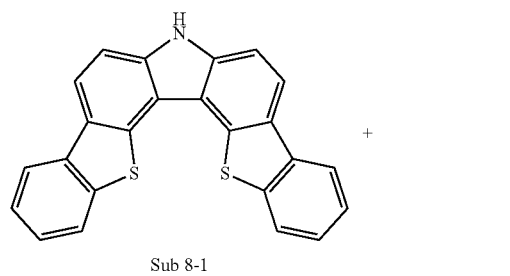
Sub 8-1

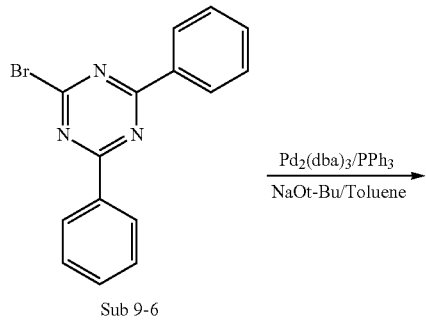
Sub 9-6

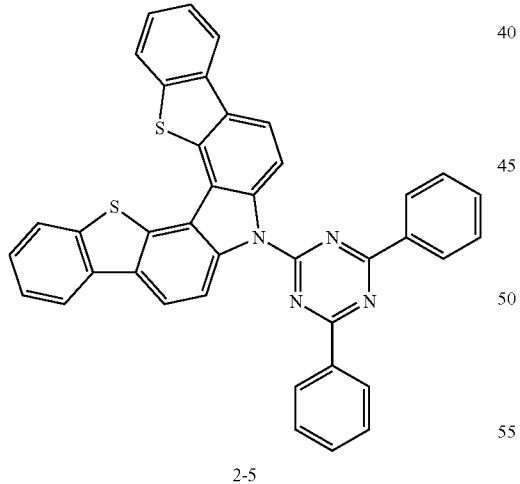
2-5

A solution of Sub 8-1 (7.6 g, 20 mmol), Sub 9-6 (7.5 g, 20 mmol), Pd₂(dba)₃ (0.9 g, 1 mmol), PPh₃ (0.5 g, 2 mmol), NaOt-Bu (5.8 g, 60 mmol), toluene (210 mL) in a round bottom flask was refluxed at 100° C. for 24 hr. Upon completion of the reaction, it was extracted with ether and water, dried over MgSO₄. After concentrating, the residue was purified by silica gel column and recrystallization to obtain final product 2-5 (8.8 g, 72%).

(2) Synthesis Example of Product 4-16

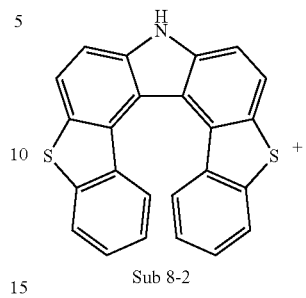
Sub 8-2

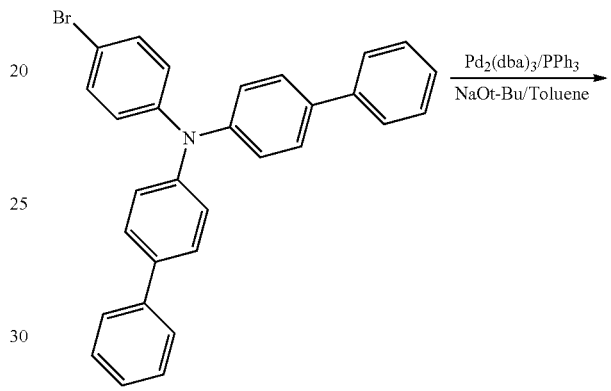
Sub 9-28

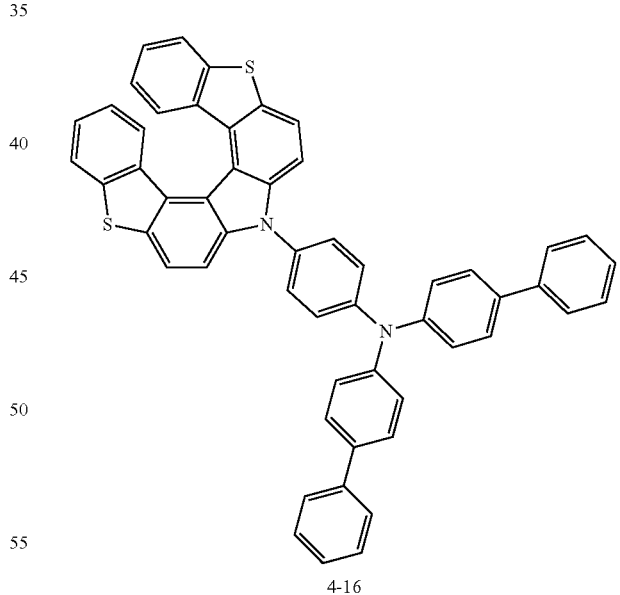
4-16

A solution of Sub 8-2 (7.6 g, 20 mmol), Sub 9-28 (11.4 g, 20 mmol), Pd₂(dba)₃ (0.9 g, 1 mmol), PPh₃ (0.5 g, 2 mmol), NaOt-Bu (5.8 g, 60 mmol), toluene (210 mL) in a round bottom flask was refluxed at 100° C. for 24 hr. Upon completion of the reaction, it was extracted with ether and water, dried over MgSO₄. After concentrating, the residue was purified by silica gel column and recrystallization to obtain final product 4-16 (10.8 g, 70%).

(3) Synthesis Example of Product 6-33

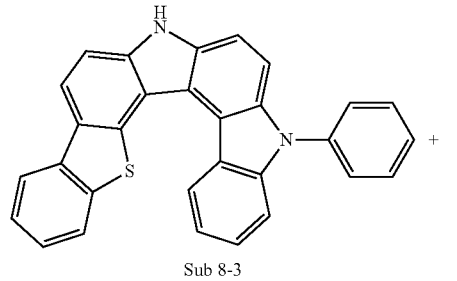
Sub 8-3

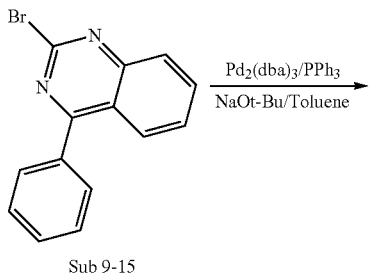
Sub 9-15

$\xrightarrow{\text{Pd}_2(\text{dba})_3/\text{PPh}_3}{\text{NaOt-Bu/Toluene}}$

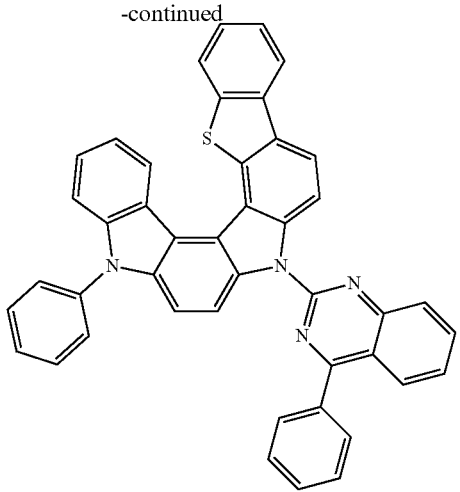
6-33

A solution of Sub 8-3 (8.8 g, 20 mmol), Sub 9-15 (6.8 g, 20 mmol), Pd$_2$(dba)$_3$ (0.9 g, 1 mmol), PPh$_3$ (0.5 g, 2 mmol), NaOt-Bu (5.8 g, 60 mmol), toluene (210 mL) in a round bottom flask was refluxed at 100° C. for 24 hr. Upon completion of the reaction, it was extracted with ether and water, dried over MgSO$_4$. After concentrating, the residue was purified by silica gel column and recrystallization to obtain final product 6-33 (8.9 g, 69%).

TABLE 3

| Compound | FD-MS | Compound | FD-MS |
|---|---|---|---|
| 1-1 | m/z = 669.20(C$_{45}$H$_{27}$N$_5$S = 669.79) | 1-2 | m/z = 668.20(C$_{46}$H$_{28}$N$_4$S = 668.81) |
| 1-3 | m/z = 668.20(C$_{46}$H$_{28}$N$_4$S = 668.81) | 1-4 | m/z = 642.19(C$_{44}$H$_{26}$N$_4$S = 642.77) |
| 1-5 | m/z = 745.23(C$_{51}$H$_{31}$N$_5$S = 745.89) | 1-6 | m/z = 744.23(C$_{52}$H$_{32}$N$_4$S = 744.90) |
| 1-7 | m/z = 744.23(C$_{52}$H$_{32}$N$_4$S = 744.90) | 1-8 | m/z = 718.22(C$_{50}$H$_{30}$N$_4$S = 718.87) |
| 1-9 | m/z = 745.23(C$_{51}$H$_{31}$N$_5$S = 745.89) | 1-10 | m/z = 744.23(C$_{52}$H$_{32}$N$_4$S = 744.90) |
| 1-11 | m/z = 744.23(C$_{52}$H$_{32}$N$_4$S = 744.90) | 1-12 | m/z = 718.22(C$_{50}$H$_{30}$N$_4$S = 718.87) |
| 1-13 | m/z = 719.21(C$_{49}$H$_{29}$N$_5$S = 719.85) | 1-14 | m/z = 178.22(C$_{50}$H$_{30}$N$_4$S = 718.87) |
| 1-15 | m/z = 178.22(C$_{50}$H$_{30}$N$_4$S = 718.87) | 1-16 | m/z = 692.20(C$_{48}$H$_{28}$N$_4$S = 692.83) |
| 1-17 | m/z = 719.21(C$_{49}$H$_{29}$N$_5$S = 719.85) | 1-18 | m/z = 178.22(C$_{50}$H$_{30}$N$_4$S = 718.87) |
| 1-19 | m/z = 178.22(C$_{50}$H$_{30}$N$_4$S = 718.87) | 1-20 | m/z = 692.20(C$_{48}$H$_{28}$N$_4$S = 692.83) |
| 1-21 | m/z = 590.18(C$_{42}$H$_{26}$N$_2$S = 590.73) | 1-22 | m/z = 755.24(C$_{54}$H$_{33}$N$_3$S = 755.92) |
| 1-23 | m/z = 591.18(C$_{41}$H$_{25}$N$_3$S = 591.72) | 1-24 | m/z = 681.22(C$_{48}$H$_{31}$N$_3$S = 681.84) |
| 2-1 | m/z = 455.08(C$_{30}$H$_{17}$NS$_2$ = 455.59) | 2-2 | m/z = 777.31(C$_{58}$H$_{39}$N$_3$ = 777.95) |
| 2-3 | m/z = 455.08(C$_{30}$H$_{17}$NS$_2$ = 455.59) | 2-4 | m/z = 531.11(C$_{36}$H$_{21}$NS$_2$ = 531.69) |
| 2-5 | m/z = 610.13(C$_{39}$H$_{22}$N$_4$S$_2$ = 610.75) | 2-6 | m/z = 609.13(C$_{40}$H$_{23}$N$_3$S$_2$ = 609.76) |
| 2-7 | m/z = 609.13(C$_{40}$H$_{23}$N$_3$S$_2$ = 609.76) | 2-8 | m/z = 583.12(C$_{38}$H$_{21}$N$_3$S$_2$ = 583.72) |
| 2-9 | m/z = 561.07(C$_{36}$H$_{19}$NS$_3$ = 561.74) | 2-10 | m/z = 571.14(C$_{39}$H$_{25}$NS$_2$ = 571.75) |
| 2-11 | m/z = 695.17(C$_{49}$H$_{29}$NS$_2$ = 695.89) | 2-12 | m/z = 693.16(C$_{49}$H$_{27}$NS$_2$ = 693.88) |
| 2-13 | m/z = 622.15(C$_{42}$H$_{26}$N$_2$S$_2$ = 622.80) | 2-14 | m/z = 672.17(C$_{46}$H$_{28}$N$_2$S$_2$ = 672.86) |
| 2-15 | m/z = 698.19(C$_{48}$H$_{30}$N$_2$S$_2$ = 698.90) | 2-16 | m/z = 774.22(C$_{54}$H$_{34}$N$_2$S$_2$ = 774.99) |
| 2-17 | m/z = 698.19(C$_{48}$H$_{30}$N$_2$S$_2$ = 698.90) | 2-18 | m/z = 748.20(C$_{52}$H$_{32}$N$_2$S$_2$ = 748.95) |
| 2-19 | m/z = 748.20(C$_{52}$H$_{32}$N$_2$S$_2$ = 748.95) | 2-20 | m/z = 774.22(C$_{54}$H$_{34}$N$_2$S$_2$ = 774.99) |
| 2-21 | m/z = 853.23(C$_{57}$H$_{35}$N$_5$S$_2$ = 854.05) | 2-22 | m/z = 774.22(C$_{54}$H$_{34}$N$_2$S$_2$ = 774.99) |
| 2-23 | m/z = 824.23(C$_{58}$H$_{36}$N$_2$S$_2$ = 825.05) | 2-24 | m/z = 824.23(C$_{58}$H$_{36}$N$_2$S$_2$ = 825.05) |
| 2-25 | m/z = 850.25(C$_{60}$H$_{38}$N$_2$S$_2$ = 851.09) | 2-26 | m/z = 890.28(C$_{63}$H$_{42}$N$_2$S$_2$ = 891.15) |
| 2-27 | m/z = 880.20(C$_{60}$H$_{36}$N$_2$S$_3$ = 881.14) | 2-28 | m/z = 1014.31(C$_{73}$H$_{46}$N$_2$S$_2$ = 1015.29) |
| 2-29 | m/z = 890.28(C$_{63}$H$_{42}$N$_2$S$_2$ = 891.15) | 2-30 | m/z = 776.21(C$_{52}$H$_{32}$N$_4$S$_2$ = 776.97) |
| 2-31 | m/z = 880.20(C$_{60}$H$_{36}$N$_2$S$_3$ = 881.14) | 2-32 | m/z = 939.27(C$_{66}$H$_{41}$N$_3$S$_2$ = 940.18) |
| 2-33 | m/z = 642.19(C$_{44}$H$_{26}$N$_4$S = 642.77) | 2-34 | m/z = 626.21(C$_{44}$H$_{26}$N$_4$O = 626.70) |
| 2-35 | m/z = 567.14(C$_{38}$H$_{21}$N$_3$OS = 567.66) | 2-36 | m/z = 551.16(C$_{38}$H$_{21}$N$_3$O$_2$ = 551.59) |
| 2-37 | m/z = 567.14(C$_{38}$H$_{21}$N$_3$OS = 567.66) | 2-38 | m/z = 583.12(C$_{38}$H$_{21}$N$_3$S$_2$ = 583.72) |
| 2-39 | m/z = 380.03(C$_{24}$H$_{12}$OS$_2$ = 380.48) | 2-40 | m/z = 364.06(C$_{24}$H$_{12}$O$_2$S = 364.42) |
| 3-1 | m/z = 669.20(C$_{45}$H$_{27}$N$_5$S = 669.79) | 3-2 | m/z = 668.20(C$_{46}$H$_{28}$N$_4$S = 668.81) |
| 3-3 | m/z = 668.20(C$_{46}$H$_{28}$N$_4$S = 668.81) | 3-4 | m/z = 642.19(C$_{44}$H$_{26}$N$_4$S = 642.77) |
| 3-5 | m/z = 745.23(C$_{51}$H$_{31}$N$_5$S = 745.89) | 3-6 | m/z = 744.23(C$_{52}$H$_{32}$N$_4$S = 744.90) |
| 3-7 | m/z = 744.23(C$_{52}$H$_{32}$N$_4$S = 744.90) | 3-8 | m/z = 718.22(C$_{50}$H$_{30}$N$_4$S = 718.87) |
| 3-9 | m/z = 745.23(C$_{51}$H$_{31}$N$_5$S = 745.89) | 3-10 | m/z = 744.23(C$_{52}$H$_{32}$N$_4$S = 744.90) |
| 3-11 | m/z = 744.23(C$_{52}$H$_{32}$N$_4$S = 744.90) | 3-12 | m/z = 718.22(C$_{50}$H$_{30}$N$_4$S = 718.87) |
| 3-13 | m/z = 719.21(C$_{49}$H$_{29}$N$_5$S = 719.85) | 3-14 | m/z = 178.22(C$_{50}$H$_{30}$N$_4$S = 718.87) |
| 3-15 | m/z = 178.22(C$_{50}$H$_{30}$N$_4$S = 718.87) | 3-16 | m/z = 692.20(C$_{48}$H$_{28}$N$_4$S = 692.83) |
| 3-17 | m/z = 719.21(C$_{49}$H$_{29}$N$_5$S = 719.85) | 3-18 | m/z = 178.22(C$_{50}$H$_{30}$N$_4$S = 718.87) |

TABLE 3-continued

| Compound | FD-MS | Compound | FD-MS |
|---|---|---|---|
| 3-19 | m/z = 178.22($C_{50}H_{30}N_4S$ = 718.87) | 3-20 | m/z = 692.20($C_{48}H_{28}N_4S$ = 692.83) |
| 3-21 | m/z = 590.18($C_{42}H_{26}N_2S$ = 590.73) | 3-22 | m/z = 755.24($C_{54}H_{33}N_3S$ = 755.92) |
| 3-23 | m/z = 591.18($C_{41}H_{25}N_3S$ = 591.72) | 3-24 | m/z = 681.22($C_{48}H_{31}N_3S$ = 681.84) |
| 4-1 | m/z = 455.08($C_{30}H_{17}NS_2$ = 455.59) | 4-2 | m/z = 777.31($C_{58}H_{39}N_3$ = 777.95) |
| 4-3 | m/z = 455.08($C_{30}H_{17}NS_2$ = 455.59) | 4-4 | m/z = 531.11($C_{36}H_{21}NS_2$ = 531.69) |
| 4-5 | m/z = 610.13($C_{39}H_{22}N_4S_2$ = 610.75) | 4-6 | m/z = 609.13($C_{40}H_{23}N_3S_2$ = 609.76) |
| 4-7 | m/z = 609.13($C_{40}H_{23}N_3S_2$ = 609.76) | 4-8 | m/z = 583.12($C_{38}H_{21}N_3S_2$ = 583.72) |
| 4-9 | m/z = 561.07($C_{36}H_{19}NS_3$ = 561.74) | 4-10 | m/z = 571.14($C_{39}H_{25}NS_2$ = 571.75) |
| 4-11 | m/z = 695.17($C_{49}H_{29}NS_2$ = 695.89) | 4-12 | m/z = 693.16($C_{49}H_{27}NS_2$ = 693.88) |
| 4-13 | m/z = 622.15($C_{42}H_{26}N_2S_2$ = 622.80) | 4-14 | m/z = 672.17($C_{46}H_{28}N_2S_2$ = 672.86) |
| 4-15 | m/z = 698.19($C_{48}H_{30}N_2S_2$ = 698.90) | 4-16 | m/z = 774.22($C_{54}H_{34}N_2S_2$ = 774.99) |
| 4-17 | m/z = 698.19($C_{48}H_{30}N_2S_2$ = 698.90) | 4-18 | m/z = 748.20($C_{52}H_{32}N_2S_2$ = 748.95) |
| 4-19 | m/z = 748.20($C_{52}H_{32}N_2S_2$ = 748.95) | 4-20 | m/z = 774.22($C_{54}H_{34}N_2S_2$ = 774.99) |
| 4-21 | m/z = 853.23($C_{57}H_{35}N_5S$ = 854.05) | 4-22 | m/z = 774.22($C_{54}H_{34}N_2S_2$ = 774.99) |
| 4-23 | m/z = 824.23($C_{58}H_{36}N_2S_2$ = 825.05) | 4-24 | m/z = 824.23($C_{58}H_{36}N_2S_2$ = 825.05) |
| 4-25 | m/z = 850.25($C_{60}H_{38}N_2S_2$ = 851.09) | 4-26 | m/z = 890.28($C_{63}H_{42}N_2S_2$ = 891.15) |
| 4-27 | m/z = 880.20($C_{60}H_{36}N_2S_3$ = 881.14) | 4-28 | m/z = 1014.31($C_{73}H_{46}N_2S_2$ = 1015.29) |
| 4-29 | m/z = 890.28($C_{63}H_{42}N_2S_2$ = 891.15) | 4-30 | m/z = 776.21($C_{52}H_{32}N_4S_2$ = 776.97) |
| 4-31 | m/z = 880.20($C_{60}H_{36}N_2S_3$ = 881.14) | 4-32 | m/z = 939.27($C_{66}H_{41}N_3S_2$ = 940.18) |
| 4-33 | m/z = 642.19($C_{44}H_{26}N_4S$ = 642.77) | 4-34 | m/z = 626.21($C_{44}H_{26}N_4O$ = 626.70) |
| 4-35 | m/z = 567.14($C_{38}H_{21}N_3OS$ = 567.66) | 4-36 | m/z = 551.16($C_{38}H_{21}N_3O_2$ = 551.59) |
| 4-37 | m/z = 567.14($C_{38}H_{21}N_3OS$ = 567.66) | 4-38 | m/z = 583.12($C_{38}H_{21}N_3S_2$ = 583.72) |
| 4-39 | m/z = 380.03($C_{24}H_{12}OS_2$ = 380.48) | 4-40 | m/z = 364.06($C_{24}H_{12}O_2S$ = 364.42) |
| 5-1 | m/z = 669.20($C_{45}H_{27}N_5S$ = 669.79) | 5-2 | m/z = 668.20($C_{46}H_{28}N_4S$ = 668.81) |
| 5-3 | m/z = 668.20($C_{46}H_{28}N_4S$ = 668.81) | 5-4 | m/z = 642.19($C_{44}H_{26}N_4S$ = 642.77) |
| 5-5 | m/z = 745.23($C_{51}H_{31}N_5S$ = 745.89) | 5-6 | m/z = 744.23($C_{52}H_{32}N_4S$ = 744.90) |
| 5-7 | m/z = 744.23($C_{52}H_{32}N_4S$ = 744.90) | 5-8 | m/z = 718.22($C_{50}H_{30}N_4S$ = 718.87) |
| 5-9 | m/z = 745.23($C_{51}H_{31}N_5S$ = 745.89) | 5-10 | m/z = 744.23($C_{52}H_{32}N_4S$ = 744.90) |
| 5-11 | m/z = 744.23($C_{52}H_{32}N_4S$ = 744.90) | 5-12 | m/z = 718.22($C_{50}H_{30}N_4S$ = 718.87) |
| 5-13 | m/z = 719.21($C_{49}H_{29}N_5S$ = 719.85) | 5-14 | m/z = 178.22($C_{50}H_{30}N_4S$ = 718.87) |
| 5-15 | m/z = 178.22($C_{50}H_{30}N_4S$ = 718.87) | 5-16 | m/z = 692.20($C_{48}H_{28}N_4S$ = 692.83) |
| 5-17 | m/z = 719.21($C_{49}H_{29}N_5S$ = 719.85) | 5-18 | m/z = 178.22($C_{50}H_{30}N_4S$ = 718.87) |
| 5-19 | m/z = 178.22($C_{50}H_{30}N_4S$ = 718.87) | 5-20 | m/z = 692.20($C_{48}H_{28}N_4S$ = 692.83) |
| 5-21 | m/z = 590.18($C_{42}H_{26}N_2S$ = 590.73) | 5-22 | m/z = 755.24($C_{54}H_{33}N_3S$ = 755.92) |
| 5-23 | m/z = 591.18($C_{41}H_{25}N_3S$ = 591.72) | 5-24 | m/z = 681.22($C_{48}H_{31}N_3S$ = 681.84) |
| 6-1 | m/z = 455.08($C_{30}H_{17}NS_2$ = 455.59) | 6-2 | m/z = 777.31($C_{58}H_{39}N_3$ = 777.95) |
| 6-3 | m/z = 455.08($C_{30}H_{17}NS_2$ = 455.59) | 6-4 | m/z = 531.11($C_{36}H_{21}NS_2$ = 531.69) |
| 6-5 | m/z = 610.13($C_{39}H_{22}N_4S_2$ = 610.75) | 6-6 | m/z = 609.13($C_{40}H_{23}N_3S_2$ = 609.76) |
| 6-7 | m/z = 609.13($C_{40}H_{23}N_3S_2$ = 609.76) | 6-8 | m/z = 583.12($C_{38}H_{21}N_3S_2$ = 583.72) |
| 6-9 | m/z = 561.07($C_{36}H_{19}NS_3$ = 561.74) | 6-10 | m/z = 571.14($C_{39}H_{25}NS_2$ = 571.75) |
| 6-11 | m/z = 695.17($C_{49}H_{29}NS_2$ = 695.89) | 6-12 | m/z = 693.16($C_{49}H_{27}NS_2$ = 693.88) |
| 6-13 | m/z = 622.15($C_{42}H_{26}N_2S_2$ = 622.80) | 6-14 | m/z = 672.17($C_{46}H_{28}N_2S_2$ = 672.86) |
| 6-15 | m/z = 698.19($C_{48}H_{30}N_2S_2$ = 698.90) | 6-16 | m/z = 774.22($C_{54}H_{34}N_2S_2$ = 774.99) |
| 6-17 | m/z = 698.19($C_{48}H_{30}N_2S_2$ = 698.90) | 6-18 | m/z = 748.20($C_{52}H_{32}N_2S_2$ = 748.95) |
| 6-19 | m/z = 748.20($C_{52}H_{32}N_2S_2$ = 748.95) | 6-20 | m/z = 774.22($C_{54}H_{34}N_2S_2$ = 774.99) |
| 6-21 | m/z = 853.23($C_{57}H_{35}N_5S$ = 854.05) | 6-22 | m/z = 774.22($C_{54}H_{34}N_2S_2$ = 774.99) |
| 6-23 | m/z = 824.23($C_{58}H_{36}N_2S_2$ = 825.05) | 6-24 | m/z = 824.23($C_{58}H_{36}N_2S_2$ = 825.05) |
| 6-25 | m/z = 850.25($C_{60}H_{38}N_2S_2$ = 851.09) | 6-26 | m/z = 890.28($C_{63}H_{42}N_2S_2$ = 891.15) |
| 6-27 | m/z = 880.20($C_{60}H_{36}N_2S_3$ = 881.14) | 6-28 | m/z = 1014.31($C_{73}H_{46}N_2S_2$ = 1015.29) |
| 6-29 | m/z = 890.28($C_{63}H_{42}N_2S_2$ = 891.15) | 6-30 | m/z = 776.21($C_{52}H_{32}N_4S_2$ = 776.97) |
| 6-31 | m/z = 880.20($C_{60}H_{36}N_2S_3$ = 881.14) | 6-32 | m/z = 939.27($C_{66}H_{41}N_3S_2$ = 940.18) |
| 6-33 | m/z = 642.19($C_{44}H_{26}N_4S$ = 642.77) | 6-34 | m/z = 626.21($C_{44}H_{26}N_4O$ = 626.70) |
| 6-35 | m/z = 567.14($C_{38}H_{21}N_3OS$ = 567.66) | 6-36 | m/z = 551.16($C_{38}H_{21}N_3O_2$ = 551.59) |
| 6-37 | m/z = 567.14($C_{38}H_{21}N_3OS$ = 567.66) | 6-38 | m/z = 583.12($C_{38}H_{21}N_3S_2$ = 583.72) |
| 6-39 | m/z = 380.03($C_{24}H_{12}OS_2$ = 380.48) | 6-40 | m/z = 364.06($C_{24}H_{12}O_2S$ = 364.42) |
| 7-1 | m/z = 669.20($C_{45}H_{27}N_5S$ = 669.79) | 7-2 | m/z = 668.20($C_{46}H_{28}N_4S$ = 668.81) |
| 7-3 | m/z = 668.20($C_{46}H_{28}N_4S$ = 668.81) | 7-4 | m/z = 642.19($C_{44}H_{26}N_4S$ = 642.77) |
| 7-5 | m/z = 745.23($C_{51}H_{31}N_5S$ = 745.89) | 7-6 | m/z = 744.23($C_{52}H_{32}N_4S$ = 744.90) |
| 7-7 | m/z = 744.23($C_{52}H_{32}N_4S$ = 744.90) | 7-8 | m/z = 718.22($C_{50}H_{30}N_4S$ = 718.87) |
| 7-9 | m/z = 745.23($C_{51}H_{31}N_5S$ = 745.89) | 7-10 | m/z = 744.23($C_{52}H_{32}N_4S$ = 744.90) |
| 7-11 | m/z = 744.23($C_{52}H_{32}N_4S$ = 744.90) | 7-12 | m/z = 718.22($C_{50}H_{30}N_4S$ = 718.87) |
| 7-13 | m/z = 719.21($C_{49}H_{29}N_5S$ = 719.85) | 7-14 | m/z = 178.22($C_{50}H_{30}N_4S$ = 718.87) |
| 7-15 | m/z = 178.22($C_{50}H_{30}N_4S$ = 718.87) | 7-16 | m/z = 692.20($C_{48}H_{28}N_4S$ = 692.83) |
| 7-17 | m/z = 719.21($C_{49}H_{29}N_5S$ = 719.85) | 7-18 | m/z = 178.22($C_{50}H_{30}N_4S$ = 718.87) |
| 7-19 | m/z = 178.22($C_{50}H_{30}N_4S$ = 718.87) | 7-20 | m/z = 692.20($C_{48}H_{28}N_4S$ = 692.83) |
| 7-21 | m/z = 590.18($C_{42}H_{28}N_2S$ = 590.73) | 7-22 | m/z = 755.24($C_{54}H_{33}N_3S$ = 755.92) |
| 7-23 | m/z = 591.18($C_{41}H_{25}N_3S$ = 591.72) | 7-24 | m/z = 681.22($C_{48}H_{31}N_3S$ = 681.84) |
| 8-1 | m/z = 455.08($C_{30}H_{17}NS_2$ = 455.59) | 8-2 | m/z = 777.31($C_{58}H_{39}N_3$ = 777.95) |
| 8-3 | m/z = 455.08($C_{30}H_{17}NS_2$ = 455.59) | 8-4 | m/z = 531.11($C_{36}H_{21}NS_2$ = 531.69) |
| 8-5 | m/z = 610.13($C_{39}H_{22}N_4S_2$ = 610.75) | 8-6 | m/z = 609.13($C_{40}H_{23}N_3S_2$ = 609.76) |
| 8-7 | m/z = 609.13($C_{40}H_{23}N_3S_2$ = 609.76) | 8-8 | m/z = 583.12($C_{38}H_{21}N_3S_2$ = 583.72) |
| 8-9 | m/z = 561.07($C_{38}H_{19}NS_3$ = 561.74) | 8-10 | m/z = 571.14($C_{39}H_{25}NS_2$ = 571.75) |
| 8-11 | m/z = 695.17($C_{49}H_{29}NS_2$ = 695.89) | 8-12 | m/z = 693.16($C_{49}H_{27}NS_2$ = 693.88) |
| 8-13 | m/z = 622.15($C_{42}H_{26}N_2S_2$ = 622.80) | 8-14 | m/z = 672.17($C_{48}H_{28}N_2S_2$ = 672.86) |
| 8-15 | m/z = 698.19($C_{48}H_{30}N_2S_2$ = 698.90) | 8-16 | m/z = 774.22($C_{54}H_{34}N_2S_2$ = 774.99) |
| 8-17 | m/z = 698.19($C_{48}H_{30}N_2S_2$ = 698.90) | 8-18 | m/z = 748.20($C_{52}H_{32}N_2S_2$ = 748.95) |
| 8-19 | m/z = 748.20($C_{52}H_{32}N_2S_2$ = 748.95) | 8-20 | m/z = 774.22($C_{54}H_{34}N_2S_2$ = 774.99) |

Fabrication and Evaluation of Organic Electronic Element

[Example 1] Red Organic Light Emitting Diode (a Phosphorescent Host)

Organic light emitting diodes (OLEDs) were fabricated according to a conventional method by using a compound of the present invention as a phosphorescent host material.

First, an ITO layer (anode) was formed on a glass substrate, and a film of $N^1$-(naphthalen-2-yl)-$N^4$,$N^4$-bis (4-(naphthalen-2-yl(phenyl)amino)phenyl)-$N^1$-phenylbenzene-1,4-diamine (hereinafter abbreviated as "2-TNATA") was vacuum-deposited on the ITO layer to form a hole injection layer with a thickness of 60 nm. Subsequently, 4,4-bis[N-(1-naphthyl)-N-phenylamino]biphenyl (hereinafter abbreviated as "NPD") was vacuum-deposited with a thickness of 60 nm on the hole injection layer to form a hole transport layer. Subsequently, a light emitting layer with a thickness of 30 nm was deposited on the hole transport layer by doping the hole transport layer with the compound 1-4 of the present invention as a host material and bis-(1-phenylisoquinolyl)iridium(III)acetylacetonate (hereinafter abbreviated as "(piq)$_2$Ir(acac)" as a dopant material in a weight ratio of 95:5.

Next, a film of ((1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and a film of tris(8-quinolinolato)aluminum (hereinafter abbreviated as "Alq$_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 36] Red Organic Light Emitting Diode (a Phosphorescent Host)

The OLEDs were manufactured in the same manner as described in Example 1, except that any one of the compounds 1-8, 1-12, 1-16, 1-20, 2-8, 2-33 to 2-38, 3-4, 3-8, 3-12, 3-16, 3-20, 4-8, 4-33 to 4-38, 5-4, 5-8, 5-12, 5-16, 5-20, 6-8, 6-33 to 6-38 of the present invention in the Table 4 below was used as the host material of the light emitting layer, instead of the inventive compound 1-4.

Comparative Example 1

An OLED was manufactured in the same manner as described in Example 1, except that the following Comparative Compound A was used as the host material of the light emitting layer, instead of the inventive compound 1-4.

<Comparative Compound A>

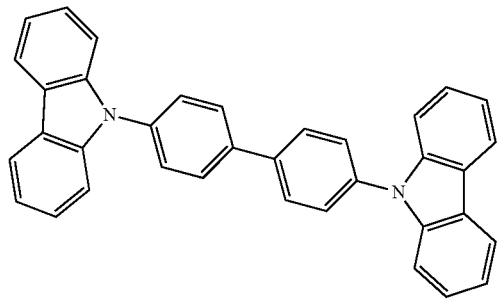

Comparative Example 2

An OLED was manufactured in the same manner as described in Example 1, except that the following Comparative Compound B was used as the host material of the light emitting layer, instead of the inventive compound 1-4.

<Comparative Compound B>

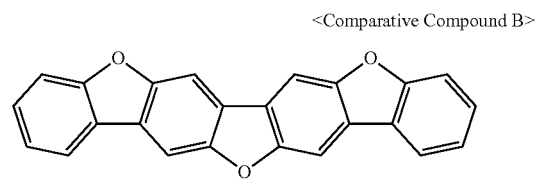 [SMILES: c1ccc2c(c1)oc1cc3c(cc12)oc1cc2c(cc13)oc1ccccc12]

Comparative Example 3

An OLED was manufactured in the same manner as described in Example 1, except that the following Comparative Compound C was used as the host material of the light emitting layer, instead of the inventive compound 1-4.

<Comparative Compound C>

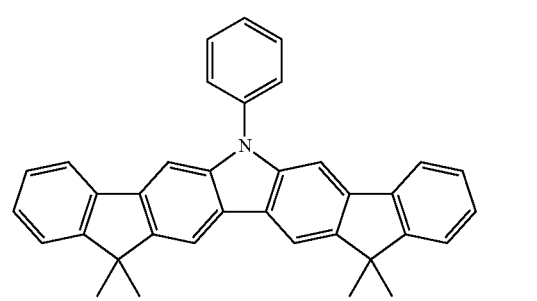

Comparative Example 4

An OLED was manufactured in the same manner as described in Example 1, except that the following Comparative Compound D was used as the host material of the light emitting layer, instead of the inventive compound 1-4.

<Comparative Compound D>

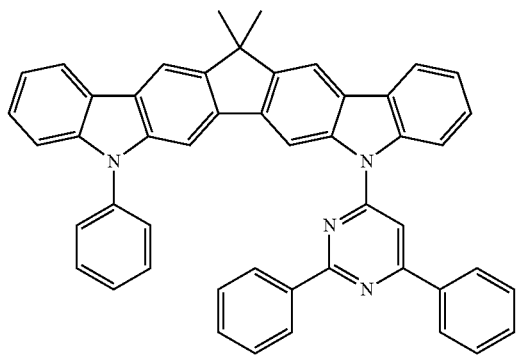

Comparative Example 5

An OLED was manufactured in the same manner as described in Example 1, except that the following Comparative Compound E was used as the host material of the light emitting layer, instead of the inventive compound 1-4.

<Comparative Compound E>

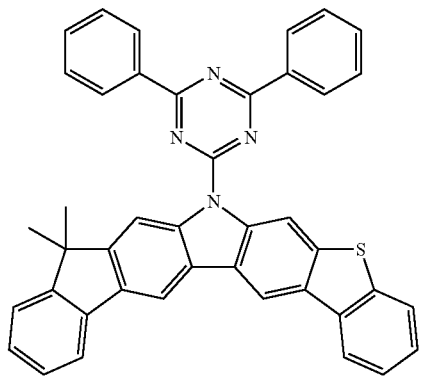

Comparative Example 6

An OLED was manufactured in the same manner as described in Example 1, except that the following Comparative Compound F was used as the host material of the light emitting layer, instead of the inventive compound 1-4.

<Comparative Compound F>

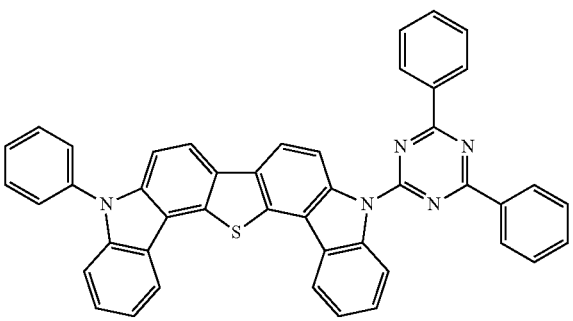

A forward bias DC voltage was applied to each of the OLEDs manufactured through the Examples 1 to 36 and the Comparative Examples 1 to 6, and electro-luminescence (EL) characteristics of the OLED were measured by PR-650 (Photoresearch). Also, T90 life span was measured by life span measuring equipment (Mcscience) at the reference brightness of 2500 cd/m$^2$. Evaluation results are in the Table 4 below.

TABLE 4

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Com. Ex (1) | Com. Com A | 6.8 | 34.2 | 2500.0 | 7.3 | 51.6 | (0.66, 0.32) |
| Com. Ex (2) | Com. Com B | 6.9 | 31.3 | 2500.0 | 8.0 | 76.6 | (0.67, 0.32) |
| Com. Ex (3) | Com. Com C | 6.7 | 30.1 | 2500.0 | 8.3 | 74.3 | (0.66, 0.32) |
| Com. Ex (4) | Com. Com D | 6.5 | 28.7 | 2500.0 | 8.7 | 71.3 | (0.66, 0.33) |
| Com. Ex (5) | Com. Com E | 6.3 | 26.9 | 2500.0 | 9.3 | 72.5 | (0.65, 0.32) |
| Com. Ex (6) | Com. Com F | 6.1 | 25.6 | 2500.0 | 9.8 | 85.8 | (0.66, 0.32) |
| Ex. (1) | 1-4 | 5.8 | 23.3 | 2500.0 | 10.7 | 117.7 | (0.66, 0.33) |
| Ex. (2) | 1-8 | 5.6 | 16.9 | 2500.0 | 14.8 | 103.6 | (0.66, 0.32) |
| Ex. (3) | 1-12 | 5.3 | 20.0 | 2500.0 | 12.5 | 95.6 | (0.65, 0.32) |
| Ex. (4) | 1-16 | 5.7 | 16.7 | 2500.0 | 15.0 | 128.2 | (0.66, 0.32) |
| Ex. (5) | 1-20 | 5.4 | 23.5 | 2500.0 | 10.6 | 105.9 | (0.66, 0.32) |
| Ex. (6) | 2-8 | 5.3 | 21.7 | 2500.0 | 11.5 | 109.8 | (0.67, 0.32) |
| Ex. (7) | 2-33 | 5.5 | 18.3 | 2500.0 | 13.7 | 99.9 | (0.66, 0.32) |
| Ex. (8) | 2-34 | 5.6 | 18.4 | 2500.0 | 13.6 | 98.0 | (0.66, 0.32) |
| Ex. (9) | 2-35 | 5.4 | 19.4 | 2500.0 | 12.9 | 98.6 | (0.66, 0.33) |
| Ex. (10) | 2-36 | 5.4 | 19.5 | 2500.0 | 12.8 | 129.7 | (0.66, 0.32) |
| Ex. (11) | 2-37 | 5.3 | 17.3 | 2500.0 | 14.5 | 136.3 | (0.65, 0.32) |
| Ex. (12) | 2-38 | 5.6 | 19.9 | 2500.0 | 12.5 | 123.3 | (0.66, 0.32) |
| Ex. (13) | 3-4 | 5.8 | 23.6 | 2500.0 | 10.6 | 90.7 | (0.66, 0.32) |
| Ex. (14) | 3-8 | 5.3 | 18.0 | 2500.0 | 13.9 | 126.9 | (0.67, 0.32) |
| Ex. (15) | 3-12 | 5.6 | 22.7 | 2500.0 | 11.0 | 137.8 | (0.66, 0.32) |
| Ex. (16) | 3-16 | 5.6 | 24.6 | 2500.0 | 10.2 | 126.8 | (0.67, 0.32) |

TABLE 4-continued

|  | Compound | Voltage (V) | Current Density (mA/cm²) | Brightness (cd/m²) | Efficiency (cd/A) | Lifetime T(95) | CIE (x, y) |
|---|---|---|---|---|---|---|---|
| Ex. (17) | 3-20 | 5.8 | 22.2 | 2500.0 | 11.2 | 145.7 | (0.66, 0.32) |
| Ex. (18) | 4-8 | 5.7 | 18.9 | 2500.0 | 13.2 | 108.5 | (0.66, 0.32) |
| Ex. (19) | 4-33 | 5.7 | 18.2 | 2500.0 | 13.8 | 97.7 | (0.66, 0.33) |
| Ex. (20) | 4-34 | 5.7 | 19.6 | 2500.0 | 12.8 | 118.5 | (0.66, 0.32) |
| Ex. (21) | 4-35 | 5.5 | 23.7 | 2500.0 | 10.5 | 132.4 | (0.65, 0.32) |
| Ex. (22) | 4-36 | 5.7 | 17.4 | 2500.0 | 14.3 | 114.4 | (0.66, 0.32) |
| Ex. (23) | 4-37 | 5.5 | 18.9 | 2500.0 | 13.2 | 131.1 | (0.66, 0.32) |
| Ex. (24) | 4-38 | 5.4 | 20.6 | 2500.0 | 12.2 | 118.8 | (0.67, 0.32) |
| Ex. (25) | 5-4 | 5.7 | 19.1 | 2500.0 | 13.1 | 96.2 | (0.66, 0.32) |
| Ex. (26) | 5-8 | 5.6 | 21.6 | 2500.0 | 11.6 | 138.3 | (0.67, 0.32) |
| Ex. (27) | 5-12 | 5.7 | 20.5 | 2500.0 | 12.2 | 141.1 | (0.66, 0.32) |
| Ex. (28) | 5-16 | 5.6 | 19.5 | 2500.0 | 12.8 | 119.0 | (0.66, 0.32) |
| Ex. (29) | 5-20 | 5.5 | 17.3 | 2500.0 | 14.5 | 145.5 | (0.66, 0.33) |
| Ex. (30) | 6-8 | 5.7 | 21.2 | 2500.0 | 11.8 | 105.1 | (0.66, 0.32) |
| Ex. (31) | 6-33 | 5.5 | 20.8 | 2500.0 | 12.0 | 145.9 | (0.65, 0.32) |
| Ex. (32) | 6-34 | 5.6 | 20.1 | 2500.0 | 12.5 | 133.8 | (0.66, 0.32) |
| Ex. (33) | 6-35 | 5.4 | 24.3 | 2500.0 | 10.3 | 99.0 | (0.66, 0.32) |
| Ex. (34) | 6-36 | 5.6 | 17.0 | 2500.0 | 14.7 | 105.7 | (0.67, 0.32) |
| Ex. (35) | 6-37 | 5.4 | 17.0 | 2500.0 | 14.7 | 145.8 | (0.66, 0.32) |
| Ex. (36) | 6-38 | 5.4 | 19.9 | 2500.0 | 12.5 | 105.8 | (0.67, 0.32) |

[Example 37] Green Organic Light Emitting Diode (a Phosphorescent Host)

Organic light emitting diodes (OLEDs) were fabricated according to a conventional method by using a compound of the present invention as a phosphorescent host material. First, an ITO layer (anode) was formed on a glass substrate, and a film of 2-TNATA was vacuum-deposited on the ITO layer to form a hole injection layer with a thickness of 60 nm. Subsequently, NPD was vacuum-deposited with a thickness of 60 nm on the hole injection layer to form a hole transport layer. Subsequently, a light emitting layer with a thickness of 30 nm was deposited on the hole transport layer by doping the hole transport layer with the compound 1-1 of the present invention as a host material and tris(2-phenylpyridine)-iridium (hereinafter abbreviated as "Ir(ppy)₃") as a dopant material in a weight ratio of 95:5.

Next, a film of BAlq was vacuum-deposited with a thickness of 10 nm on the light emitting layer to form a hole blocking layer, and a film of Alq₃ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 38] to [Example 192] Green Organic Light Emitting Diode (a Phosphorescent Host)

The OLEDs were manufactured in the same manner as described in Example 37, except that any one of the compounds 1-2, 1-3, 1-5 to 1-7, 1-9 to 1-11, 1-13 to 1-15, 1-17 to 1-19, 1-21 to 1-24, 2-1 to 2-7, 2-9 to 4-32, 2-39 to 2-40, 3-1 to 3-3, 3-5 to 3-7, 3-9 to 3-11, 3-13 to 3-15, 3-17 to 3-19, 3-21 to 3-24, 4-1 to 4-7, 4-9 to 4-32, 4-39, 4-40, 5-1 to 5-3, 5-5 to 5-7, 5-9 to 5-11, 5-13 to 5-15, 5-17 to 5-19, 5-21 to 5-24, 6-1 to 6-7, 6-9 to 6-32, 6-39, 6-40 of the present invention in the Table 5 below was used as the host material of the light emitting layer, instead of the inventive compound 1-1.

Comparative Example 7

An OLED was manufactured in the same manner as described in Example 37, except that the Comparative Compound A above was used as the host material of the light emitting layer, instead of the inventive compound 1-1.

Comparative Example 8

An OLED was manufactured in the same manner as described in Example 37, except that the Comparative Compound B above was used as the host material of the light emitting layer, instead of the inventive compound 1-1.

Comparative Example 9

An OLED was manufactured in the same manner as described in Example 37, except that the Comparative Compound C above was used as the host material of the light emitting layer, instead of the inventive compound 1-1.

Comparative Example 10

An OLED was manufactured in the same manner as described in Example 37, except that the Comparative Compound D above was used as the host material of the light emitting layer, instead of the inventive compound 1-1.

Comparative Example 11

An OLED was manufactured in the same manner as described in Example 37, except that the Comparative Compound E above was used as the host material of the light emitting layer, instead of the inventive compound 1-1.

Comparative Example 6

An OLED was manufactured in the same manner as described in Example 37, except that the Comparative Compound F above was used as the host material of the light emitting layer, instead of the inventive compound 1-1.

A forward bias DC voltage was applied to each of the OLEDs manufactured through the Examples 37 to 192 and the Comparative Examples 7 to 12, and electro-luminescence (EL) characteristics of the OLED were measured by PR-650 (Photoresearch). Also, T90 life span was measured by life span measuring equipment (Mcscience) at the reference brightness of 5000 cd/m². Evaluation results are in the Table 5 below.

TABLE 5

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Com. Ex (7) | Com. Com A | 6.5 | 20.0 | 5000.0 | 25.0 | 73.8 | (0.31, 0.60) |
| Com. Ex (8) | Com. Com B | 6.5 | 15.1 | 5000.0 | 33.1 | 63.8 | (0.31, 0.61) |
| Com. Ex (9) | Com. Com C | 6.4 | 14.2 | 5000.0 | 35.3 | 75.7 | (0.31, 0.60) |
| Com. Ex (10) | Com. Com D | 6.3 | 13.6 | 5000.0 | 36.8 | 73.1 | (0.33, 0.61) |
| Com. Ex (11) | Com. Com E | 6.2 | 12.9 | 5000.0 | 38.7 | 59.1 | (0.30, 0.60) |
| Com. Ex (12) | Com. Com F | 6.0 | 12.5 | 5000.0 | 40.1 | 74.7 | (0.31, 0.61) |
| Ex. (37) | 1-1 | 5.4 | 9.5 | 5000.0 | 52.5 | 140.7 | (0.31, 0.60) |
| Ex. (38) | 1-2 | 5.3 | 10.0 | 5000.0 | 50.2 | 118.1 | (0.33, 0.61) |
| Ex. (39) | 1-3 | 5.2 | 9.4 | 5000.0 | 53.0 | 141.8 | (0.32, 0.61) |
| Ex. (40) | 1-5 | 5.4 | 10.4 | 5000.0 | 48.0 | 144.6 | (0.33, 0.61) |
| Ex. (41) | 1-6 | 5.4 | 11.1 | 5000.0 | 44.9 | 123.6 | (0.32, 0.61) |
| Ex. (42) | 1-7 | 5.1 | 10.8 | 5000.0 | 46.4 | 127.5 | (0.31, 0.60) |
| Ex. (43) | 1-9 | 5.2 | 11.3 | 5000.0 | 44.4 | 139.7 | (0.31, 0.61) |
| Ex. (44) | 1-10 | 5.3 | 10.4 | 5000.0 | 47.9 | 127.4 | (0.31, 0.60) |
| Ex. (45) | 1-11 | 5.3 | 9.3 | 5000.0 | 53.6 | 149.6 | (0.33, 0.61) |
| Ex. (46) | 1-13 | 5.0 | 11.2 | 5000.0 | 44.6 | 122.9 | (0.30, 0.60) |
| Ex. (47) | 1-14 | 5.1 | 9.5 | 5000.0 | 52.5 | 148.1 | (0.31, 0.61) |
| Ex. (48) | 1-15 | 5.2 | 9.5 | 5000.0 | 52.5 | 123.8 | (0.31, 0.61) |
| Ex. (49) | 1-17 | 5.0 | 10.1 | 5000.0 | 49.7 | 129.0 | (0.33, 0.61) |
| Ex. (50) | 1-18 | 5.0 | 10.1 | 5000.0 | 49.4 | 110.1 | (0.32, 0.61) |
| Ex. (51) | 1-19 | 5.2 | 11.6 | 5000.0 | 43.0 | 140.4 | (0.33, 0.60) |
| Ex. (52) | 1-21 | 5.2 | 11.4 | 5000.0 | 44.0 | 105.5 | (0.32, 0.61) |
| Ex. (53) | 1-22 | 5.1 | 10.3 | 5000.0 | 48.6 | 123.5 | (0.31, 0.60) |
| Ex. (54) | 1-23 | 5.1 | 9.9 | 5000.0 | 50.5 | 112.3 | (0.31, 0.61) |
| Ex. (55) | 1-24 | 5.2 | 11.3 | 5000.0 | 44.1 | 115.3 | (0.31, 0.60) |
| Ex. (56) | 2-1 | 5.4 | 11.4 | 5000.0 | 44.0 | 126.4 | (0.33, 0.61) |
| Ex. (57) | 2-2 | 5.2 | 10.0 | 5000.0 | 50.2 | 118.1 | (0.30, 0.60) |
| Ex. (58) | 2-3 | 5.0 | 9.6 | 5000.0 | 52.1 | 91.9 | (0.31, 0.61) |
| Ex. (59) | 2-4 | 5.4 | 9.3 | 5000.0 | 54.0 | 102.9 | (0.31, 0.60) |
| Ex. (60) | 2-5 | 5.5 | 10.9 | 5000.0 | 45.9 | 137.6 | (0.33, 0.61) |
| Ex. (61) | 2-6 | 5.0 | 9.9 | 5000.0 | 50.4 | 138.3 | (0.32, 0.61) |
| Ex. (62) | 2-7 | 5.4 | 10.7 | 5000.0 | 46.8 | 112.7 | (0.33, 0.61) |
| Ex. (63) | 2-9 | 5.2 | 10.8 | 5000.0 | 46.3 | 123.6 | (0.31, 0.60) |
| Ex. (64) | 2-10 | 5.1 | 10.2 | 5000.0 | 49.1 | 148.0 | (0.31, 0.61) |
| Ex. (65) | 2-11 | 5.3 | 9.1 | 5000.0 | 54.7 | 96.8 | (0.31, 0.61) |
| Ex. (66) | 2-12 | 5.3 | 9.3 | 5000.0 | 53.5 | 100.6 | (0.33, 0.61) |
| Ex. (67) | 2-13 | 5.2 | 9.3 | 5000.0 | 53.7 | 106.0 | (0.30, 0.60) |
| Ex. (68) | 2-14 | 5.2 | 9.9 | 5000.0 | 50.7 | 102.6 | (0.31, 0.61) |
| Ex. (69) | 2-15 | 5.0 | 9.5 | 5000.0 | 52.6 | 108.5 | (0.31, 0.61) |
| Ex. (70) | 2-16 | 5.2 | 9.7 | 5000.0 | 51.7 | 103.5 | (0.33, 0.61) |
| Ex. (71) | 2-17 | 5.3 | 10.8 | 5000.0 | 46.4 | 127.3 | (0.32, 0.61) |
| Ex. (72) | 2-18 | 5.2 | 9.3 | 5000.0 | 53.9 | 134.2 | (0.33, 0.60) |
| Ex. (73) | 2-19 | 5.4 | 11.2 | 5000.0 | 44.5 | 147.8 | (0.32, 0.61) |
| Ex. (74) | 2-20 | 5.2 | 9.6 | 5000.0 | 52.1 | 134.4 | (0.31, 0.60) |
| Ex. (75) | 2-21 | 5.3 | 11.6 | 5000.0 | 43.1 | 133.7 | (0.31, 0.61) |
| Ex. (76) | 2-22 | 5.0 | 9.3 | 5000.0 | 53.6 | 146.7 | (0.31, 0.60) |
| Ex. (77) | 2-23 | 5.2 | 11.4 | 5000.0 | 43.9 | 130.3 | (0.33, 0.61) |
| Ex. (78) | 2-24 | 5.1 | 11.2 | 5000.0 | 44.7 | 90.1 | (0.30, 0.60) |
| Ex. (79) | 2-25 | 5.2 | 10.3 | 5000.0 | 48.6 | 96.7 | (0.31, 0.61) |
| Ex. (80) | 2-26 | 5.3 | 9.6 | 5000.0 | 52.2 | 138.0 | (0.31, 0.60) |
| Ex. (81) | 2-27 | 5.0 | 11.3 | 5000.0 | 44.3 | 136.1 | (0.33, 0.61) |
| Ex. (82) | 2-28 | 5.0 | 11.4 | 5000.0 | 44.0 | 125.1 | (0.32, 0.61) |
| Ex. (83) | 2-29 | 5.4 | 9.7 | 5000.0 | 51.8 | 115.9 | (0.33, 0.60) |
| Ex. (84) | 2-30 | 5.2 | 9.6 | 5000.0 | 51.9 | 114.2 | (0.32, 0.61) |
| Ex. (85) | 2-31 | 5.2 | 10.5 | 5000.0 | 47.7 | 95.5 | (0.31, 0.61) |
| Ex. (86) | 2-32 | 5.3 | 9.6 | 5000.0 | 52.1 | 146.9 | (0.31, 0.61) |
| Ex. (87) | 2-39 | 5.0 | 11.0 | 5000.0 | 45.5 | 145.9 | (0.31, 0.61) |
| Ex. (88) | 2-40 | 5.3 | 11.1 | 5000.0 | 45.0 | 143.1 | (0.33, 0.61) |
| Ex. (89) | 3-1 | 5.1 | 10.7 | 5000.0 | 46.8 | 144.0 | (0.31, 0.60) |
| Ex. (90) | 3-2 | 5.4 | 10.1 | 5000.0 | 49.5 | 134.0 | (0.33, 0.61) |
| Ex. (91) | 3-3 | 5.4 | 10.0 | 5000.0 | 50.1 | 123.6 | (0.32, 0.61) |
| Ex. (92) | 3-5 | 5.3 | 10.3 | 5000.0 | 48.6 | 135.1 | (0.33, 0.60) |
| Ex. (93) | 3-6 | 5.4 | 10.9 | 5000.0 | 46.0 | 115.5 | (0.32, 0.61) |
| Ex. (94) | 3-7 | 5.1 | 10.6 | 5000.0 | 47.1 | 124.5 | (0.31, 0.61) |
| Ex. (95) | 3-9 | 5.1 | 11.0 | 5000.0 | 45.4 | 120.1 | (0.31, 0.61) |
| Ex. (96) | 3-10 | 5.4 | 10.0 | 5000.0 | 50.2 | 97.9 | (0.31, 0.60) |
| Ex. (97) | 3-11 | 5.2 | 9.6 | 5000.0 | 52.2 | 97.0 | (0.33, 0.61) |
| Ex. (98) | 3-13 | 5.3 | 9.5 | 5000.0 | 52.6 | 99.0 | (0.30, 0.60) |
| Ex. (99) | 3-14 | 5.4 | 11.5 | 5000.0 | 43.6 | 114.9 | (0.31, 0.61) |
| Ex. (100) | 3-15 | 5.3 | 11.0 | 5000.0 | 45.4 | 142.6 | (0.31, 0.61) |
| Ex. (101) | 3-17 | 5.2 | 10.2 | 5000.0 | 48.9 | 104.4 | (0.33, 0.61) |
| Ex. (102) | 3-18 | 5.1 | 9.9 | 5000.0 | 50.7 | 120.4 | (0.32, 0.61) |
| Ex. (103) | 3-19 | 5.4 | 10.1 | 5000.0 | 49.5 | 111.6 | (0.33, 0.61) |
| Ex. (104) | 3-21 | 5.1 | 9.9 | 5000.0 | 50.6 | 121.6 | (0.32, 0.61) |
| Ex. (105) | 3-22 | 5.4 | 9.2 | 5000.0 | 54.3 | 90.4 | (0.31, 0.60) |
| Ex. (106) | 3-23 | 5.0 | 9.2 | 5000.0 | 54.4 | 121.2 | (0.31, 0.61) |
| Ex. (107) | 3-24 | 5.4 | 10.8 | 5000.0 | 46.2 | 129.9 | (0.31, 0.60) |

TABLE 5-continued

|  | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex. (108) | 4-1 | 5.0 | 11.5 | 5000.0 | 43.5 | 123.2 | (0.33, 0.61) |
| Ex. (109) | 4-2 | 5.3 | 11.1 | 5000.0 | 44.9 | 134.4 | (0.30, 0.60) |
| Ex. (110) | 4-3 | 5.2 | 11.1 | 5000.0 | 45.2 | 94.7 | (0.31, 0.61) |
| Ex. (111) | 4-4 | 5.4 | 11.2 | 5000.0 | 44.5 | 144.2 | (0.31, 0.60) |
| Ex. (112) | 4-5 | 5.3 | 9.9 | 5000.0 | 50.8 | 115.9 | (0.33, 0.61) |
| Ex. (113) | 4-6 | 5.2 | 11.5 | 5000.0 | 43.7 | 108.0 | (0.32, 0.61) |
| Ex. (114) | 4-7 | 5.3 | 10.0 | 5000.0 | 50.1 | 119.9 | (0.33, 0.60) |
| Ex. (115) | 4-9 | 5.2 | 10.1 | 5000.0 | 49.7 | 126.1 | (0.31, 0.60) |
| Ex. (116) | 4-10 | 5.1 | 10.8 | 5000.0 | 46.3 | 109.9 | (0.31, 0.61) |
| Ex. (117) | 4-11 | 5.3 | 9.2 | 5000.0 | 54.2 | 146.3 | (0.31, 0.60) |
| Ex. (118) | 4-12 | 5.2 | 10.7 | 5000.0 | 46.8 | 133.4 | (0.33, 0.61) |
| Ex. (119) | 4-13 | 5.2 | 11.3 | 5000.0 | 44.1 | 112.3 | (0.30, 0.60) |
| Ex. (120) | 4-14 | 5.4 | 10.9 | 5000.0 | 45.9 | 92.2 | (0.31, 0.61) |
| Ex. (121) | 4-15 | 5.2 | 10.6 | 5000.0 | 47.3 | 132.5 | (0.31, 0.61) |
| Ex. (122) | 4-16 | 5.2 | 10.5 | 5000.0 | 47.5 | 108.4 | (0.33, 0.61) |
| Ex. (123) | 4-17 | 5.0 | 9.7 | 5000.0 | 51.6 | 95.8 | (0.32, 0.61) |
| Ex. (124) | 4-18 | 5.5 | 10.6 | 5000.0 | 47.1 | 142.4 | (0.33, 0.60) |
| Ex. (125) | 4-19 | 5.0 | 10.8 | 5000.0 | 46.5 | 128.3 | (0.32, 0.61) |
| Ex. (126) | 4-20 | 5.3 | 11.3 | 5000.0 | 44.1 | 132.5 | (0.31, 0.60) |
| Ex. (127) | 4-21 | 5.0 | 10.3 | 5000.0 | 48.7 | 106.4 | (0.31, 0.61) |
| Ex. (128) | 4-22 | 5.1 | 9.3 | 5000.0 | 54.0 | 95.5 | (0.31, 0.60) |
| Ex. (129) | 4-23 | 5.1 | 9.1 | 5000.0 | 54.8 | 114.4 | (0.33, 0.61) |
| Ex. (130) | 4-24 | 5.1 | 9.5 | 5000.0 | 52.4 | 101.6 | (0.30, 0.60) |
| Ex. (131) | 4-25 | 5.4 | 10.5 | 5000.0 | 47.7 | 99.2 | (0.31, 0.61) |
| Ex. (132) | 4-26 | 5.0 | 9.4 | 5000.0 | 53.4 | 118.4 | (0.31, 0.60) |
| Ex. (133) | 4-27 | 5.4 | 9.4 | 5000.0 | 53.1 | 136.7 | (0.33, 0.61) |
| Ex. (134) | 4-28 | 5.4 | 9.4 | 5000.0 | 53.1 | 126.4 | (0.32, 0.61) |
| Ex. (135) | 4-29 | 5.2 | 9.2 | 5000.0 | 54.1 | 106.6 | (0.33, 0.60) |
| Ex. (136) | 4-30 | 5.0 | 10.1 | 5000.0 | 49.4 | 112.6 | (0.32, 0.61) |
| Ex. (137) | 4-31 | 5.4 | 10.2 | 5000.0 | 48.9 | 140.3 | (0.31, 0.60) |
| Ex. (138) | 4-32 | 5.1 | 10.9 | 5000.0 | 45.8 | 92.3 | (0.31, 0.61) |
| Ex. (139) | 4-39 | 5.3 | 10.9 | 5000.0 | 45.9 | 91.8 | (0.31, 0.61) |
| Ex. (140) | 4-40 | 5.1 | 9.7 | 5000.0 | 51.7 | 112.5 | (0.33, 0.61) |
| Ex. (141) | 5-1 | 5.2 | 9.8 | 5000.0 | 50.8 | 136.7 | (0.31, 0.60) |
| Ex. (142) | 5-2 | 5.2 | 10.9 | 5000.0 | 46.0 | 115.6 | (0.33, 0.61) |
| Ex. (143) | 5-3 | 5.1 | 9.3 | 5000.0 | 53.6 | 110.2 | (0.32, 0.61) |
| Ex. (144) | 5-5 | 5.0 | 10.1 | 5000.0 | 49.6 | 99.5 | (0.33, 0.61) |
| Ex. (145) | 5-6 | 5.2 | 9.6 | 5000.0 | 51.9 | 100.4 | (0.32, 0.61) |
| Ex. (146) | 5-7 | 5.4 | 9.7 | 5000.0 | 51.6 | 106.8 | (0.31, 0.61) |
| Ex. (147) | 5-9 | 5.5 | 9.1 | 5000.0 | 54.9 | 128.6 | (0.31, 0.61) |
| Ex. (148) | 5-10 | 5.4 | 9.9 | 5000.0 | 50.6 | 136.1 | (0.31, 0.60) |
| Ex. (149) | 5-11 | 5.3 | 9.7 | 5000.0 | 51.4 | 149.2 | (0.33, 0.61) |
| Ex. (150) | 5-13 | 5.3 | 11.6 | 5000.0 | 43.1 | 111.0 | (0.30, 0.60) |
| Ex. (151) | 5-14 | 5.5 | 10.4 | 5000.0 | 48.1 | 136.1 | (0.31, 0.61) |
| Ex. (152) | 5-15 | 5.4 | 10.6 | 5000.0 | 47.0 | 134.0 | (0.31, 0.61) |
| Ex. (153) | 5-17 | 5.3 | 9.7 | 5000.0 | 51.7 | 125.5 | (0.33, 0.61) |
| Ex. (154) | 5-18 | 5.3 | 10.1 | 5000.0 | 49.3 | 112.2 | (0.32, 0.61) |
| Ex. (155) | 5-19 | 5.1 | 10.5 | 5000.0 | 47.6 | 91.0 | (0.33, 0.60) |
| Ex. (156) | 5-21 | 5.1 | 10.3 | 5000.0 | 48.4 | 94.0 | (0.32, 0.61) |
| Ex. (157) | 5-22 | 5.0 | 9.4 | 5000.0 | 53.4 | 119.4 | (0.31, 0.60) |
| Ex. (158) | 5-23 | 5.5 | 11.0 | 5000.0 | 45.6 | 104.0 | (0.31, 0.61) |
| Ex. (159) | 5-24 | 5.3 | 9.6 | 5000.0 | 52.0 | 135.5 | (0.31, 0.60) |
| Ex. (160) | 6-1 | 5.0 | 10.2 | 5000.0 | 49.0 | 142.0 | (0.33, 0.61) |
| Ex. (161) | 6-2 | 5.1 | 9.9 | 5000.0 | 50.5 | 123.9 | (0.30, 0.60) |
| Ex. (162) | 6-3 | 5.4 | 10.8 | 5000.0 | 46.4 | 116.5 | (0.31, 0.61) |
| Ex. (163) | 6-4 | 5.3 | 10.8 | 5000.0 | 46.2 | 92.2 | (0.31, 0.60) |
| Ex. (164) | 6-5 | 5.3 | 11.3 | 5000.0 | 44.3 | 138.4 | (0.33, 0.61) |
| Ex. (165) | 6-6 | 5.0 | 9.8 | 5000.0 | 51.2 | 128.9 | (0.32, 0.61) |
| Ex. (166) | 6-7 | 5.4 | 10.8 | 5000.0 | 46.3 | 100.2 | (0.33, 0.61) |
| Ex. (167) | 6-9 | 5.2 | 9.9 | 5000.0 | 50.7 | 134.9 | (0.31, 0.61) |
| Ex. (168) | 6-10 | 5.1 | 9.4 | 5000.0 | 53.0 | 148.8 | (0.31, 0.61) |
| Ex. (169) | 6-11 | 5.4 | 9.3 | 5000.0 | 53.8 | 106.7 | (0.31, 0.60) |
| Ex. (170) | 6-12 | 5.1 | 10.1 | 5000.0 | 49.4 | 149.0 | (0.33, 0.61) |
| Ex. (171) | 6-13 | 5.4 | 10.1 | 5000.0 | 49.5 | 133.3 | (0.30, 0.60) |
| Ex. (172) | 6-14 | 5.0 | 11.0 | 5000.0 | 45.5 | 147.1 | (0.31, 0.61) |
| Ex. (173) | 6-15 | 5.0 | 10.7 | 5000.0 | 46.6 | 93.4 | (0.31, 0.61) |
| Ex. (174) | 6-16 | 5.2 | 10.7 | 5000.0 | 46.9 | 94.8 | (0.33, 0.61) |
| Ex. (175) | 6-17 | 5.5 | 10.1 | 5000.0 | 49.6 | 130.7 | (0.32, 0.61) |
| Ex. (176) | 6-18 | 5.1 | 9.5 | 5000.0 | 52.7 | 145.0 | (0.33, 0.61) |
| Ex. (177) | 6-19 | 5.2 | 9.2 | 5000.0 | 54.6 | 127.1 | (0.32, 0.61) |
| Ex. (178) | 6-20 | 5.4 | 11.6 | 5000.0 | 43.2 | 137.9 | (0.31, 0.60) |
| Ex. (179) | 6-21 | 5.4 | 9.1 | 5000.0 | 54.8 | 142.9 | (0.31, 0.61) |
| Ex. (180) | 6-22 | 5.4 | 10.5 | 5000.0 | 47.8 | 116.6 | (0.31, 0.61) |
| Ex. (181) | 6-23 | 5.1 | 11.1 | 5000.0 | 45.0 | 125.9 | (0.33, 0.61) |
| Ex. (182) | 6-24 | 5.4 | 11.2 | 5000.0 | 44.6 | 107.2 | (0.30, 0.60) |
| Ex. (183) | 6-25 | 5.2 | 10.9 | 5000.0 | 46.0 | 104.6 | (0.31, 0.61) |
| Ex. (184) | 6-26 | 5.1 | 9.6 | 5000.0 | 52.1 | 133.2 | (0.31, 0.60) |

TABLE 5-continued

|  | Compound | Voltage (V) | Current Density (mA/cm$^2$) | Brightness (cd/m$^2$) | Efficiency (cd/A) | Lifetime T(95) | CIE (x, y) |
| --- | --- | --- | --- | --- | --- | --- | --- |
| Ex. (185) | 6-27 | 5.0 | 10.4 | 5000.0 | 48.0 | 112.5 | (0.33, 0.61) |
| Ex. (186) | 6-28 | 5.2 | 11.4 | 5000.0 | 43.8 | 130.6 | (0.32, 0.61) |
| Ex. (187) | 6-29 | 5.5 | 10.8 | 5000.0 | 46.3 | 101.5 | (0.33, 0.60) |
| Ex. (188) | 6-30 | 5.0 | 10.6 | 5000.0 | 47.0 | 115.1 | (0.32, 0.61) |
| Ex. (189) | 6-31 | 5.4 | 11.6 | 5000.0 | 43.2 | 109.1 | (0.31, 0.60) |
| Ex. (190) | 6-32 | 5.0 | 11.5 | 5000.0 | 43.6 | 125.1 | (0.31, 0.61) |
| Ex. (191) | 6-39 | 5.1 | 11.1 | 5000.0 | 44.9 | 94.6 | (0.31, 0.60) |
| Ex. (192) | 6-40 | 5.5 | 11.3 | 5000.0 | 44.1 | 117.5 | (0.33, 0.61) |

It can be seen from the results in Tables 4 and 5, above, that the OLEDs using the inventive compounds as the light-emitting host material (phosphorescent host material) showed the improved efficiency, lifespan and driving voltage, compared to the OLEDs using the comparative compounds A to F as the light-emitting host material.

That is, the OLEDs using the inventive compounds as the light-emitting host material showed the improved results, compared to the OLEDs using the comparative compound A being NPB or the comparative compounds B to F being the seven-membered ring. This result indicates that the electric properties depend on the hetero atom(s) forming the ring and the fused position: the OLED using the comparative compound F that is a seven-membered ring comprising N and S, among the comparative compounds, showed the improved results; however, the inventive compounds comprising N and S, like the comparative compounds, and having a different fused-position showed improved results, compared to the comparative compound F. This indicates that the properties of the compounds strongly depend on the kind of the hetero atom(s) forming the ring and the fused position.

[Example 193] Red Organic Light Emitting Diode (Emission-Auxiliary Layer)

Organic light emitting diodes (OLEDs) were fabricated according to a conventional method by using a compound of the present invention as an emission-auxiliary layer material First, an ITO layer (anode) was formed on a glass substrate, and a film of 2-TNATA was vacuum-deposited on the ITO layer to form a hole injection layer with a thickness of 60 nm. Subsequently, NPD was vacuum-deposited with a thickness of 60 nm on the hole injection layer to form a hole transport layer.

Subsequently, a film of the compound 1-24 of the present invention was vacuum-deposited on the hole transport layer to form a emission-auxiliary layer with a thickness of 20 nm.

a light emitting layer with a thickness of 30 nm was deposited on the emission-auxiliary layer by using the 4,4'-N,N'-dicarbazole-biphenyl (hereinafter abbreviated as "CBP") as a host material and (piq)$_2$Ir(acac) as a dopant material in a weight ratio of 95:5.

Next, a film of BAlq was vacuum-deposited with a thickness of 10 nm on the light emitting layer to form a hole blocking layer, and a film of Alq$_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 194] to [Example 255] Red Organic Light Emitting Diode (Emission-Auxiliary Layer)

The OLED was manufactured in the same manner as described in Test Example 193, except that any one of the compounds 2-13 to 2-32, 3-24, 4-13 to 4-32, 5-24, 6-13 to 6-32 of the present invention in the Table 6 below was used as the emission-auxiliary layer material, instead of the inventive compound 1-24.

Comparative Example 13

An OLED was manufactured in the same manner as described in Test Example 193, except not to form the emission-auxiliary layer.

Comparative Example 14

An OLED was manufactured in the same manner as described in Test Example 193, except that Comparative Compound B above was used as the emission-auxiliary layer material, instead of the inventive compound 1-24.

Comparative Example 15

An OLED was manufactured in the same manner as described in Test Example 193, except that Comparative Compound C above was used as the emission-auxiliary layer material, instead of the inventive compound 1-24.

Comparative Example 16

An OLED was manufactured in the same manner as described in Test Example 193, except that Comparative Compound D above was used as the emission-auxiliary layer material, instead of the inventive compound 1-24.

Comparative Example 17

An OLED was manufactured in the same manner as described in Test Example 193, except that Comparative Compound E above was used as the emission-auxiliary layer material, instead of the inventive compound 1-24.

Comparative Example 18

An OLED was manufactured in the same manner as described in Test Example 193, except that Comparative Compound F above was used as the emission-auxiliary layer material, instead of the inventive compound 1-24.

A forward bias DC voltage was applied to each of the OLEDs manufactured through Test Examples 193 to 255 and Comparative Example 13 to 18, and electro-luminescence (EL) characteristics of the OLED were measured by PR-650 (Photoresearch). Also, T95 life span was measured by life span measuring equipment (Mcscience) at a reference brightness of 2500 cd/m$^2$. Table 6 below shows evaluation results of OLEDs manufactured Test Examples and Comparative Examples.

TABLE 6

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Com. Ex (13) | — | 6.8 | 34.2 | 2500.0 | 7.3 | 51.6 | (0.66, 0.32) |
| Com. Ex (14) | Com. Com B | 6.8 | 27.6 | 2500.0 | 9.1 | 65.4 | (0.67, 0.32) |
| Com. Ex (15) | Com. Com C | 6.8 | 25.9 | 2500.0 | 9.6 | 53.9 | (0.66, 0.32) |
| Com. Ex (16) | Com. Com D | 6.9 | 26.8 | 2500.0 | 9.3 | 69.5 | (0.66, 0.33) |
| Com. Ex (17) | Com. Com E | 6.9 | 26.3 | 2500.0 | 9.5 | 71.0 | (0.65, 0.32) |
| Com. Ex (18) | Com. Com F | 7.0 | 25.1 | 2500.0 | 10.0 | 89.0 | (0.66, 0.32) |
| Ex. (193) | 1-24 | 6.8 | 13.2 | 2500.0 | 19.0 | 143.9 | (0.67, 0.32) |
| Ex. (194) | 2-13 | 6.8 | 16.4 | 2500.0 | 15.2 | 149.3 | (0.66, 0.32) |
| Ex. (195) | 2-14 | 6.8 | 12.6 | 2500.0 | 19.8 | 91.0 | (0.66, 0.32) |
| Ex. (196) | 2-15 | 6.9 | 13.4 | 2500.0 | 18.7 | 131.2 | (0.66, 0.33) |
| Ex. (197) | 2-16 | 6.9 | 14.9 | 2500.0 | 16.7 | 111.6 | (0.66, 0.32) |
| Ex. (198) | 2-17 | 7.0 | 13.2 | 2500.0 | 18.9 | 92.1 | (0.65, 0.32) |
| Ex. (199) | 2-18 | 6.9 | 13.0 | 2500.0 | 19.2 | 103.6 | (0.66, 0.32) |
| Ex. (200) | 2-19 | 7.0 | 12.8 | 2500.0 | 19.5 | 103.6 | (0.66, 0.32) |
| Ex. (201) | 2-20 | 6.9 | 13.1 | 2500.0 | 19.0 | 91.8 | (0.67, 0.32) |
| Ex. (202) | 2-21 | 6.8 | 16.2 | 2500.0 | 15.5 | 111.4 | (0.66, 0.32) |
| Ex. (203) | 2-22 | 6.9 | 15.2 | 2500.0 | 16.5 | 115.7 | (0.67, 0.32) |
| Ex. (204) | 2-23 | 6.8 | 14.7 | 2500.0 | 17.0 | 142.0 | (0.66, 0.32) |
| Ex. (205) | 2-24 | 6.9 | 12.6 | 2500.0 | 19.9 | 135.0 | (0.66, 0.32) |
| Ex. (206) | 2-25 | 6.9 | 15.8 | 2500.0 | 15.8 | 94.6 | (0.66, 0.33) |
| Ex. (207) | 2-26 | 6.9 | 15.2 | 2500.0 | 16.5 | 98.8 | (0.66, 0.32) |
| Ex. (208) | 2-27 | 7.0 | 12.8 | 2500.0 | 19.5 | 131.6 | (0.65, 0.32) |
| Ex. (209) | 2-28 | 6.9 | 13.7 | 2500.0 | 18.2 | 141.9 | (0.66, 0.32) |
| Ex. (210) | 2-2) | 6.9 | 12.9 | 2500.0 | 19.4 | 97.5 | (0.66, 0.32) |
| Ex. (211) | 2-30 | 6.9 | 15.7 | 2500.0 | 16.0 | 124.4 | (0.67, 0.32) |
| Ex. (212) | 2-31 | 6.8 | 14.4 | 2500.0 | 17.4 | 97.8 | (0.66, 0.32) |
| Ex. (213) | 2-32 | 6.9 | 14.0 | 2500.0 | 17.9 | 137.0 | (0.67, 0.32) |
| Ex. (214) | 3-24 | 6.9 | 15.3 | 2500.0 | 16.3 | 98.2 | (0.66, 0.32) |
| Ex. (215) | 4-13 | 6.9 | 14.3 | 2500.0 | 17.4 | 103.3 | (0.66, 0.32) |
| Ex. (216) | 4-14 | 6.9 | 14.0 | 2500.0 | 17.8 | 116.5 | (0.66, 0.33) |
| Ex. (217) | 4-15 | 6.9 | 13.7 | 2500.0 | 18.3 | 92.8 | (0.66, 0.32) |
| Ex. (218) | 4-16 | 6.9 | 12.7 | 2500.0 | 19.7 | 142.7 | (0.65, 0.32) |
| Ex. (219) | 4-17 | 6.8 | 16.5 | 2500.0 | 15.1 | 147.2 | (0.66, 0.32) |
| Ex. (220) | 4-18 | 6.9 | 16.2 | 2500.0 | 15.4 | 141.6 | (0.66, 0.32) |
| Ex. (221) | 4-19 | 6.9 | 16.0 | 2500.0 | 15.6 | 126.5 | (0.67, 0.32) |
| Ex. (222) | 4-20 | 6.9 | 13.4 | 2500.0 | 18.7 | 145.7 | (0.66, 0.32) |
| Ex. (223) | 4-21 | 6.9 | 16.3 | 2500.0 | 15.4 | 134.4 | (0.67, 0.32) |
| Ex. (224) | 4-22 | 6.9 | 14.7 | 2500.0 | 17.0 | 142.4 | (0.66, 0.32) |
| Ex. (225) | 4-23 | 7.0 | 13.6 | 2500.0 | 18.3 | 117.3 | (0.67, 0.32) |
| Ex. (226) | 4-24 | 6.9 | 14.7 | 2500.0 | 17.0 | 92.2 | (0.66, 0.32) |
| Ex. (227) | 4-25 | 6.9 | 16.0 | 2500.0 | 15.6 | 98.5 | (0.66, 0.33) |
| Ex. (228) | 4-26 | 7.0 | 14.8 | 2500.0 | 16.9 | 136.4 | (0.65, 0.32) |
| Ex. (229) | 4-27 | 6.8 | 15.8 | 2500.0 | 15.8 | 135.9 | (0.66, 0.32) |
| Ex. (230) | 4-28 | 6.9 | 13.2 | 2500.0 | 18.9 | 99.2 | (0.67, 0.32) |
| Ex. (231) | 4-29 | 6.9 | 16.5 | 2500.0 | 15.1 | 121.3 | (0.66, 0.32) |
| Ex. (232) | 4-30 | 6.8 | 15.0 | 2500.0 | 16.7 | 132.9 | (0.66, 0.32) |
| Ex. (233) | 4-31 | 6.9 | 13.1 | 2500.0 | 19.0 | 91.5 | (0.66, 0.33) |
| Ex. (234) | 4-32 | 6.9 | 14.6 | 2500.0 | 17.2 | 108.5 | (0.66, 0.32) |
| Ex. (235) | 5-24 | 6.9 | 12.5 | 2500.0 | 20.0 | 135.0 | (0.65, 0.32) |
| Ex. (236) | 6-13 | 6.9 | 16.4 | 2500.0 | 15.2 | 133.6 | (0.66, 0.32) |
| Ex. (237) | 6-14 | 6.9 | 13.9 | 2500.0 | 18.0 | 135.7 | (0.66, 0.32) |
| Ex. (238) | 6-15 | 7.0 | 13.4 | 2500.0 | 18.7 | 101.7 | (0.67, 0.32) |
| Ex. (239) | 6-16 | 6.8 | 13.6 | 2500.0 | 18.3 | 91.5 | (0.66, 0.32) |
| Ex. (240) | 6-17 | 6.9 | 14.1 | 2500.0 | 17.7 | 92.0 | (0.67, 0.32) |
| Ex. (241) | 6-18 | 6.9 | 12.9 | 2500.0 | 19.4 | 98.4 | (0.66, 0.32) |
| Ex. (242) | 6-19 | 7.0 | 13.4 | 2500.0 | 18.6 | 113.3 | (0.66, 0.32) |
| Ex. (243) | 6-20 | 6.9 | 13.1 | 2500.0 | 19.1 | 93.0 | (0.66, 0.33) |
| Ex. (244) | 6-21 | 7.0 | 13.2 | 2500.0 | 18.9 | 109.9 | (0.66, 0.32) |
| Ex. (245) | 6-22 | 6.8 | 15.4 | 2500.0 | 16.2 | 100.8 | (0.65, 0.32) |
| Ex. (246) | 6-23 | 6.8 | 15.4 | 2500.0 | 16.2 | 112.3 | (0.66, 0.32) |
| Ex. (247) | 6-24 | 6.9 | 13.3 | 2500.0 | 18.7 | 96.1 | (0.66, 0.32) |
| Ex. (248) | 6-25 | 7.0 | 13.3 | 2500.0 | 18.8 | 112.5 | (0.67, 0.32) |
| Ex. (249) | 6-26 | 7.0 | 13.6 | 2500.0 | 18.4 | 123.4 | (0.66, 0.32) |
| Ex. (250) | 6-27 | 6.9 | 14.6 | 2500.0 | 17.2 | 121.0 | (0.67, 0.32) |
| Ex. (251) | 6-28 | 6.9 | 16.4 | 2500.0 | 15.3 | 97.2 | (0.66, 0.32) |
| Ex. (252) | 6-29 | 7.0 | 13.8 | 2500.0 | 18.1 | 121.6 | (0.66, 0.32) |
| Ex. (253) | 6-30 | 7.0 | 16.5 | 2500.0 | 15.1 | 109.5 | (0.66, 0.33) |
| Ex. (254) | 6-31 | 6.9 | 16.1 | 2500.0 | 15.6 | 132.7 | (0.66, 0.32) |
| Ex. (255) | 6-32 | 6.9 | 14.9 | 2500.0 | 16.8 | 113.1 | (0.65, 0.32) |

[Example 256] Green Organic Light Emitting Diode (an Emission-Auxiliary Layer)

Organic light emitting diodes (OLEDs) were fabricated according to a conventional method by using a compound of the present invention as an emission-auxiliary layer material First, an ITO layer (anode) was formed on a glass substrate, and a film of 2-TNATA was vacuum-deposited on the ITO layer to form a hole injection layer with a thickness of 60 nm. Subsequently, NPD was vacuum-deposited with a thickness of 60 nm on the hole injection layer to form a hole transport layer.

Subsequently, a film of the compound 1-24 of the present invention was vacuum-deposited on the hole transport layer to form a emission-auxiliary layer with a thickness of 20 nm. A light emitting layer with a thickness of 30 nm was deposited on the emission-auxiliary layer by using the CBP as a host material and Ir(ppy)$_3$ as a dopant material in a weight ratio of 95:5.

Next, a film of BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 257] to [Example 318] Green Organic Light Emitting Diode (an Emission-Auxiliary Layer)

The OLED was manufactured in the same manner as described in Test Example 256, except that any one of the compounds 2-13 to 2-32, 3-24, 4-13 to 4-32, 5-24, 6-13 to 6-32 of the present invention in the Table 7 below was used as the emission-auxiliary layer material, instead of the inventive compound 1-24.

Comparative Example 19

An OLED was manufactured in the same manner as described in Test Example 256, except not to form the emission-auxiliary layer.

Comparative Example 20

An OLED was manufactured in the same manner as described in Test Example 256, except that Comparative Compound B above was used as the emission-auxiliary layer material, instead of the inventive compound 1-24.

Comparative Example 21

An OLED was manufactured in the same manner as described in Test Example 256, except that Comparative Compound C above was used as the emission-auxiliary layer material, instead of the inventive compound 1-24.

Comparative Example 22

An OLED was manufactured in the same manner as described in Test Example 256, except that Comparative Compound D above was used as the emission-auxiliary layer material, instead of the inventive compound 1-24.

Comparative Example 23

An OLED was manufactured in the same manner as described in Test Example 256, except that Comparative Compound E above was used as the emission-auxiliary layer material, instead of the inventive compound 1-24.

Comparative Example 24

An OLED was manufactured in the same manner as described in Test Example 256, except that Comparative Compound F above was used as the emission-auxiliary layer material, instead of the inventive compound 1-24.

A forward bias DC voltage was applied to each of the OLEDs manufactured through Test Examples 256 to 318 and Comparative Example 19 to 24, and electro-luminescence (EL) characteristics of the OLED were measured by PR-650 (Photoresearch). Also, T95 life span was measured by life span measuring equipment (Mcscience) at a reference brightness of 5000 cd/m$^2$. Table 7 below shows evaluation results of OLEDs manufactured Test Examples and Comparative Examples.

TABLE 7

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Com. Ex (19) | — | 6.5 | 20.0 | 5000.0 | 25.0 | 73.8 | (0.31, 0.60) |
| Com. Ex (20) | Com. Com B | 6.8 | 13.0 | 5000.0 | 38.4 | 80.4 | (0.31, 0.61) |
| Com. Ex (21) | Com. Com C | 7.0 | 13.9 | 5000.0 | 36.0 | 85.3 | (0.31, 0.60) |
| Com. Ex (22) | Com. Com D | 6.7 | 13.6 | 5000.0 | 36.9 | 85.5 | (0.33, 0.61) |
| Com. Ex (23) | Com. Com E | 7.0 | 13.0 | 5000.0 | 38.5 | 84.3 | (0.30, 0.60) |
| Com. Ex (24) | Com. Com F | 6.6 | 13.4 | 5000.0 | 37.3 | 83.6 | (0.31, 0.61) |
| Ex. (256) | 1-24 | 6.8 | 9.1 | 5000.0 | 54.7 | 111.5 | (0.31, 0.60) |
| Ex. (257) | 2-13 | 6.8 | 11.1 | 5000.0 | 45.1 | 147.6 | (0.33, 0.61) |
| Ex. (258) | 2-14 | 6.8 | 10.7 | 5000.0 | 46.7 | 129.7 | (0.32, 0.61) |
| Ex. (259) | 2-15 | 6.9 | 9.5 | 5000.0 | 52.9 | 137.2 | (0.33, 0.60) |
| Ex. (260) | 2-16 | 6.6 | 10.9 | 5000.0 | 46.0 | 114.4 | (0.32, 0.61) |
| Ex. (261) | 2-17 | 6.7 | 10.5 | 5000.0 | 47.8 | 125.5 | (0.31, 0.60) |
| Ex. (262) | 2-18 | 6.6 | 10.1 | 5000.0 | 49.5 | 111.8 | (0.31, 0.61) |
| Ex. (263) | 2-19 | 6.6 | 9.7 | 5000.0 | 51.6 | 137.3 | (0.31, 0.60) |
| Ex. (264) | 2-20 | 6.8 | 9.5 | 5000.0 | 52.4 | 108.6 | (0.33, 0.61) |
| Ex. (265) | 2-21 | 6.5 | 11.0 | 5000.0 | 45.7 | 144.1 | (0.30, 0.60) |
| Ex. (266) | 2-22 | 7.0 | 10.4 | 5000.0 | 48.3 | 145.5 | (0.31, 0.61) |
| Ex. (267) | 2-23 | 6.6 | 10.3 | 5000.0 | 48.5 | 147.3 | (0.31, 0.60) |
| Ex. (268) | 2-24 | 6.6 | 9.1 | 5000.0 | 55.0 | 142.1 | (0.33, 0.61) |
| Ex. (269) | 2-25 | 6.8 | 10.5 | 5000.0 | 47.7 | 92.0 | (0.32, 0.61) |
| Ex. (270) | 2-26 | 6.6 | 10.1 | 5000.0 | 49.5 | 96.7 | (0.33, 0.60) |

TABLE 7-continued

|  | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex. (271) | 2-27 | 6.9 | 9.2 | 5000.0 | 54.6 | 144.3 | (0.32, 0.61) |
| Ex. (272) | 2-28 | 6.9 | 10.0 | 5000.0 | 49.9 | 103.5 | (0.31, 0.60) |
| Ex. (273) | 2-29 | 6.7 | 9.4 | 5000.0 | 53.2 | 93.1 | (0.31, 0.61) |
| Ex. (274) | 2-30 | 6.6 | 11.0 | 5000.0 | 45.6 | 135.7 | (0.31, 0.60) |
| Ex. (275) | 2-31 | 6.8 | 10.0 | 5000.0 | 50.2 | 108.4 | (0.33, 0.61) |
| Ex. (276) | 2-32 | 7.0 | 10.8 | 5000.0 | 46.4 | 149.4 | (0.30, 0.60) |
| Ex. (277) | 3-24 | 6.8 | 9.9 | 5000.0 | 50.5 | 120.4 | (0.31, 0.61) |
| Ex. (278) | 4-13 | 7.0 | 9.2 | 5000.0 | 54.6 | 117.8 | (0.31, 0.60) |
| Ex. (279) | 4-14 | 6.5 | 9.1 | 5000.0 | 54.7 | 105.8 | (0.33, 0.61) |
| Ex. (280) | 4-15 | 6.9 | 10.8 | 5000.0 | 46.2 | 125.1 | (0.32, 0.61) |
| Ex. (281) | 4-16 | 6.6 | 11.0 | 5000.0 | 45.5 | 116.9 | (0.33, 0.60) |
| Ex. (282) | 4-17 | 6.9 | 10.6 | 5000.0 | 47.3 | 90.8 | (0.31, 0.60) |
| Ex. (283) | 4-18 | 6.9 | 9.1 | 5000.0 | 54.9 | 140.7 | (0.31, 0.61) |
| Ex. (284) | 4-19 | 6.8 | 10.6 | 5000.0 | 47.1 | 141.8 | (0.31, 0.60) |
| Ex. (285) | 4-20 | 6.9 | 11.1 | 5000.0 | 45.2 | 134.9 | (0.33, 0.61) |
| Ex. (286) | 4-21 | 6.9 | 9.7 | 5000.0 | 51.5 | 110.7 | (0.30, 0.60) |
| Ex. (287) | 4-22 | 7.0 | 9.8 | 5000.0 | 51.1 | 93.7 | (0.31, 0.61) |
| Ex. (288) | 4-23 | 6.8 | 9.5 | 5000.0 | 52.9 | 105.9 | (0.31, 0.60) |
| Ex. (289) | 4-24 | 7.0 | 9.7 | 5000.0 | 51.5 | 110.7 | (0.33, 0.61) |
| Ex. (290) | 4-25 | 6.9 | 9.3 | 5000.0 | 53.8 | 122.4 | (0.32, 0.61) |
| Ex. (291) | 4-26 | 6.8 | 9.8 | 5000.0 | 51.0 | 94.4 | (0.33, 0.60) |
| Ex. (292) | 4-27 | 6.9 | 10.5 | 5000.0 | 47.6 | 102.8 | (0.32, 0.61) |
| Ex. (293) | 4-28 | 6.6 | 9.4 | 5000.0 | 53.4 | 98.7 | (0.31, 0.60) |
| Ex. (294) | 4-29 | 6.6 | 10.9 | 5000.0 | 45.7 | 129.0 | (0.31, 0.61) |
| Ex. (295) | 4-30 | 6.6 | 10.2 | 5000.0 | 48.8 | 125.1 | (0.31, 0.60) |
| Ex. (296) | 4-31 | 6.7 | 10.5 | 5000.0 | 47.4 | 133.2 | (0.33, 0.61) |
| Ex. (297) | 4-32 | 6.6 | 11.1 | 5000.0 | 45.0 | 124.7 | (0.30, 0.60) |
| Ex. (298) | 5-24 | 6.5 | 9.1 | 5000.0 | 54.8 | 92.3 | (0.31, 0.61) |
| Ex. (299) | 6-13 | 7.0 | 9.8 | 5000.0 | 50.9 | 91.4 | (0.31, 0.60) |
| Ex. (300) | 6-14 | 6.6 | 9.5 | 5000.0 | 52.8 | 119.5 | (0.33, 0.61) |
| Ex. (301) | 6-15 | 6.5 | 11.0 | 5000.0 | 45.4 | 129.4 | (0.32, 0.61) |
| Ex. (302) | 6-16 | 7.0 | 9.6 | 5000.0 | 52.3 | 132.2 | (0.33, 0.60) |
| Ex. (303) | 6-17 | 6.6 | 9.4 | 5000.0 | 53.4 | 118.4 | (0.32, 0.61) |
| Ex. (304) | 6-18 | 7.0 | 9.5 | 5000.0 | 52.5 | 92.7 | (0.31, 0.60) |
| Ex. (305) | 6-19) | 6.8 | 10.4 | 5000.0 | 48.3 | 129.7 | (0.31, 0.61) |
| Ex. (306) | 6-20 | 7.0 | 10.5 | 5000.0 | 47.5 | 131.8 | (0.31, 0.60) |
| Ex. (307) | 6-21 | 6.8 | 10.2 | 5000.0 | 49.1 | 148.2 | (0.33, 0.61) |
| Ex. (308) | 6-22 | 6.9 | 10.6 | 5000.0 | 47.1 | 105.1 | (0.31, 0.60) |
| Ex. (309) | 6-23 | 7.0 | 10.1 | 5000.0 | 49.7 | 114.0 | (0.33, 0.61) |
| Ex. (310) | 6-24 | 6.5 | 10.2 | 5000.0 | 48.9 | 134.5 | (0.32, 0.61) |
| Ex. (311) | 6-25 | 6.5 | 11.1 | 5000.0 | 45.2 | 142.9 | (0.33, 0.60) |
| Ex. (312) | 6-26 | 6.9 | 9.5 | 5000.0 | 52.8 | 108.2 | (0.32, 0.61) |
| Ex. (313) | 6-27 | 6.9 | 11.0 | 5000.0 | 45.3 | 98.4 | (0.31, 0.60) |
| Ex. (314) | 6-28 | 6.6 | 9.5 | 5000.0 | 52.7 | 109.0 | (0.31, 0.61) |
| Ex. (315) | 6-29 | 6.8 | 11.0 | 5000.0 | 45.4 | 143.0 | (0.31, 0.60) |
| Ex. (316) | 6-30 | 6.7 | 10.1 | 5000.0 | 49.3 | 149.2 | (0.33, 0.61) |
| Ex. (317) | 6-31 | 6.8 | 10.1 | 5000.0 | 49.4 | 125.0 | (0.30, 0.60) |
| Ex. (318) | 6-32 | 6.8 | 10.0 | 5000.0 | 50.2 | 136.8 | (0.31, 0.61) |

It can be seen from the resulting data in Tables 6 and 7, above, that the efficiency and lifespan of the OLEDs having the inventive compounds as the material of the emission-auxiliary layer were remarkably improved, compared to the OLEDs not having the emission-auxiliary layer, or the comparative compounds B to F.

The driving voltage of the OLED comprising the emission-auxiliary layer was equal to or slightly higher than the OLED not having the emission-auxiliary layer, but the OLED comprising the emission-auxiliary layer showed improvement in efficiency and lifespan. That is, the inventive compounds showed improved efficiency and lifespan, compared to the comparative compounds B to F. It is believed this is because the inventive compound has the high T1 energy level and the deep HOMO energy level when it is used alone as the material of the emission-auxiliary layer, and as a result, the holes and the electrons achieve the charge balance, and thus the light emission is made efficiently in the light emitting layer, not in the interface of the hole transport layer, and thus the efficiency and lifespan are improved.

Further, as explained in Tables 4 and 5, the electric properties of OLEDs are different depending on the kind of the heteroatom and the fused position even in a similar seven-membered ring compound, which suggests that the properties of the compounds remarkably depend on the kind of the atom(s) in the heterocyclic ring and the fused position.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1:

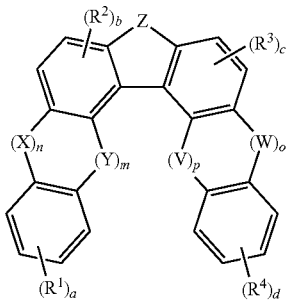

[Formula 1]

wherein Z is S or N(R$^5$),

X, Y, V and W are each independently N(R$^6$), S or O, with the proviso that: where Z is N(R$^5$) at least one of, but not all of, X, Y, V and W, is N(R$^6$), where Z is S, at least two of X, Y, V and W are N(R$^6$), and where n=o=0 (zero), X and W are each a single bond and at least one of Y and V is N(R$^6$) where Z is N(R$^5$) and both Y and V are N(R$^6$) where Z is S, m, n, o and p are each independently an integer of 0 or 1, with the proviso that m+n is 1 or more and o+p is 1 or more, R$^5$ and R$^6$ are each independently selected from the group consisting of a C$_6$-C$_{60}$ aryl group; a fluorenylene group; a C$_2$-C$_{60}$ heterocyclic group containing at least one heteroatom selected from the group consisting of O, N, S, Si, and P; a fused ring group formed by a C$_3$-C$_{60}$ aliphatic ring with a C$_6$-C$_{60}$ aromatic ring; a C$_1$-C$_{50}$ alkyl group; a C$_2$-C$_{20}$ alkenyl group; a C$_2$-C$_{20}$ alkynyl group; a C$_1$-C$_{30}$ alkoxy group; a C$_6$-C$_{30}$ aryloxy group; -L'-N(Ar$^1$) (Ar$^2$); and a combination thereof, R$^1$ to R$^4$ are each independently selected from the group consisting of deuterium; halogen; a C$_6$-C$_{60}$ aryl group; a fluorenyl group; a C$_2$-C$_{60}$ heterocyclic group containing at least one heteroatom selected from the group consisting of O, N, S, Si, and P; a fused ring group formed by a C$_3$-C$_{60}$ aliphatic ring with a C$_6$-C$_{60}$ aromatic ring; a C$_1$-C$_{50}$ alkyl group; a C$_2$-C$_{20}$ alkenyl group; a C$_2$-C$_{20}$ alkynyl group; a C$_1$-C$_{30}$ alkoxy group; a C$_6$-C$_{30}$ aryloxy group; -L'-N(Ar$^1$) (Ar$^2$); and a combination thereof, a and d are each an integer of 0 to 4, and b and c are each an integer of 0 to 2, wherein the plurality of R$^1$, R$^2$, R$^3$ and R$^4$ are each identical or different when a, b, c and d are each 2 or more, L' is selected from the group consisting of a single bond; a C$_6$-C$_{60}$ arylene group; a fluorenylene group; a fused ring group formed by a C$_3$-C$_{60}$ aliphatic ring with a C$_6$-C$_{60}$ aromatic ring; a C$_2$-C$_{60}$ heterocyclic group containing at least one heteroatom selected from the group consisting of O, N, S, Si, and P; and a combination thereof, Ar$^1$ and Ar$^2$ are each independently selected from the group consisting of a C$_6$-C$_{60}$ aryl group; a fluorenyl group; a fused ring group formed by a C$_3$-C$_{60}$ aliphatic ring with a C$_6$-C$_{60}$ aromatic ring; a C$_2$-C$_{60}$ heterocyclic group containing at least one heteroatom selected from the group consisting of O, N, S, Si, and P; and a combination thereof, wherein L' may be optionally substituted by one or more substituents selected from the group consisting of deuterium; halogen; a silane group; a siloxane group; a boron group; a germanium group; a cyano group; a nitro group; a C$_1$-C$_{20}$ alkylthio group; a C$_1$-C$_{20}$ alkoxy group; a C$_1$-C$_{20}$ alkyl group; a C$_2$-C$_{20}$ alkenyl group; a C$_2$-C$_{20}$ alkynyl group; a C$_6$-C$_{20}$ aryl group; a C$_6$-C$_{20}$ aryl group substituted with deuterium; a fluorenyl group; a C$_2$-C$_{20}$ heterocyclic group containing at least one heteroatom selected from the group consisting of O, N, S, Si, and P; a C$_3$-C$_{20}$ cycloalkyl group; a C$_7$-C$_{20}$ arylalkyl group; and a C$_8$-C$_{20}$ arylalkenyl group, and where R$^1$ to R$^6$, Ar$^1$ and Ar$^2$ are the aryl, fluorenyl, heterocyclic ring or fused ring, and where R$^5$ and R$^6$ are the alkyl, alkenyl, alkynyl, alkoxy or aryloxy, each of the R$^1$ to R$^6$, Ar$^1$, Ar$^2$, R$^5$ and R$^6$ may be optionally substituted with one or more substituents selected from the group consisting of deuterium; halogen; a silane group; a siloxane group; a boron group; a germanium group; a cyano group; a nitro group; a C$_1$-C$_{20}$ alkylthio group; a C$_1$-C$_{20}$ alkoxy group; a C$_1$-C$_{20}$ alkyl group; a C$_2$-C$_{20}$ alkenyl group; a C$_2$-C$_{20}$ alkynyl group; a C$_6$-C$_{20}$ aryl group; a C$_6$-C$_{20}$ aryl group substituted with deuterium; a fluorenyl group; a C$_2$-C$_{20}$ heterocyclic group containing at least one heteroatom selected from the group consisting of O, N, S, Si, and P; a C$_3$-C$_{20}$ cycloalkyl group; a C$_7$-C$_{20}$ arylalkyl group; and a C$_8$-C$_{20}$ arylalkenyl group.

2. The compound of claim 1, wherein Formula 1 is represented by one of Formulas 2 to 4:

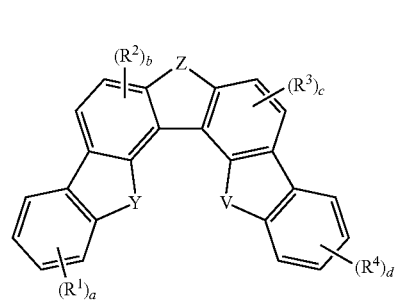

[Formula 2]

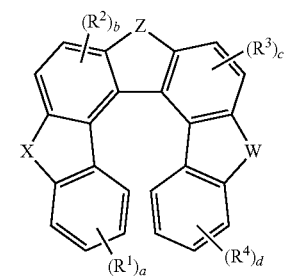

[Formula 3]

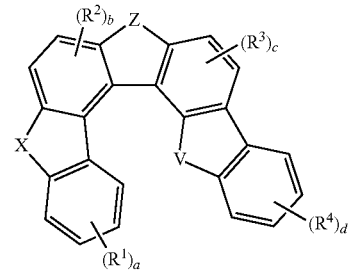

[Formula 4]

wherein V, W, X, Y, Z, R¹ to R⁴, a, b, c and d are the same as defined in claim 1.
3. The compound of claim 1 selected from the group consisting of:
1-1
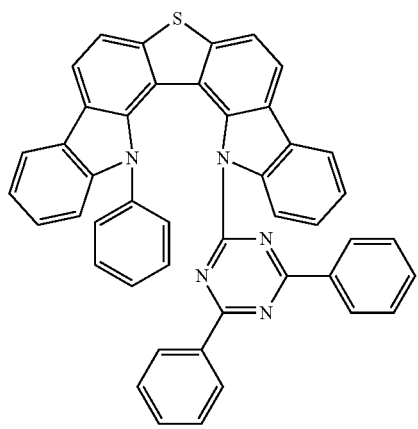
1-2
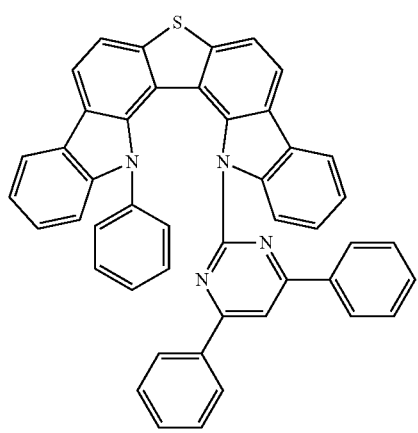
1-3
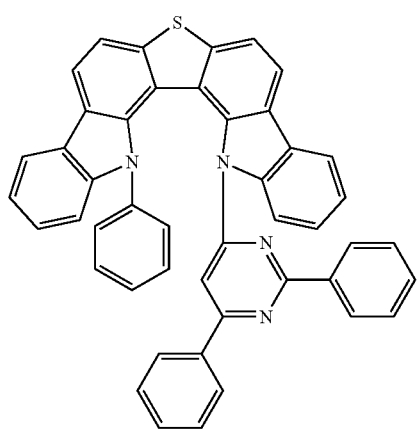
1-4
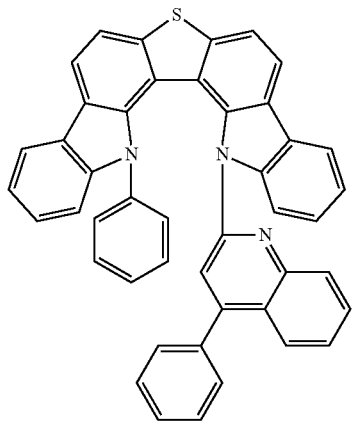
1-5
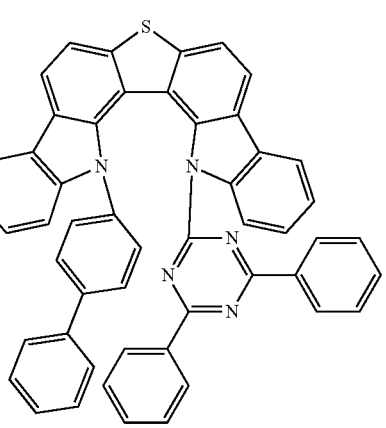
1-6
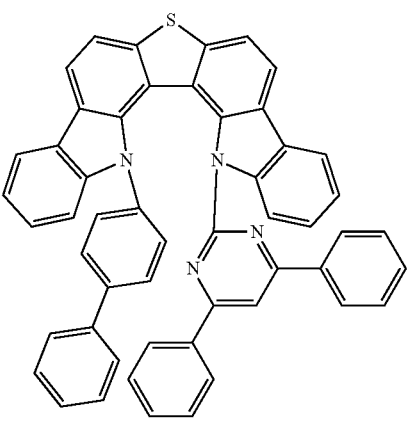

1-7
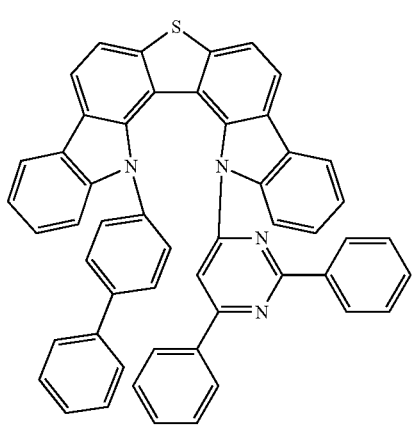
1-8
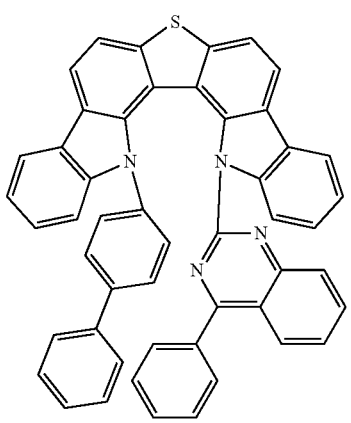
1-9
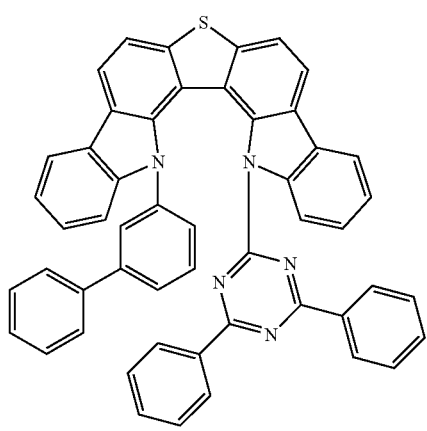
1-10
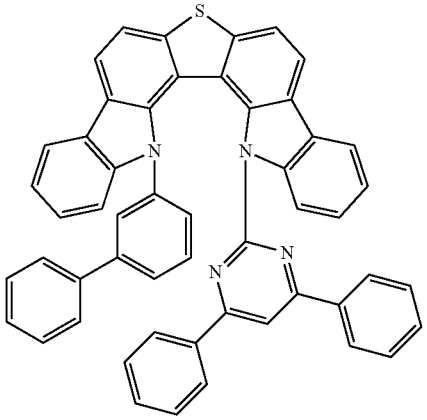
1-11
1-12
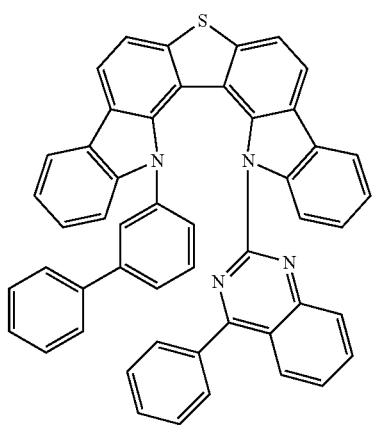

-continued
1-13
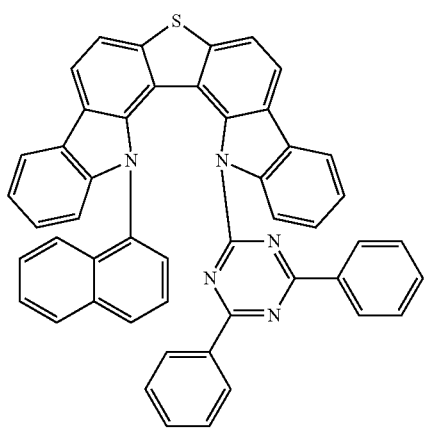
1-14
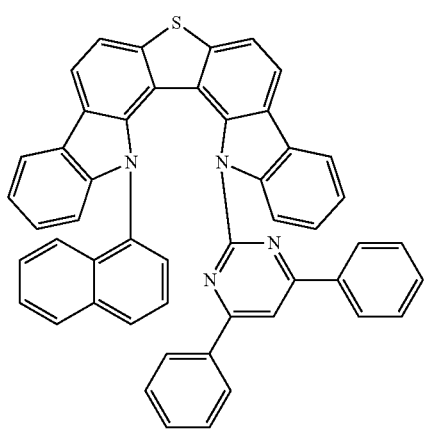
1-15
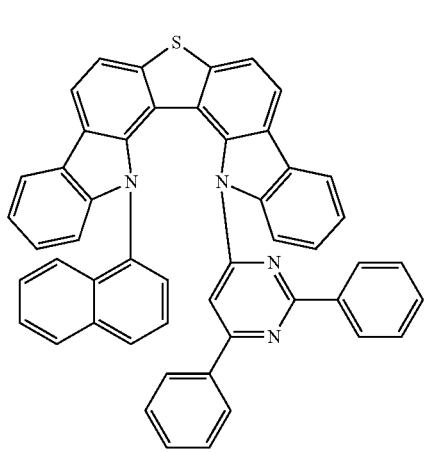
-continued
1-16
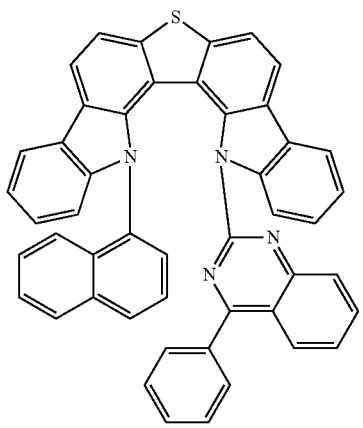
1-17
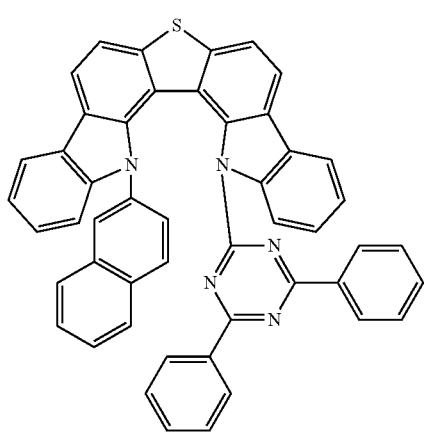
1-18
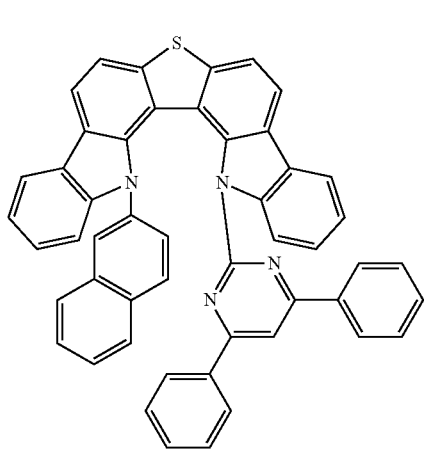

1-19
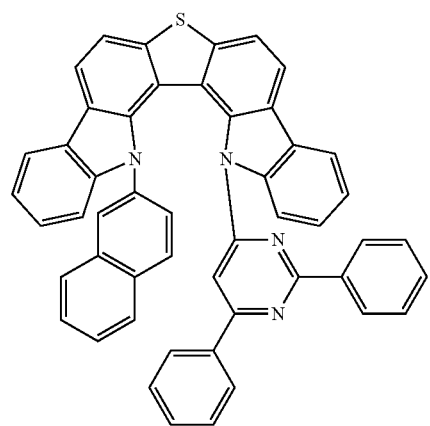
1-20
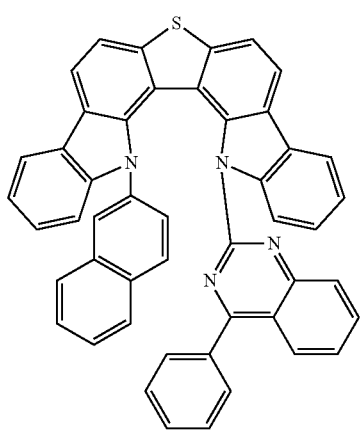
1-21
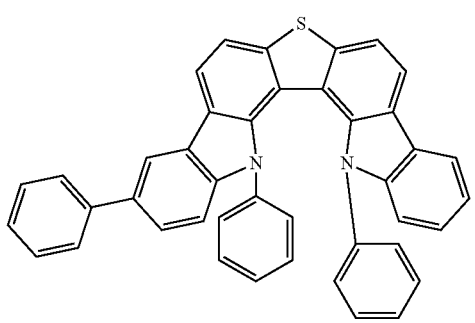
1-22
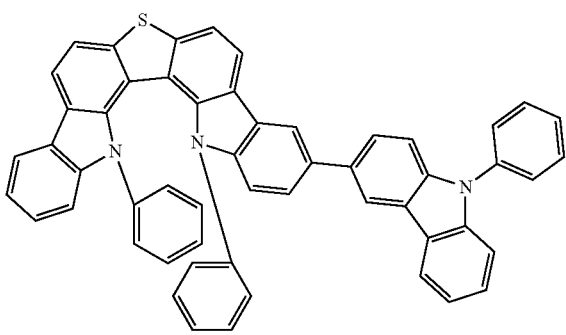
1-23
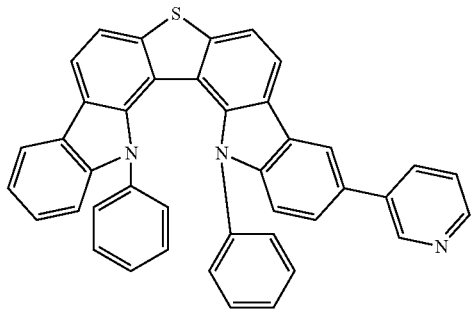
1-24
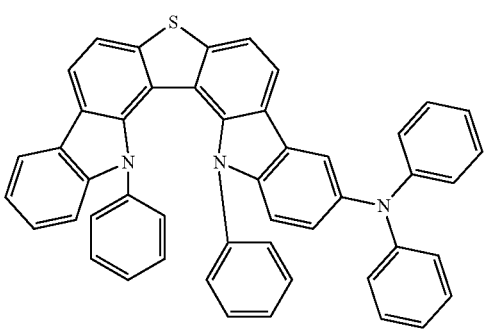
2-1
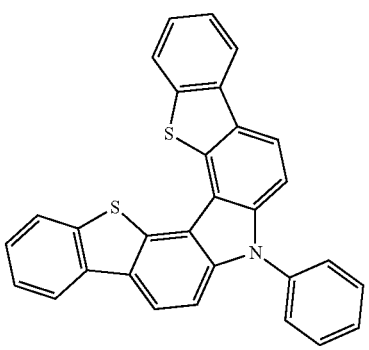
2-2
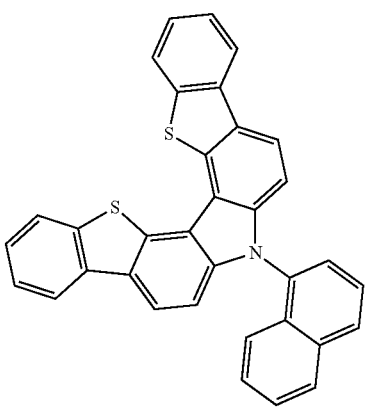

-continued
2-3
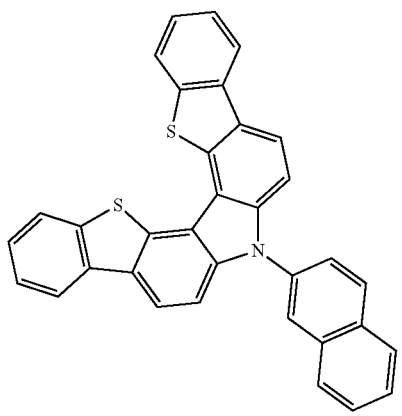
2-6
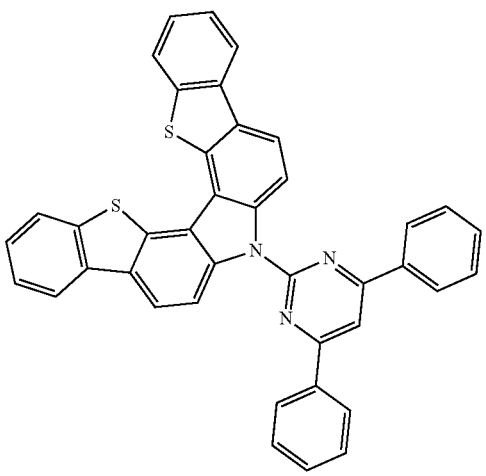
2-4
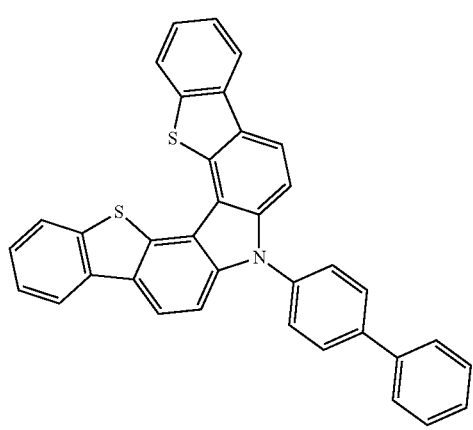
2-7
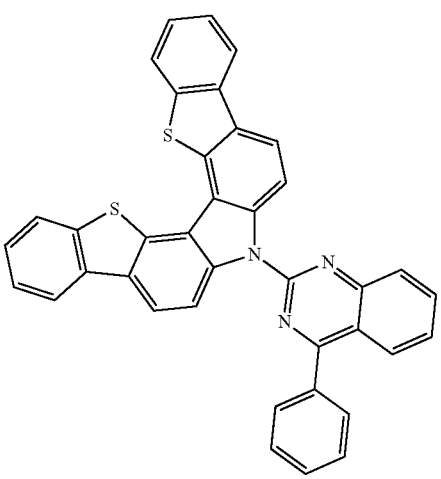
2-5
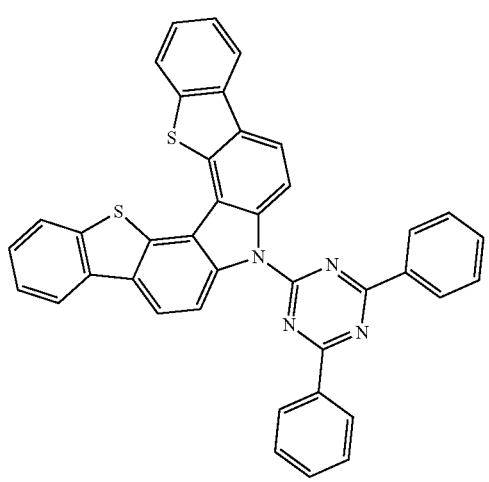
2-8

2-9
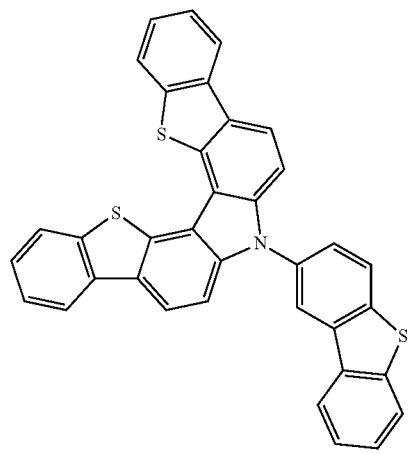
2-10
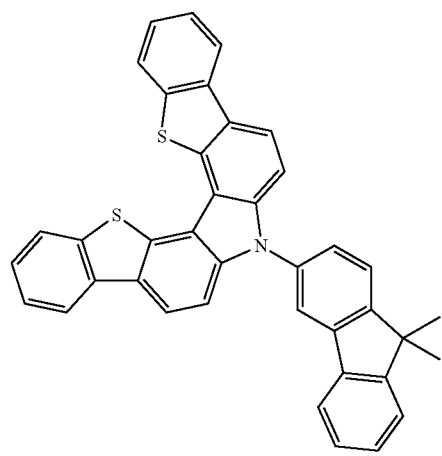
2-11
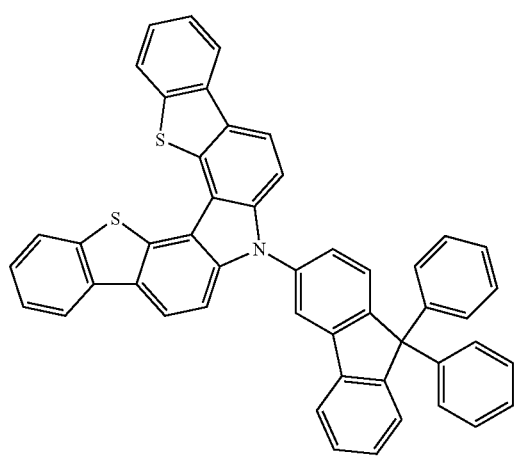
2-12
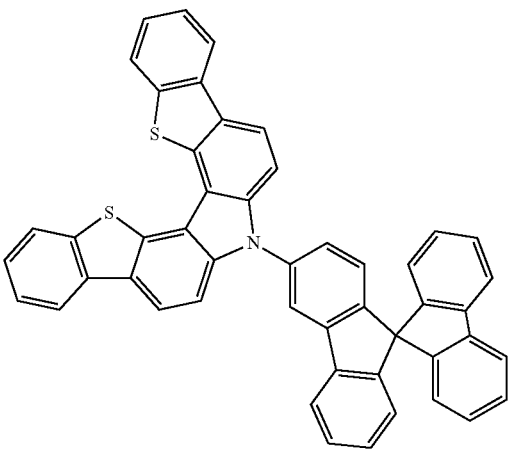
2-13
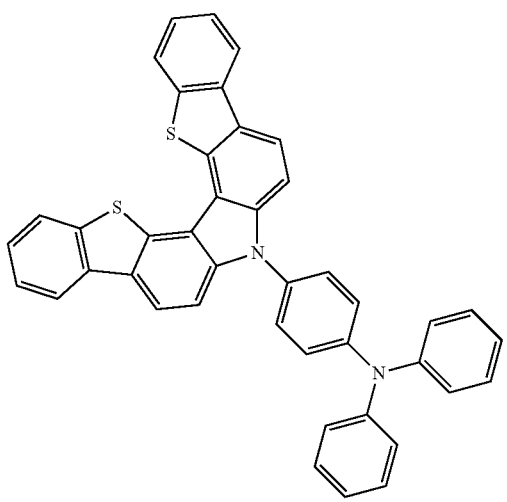
2-14
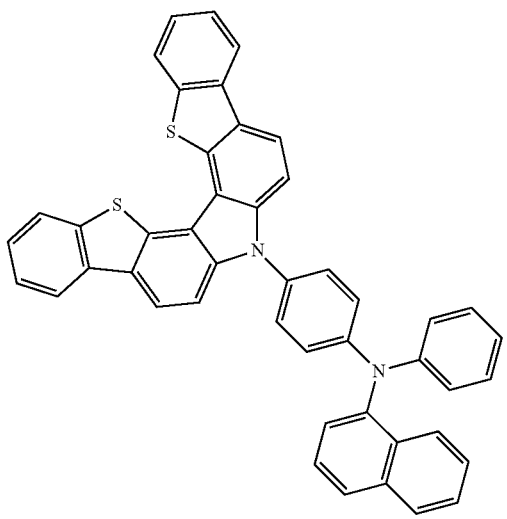

2-15
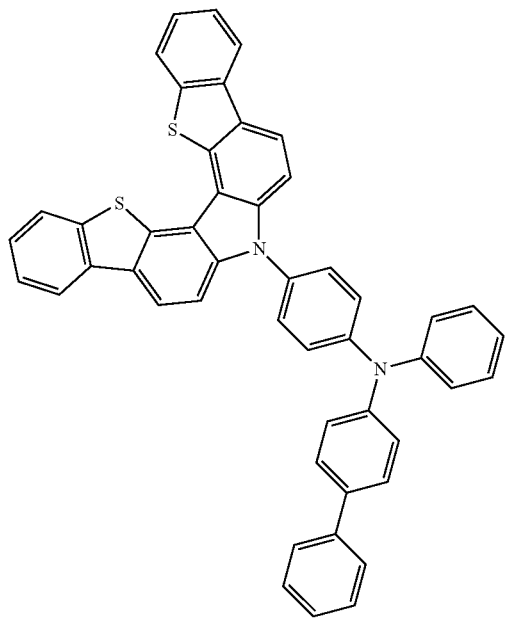
2-17
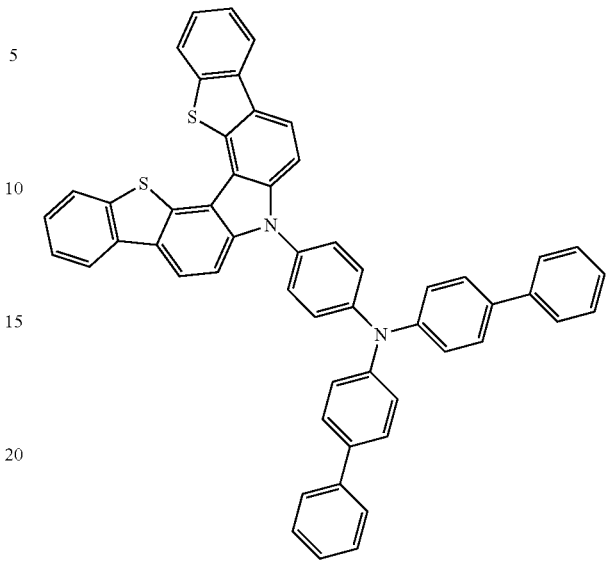
2-18
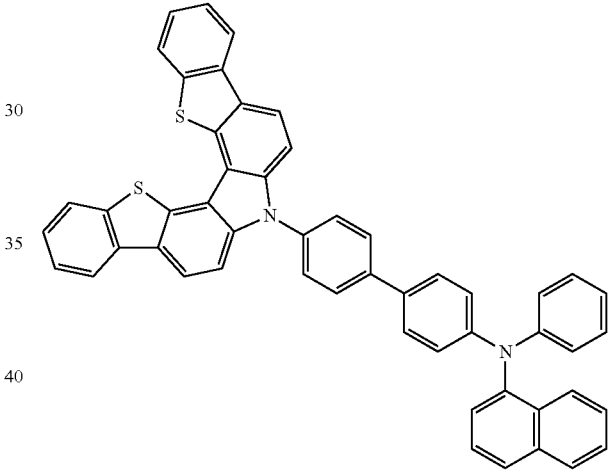
2-16
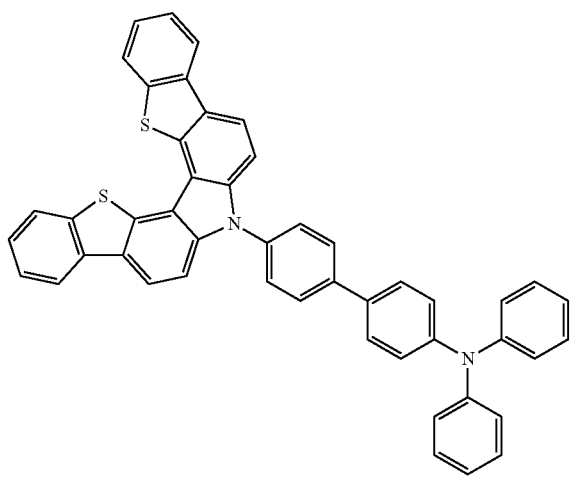
2-19
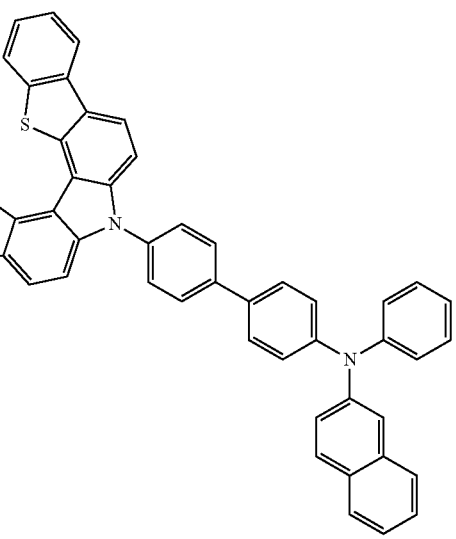

2-20
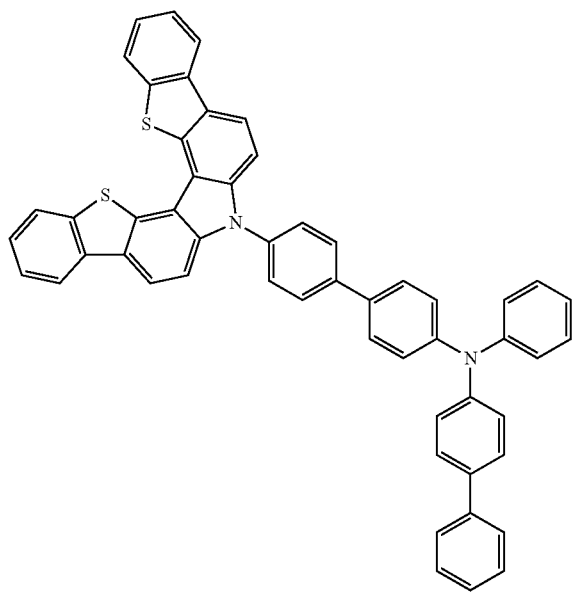
2-22
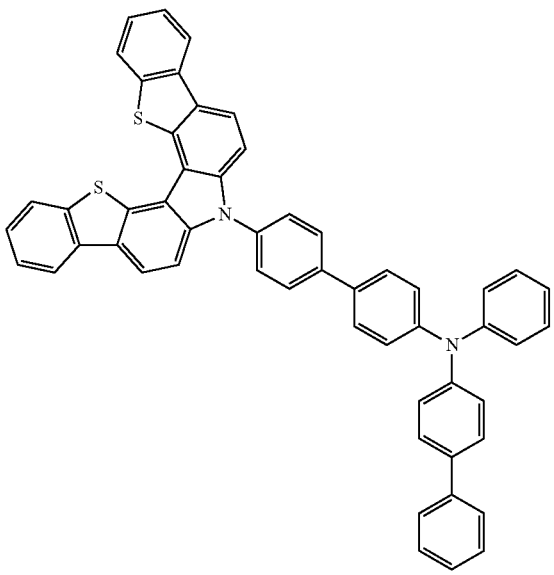
2-23
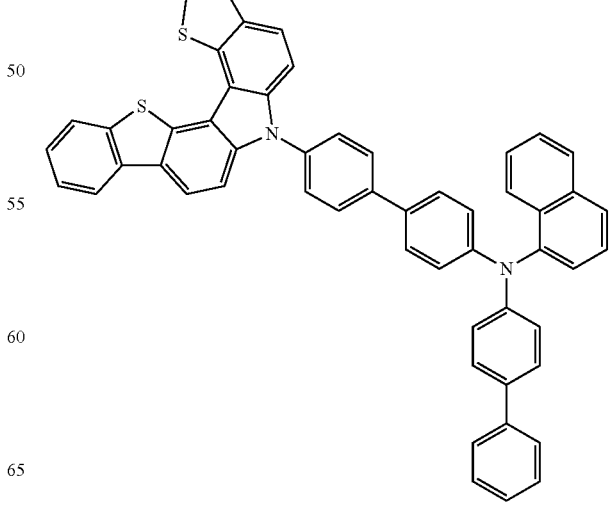
2-21
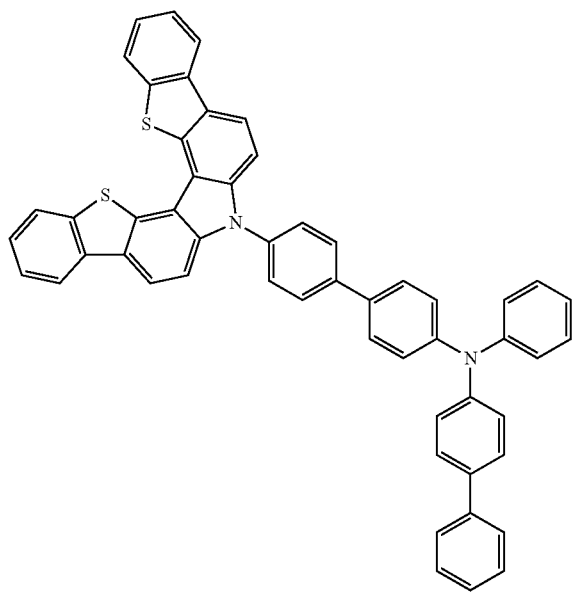

2-24
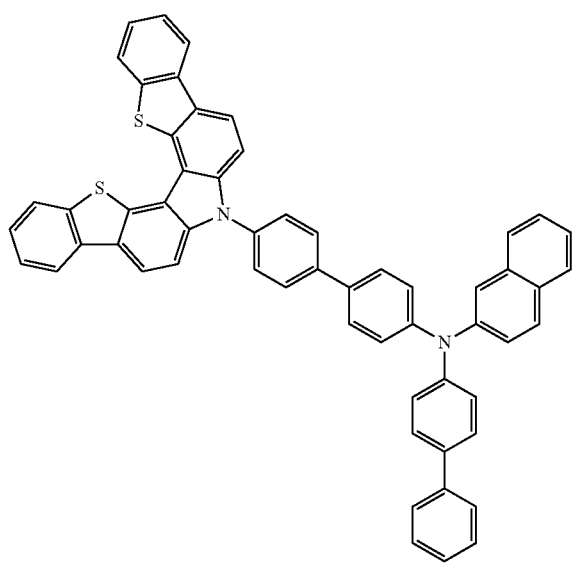
2-27
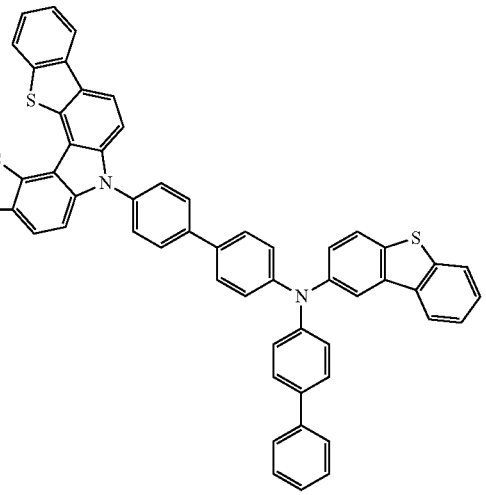
2-25
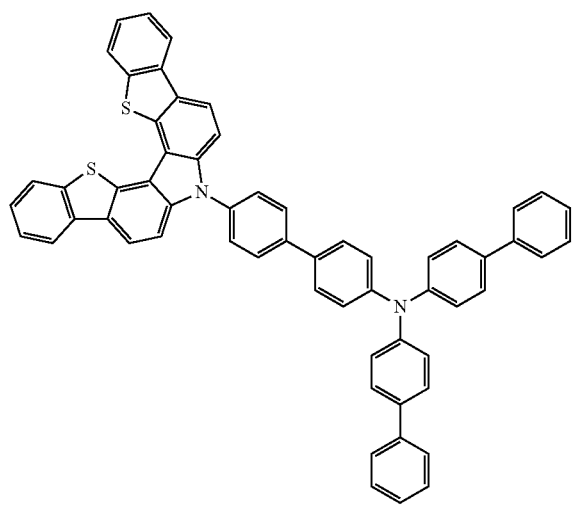
2-28
2-26
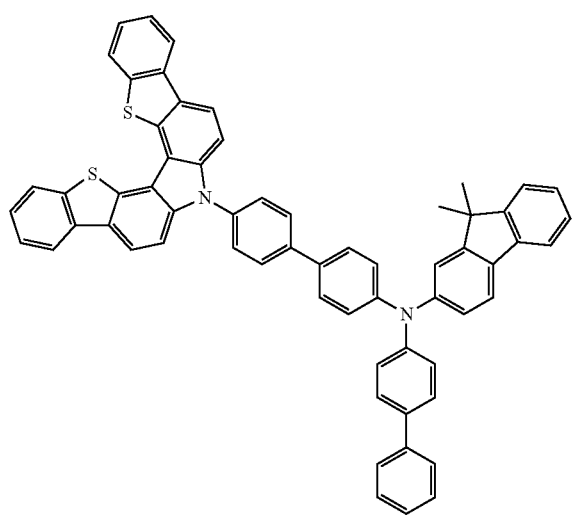
2-29
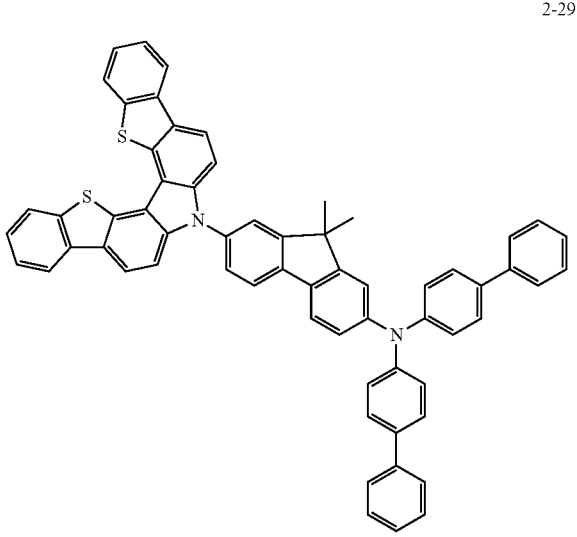

2-30
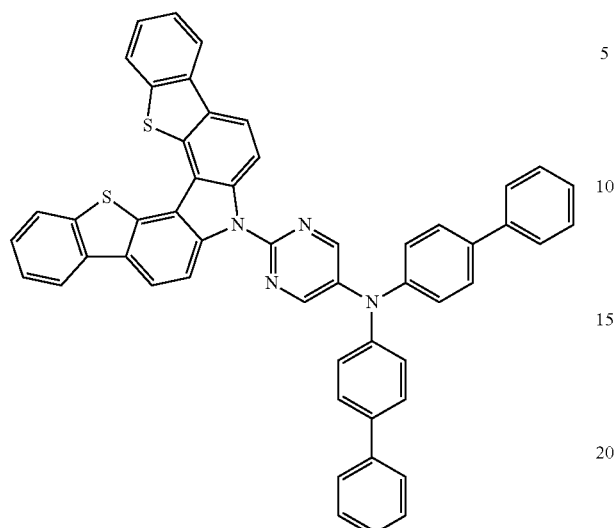
2-31
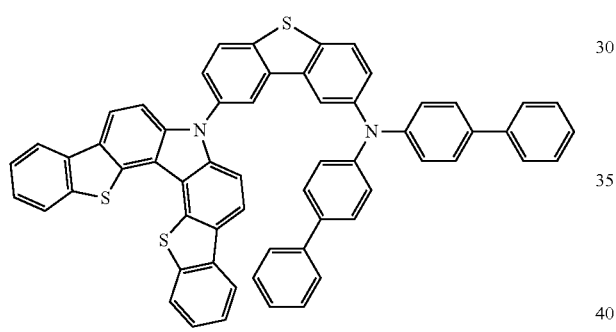
2-32
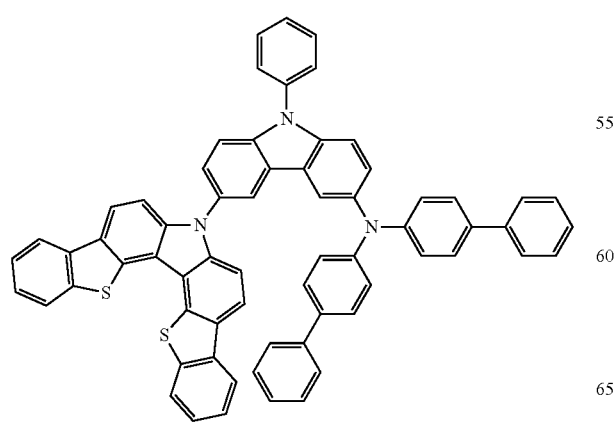
2-33
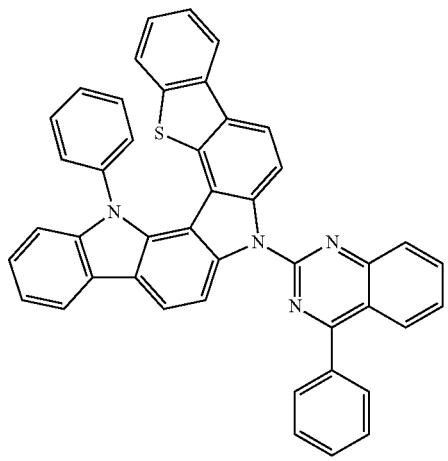
2-34
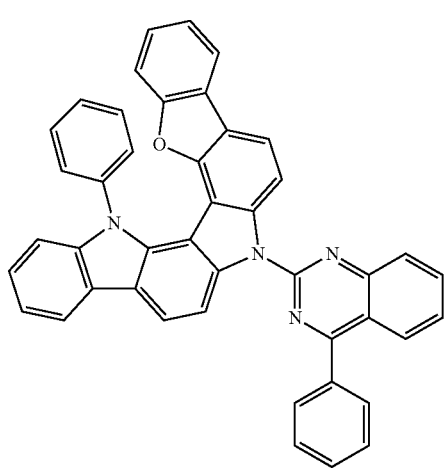
2-35
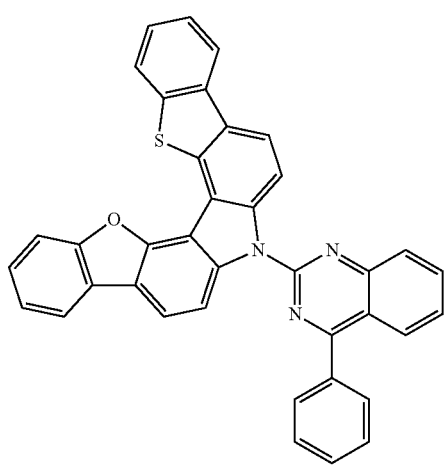

-continued
2-36
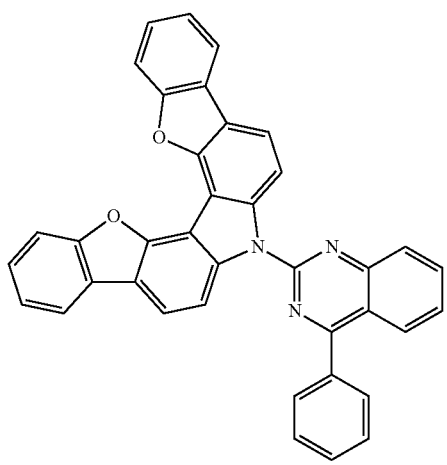
2-37
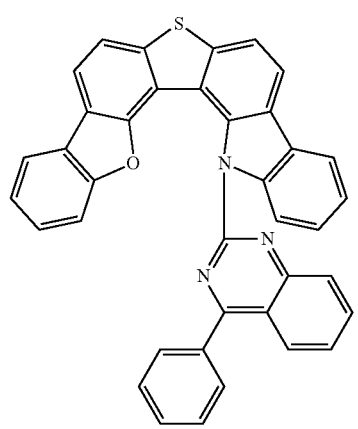
2-38
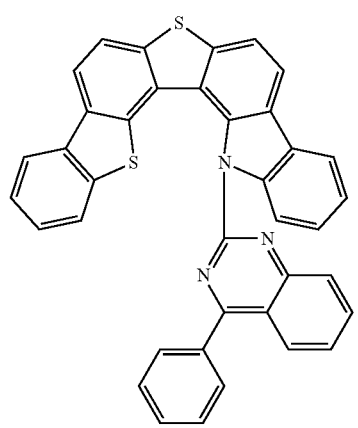
2-39
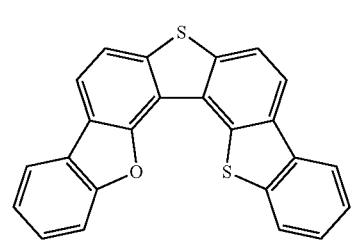
-continued
2-40
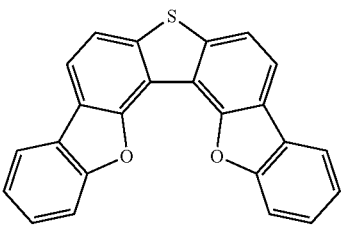
3-1
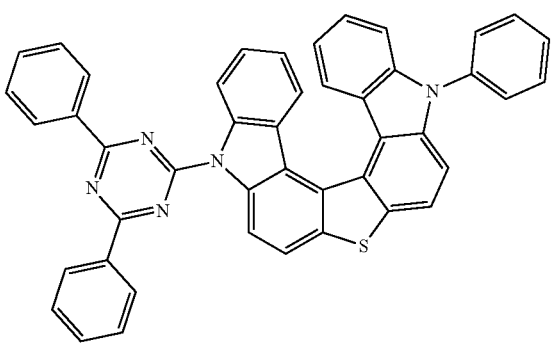
3-2
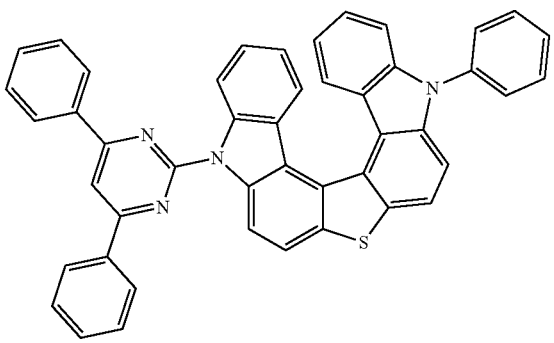
3-3
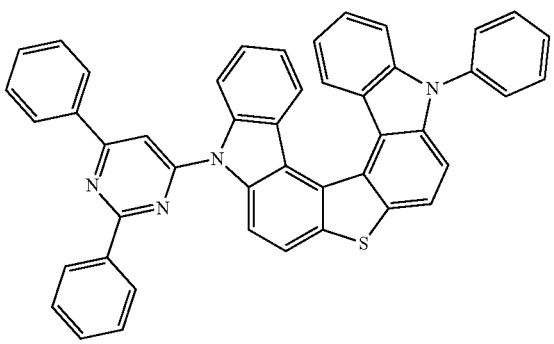

3-4
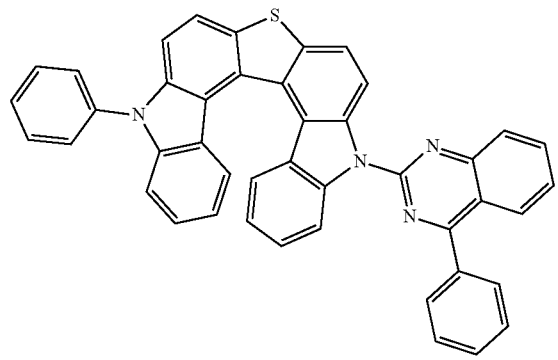
3-5
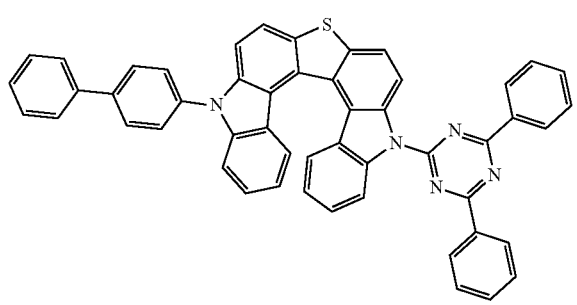
3-6
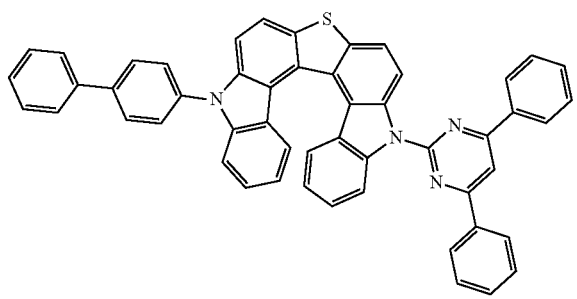
3-7
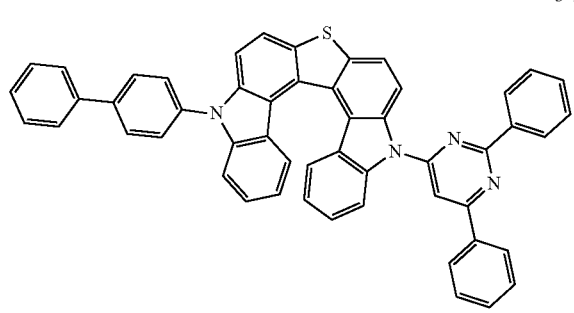
3-8
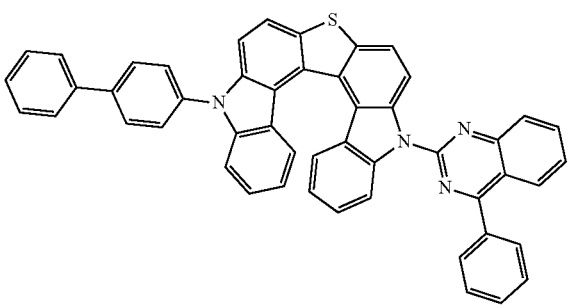
3-9
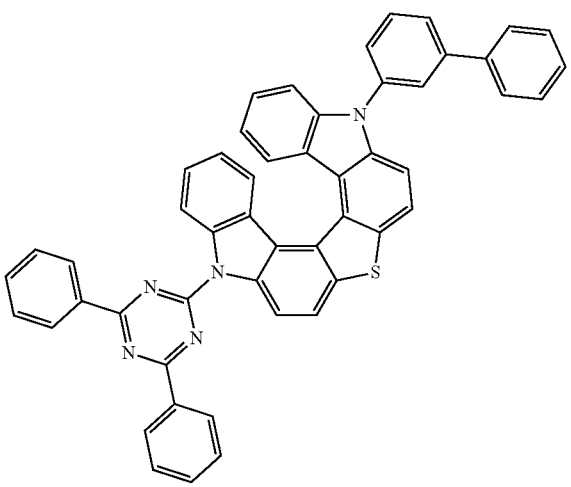
3-10
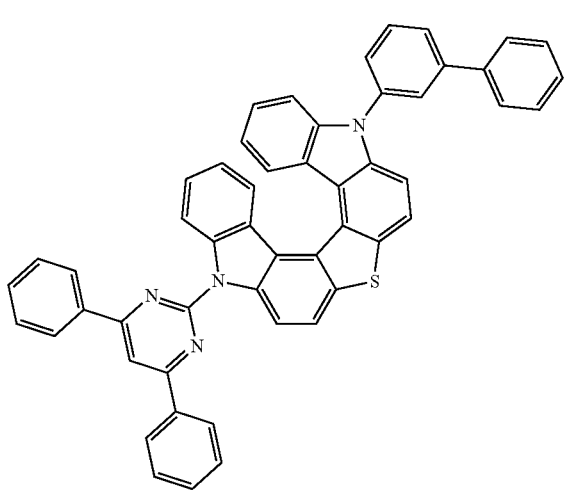

3-11
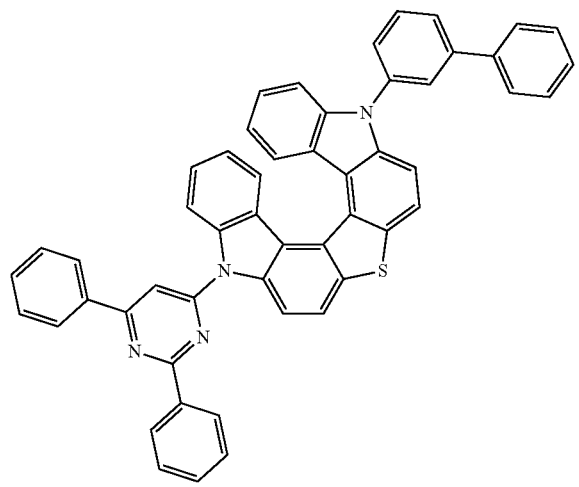
3-12
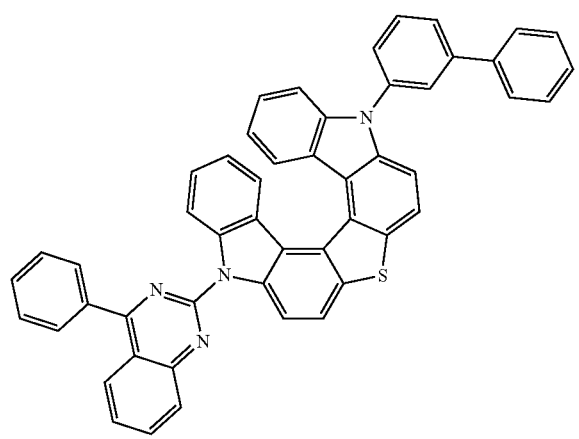
3-13
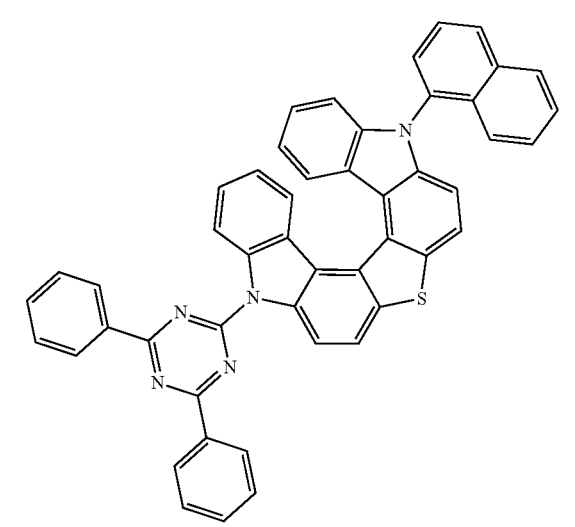
3-14
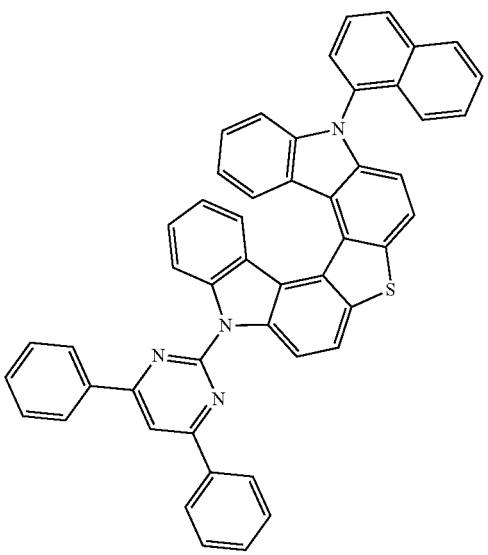
3-15
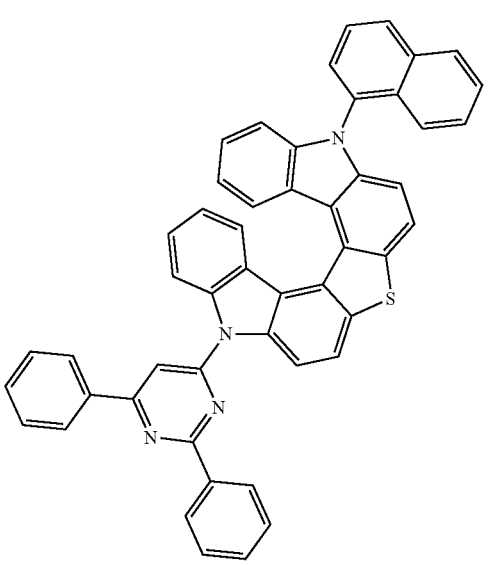
3-16
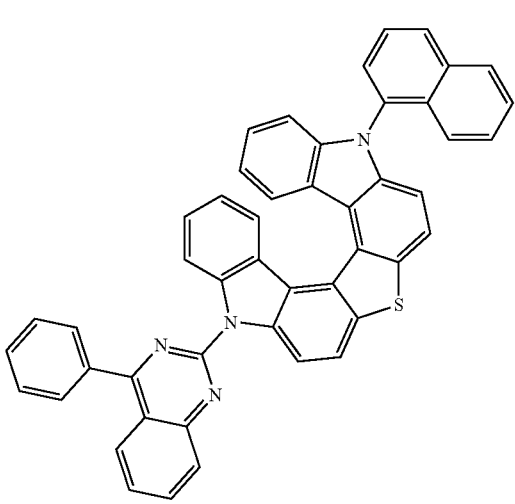

3-17
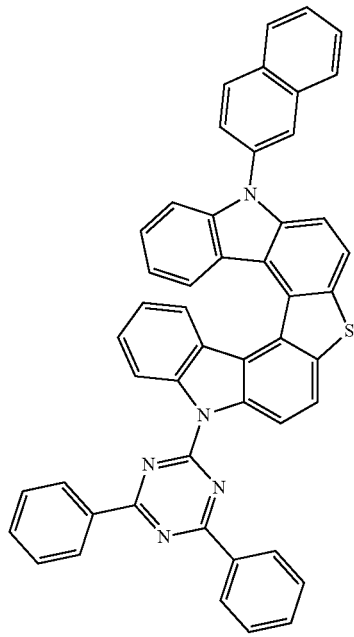
3-18
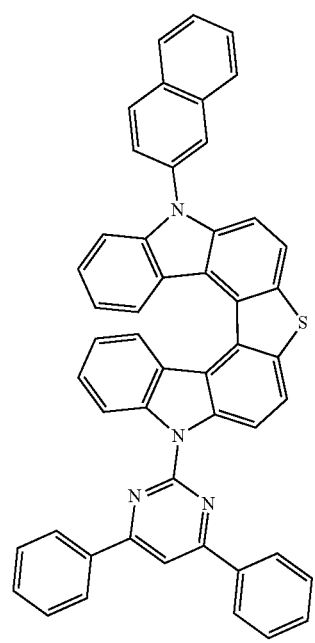
3-19
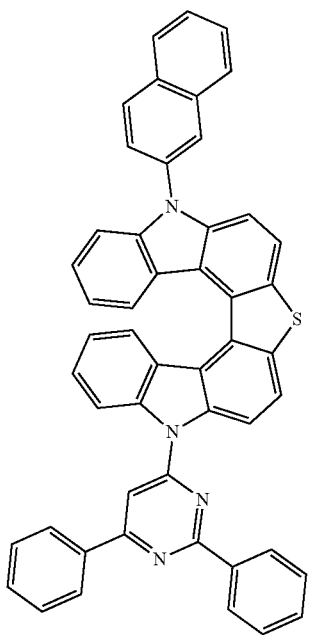
3-20
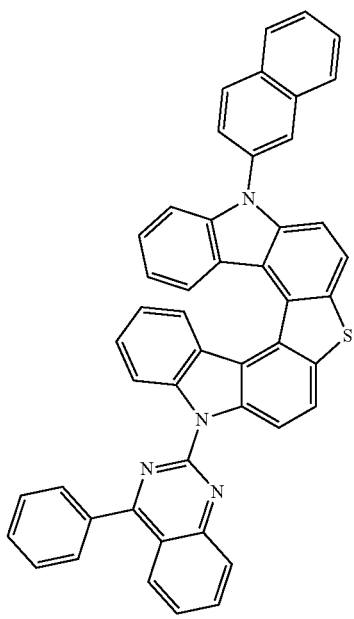

3-21
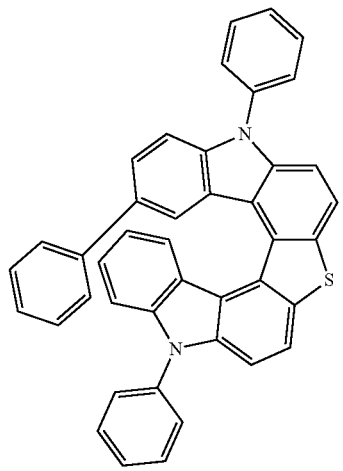
3-22
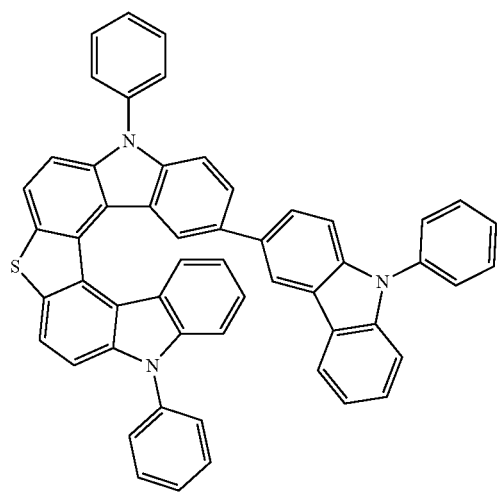
3-23
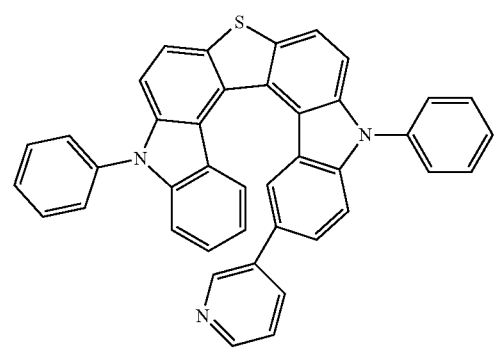
3-24
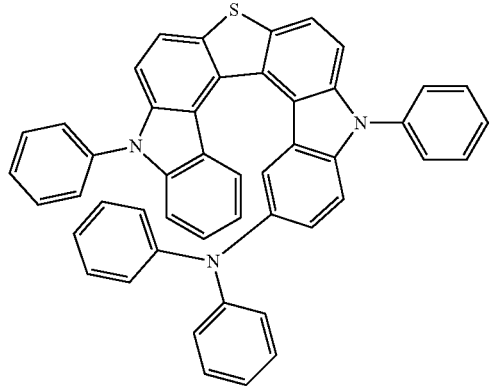
4-1
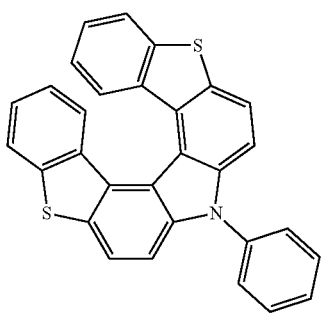
4-2
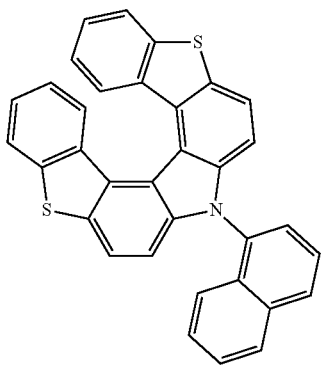
4-3
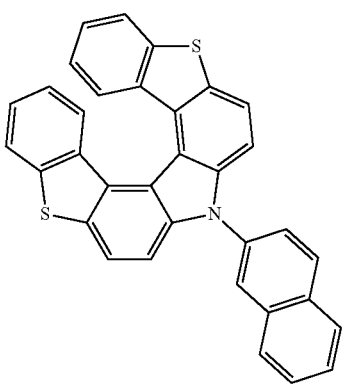

177
-continued
178
-continued
4-4
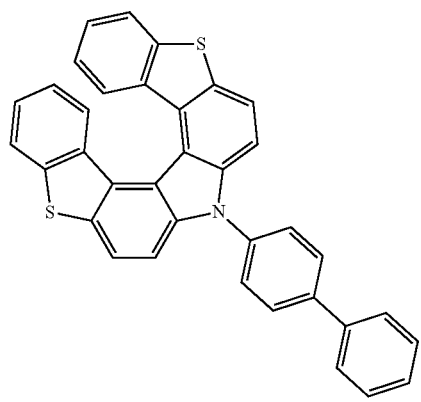
4-7
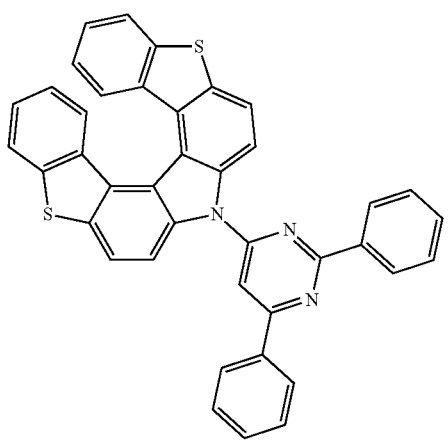
4-5
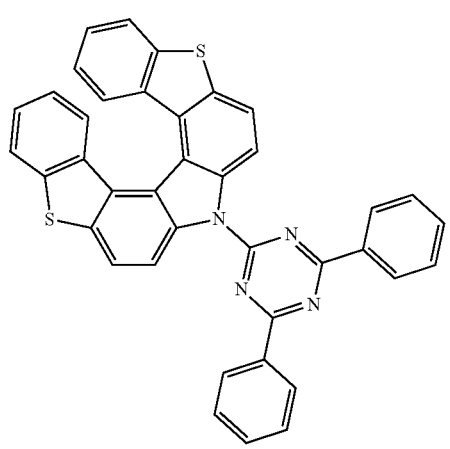
4-8
4-6
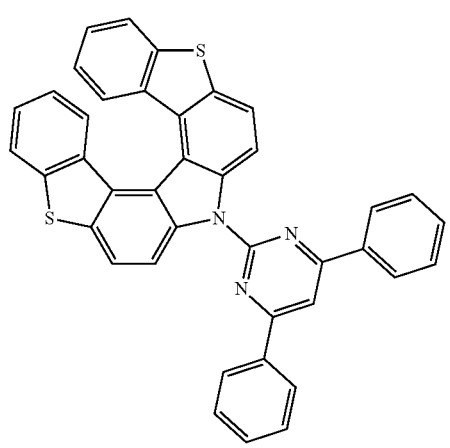
4-9
4-10

-continued
4-11
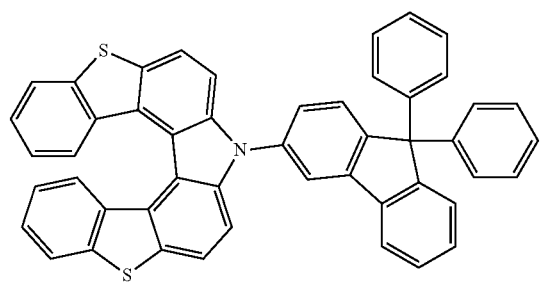
4-12
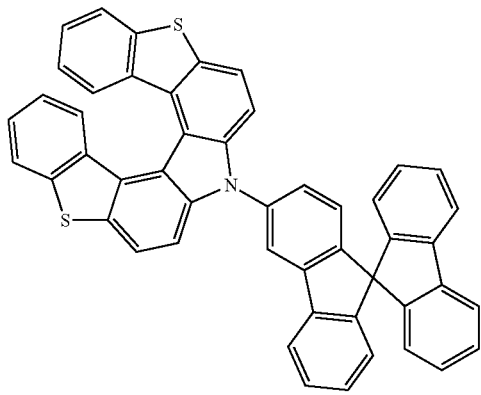
4-13
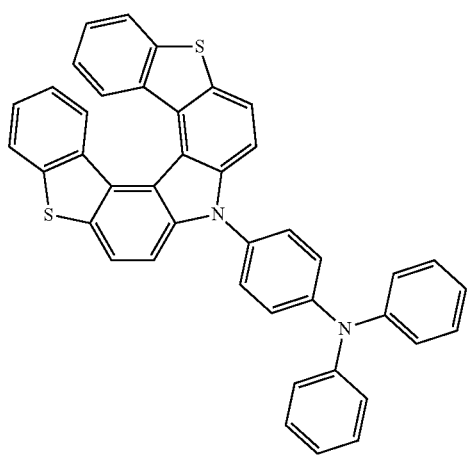
4-14
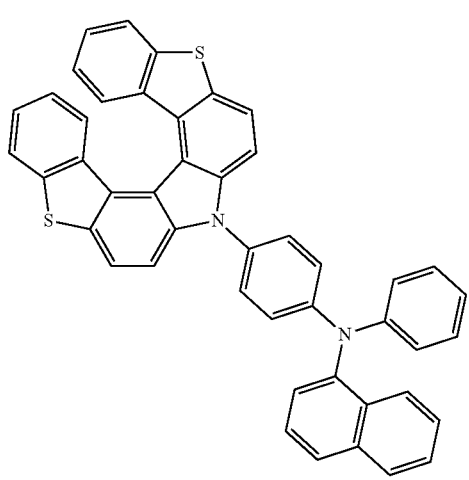
-continued
4-15
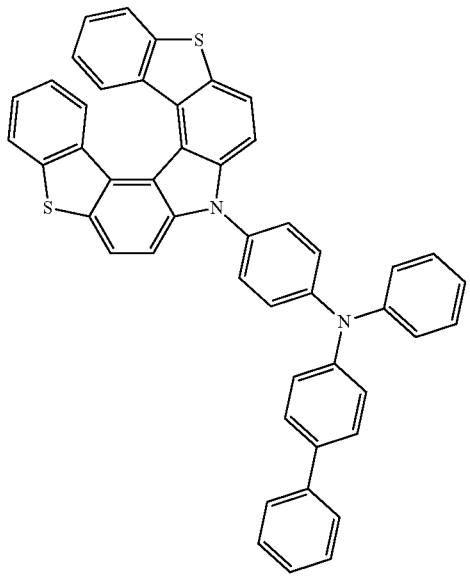
4-16
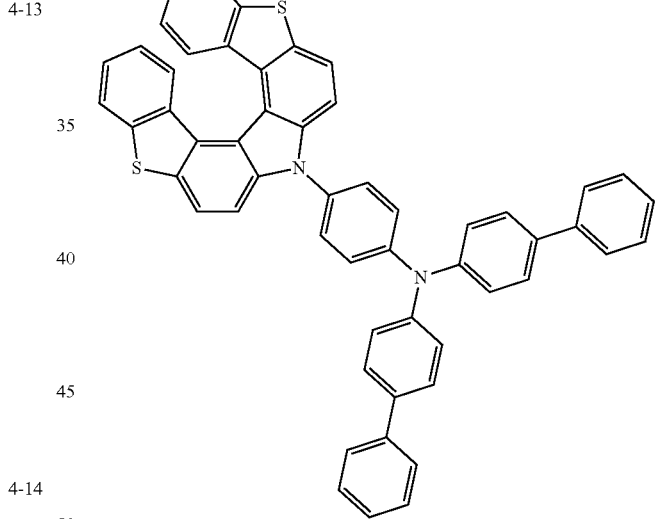
4-17
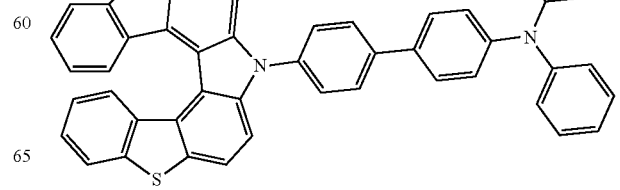

4-18
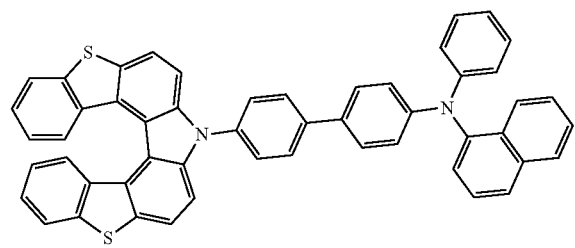
4-19
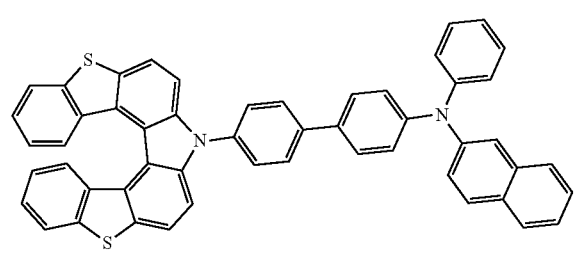
4-20
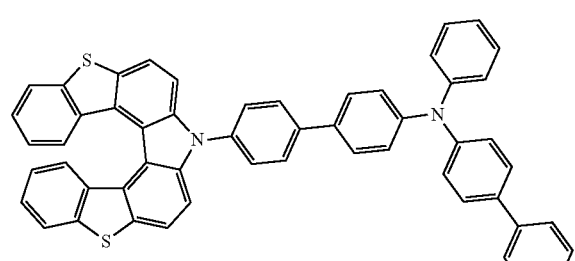
4-21
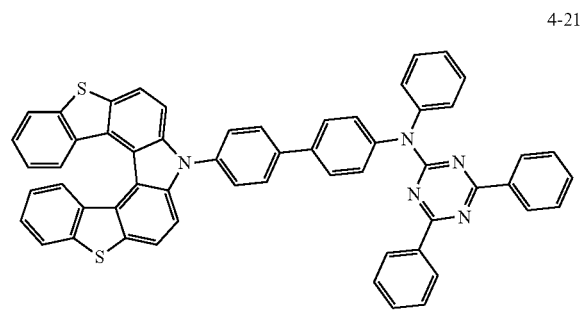
4-22
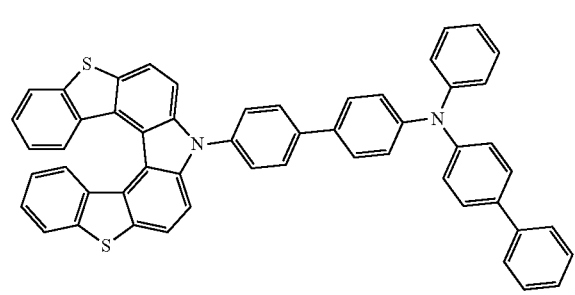
4-23
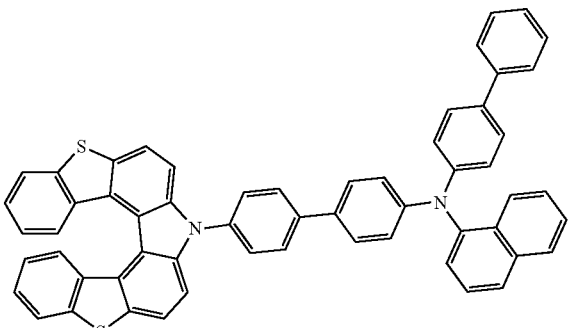
4-24
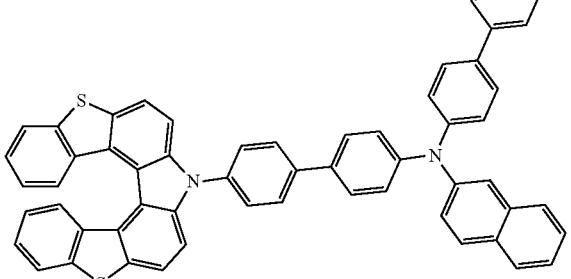
4-25
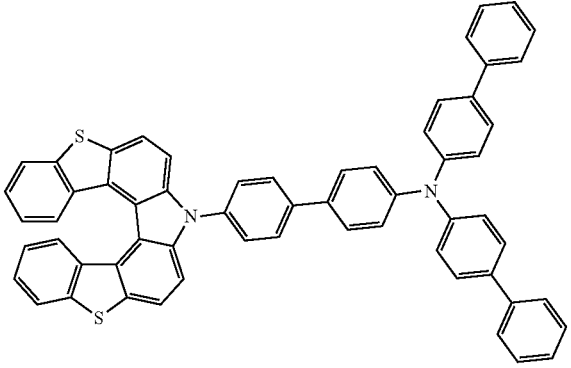
4-26
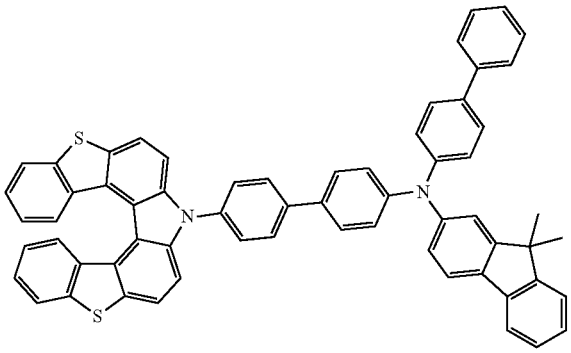

4-27
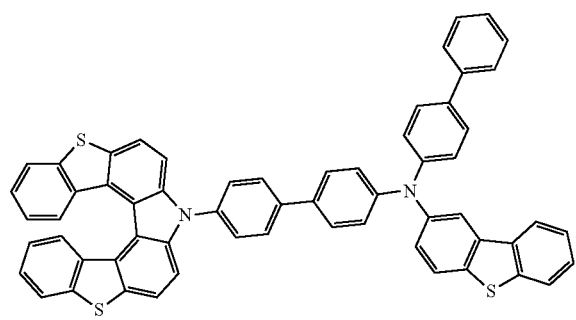
4-28
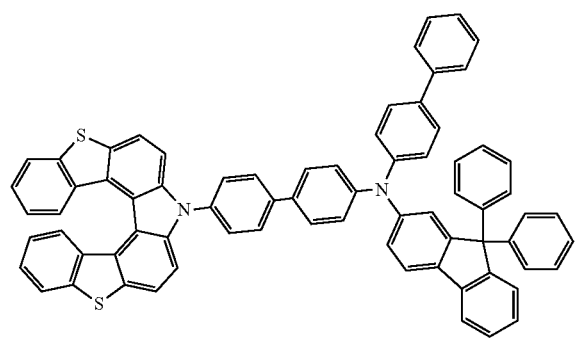
4-29
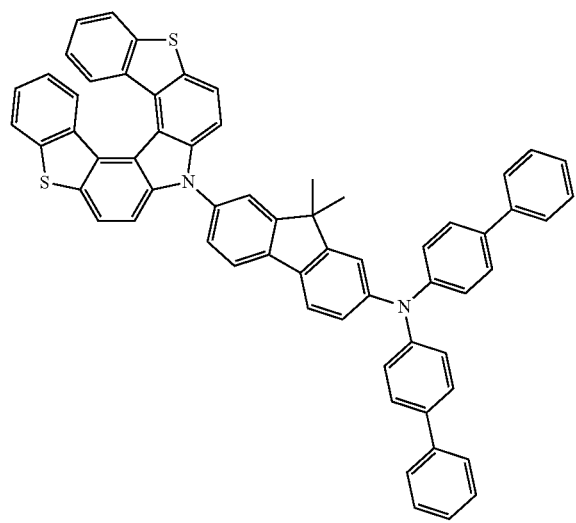
4-30
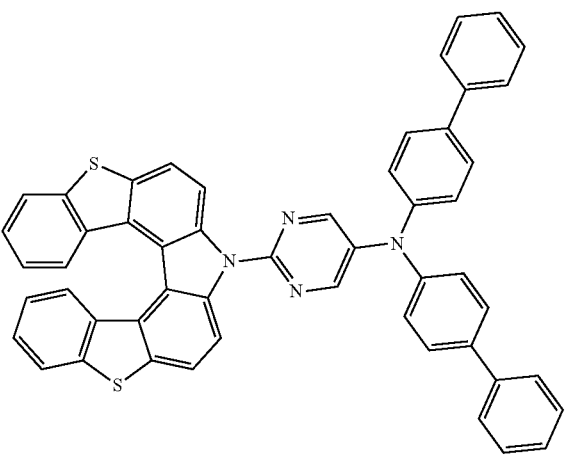
4-31
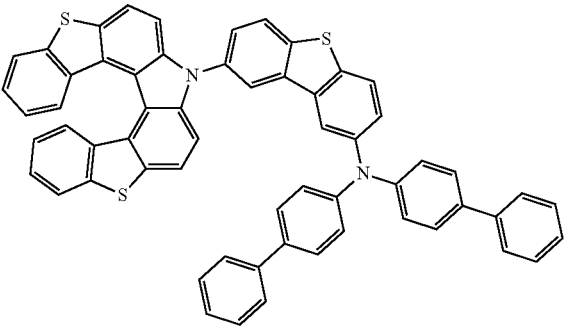
4-32
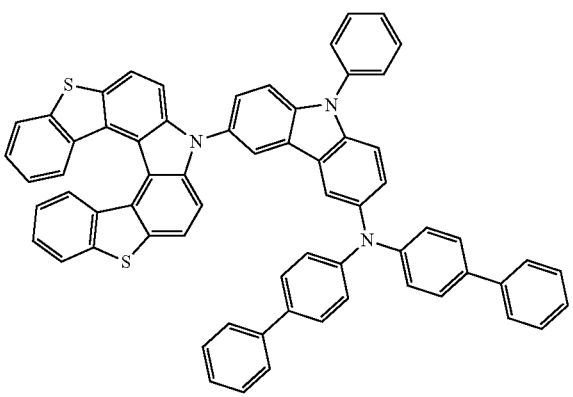

-continued
4-33
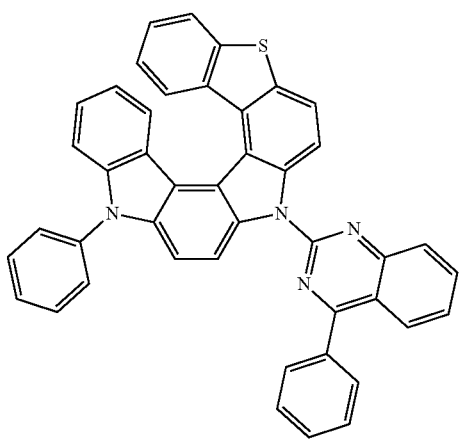
4-34
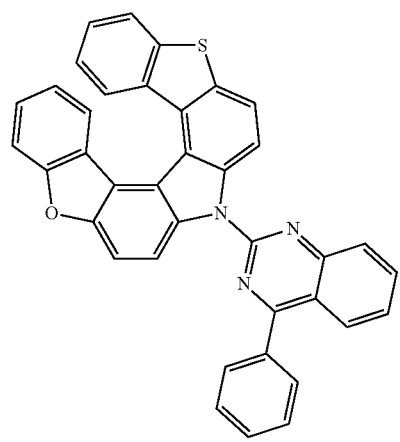
4-35
4-36
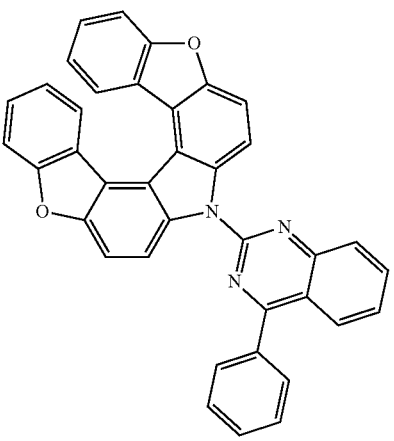
4-37
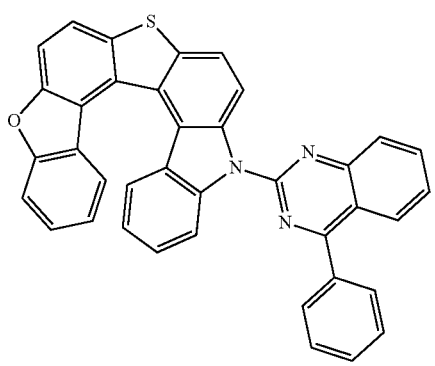
4-38
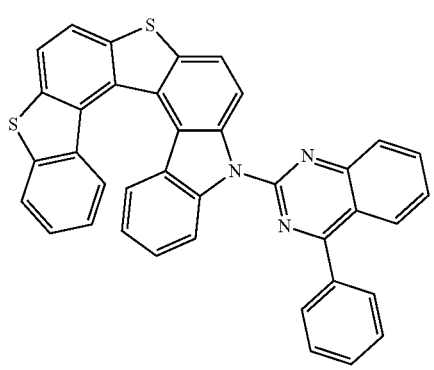
4-39
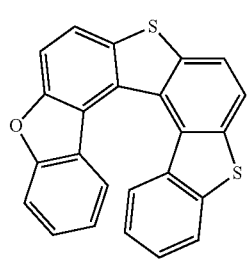

4-40
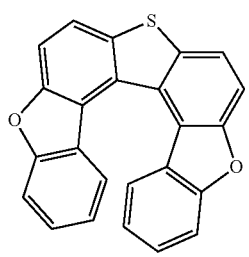
5-1
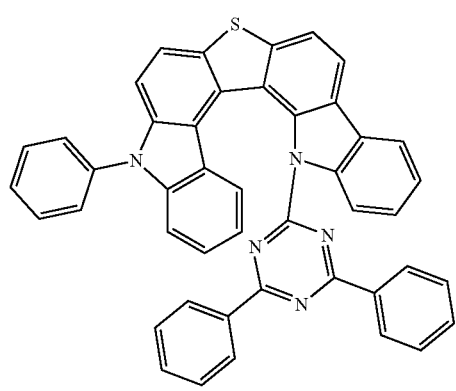
5-2
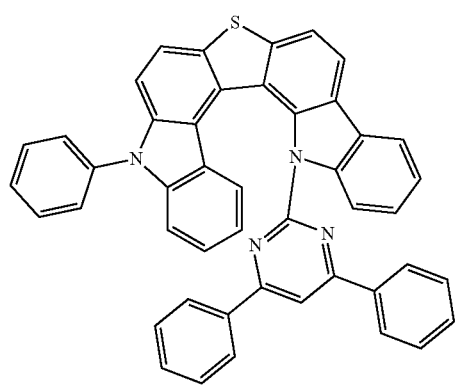
5-3
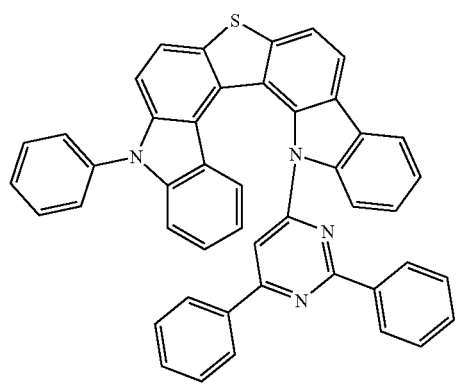
5-4
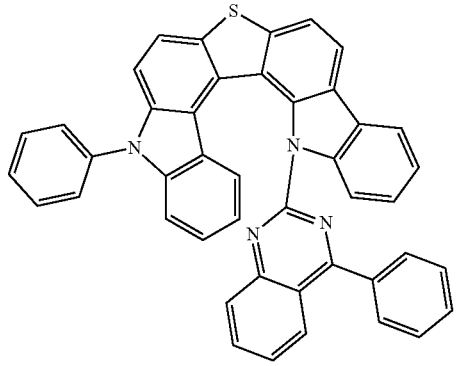
5-5
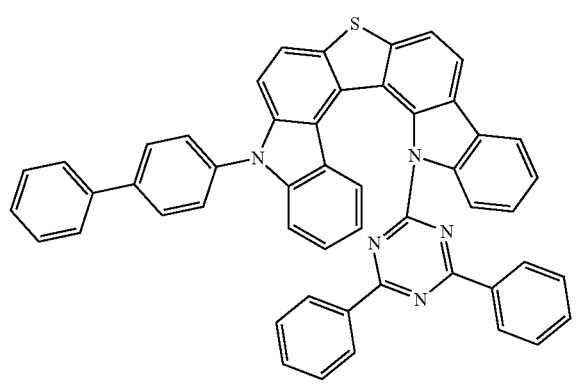
5-6
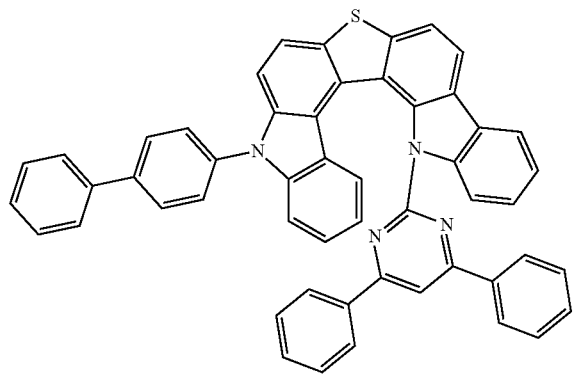
5-7
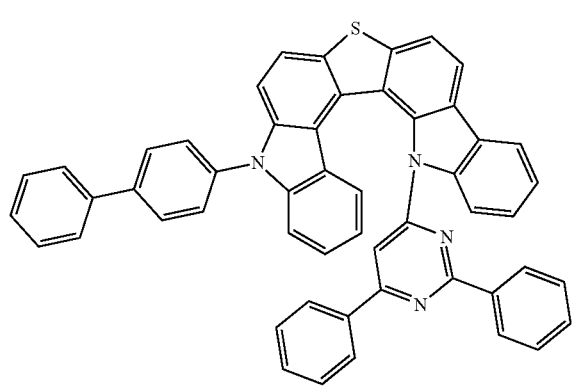

-continued
5-8
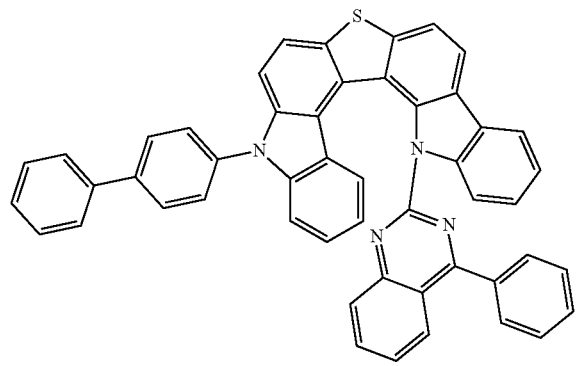
5-9
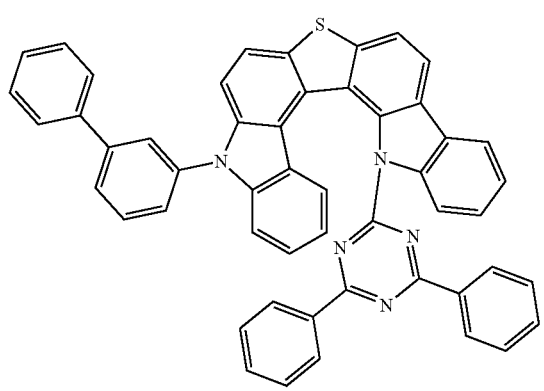
5-10
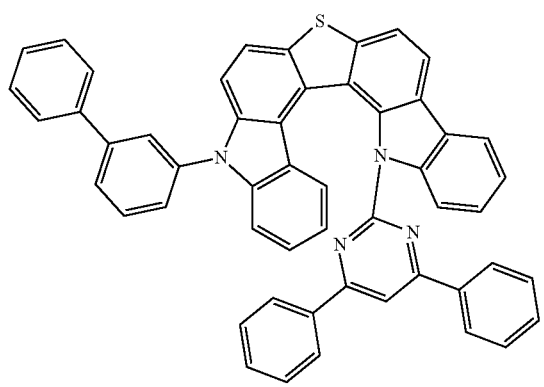
5-11
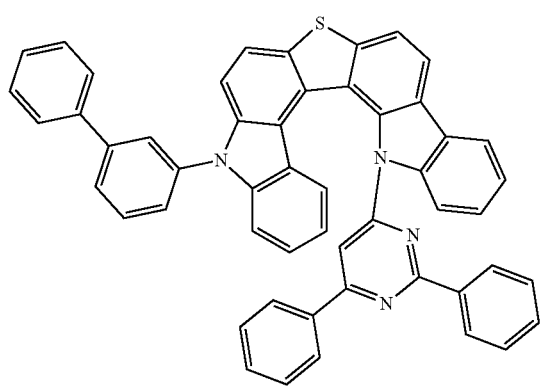
-continued
5-12
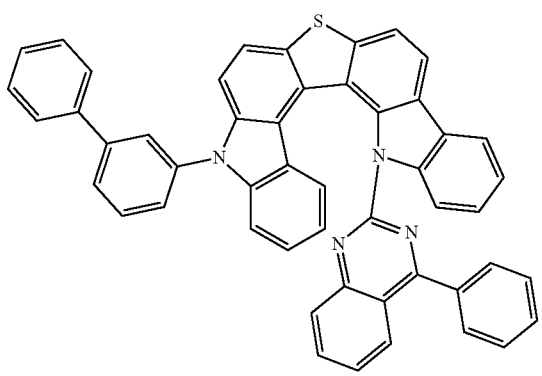
5-13
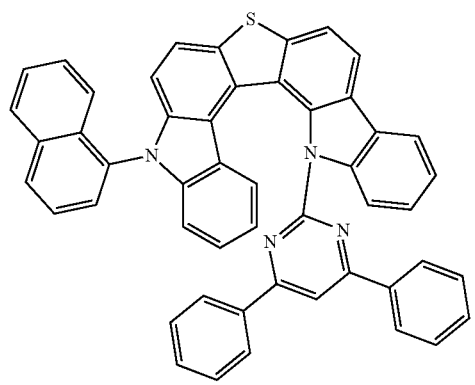
5-14
5-15
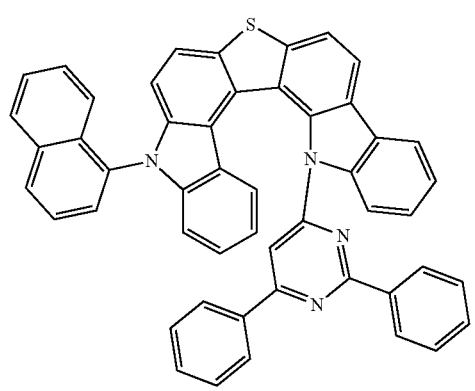

-continued
5-16
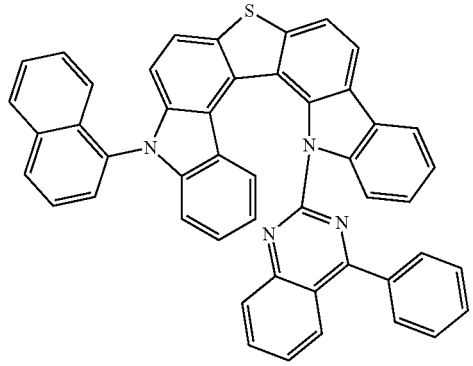
5-17
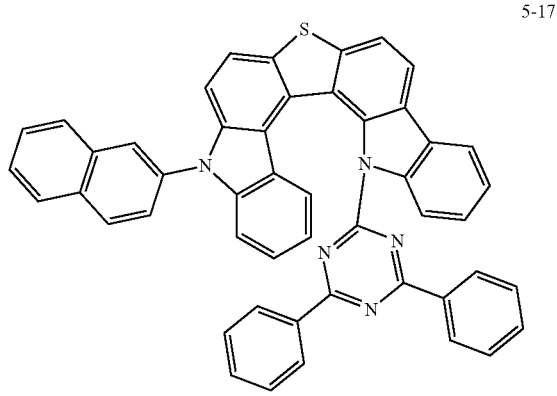
5-18
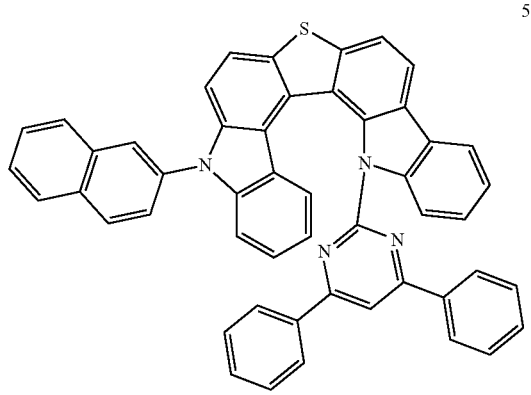
5-19
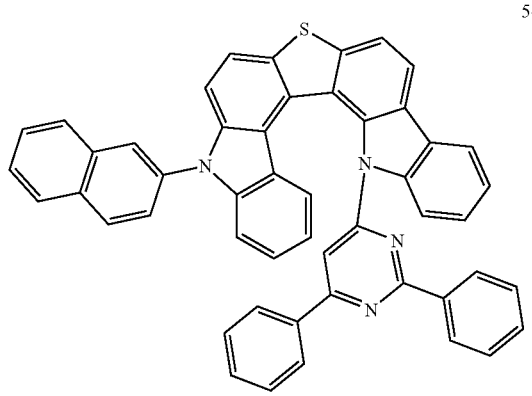
-continued
5-20
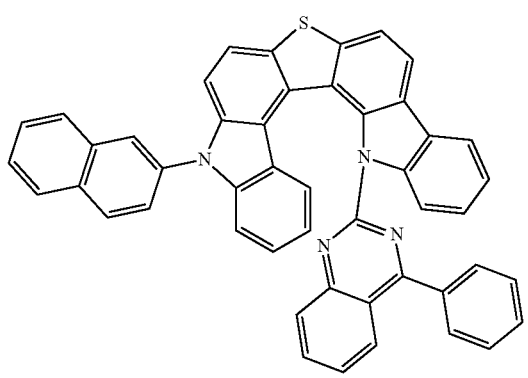
5-21
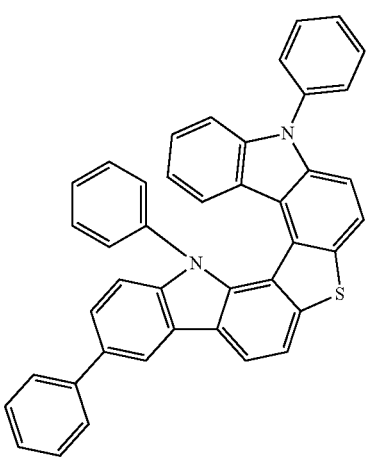
5-22
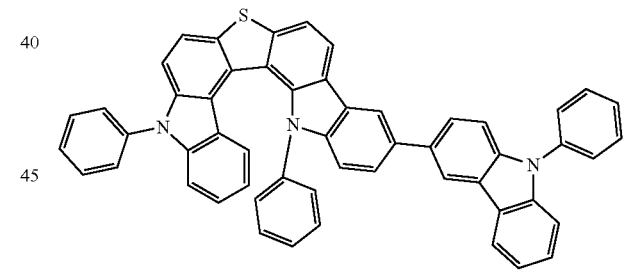
5-23
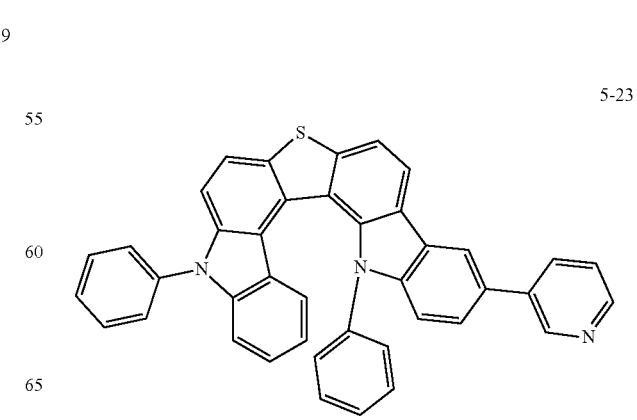

-continued
5-24
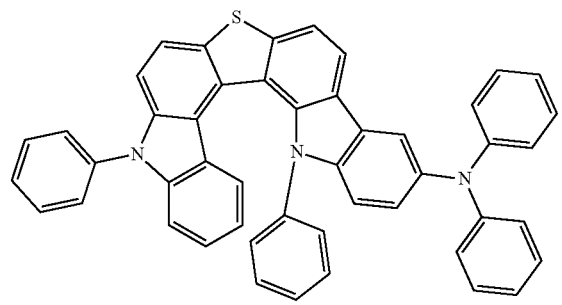
6-1
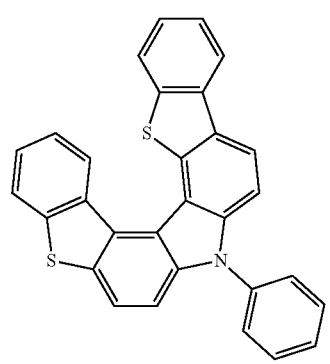
6-2
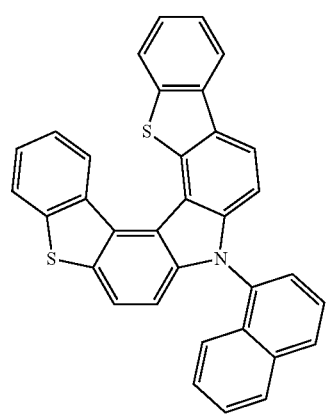
6-3
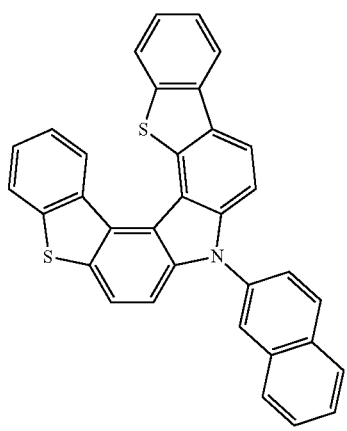
-continued
6-4
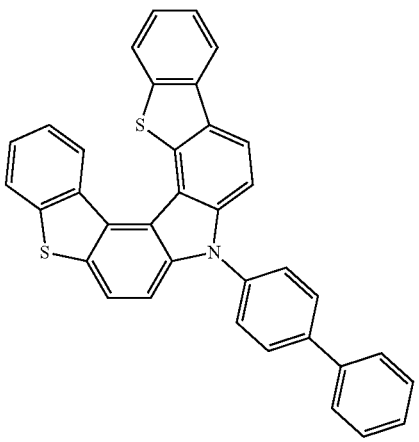
6-5
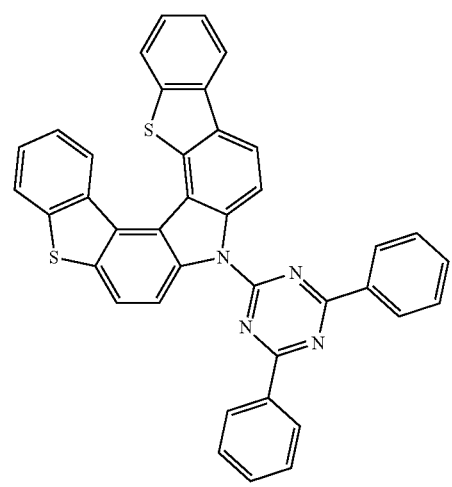
6-6
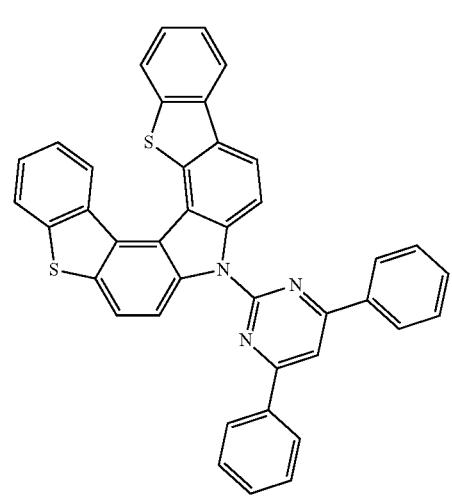

6-7
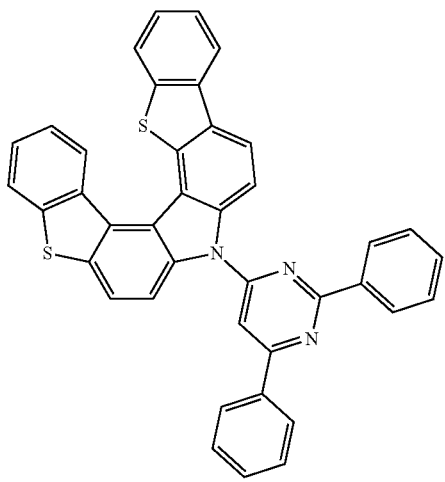
6-8
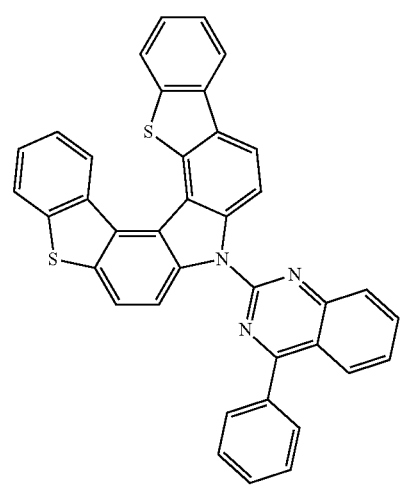
6-9
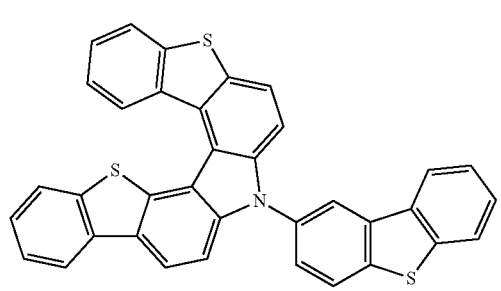
6-10
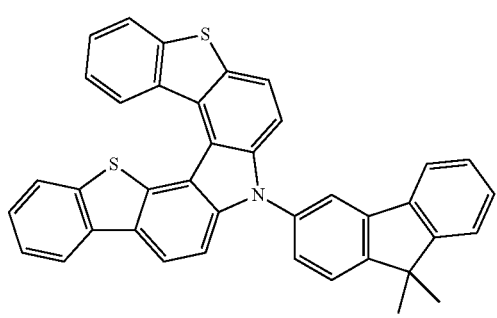
6-11
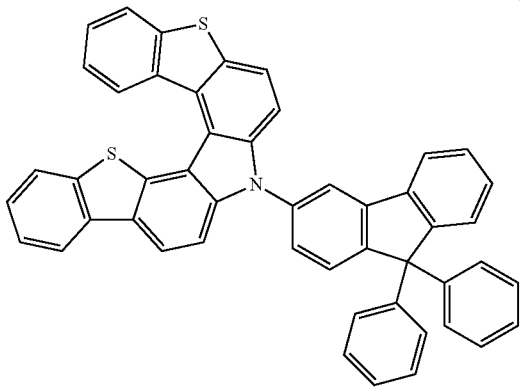
6-12
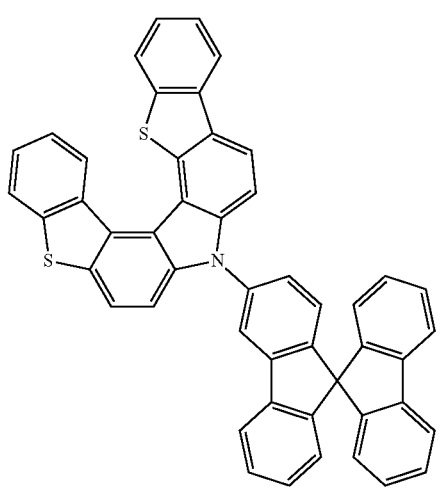
6-13
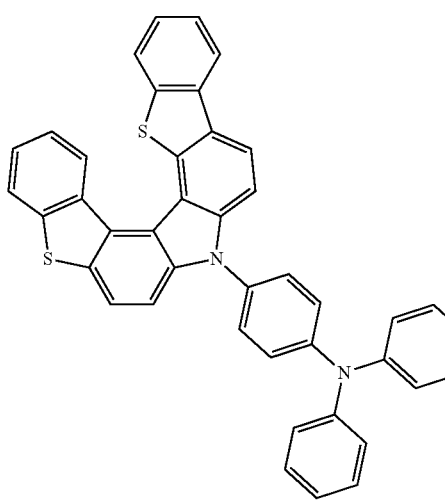

6-14
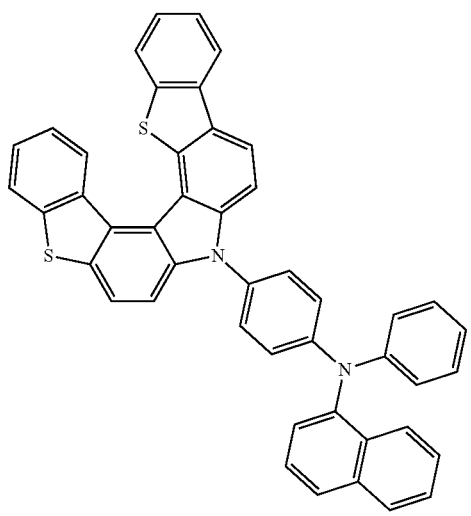
6-16
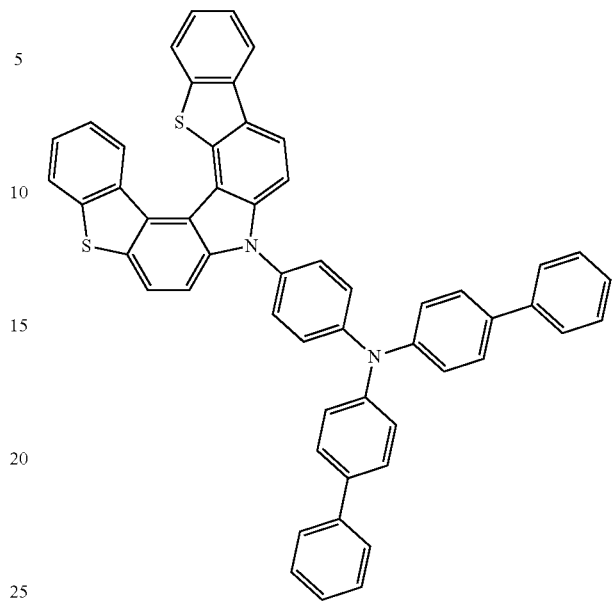
6-17
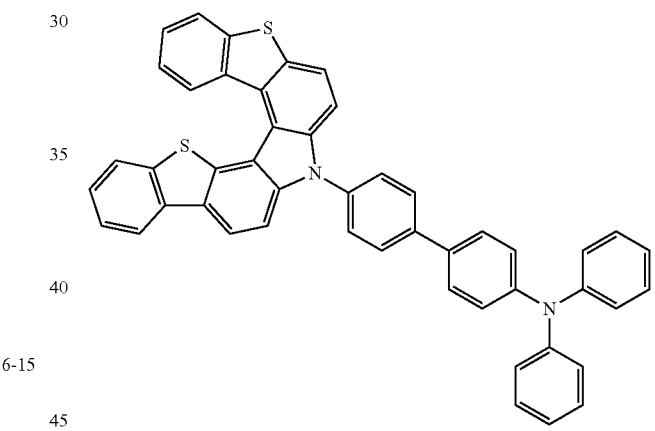
6-15
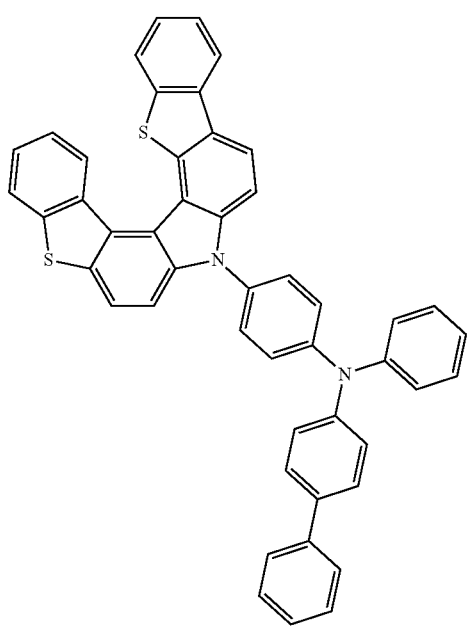
6-18
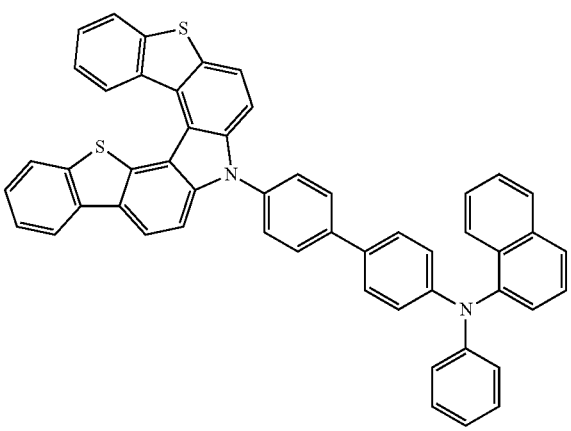

6-19
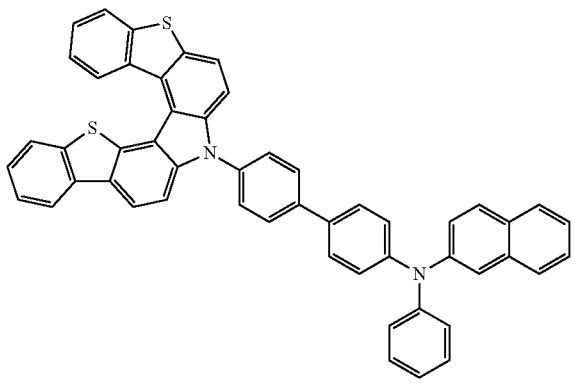
6-20
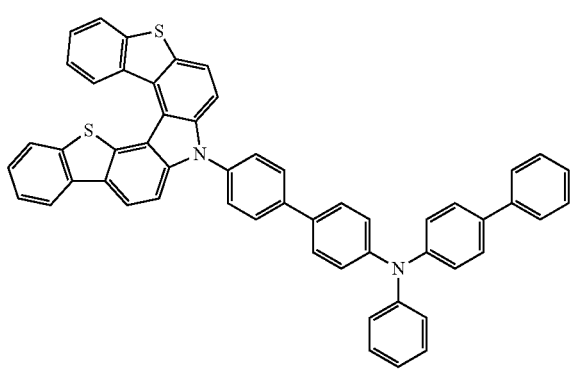
6-21
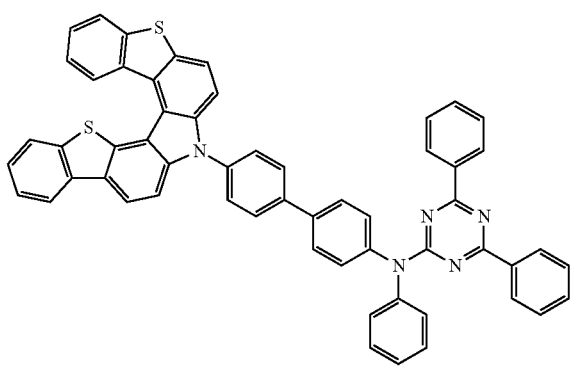
6-22
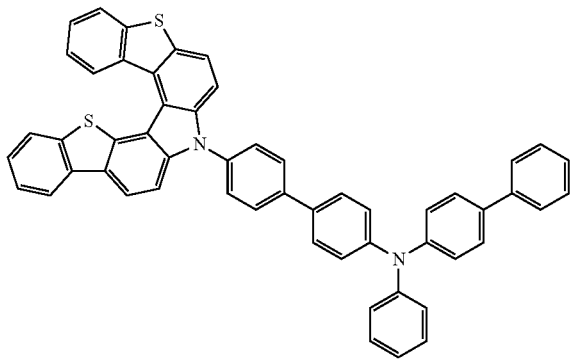
6-23
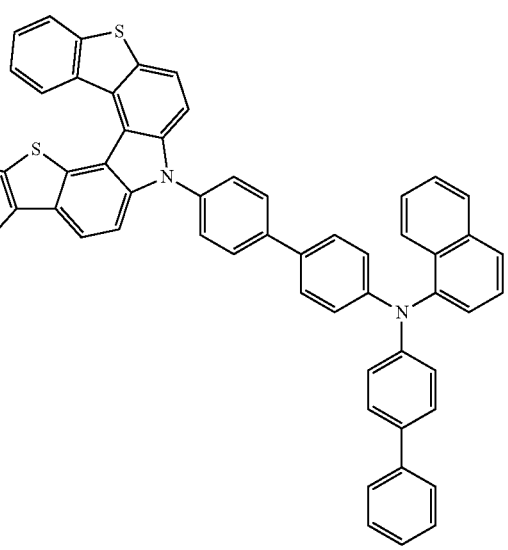
6-24
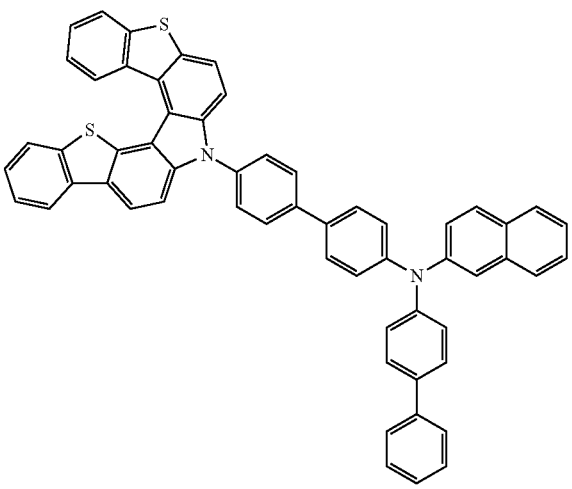
6-25
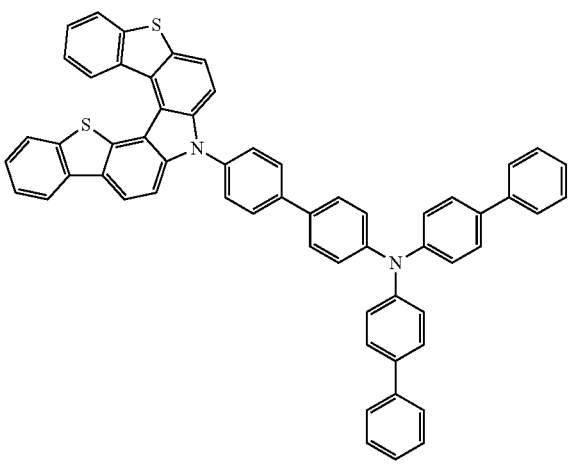

-continued
6-26
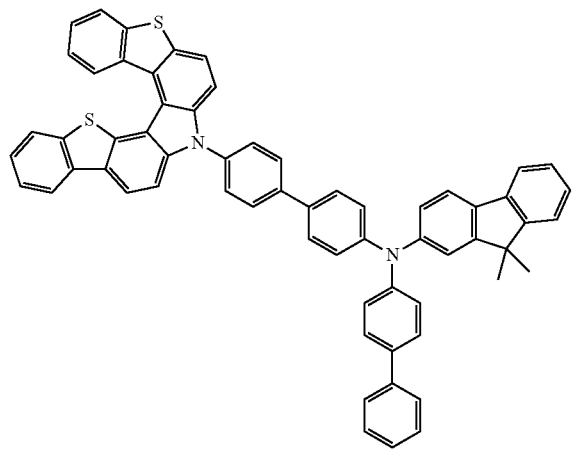
6-27
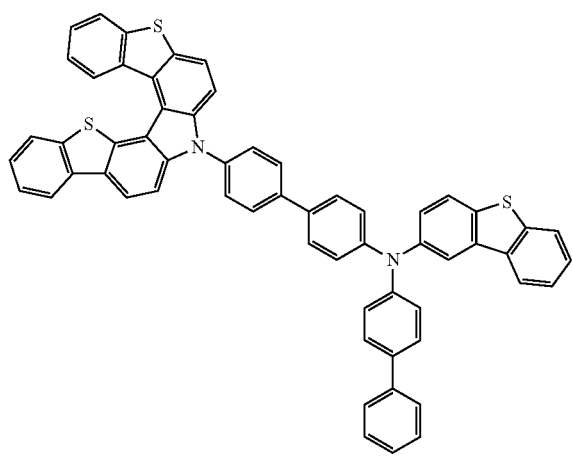
6-28
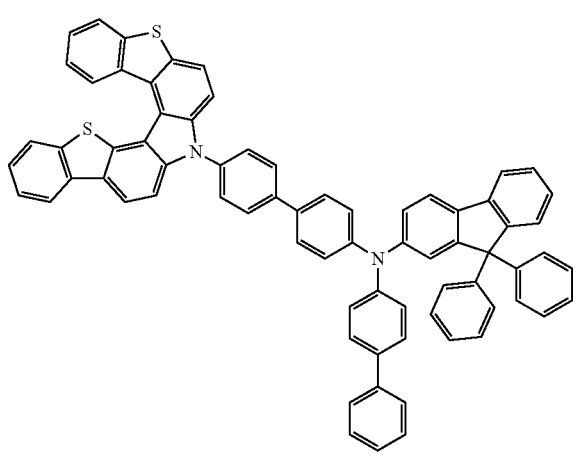
-continued
6-29
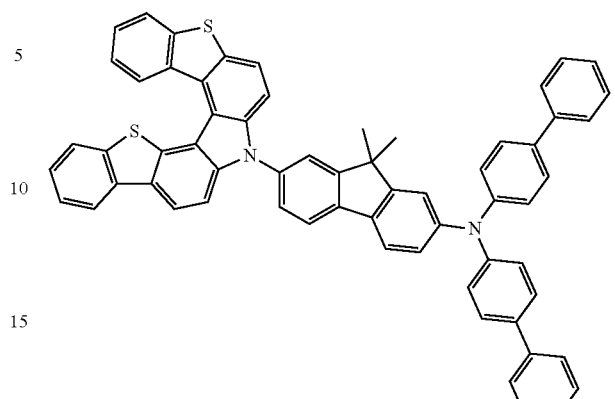
6-30
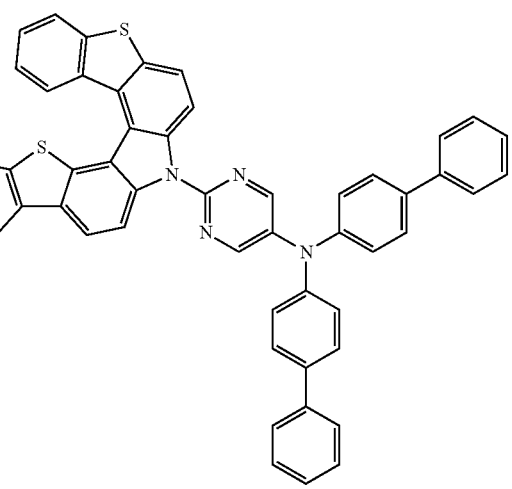
6-31
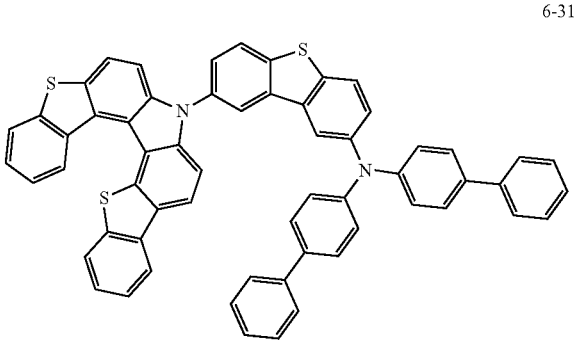

6-32
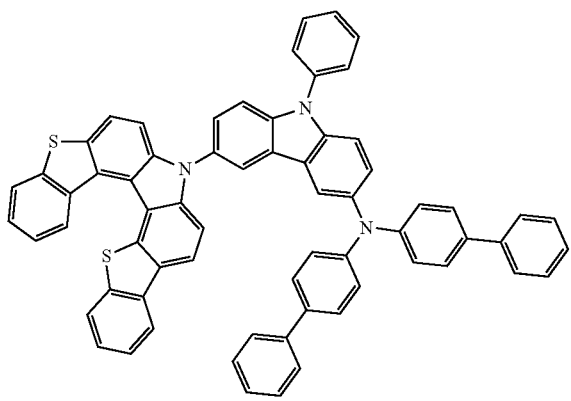
6-33
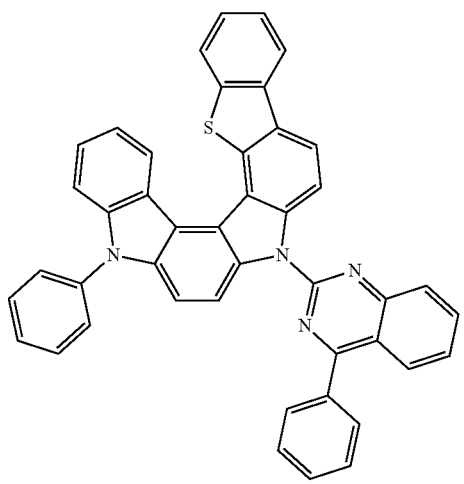
6-34
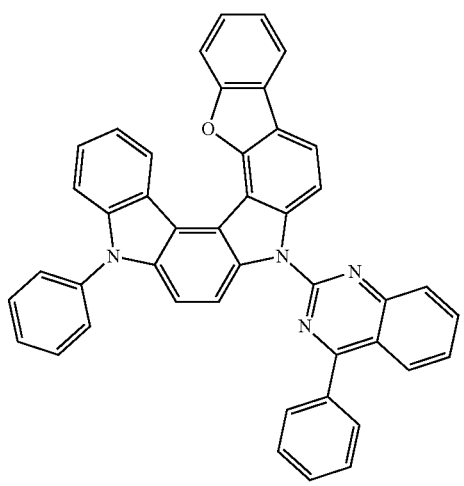
6-35
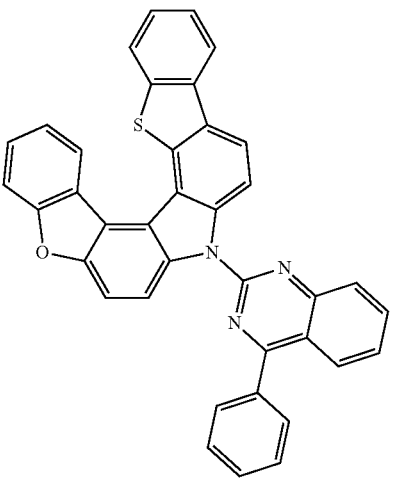
6-36
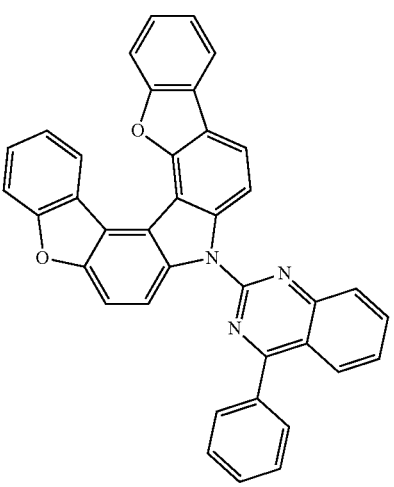
6-37
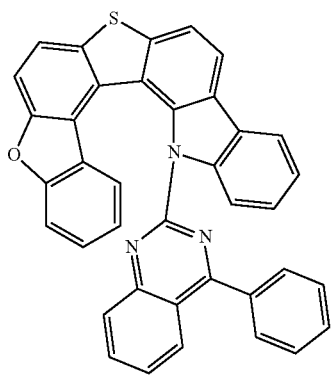

6-38
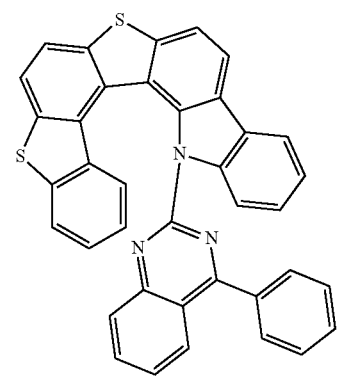
6-39
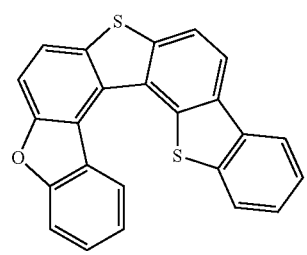
6-40
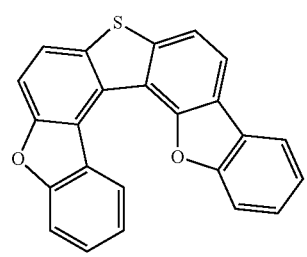
7-1
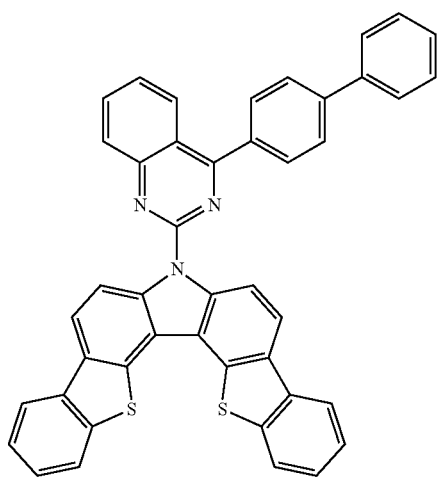
7-2
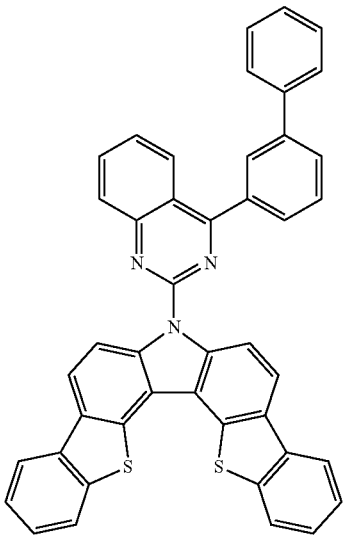
7-3
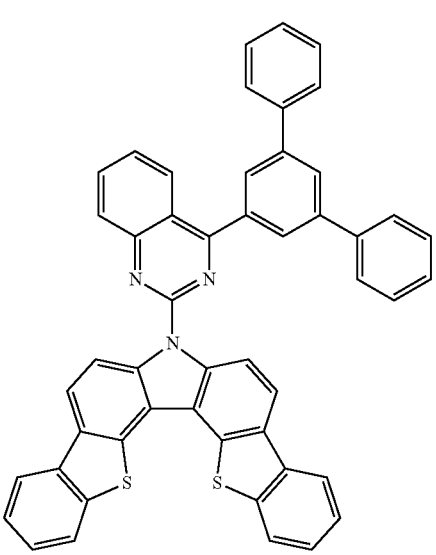
7-4
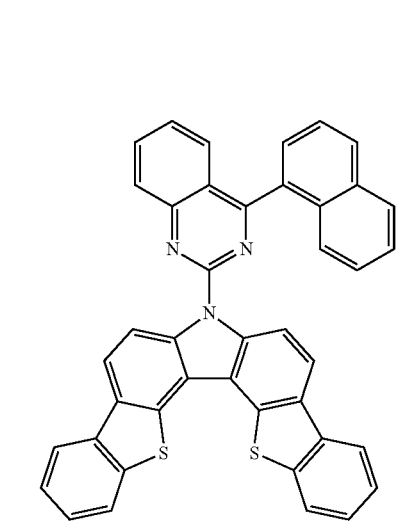

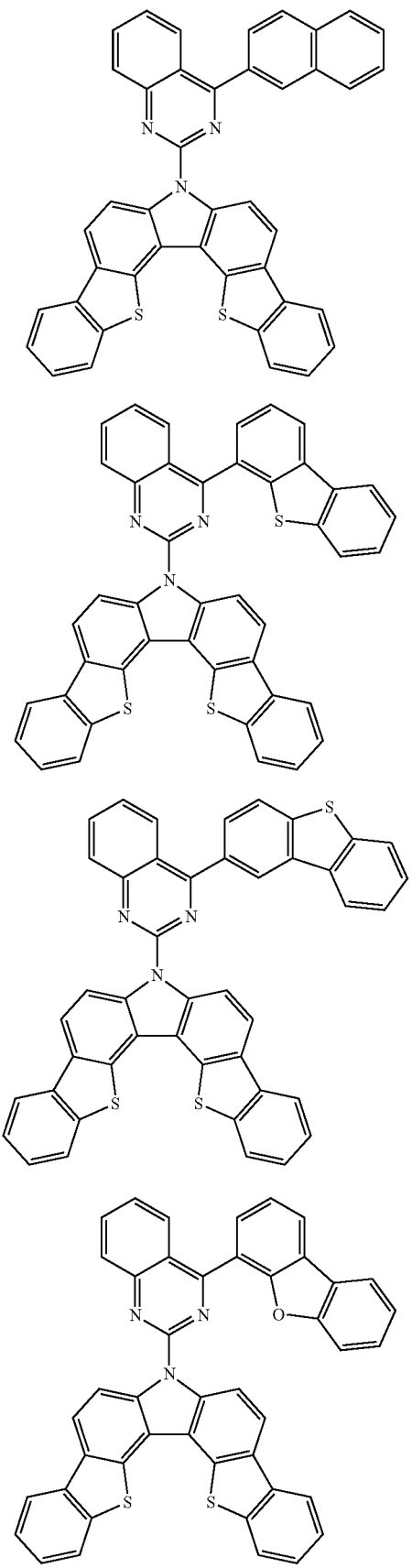
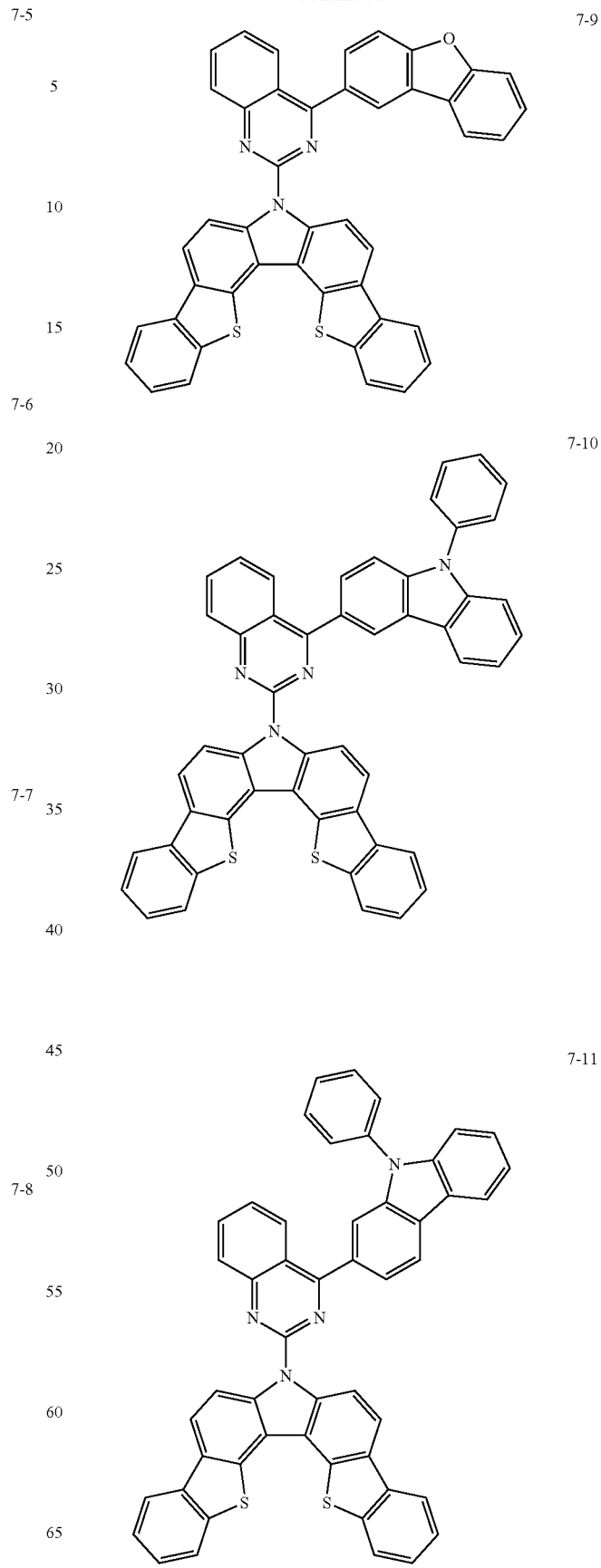

7-12
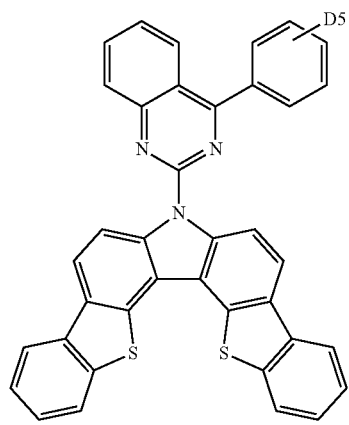
7-13
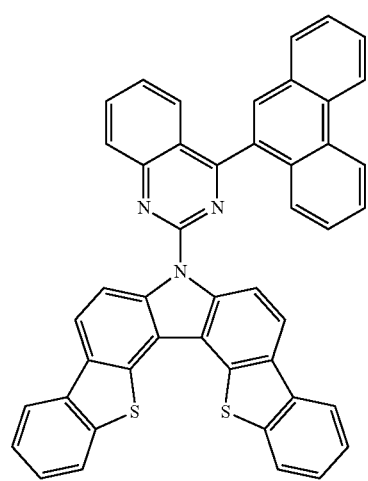
7-14
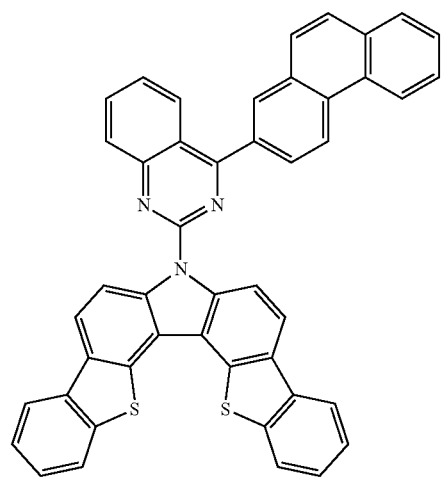
7-15
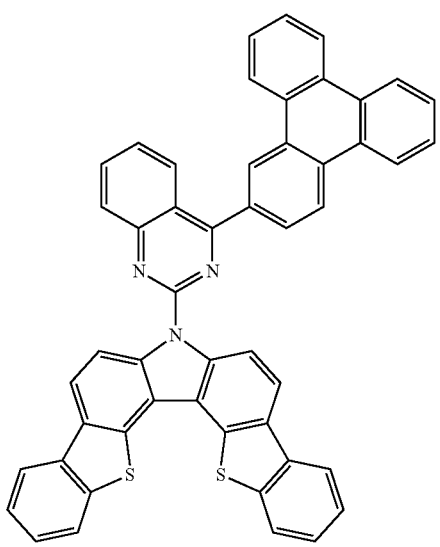
7-16
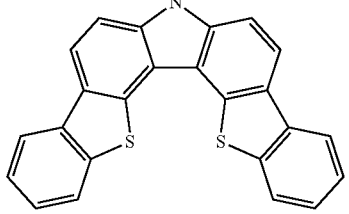
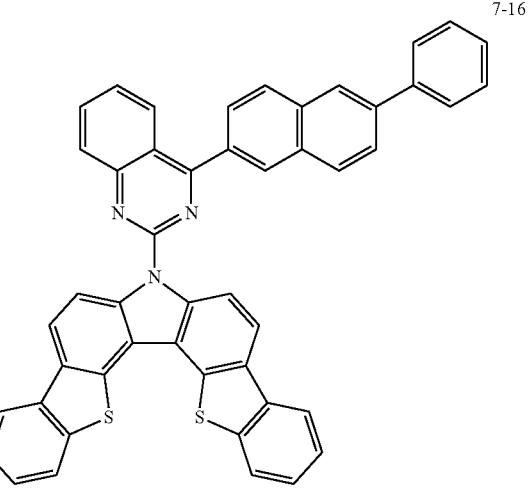
7-17
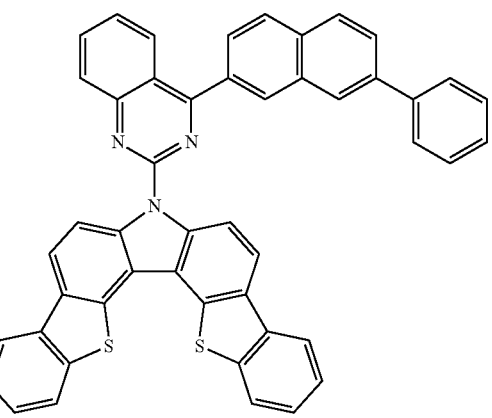

211
-continued
7-18
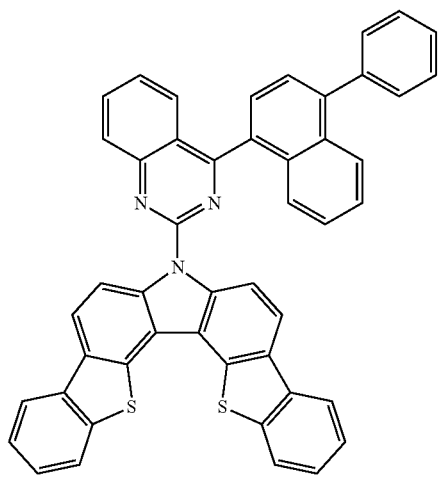
7-19
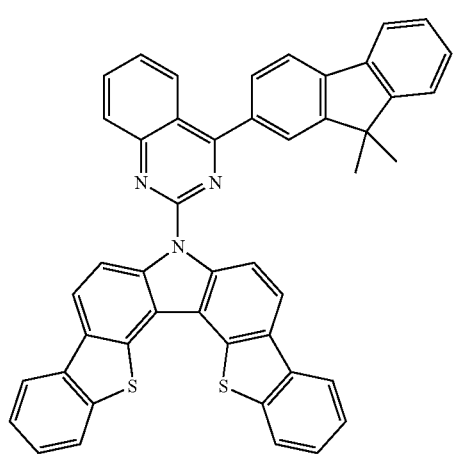
7-20
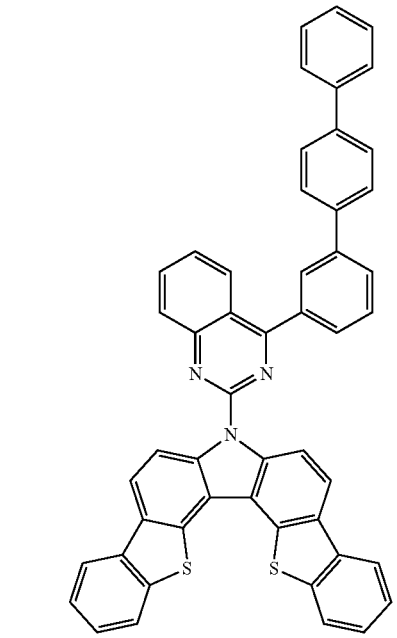
212
-continued
7-21
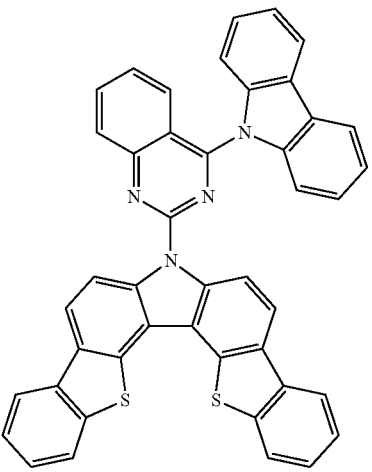
7-22
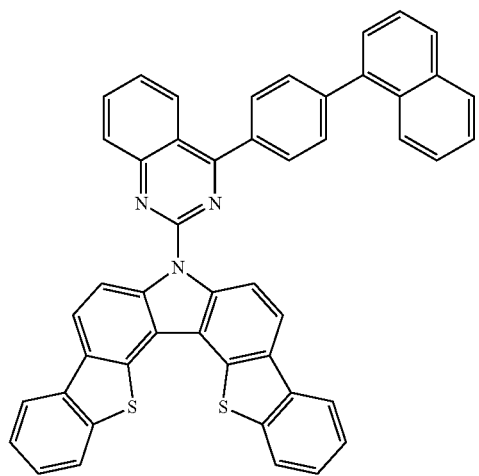
7-23
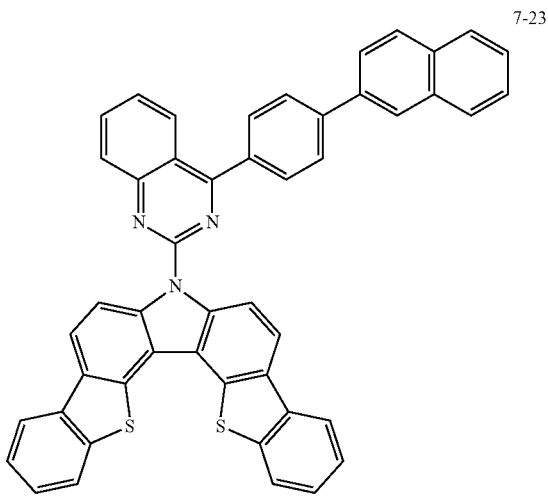

7-24
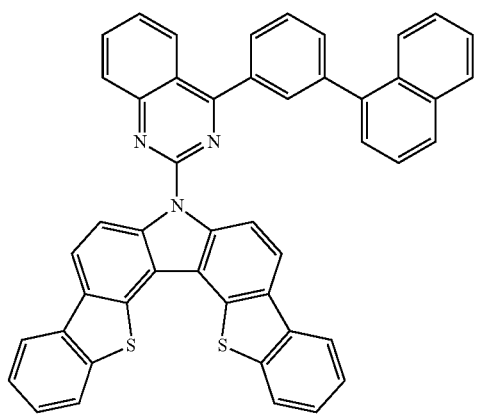
8-1
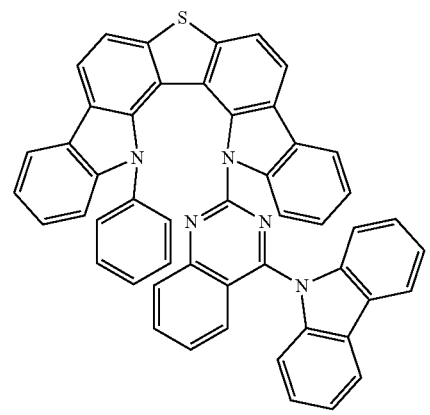
8-2
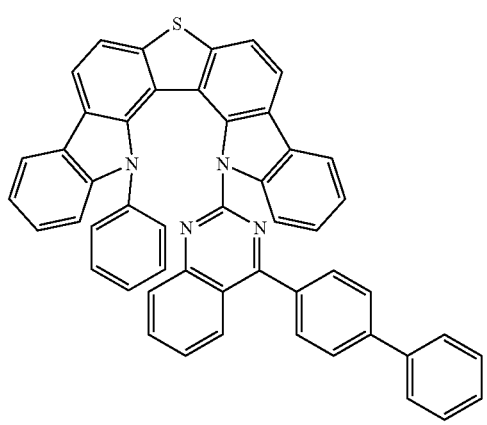
8-3
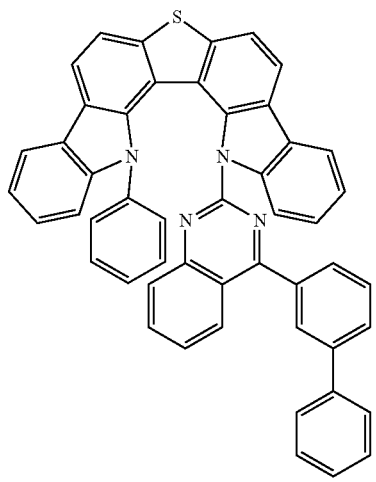
8-4
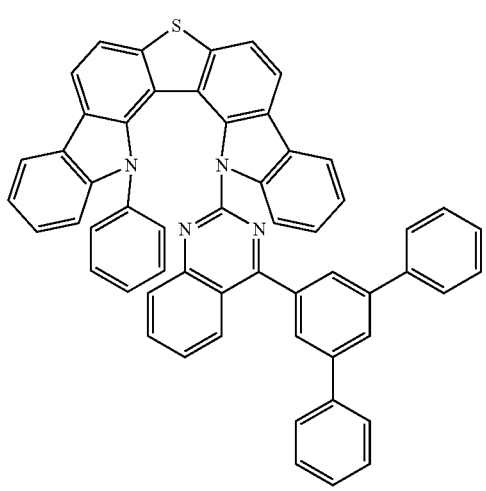
8-5
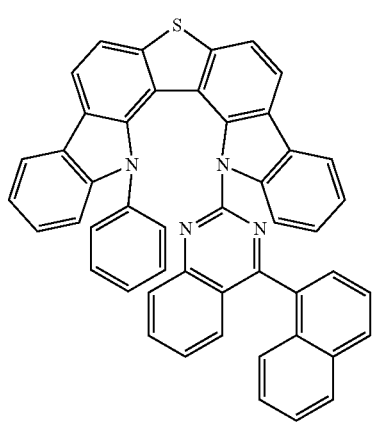

-continued
8-6
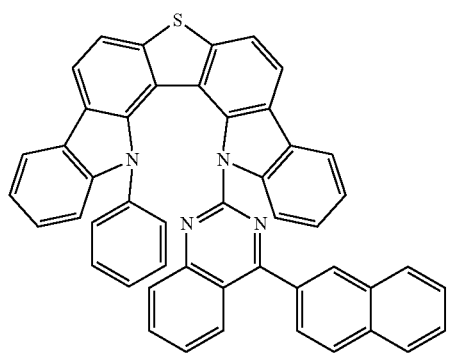
8-7
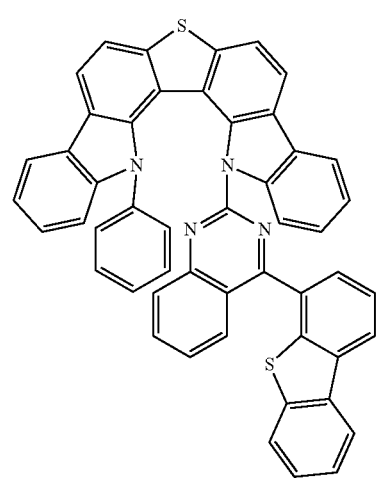
8-8
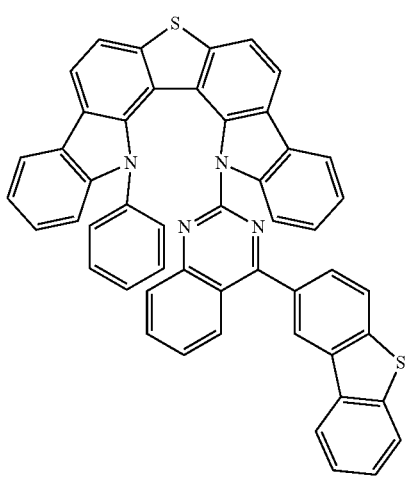
-continued
8-9
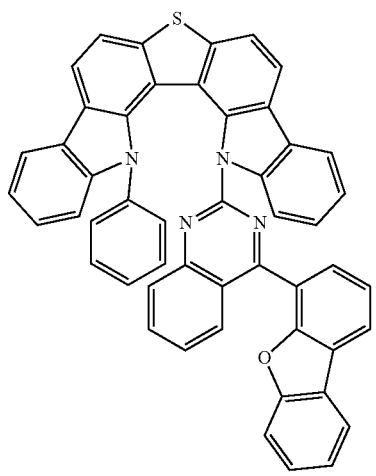
8-10
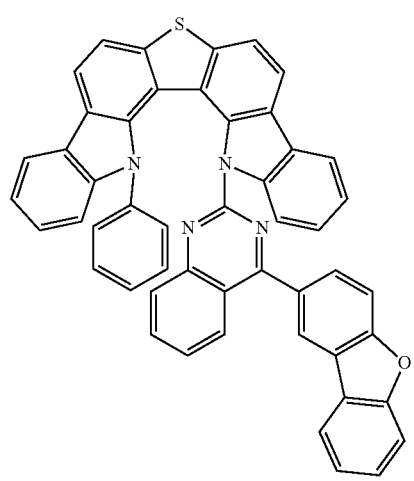
8-11
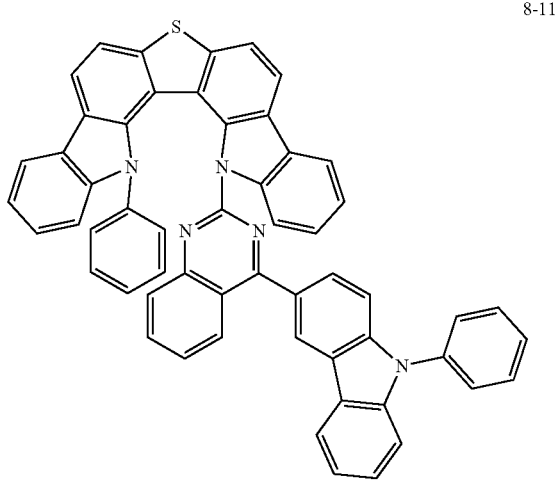

217
-continued
8-12
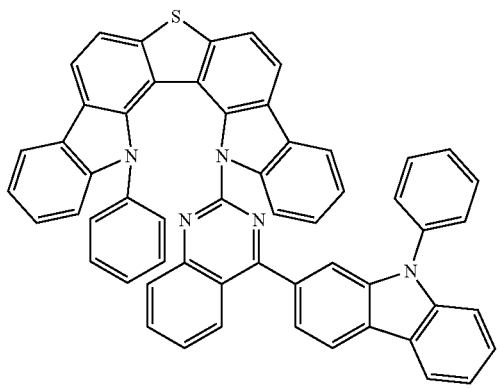
8-13
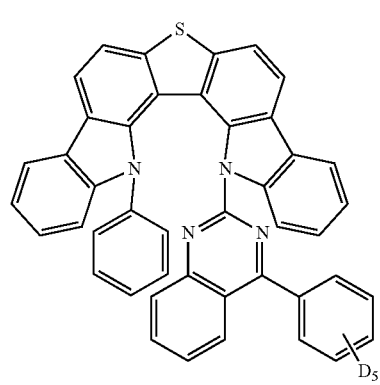
8-14
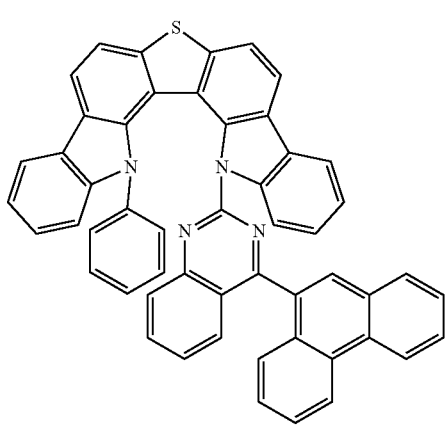
8-15
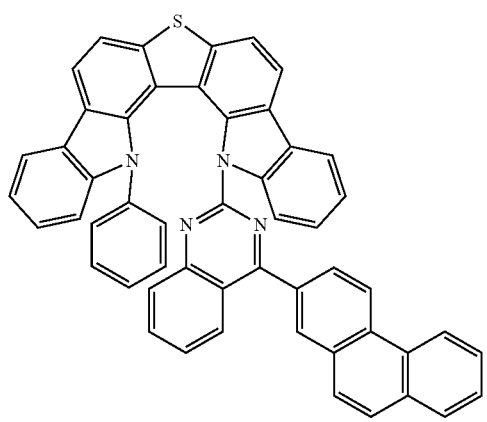
218
-continued
8-16
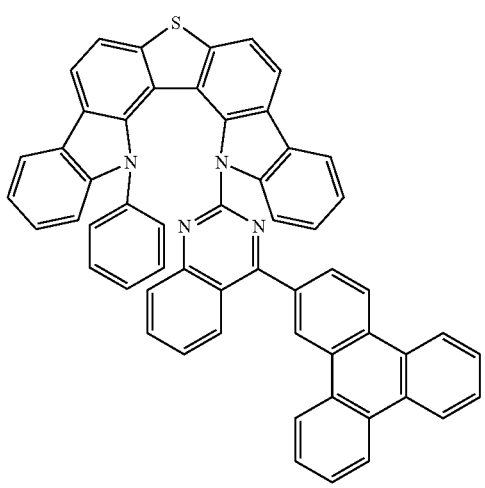
8-17
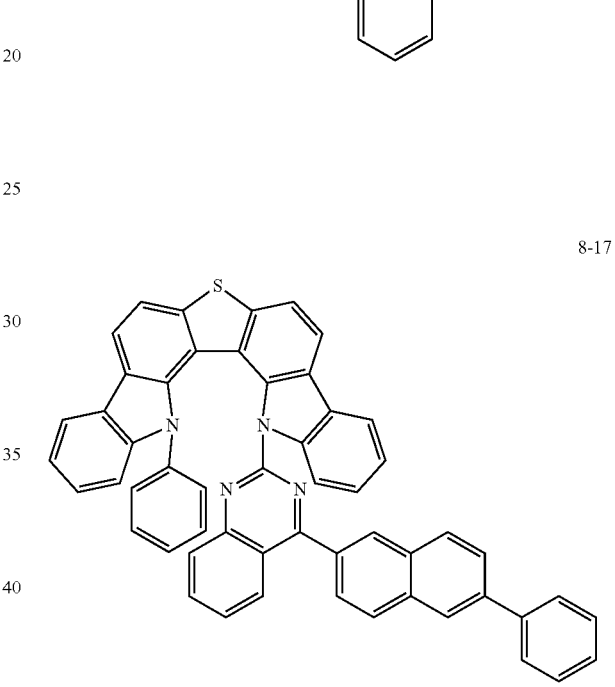
8-18
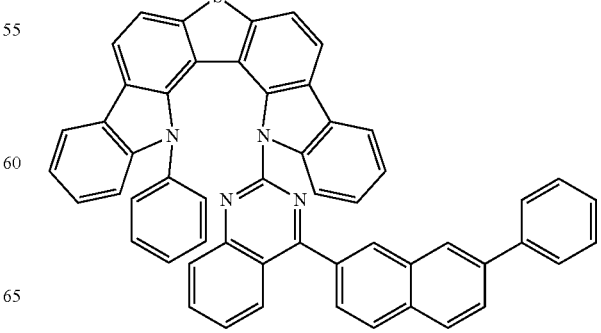

8-19

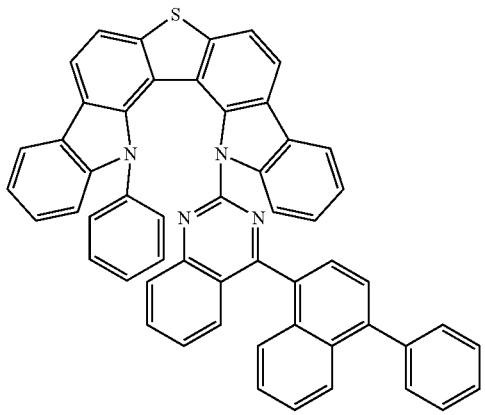

8-20

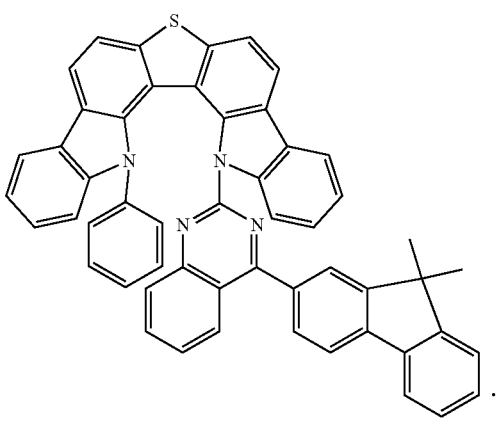

4. An organic electric element comprising a first electrode, a second electrode, and an organic material layer disposed between the first electrode and the second electrode and comprising the compounds of claim 1, wherein the compounds are the same kind or two or more different kind.

5. The organic electric element of claim 4, wherein the organic material layer comprises at least one of, a hole injection layer, a hole transport layer, an emission-auxiliary layer and a light emitting layer.

6. The organic electric element of claim 4, wherein the organic electric element further comprising at least one layer to improve luminescence efficiency which is formed on at least one of the sides of the first and second electrodes, which is opposite to the organic material layer.

7. The organic electric element of claim 4, wherein the organic material layer is formed by any one of the process of spin coating, nozzle printing, inkjet printing, slot coating, dip coating and roll-to-roll.

8. An electronic device comprising a display device, which comprises the organic electric element of claim 4, and a control unit for driving the display device.

9. The electronic device of claim 8, wherein the organic electric element comprises at least one of an organic light emitting diode, an organic solar cell, an organic photo conductor, an organic transistor, and an element for monochromatic or white illumination.

* * * * *

UNITED STATES PATENT AND TRADEMARK OFFICE
CERTIFICATE OF CORRECTION

Page 1 of 2

PATENT NO. : 10,741,771 B2
APPLICATION NO. : 15/112115
DATED : August 11, 2020
INVENTOR(S) : Kim et al.

It is certified that error appears in the above-identified patent and that said Letters Patent is hereby corrected as shown below:

In the Claims

Claim 1, Column 145, Line 21:
Please delete "N($R^5$) at least" and replace with -- N($R^5$), at least --

Claim 3, Column 148, Formula 1-4:

Please delete " 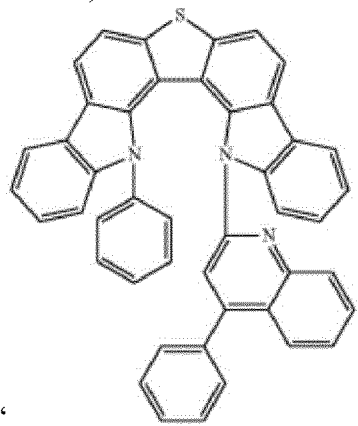 " and replace with -- 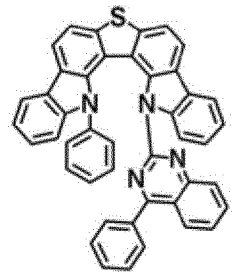 --

Claim 3, Columns 154-165:
Please delete Formulas 2-1 to 2-32

Claim 3, Columns 166-168:
Please delete Formulas 2-35 to 2-40

Claim 3, Columns 176-184:
Please delete Formulas 4-1 to 4-32

Claim 3, Columns 185-187:
Please delete Formulas 4-35 to 4-40

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,741,771 B2

Claim 3, Columns 193-203:
Please delete Formulas 6-1 to 6-32

Claim 3, Columns 204-213:
Please delete Formulas 6-35 to 6-40 and 7-1 to 7-24